US011510977B2

(12) United States Patent
Ying

(10) Patent No.: US 11,510,977 B2

(45) Date of Patent: Nov. 29, 2022

(54) NUCLEIC ACID VACCINES FOR CORONAVIRUS

(71) Applicant: Suzhou Abogen Biosciences Co., Ltd., Suzhou (CN)

(72) Inventor: Bo Ying, Suzhou (CN)

(73) Assignee: Suzhou Abogen Biosciences Co., Ltd., Suzhou (CN)

(*) Notice: Subject to any disclaimer, the term of this patent is extended or adjusted under 35 U.S.C. 154(b) by 0 days.

(21) Appl. No.: 17/589,703

(22) Filed: Jan. 31, 2022

(65) Prior Publication Data

US 2022/0218816 A1 Jul. 14, 2022

Related U.S. Application Data

(63) Continuation of application No. PCT/CN2021/085883, filed on Apr. 8, 2021.

(60) Provisional application No. 63/011,116, filed on Apr. 16, 2020.

(30) Foreign Application Priority Data

Apr. 9, 2020 (CN) ......................... 202010276288.0
Mar. 19, 2021 (CN) ......................... 202110293284.8

(51) Int. Cl.
*A61K 39/215* (2006.01)
*A61P 31/14* (2006.01)
*A61K 39/00* (2006.01)

(52) U.S. Cl.
CPC ............ *A61K 39/215* (2013.01); *A61P 31/14* (2018.01); *A61K 2039/53* (2013.01); *A61K 2039/6018* (2013.01); *A61K 2039/6056* (2013.01)

(58) Field of Classification Search
None
See application file for complete search history.

(56) References Cited

U.S. PATENT DOCUMENTS 9,296,698 B2 3/2016 Cheng et al.
9,868,693 B2 1/2018 Benenato
10,106,490 B2 10/2018 Du
10,285,950 B2 5/2019 Frederick et al.
10,406,112 B2 9/2019 Martini et al.
10,494,636 B2 12/2019 Martini et al.
10,881,730 B2 * 1/2021 Huang ................. A61K 9/0019
2003/0236266 A1 12/2003 Friebe et al.
2013/0022665 A1 1/2013 Nittsu et al.
2013/0115274 A1 5/2013 Knopov et al.
2014/0308304 A1 10/2014 Manohoran et al.
2016/0376224 A1 12/2016 Du et al.
2017/0144967 A1 5/2017 Payne et al.
2017/0340725 A1 * 11/2017 Ciaramella ............ C07K 16/10
2018/0170866 A1 6/2018 Payne et al.
2018/0185516 A1 7/2018 Ansell et al.
2019/0125839 A1 5/2019 Frederick et al.
2019/0167811 A1 6/2019 Benenato et al.
2019/0175517 A1 6/2019 Martini et al.
2019/0275170 A1 9/2019 Benenato et al.
2019/0292130 A1 9/2019 Peer et al.
2019/0298658 A1 10/2019 Benenato et al.
2019/0300906 A1 10/2019 Martini et al.
2019/0314292 A1 10/2019 Benenato et al.
2019/0382774 A1 12/2019 Hoge et al.
2019/0390181 A1 12/2019 Benenato et al.
2020/0046838 A1 2/2020 Ansell et al.
2020/0069793 A1 3/2020 Ciaramella
2020/0085916 A1 3/2020 Martini et al.
2020/0270217 A1 8/2020 Ishihara et al.
2020/0283372 A1 9/2020 Du

FOREIGN PATENT DOCUMENTS

DE 19637043 A1 3/1998
EP 3424524 A2 1/2019
JP H 05331118 A 12/1993
WO WO 2013/016058 1/2013
WO WO 2014/028487 2/2014
WO WO 2015/199952 12/2015
WO WO 2016/210190 12/2016
WO WO 2017/049245 3/2017
WO WO 2017/180917 10/2017
WO WO 2017/201346 11/2017
WO WO 2018/078053 5/2018
WO WO 2018/170245 9/2018
WO WO 2018/170256 9/2018
WO WO 2018/170260 9/2018
WO WO 2018/170306 9/2018
WO WO 2018/200943 11/2018
WO WO 2018/231990 12/2018
WO WO 2019/036000 2/2019
WO WO 2019/036008 2/2019
WO WO 2019/089828 5/2019
WO WO 2020/039631 2/2020
WO WO 2020/061367 3/2020
WO WO 2020047201 A1 3/2020

OTHER PUBLICATIONS

Wu et al., Nature, Mar. 12, 2020, published online Feb. 3, 2020, 579:265-269, plus extended data on methods and figures 1-9. (Year: 2020).*
GenBank Accession No. QHD43416, Surface Glycoprotein of SARS Coronavirus 2, Mar. 18, 2020. (Year: 2020).*
Anonymous (2020) "BioNTech BNT162 Covid-19 Vaccine," BioNTech, pp. 1-10.
Chang et al. (2014), "The SARS coronavirus nucleocapsid protein—Forms and functions," Antiviral Research 103:39-50.

(Continued)

*Primary Examiner* — Stacy B Chen
(74) *Attorney, Agent, or Firm* — Jones Day; Wenhua Yu

(57) ABSTRACT

Provided herein are therapeutic nucleic acid molecules for managing, preventing and/or treating infectious diseases caused by coronavirus. Also provided herein are therapeutic compositions, including vaccines and lipid nanoparticles, comprising the therapeutic nucleic acids and related therapeutic methods and uses.

24 Claims, 7 Drawing Sheets

Specification includes a Sequence Listing.

(56) References Cited

OTHER PUBLICATIONS

He et al. (2004), "Receptor-binding domain of SARS-CoV spike protein induces highly potent neutralizing antibodies: implication for developing subunit vaccine," Biochemical and Biophysical Research Communication 324:773-781.
Ickenstein et al. (2019), Expert Opin Drug Deliv Actions. Nov. 2019;16(11):1205-1226. "Lipid-based nanoparticle formulations for small molecules and RNA drugs." Abstract Only.
Li (2016), "Structure, Function, and Evolution of Coronavirus Spike Proteins," Annu Rev Virol. 3(1):237-261.
Polack et al. (2020), "Safety and Efficacy of the BNT162b2 mRNA Covid-19 Vaccine," The New England Journal of Medicine, 383(27):2603-2615.
Xia et al. (2020), "Towards an effective mRNA vaccine against 2019-nCoV: demonstration of virus-like particles expressed from an modified mRNA cocktail," ChinaXiv, pp. 1-10.
Zhang (2020), "Wuhan seafood market pneumonia virus isolate Wuhan-Hu-1, complete genome," GenBank, pp. 1-11.
Zhang (2020), "A Thermostable mRNA Vaccine against COVID-19," Cell 182:1271-1283.
Zhou et al. (2020), "A pneumonia outbreak associated with a new coronavirus of probable bat origin," Nature 579, 20 pages.
International Search Report and Written Opinion for International Application No. PCT/CN2021/085883 dated Mar. 25, 2022.
U.S. Appl. No. 17/586,488, filed Jan. 27, 2022, Not yet Published, Suzhou Abogen Biosciences Co., Ltd., Lipid Nanoparticle Composition, Pending.

* cited by examiner

```
                    SEQUENCE LISTING

<160> NUMBER OF SEQ ID NOS: 59

<210> SEQ ID NO 1
<211> LENGTH: 29903
<212> TYPE: DNA
<213> ORGANISM: Severe acute respiratory syndrome coronavirus 2 (SARS-
      CoV-2)
<220> FEATURE:
<223> OTHER INFORMATION: Severe acute respiratory syndrome coronavirus 2
      isolate Wuhan-Hu-1, complete genome
<300> PUBLICATION INFORMATION:
<308> DATABASE ACCESSION NUMBER: GenBank/MN908947.3
<309> DATABASE ENTRY DATE: 2020-03-18
<313> RELEVANT RESIDUES IN SEQ ID NO: (1)..(29903)

<400> SEQUENCE: 1

attaaaggtt tataccttcc caggtaacaa accaaccaac tttcgatctc ttgtagatct      60

gttctctaaa cgaactttaa aatctgtgtg gctgtcactc ggctgcatgc ttagtgcact     120

cacgcagtat aattaataac taattactgt cgttgacagg acacgagtaa ctcgtctatc     180

ttctgcaggc tgcttacggt ttcgtccgtg ttgcagccga tcatcagcac atctaggttt     240

cgtccgggtg tgaccgaaag gtaagatgga gagccttgtc cctggtttca acgagaaaac     300

acacgtccaa ctcagtttgc ctgttttaca ggttcgcgac gtgctcgtac gtggctttgg     360

agactccgtg gaggaggtct tatcagaggc acgtcaacat cttaaagatg gcacttgtgg     420

cttagtagaa gttgaaaaag gcgttttgcc tcaacttgaa cagccctatg tgttcatcaa     480

acgttcggat gctcgaactg cacctcatgg tcatgttatg gttgagctgg tagcagaact     540

cgaaggcatt cagtacggtc gtagtggtga gacacttggt gtccttgtcc ctcatgtggg     600

cgaaatacca gtggcttacc gcaaggttct tcttcgtaag aacggtaata aaggagctgg     660

tggccatagt tacggcgccg atctaaagtc atttgactta ggcgacgagc ttggcactga     720

tccttatgaa gattttcaag aaaactggaa cactaaacat agcagtggtg ttacccgtga     780

actcatgcgt gagcttaacg gaggggcata cactcgctat gtcgataaca acttctgtgg     840

ccctgatggc taccctcttg agtgcattaa agaccttcta gcacgtgctg gtaaagcttc     900

atgcactttg tccgaacaac tggactttat tgacactaag aggggtgtat actgctgccg     960

tgaacatgag catgaaattg cttggtacac ggaacgttct gaaaagagct atgaattgca    1020

gacacctttt gaaattaaat tggcaaagaa atttgacacc ttcaatgggg aatgtccaaa    1080

ttttgtattt cccttaaatt ccataatcaa gactattcaa ccaagggttg aaaagaaaaa    1140

gcttgatggc tttatgggta gaattcgatc tgtctatcca gttgcgtcac caaatgaatg    1200

caaccaaatg tgcctttcaa ctctcatgaa gtgtgatcat tgtggtgaaa cttcatggca    1260

gacgggcgat tttgttaaag ccacttgcga attttgtggc actgagaatt tgactaaaga    1320

aggtgccact acttgtggtt acttacccca aaatgctgtt gttaaaattt attgtccagc    1380
```

-continued

```
atgtcacaat tcagaagtag gacctgagca tagtcttgcc gaataccata atgaatctgg   1440
cttgaaaacc attcttcgta agggtggtcg cactattgcc tttggaggct gtgtgttctc   1500
ttatgttggt tgccataaca agtgtgccta ttgggttcca cgtgctagcg ctaacatagg   1560
ttgtaaccat acaggtgttg ttggagaagg ttccgaaggt cttaatgaca accttcttga   1620
aatactccaa aaagagaaag tcaacatcaa tattgttggt gactttaaac ttaatgaaga   1680
gatcgccatt attttggcat ctttttctgc ttccacaagt gcttttgtgg aaactgtgaa   1740
aggtttggat tataaagcat tcaaacaaat tgttgaatcc tgtggtaatt ttaaagttac   1800
aaaaggaaaa gctaaaaaag gtgcctggaa tattggtgaa cagaaatcaa tactgagtcc   1860
tctttatgca tttgcatcag aggctgctcg tgttgtacga tcaattttct cccgcactct   1920
tgaaactgct caaaattctg tgcgtgtttt acagaaggcc gctataacaa tactagatgg   1980
aatttcacag tattcactga gactcattga tgctatgatg ttcacatctg atttggctac   2040
taacaatcta gttgtaatgg cctacattac aggtggtgtt gttcagttga cttcgcagtg   2100
gctaactaac atctttggca ctgtttatga aaaactcaaa cccgtccttg attggcttga   2160
agagaagttt aaggaaggtg tagagtttct tagagacggt tgggaaattg ttaaatttat   2220
ctcaacctgt gcttgtgaaa ttgtcggtgg acaaattgtc acctgtgcaa aggaaattaa   2280
ggagagtgtt cagacattct ttaagcttgt aaataaattt ttggctttgt gtgctgactc   2340
tatcattatt ggtggagcta aacttaaagc cttgaattta ggtgaaacat ttgtcacgca   2400
ctcaaaggga ttgtacagaa agtgtgttaa atccagagaa gaaactggcc tactcatgcc   2460
tctaaaagcc ccaaaagaaa ttatcttctt agagggagaa acacttccca cagaagtgtt   2520
aacagaggaa gttgtcttga aaactggtga tttacaacca ttagaacaac ctactagtga   2580
agctgttgaa gctccattgg ttggtacacc agtttgtatt aacgggctta tgttgctcga   2640
aatcaaagac acagaaaagt actgtgccct tgcacctaat atgatggtaa caaacaatac   2700
cttcacactc aaaggcggtg caccaacaaa ggttactttt ggtgatgaca ctgtgataga   2760
agtgcaaggt tacaagagtg tgaatatcac ttttgaactt gatgaaagga ttgataaagt   2820
acttaatgag aagtgctctg cctatacagt tgaactcggt acagaagtaa atgagttcgc   2880
ctgtgttgtg gcagatgctg tcataaaaac tttgcaacca gtatctgaat tacttacacc   2940
actgggcatt gatttagatg agtggagtat ggctacatac tacttatttg atgagtctgg   3000
tgagtttaaa ttggcttcac atatgtattg ttctttctac cctccagatg aggatgaaga   3060
agaaggtgat tgtgaagaag aagagtttga gccatcaact caatatgagt atggtactga   3120
agatgattac caaggtaaac ctttggaatt tggtgccact tctgctgctc ttcaacctga   3180
agaagagcaa gaagaagatt ggttagatga tgatagtcaa caaactgttg gtcaacaaga   3240
cggcagtgag gacaatcaga caactactat tcaaacaatt gttgaggttc aacctcaatt   3300
agagatggaa cttacaccag ttgttcagac tattgaagtg aatagtttta gtggttattt   3360
aaaacttact gacaatgtat acattaaaaa tgcagacatt gtggaagaag ctaaaaaggt   3420
aaaaccaaca gtggttgtta atgcagccaa tgtttacctt aaacatggag gaggtgttgc   3480
aggagcctta aataaggcta ctaacaatgc catgcaagtt gaatctgatg attacatagc   3540
tactaatgga ccacttaaag tgggtggtag ttgtgtttta agcggacaca atcttgctaa   3600
acactgtctt catgttgtcg gcccaaatgt taacaaaggt gaagacattc aacttcttaa   3660
gagtgcttat gaaaatttta atcagcacga agttctactt gcaccattat tatcagctgg   3720
```

-continued

```
tatttttggt gctgacccta tacattcttt aagagtttgt gtagatactg ttcgcacaaa   3780
tgtctactta gctgtctttg ataaaaatct ctatgacaaa cttgtttcaa gctttttgga   3840
aatgaagagt gaaaagcaag ttgaacaaaa gatcgctgag attcctaaag aggaagttaa   3900
gccatttata actgaaagta aaccttcagt tgaacagaga aaacaagatg ataagaaaat   3960
caaagcttgt gttgaagaag ttacaacaac tctggaagaa actaagttcc tcacagaaaa   4020
cttgttactt tatattgaca ttaatggcaa tcttcatcca gattctgcca ctcttgttag   4080
tgacattgac atcactttct taaagaaaga tgctccatat atagtgggtg atgttgttca   4140
agagggtgtt ttaactgctg tggttatacc tactaaaaag gctggtggca ctactgaaat   4200
gctagcgaaa gctttgagaa aagtgccaac agacaattat ataaccactt acccgggtca   4260
gggtttaaat ggttacactg tagaggaggc aaagacagtg cttaaaaagt gtaaaagtgc   4320
cttttacatt ctaccatcta ttatctctaa tgagaagcaa gaaattcttg gaactgtttc   4380
ttggaatttg cgagaaatgc ttgcacatgc agaagaaaca cgcaaattaa tgcctgtctg   4440
tgtggaaact aaagccatag tttcaactat acagcgtaaa tataagggta ttaaaataca   4500
agagggtgtg gttgattatg gtgctagatt ttacttttac accagtaaaa caactgtagc   4560
gtcacttatc aacacactta acgatctaaa tgaaactctt gttacaatgc cacttggcta   4620
tgtaacacat ggcttaaatt tggaagaagc tgctcggtat atgagatctc tcaaagtgcc   4680
agctacagtt tctgtttctt cacctgatgc tgttacagcg tataatggtt atcttacttc   4740
ttcttctaaa acacctgaag aacattttat tgaaaccatc tcacttgctg gttcctataa   4800
agattggtcc tattctggac aatctacaca actaggtata gaatttctta agagaggtga   4860
taaaagtgta tattacacta gtaatcctac cacattccac ctagatggtg aagttatcac   4920
ctttgacaat cttaagacac ttctttcttt gagagaagtg aggactatta aggtgtttac   4980
aacagtagac aacattaacc tccacacgca agttgtggac atgtcaatga catatggaca   5040
acagtttggt ccaacttatt tggatggagc tgatgttact aaaataaaac ctcataattc   5100
acatgaaggt aaaacatttt atgttttacc taatgatgac actctacgtg ttgaggcttt   5160
tgagtactac cacacaactg atcctagttt tctgggtagg tacatgtcag cattaaatca   5220
cactaaaaag tggaaatacc cacaagttaa tggtttaact tctattaaat gggcagataa   5280
caactgttat cttgccactg cattgttaac actccaacaa atagagttga agtttaatcc   5340
acctgctcta caagatgctt attacagagc aagggctggt gaagctgcta acttttgtgc   5400
acttatctta gcctactgta ataagacagt aggtgagtta ggtgatgtta gagaaacaat   5460
gagttacttg tttcaacatg ccaatttaga ttcttgcaaa agagtcttga acgtggtgtg   5520
taaaacttgt ggacaacagc agacaaccct taagggtgta gaagctgtta tgtacatggg   5580
cacactttct tatgaacaat ttaagaaagg tgttcagata ccttgtacgt gtggtaaaca   5640
agctacaaaa tatctagtac aacaggagtc accttttgtt atgatgtcag caccacctgc   5700
tcagtatgaa cttaagcatg gtacatttac ttgtgctagt gagtacactg gtaattacca   5760
gtgtggtcac tataaacata taacttctaa agaaactttg tattgcatag acggtgcttt   5820
acttacaaag tcctcagaat acaaaggtcc tattacggat gttttctaca aagaaaacag   5880
ttacacaaca accataaaac cagttactta taaattggat ggtgttgttt gtacagaaat   5940
tgaccctaag ttggacaatt attataagaa agacaattct tatttcacag agcaaccaat   6000
tgatcttgta ccaaaccaac catatccaaa cgcaagcttc gataatttta agtttgtatg   6060
tgataatatc aaatttgctg atgatttaaa ccagttaact ggttataaga aacctgcttc   6120
```

-continued

```
aagagagctt aaagttacat ttttccctga cttaaatggt gatgtggtgg ctattgatta   6180
taaacactac acaccctctt ttaagaaagg agctaaattg ttacataaac ctattgtttg   6240
gcatgttaac aatgcaacta ataaagccac gtataaacca aatacctggt gtatacgttg   6300
tctttggagc acaaaaccag ttgaaacatc aaattcgttt gatgtactga agtcagagga   6360
cgcgcaggga atggataatc ttgcctgcga agatctaaaa ccagtctctg aagaagtagt   6420
ggaaaatcct accatacaga aagacgttct tgagtgtaat gtgaaaacta ccgaagttgt   6480
aggagacatt atacttaaac cagcaaataa tagtttaaaa attacagaag aggttggcca   6540
cacagatcta atggctgctt atgtagacaa ttctagtctt actattaaga aacctaatga   6600
attatctaga gtattaggtt tgaaaaccct tgctactcat ggtttagctg ctgttaatag   6660
tgtcccttgg gatactatag ctaattatgc taagcctttt cttaacaaag ttgttagtac   6720
aactactaac atagttacac ggtgtttaaa ccgtgtttgt actaattata tgccttattt   6780
ctttacttta ttgctacaat tgtgtacttt tactagaagt acaaattcta gaattaaagc   6840
atctatgccg actactatag caaagaatac tgttaagagt gtcggtaaat tttgtctaga   6900
ggcttcattt aattatttga agtcacctaa tttttctaaa ctgataaata ttataatttg   6960
gtttttacta ttaagtgttt gcctaggttc tttaatctac tcaaccgctg ctttaggtgt   7020
tttaatgtct aatttaggca tgccttctta ctgtactggt tacagagaag gctatttgaa   7080
ctctactaat gtcactattg caacctactg tactggttct ataccttgta gtgtttgtct   7140
tagtggttta gattctttag acacctatcc ttctttagaa actatacaaa ttaccatttc   7200
atcttttaaa tgggatttaa ctgcttttgg cttagttgca gagtggtttt tggcatatat   7260
tcttttcact aggtttttct atgtacttgg attggctgca atcatgcaat tgtttttcag   7320
ctattttgca gtacatttta ttagtaattc ttggcttatg tggttaataa ttaatcttgt   7380
acaaatggcc ccgatttcag ctatggttag aatgtacatc ttctttgcat cattttatta   7440
tgtatggaaa agttatgtgc atgttgtaga cggttgtaat tcatcaactt gtatgatgtg   7500
ttacaaacgt aatagagcaa caagagtcga atgtacaact attgttaatg gtgttagaag   7560
gtccttttat gtctatgcta atggaggtaa aggcttttgc aaactacaca attggaattg   7620
tgttaattgt gatacattct gtgctggtag tacatttatt agtgatgaag ttgcgagaga   7680
cttgtcacta cagtttaaaa gaccaataaa tcctactgac cagtcttctt acatcgttga   7740
tagtgttaca gtgaagaatg gttccatcca tctttacttt gataaagctg gtcaaaagac   7800
ttatgaaaga cattctctct ctcattttgt taacttagac aacctgagag ctaataacac   7860
taaaggttca ttgcctatta atgttatagt tttgatggt aaatcaaaat gtgaagaatc   7920
atctgcaaaa tcagcgtctg tttactacag tcagcttatg tgtcaaccta tactgttact   7980
agatcaggca ttagtgtctg atgttggtga tagtgcggaa gttgcagtta aaatgtttga   8040
tgcttacgtt aatacgtttt catcaacttt taacgtacca atggaaaaac tcaaaacact   8100
agttgcaact gcagaagctg aacttgcaaa gaatgtgtcc ttagacaatg tcttatctac   8160
ttttatttca gcagctcggc aagggtttgt tgattcagat gtagaaacta aagatgttgt   8220
tgaatgtctt aaattgtcac atcaatctga catagaagtt actggcgata gttgtaataa   8280
ctatatgctc acctataaca aagttgaaaa catgacaccc cgtgaccttg gtgcttgtat   8340
tgactgtagt gcgcgtcata ttaatgcgca ggtagcaaaa agtcacaaca ttgctttgat   8400
atggaacgtt aaagatttca tgtcattgtc tgaacaacta cgaaaacaaa tacgtagtgc   8460
```

-continued

```
tgctaaaaag aataacttac cttttaagtt gacatgtgca actactagac aagttgttaa   8520
tgttgtaaca acaaagatag cacttaaggg tggtaaaatt gttaataatt ggttgaagca   8580
gttaattaaa gttacacttg tgttcctttt tgttgctgct attttctatt taataacacc   8640
tgttcatgtc atgtctaaac atactgactt ttcaagtgaa atcataggat acaaggctat   8700
tgatggtggt gtcactcgtg acatagcatc tacagatact tgttttgcta acaaacatgc   8760
tgattttgac acatggttta gccagcgtgg tggtagttat actaatgaca aagcttgccc   8820
attgattgct gcagtcataa caagagaagt gggttttgtc gtgcctggtt tgcctggcac   8880
gatattacgc acaactaatg gtgacttttt gcatttctta cctagagttt ttagtgcagt   8940
tggtaacatc tgttacacac catcaaaact tatagagtac actgactttg caacatcagc   9000
ttgtgttttg gctgctgaat gtacaatttt taaagatgct tctggtaagc cagtaccata   9060
ttgttatgat accaatgtac tagaaggttc tgttgcttat gaaagtttac gccctgacac   9120
acgttatgtg ctcatggatg gctctattat tcaatttcct aacacctacc ttgaaggttc   9180
tgttagagtg gtaacaactt ttgattctga gtactgtagg cacggcactt gtgaaagatc   9240
agaagctggt gtttgtgtat ctactagtgg tagatgggta cttaacaatg attattacag   9300
atctttacca ggagttttct gtggtgtaga tgctgtaaat ttacttacta atatgtttac   9360
accactaatt caacctattg gtgctttgga catatcagca tctatagtag ctggtggtat   9420
tgtagctatc gtagtaacat gccttgccta ctattttatg aggtttagaa gagcttttgg   9480
tgaatacagt catgtagttg cctttaatac tttactattc cttatgtcat tcactgtact   9540
ctgtttaaca ccagtttact cattcttacc tggtgtttat tctgttattt acttgtactt   9600
gacattttat cttactaatg atgtttcttt tttagcacat attcagtgga tggttatgtt   9660
cacaccttta gtacctttct ggataacaat tgcttatatc atttgtattt ccacaaagca   9720
tttctattgg ttctttagta attacctaaa gagacgtgta gtctttaatg gtgtttcctt   9780
tagtactttt gaagaagctg cgctgtgcac ctttttgtta aataaagaaa tgtatctaaa   9840
gttgcgtagt gatgtgctat tacctcttac gcaatataat agatacttag ctctttataa   9900
taagtacaag tattttagtg gagcaatgga tacaactagc tacagagaag ctgcttgttg   9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
```

```
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
accttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
```

-continued

```
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
gtcagctgat gcacaatcgt ttttaaacgg gtttgcggtg taagtgcagc ccgtcttaca  13500
ccgtgcggca caggcactag tactgatgtc gtatacaggg cttttgacat ctacaatgat  13560
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
```

cgcaatttac aacacagact ttatgagtgt ctctatagaa atagagatgt tgacacagac 15660
tttgtgaatg agttttacgc atatttgcgt aaacatttct caatgatgat actctctgac 15720
gatgctgttg tgtgtttcaa tagcacttat gcatctcaag gtctagtggc tagcataaag 15780
aactttaagt cagttcttta ttatcaaaac aatgttttta tgtctgaagc aaaatgttgg 15840
actgagactg accttactaa aggacctcat gaattttgct ctcaacatac aatgctagtt 15900
aaacagggtg atgattatgt gtaccttcct tacccagatc catcaagaat cctaggggcc 15960
ggctgttttg tagatgatat cgtaaaaaca gatggtacac ttatgattga acggttcgtg 16020
tctttagcta tagatgctta cccacttact aaacatccta atcaggagta tgctgatgtc 16080
tttcatttgt acttacaata cataagaaag ctacatgatg agttaacagg acacatgtta 16140
gacatgtatt ctgttatgct tactaatgat aacacttcaa ggtattggga acctgagttt 16200
tatgaggcta tgtacacacc gcatacagtc ttacaggctg ttggggcttg tgttctttgc 16260
aattcacaga cttcattaag atgtggtgct tgcatacgta gaccattctt atgttgtaaa 16320
tgctgttacg accatgtcat atcaacatca cataaattag tcttgtctgt taatccgtat 16380
gtttgcaatg ctccaggttg tgatgtcaca gatgtgactc aactttactt aggaggtatg 16440
agctattatt gtaaatcaca taaaccaccc attagttttc cattgtgtgc taatggacaa 16500
gtttttggtt tatataaaaa tacatgtgtt ggtagcgata atgttactga ctttaatgca 16560
attgcaacat gtgactggac aaatgctggt gattacattt tagctaacac ctgtactgaa 16620
agactcaagc tttttgcagc agaaacgctc aaagctactg aggagacatt taaactgtct 16680
tatggtattg ctactgtacg tgaagtgctg tctgacagag aattacatct ttcatgggaa 16740
gttggtaaac ctagaccacc acttaaccga aattatgtct ttactggtta tcgtgtaact 16800
aaaaacagta aagtacaaat aggagagtac acctttgaaa aaggtgacta tggtgatgct 16860
gttgtttacc gaggtacaac aacttacaaa ttaaatgttg gtgattattt tgtgctgaca 16920
tcacatacag taatgccatt aagtgcacct acactagtgc cacaagagca ctatgttaga 16980
attactggct tatacccaac actcaatatc tcagatgagt tttctagcaa tgttgcaaat 17040
tatcaaaagg ttggtatgca aaagtattct acactccagg gaccacctgg tactggtaag 17100
agtcattttg ctattggcct agctctctac tacccttctg ctcgcatagt gtatacagct 17160
tgctctcatg ccgctgttga tgcactatgt gagaaggcat taaaatattt gcctatagat 17220
aaatgtagta gaattatacc tgcacgtgct cgtgtagagt gttttgataa attcaaagtg 17280
aattcaacat tagaacagta tgtcttttgt actgtaaatg cattgcctga gacgacagca 17340
gatatagttg tctttgatga aatttcaatg gccacaaatt atgatttgag tgttgtcaat 17400
gccagattac gtgctaagca ctatgtgtac attggcgacc ctgctcaatt acctgcacca 17460
cgcacattgc taactaaggg cacactagaa ccagaatatt tcaattcagt gtgtagactt 17520
atgaaaacta taggtccaga catgttcctc ggaacttgtc ggcgttgtcc tgctgaaatt 17580
gttgacactg tgagtgcttt ggtttatgat aataagctta aagcacataa agacaaatca 17640
gctcaatgct ttaaaatgtt ttataagggt gttatcacgc atgatgtttc atctgcaatt 17700
aacaggccac aaataggcgt ggtaagagaa ttccttacac gtaaccctgc ttggagaaaa 17760
gctgtcttta tttcacctta taattcacag aatgctgtag cctcaaagat tttgggacta 17820
ccaactcaaa ctgttgattc atcacagggc tcagaatatg actatgtcat attcactcaa 17880
accactgaaa cagctcactc ttgtaatgta aacagattta atgttgctat taccagagca 17940

-continued

```
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat cacccgcgaa gaagctataa gacatgtacg tgcatggatt  18300
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagatttttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtcttttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
```

agtcatagtc agttaggtgg tttacatcta ctgattggac tagctaaacg ttttaaggaa 20400
tcaccttttg aattagaaga ttttattcct atggacagta cagttaaaaa ctatttcata 20460
acagatgcgc aaacaggttc atctaagtgt gtgtgttctg ttattgattt attacttgat 20520
gattttgttg aaataataaa atcccaagat ttatctgtag tttctaaggt tgtcaaagtg 20580
actattgact atacagaaat ttcatttatg ctttggtgta aagatggcca tgtagaaaca 20640
ttttacccaa aattacaatc tagtcaagcg tggcaaccgg gtgttgctat gcctaatctt 20700
tacaaaatgc aaagaatgct attagaaaag tgtgaccttc aaaattatgg tgatagtgca 20760
acattaccta aaggcataat gatgaatgtc gcaaaatata ctcaactgtg tcaatattta 20820
aacacattaa cattagctgt accctataat atgagagtta tacattttgg tgctggttct 20880
gataaaggag ttgcaccagg tacagctgtt ttaagacagt ggttgcctac gggtacgctg 20940
cttgtcgatt cagatcttaa tgactttgtc tctgatgcag attcaacttt gattggtgat 21000
tgtgcaactg tacatacagc taataaatgg gatctcatta ttagtgatat gtacgaccct 21060
aagactaaaa atgttacaaa agaaaatgac tctaaagagg gtttttcac ttacatttgt 21120
gggtttatac aacaaaagct agctcttgga ggttccgtgg ctataaagat aacagaacat 21180
tcttggaatg ctgatcttta taagctcatg ggacacttcg catggtggac agcctttgtt 21240
actaatgtga atgcgtcatc atctgaagca tttttaattg gatgtaatta tcttggcaaa 21300
ccacgcgaac aaatagatgg ttatgtcatg catgcaaatt acatattttg gaggaataca 21360
aatccaattc agttgtcttc ctattcttta tttgacatga gtaaatttcc ccttaaatta 21420
aggggtactg ctgttatgtc tttaaaagaa ggtcaaatca atgatatgat tttatctctt 21480
cttagtaaag gtagacttat aattagagaa aacaacagag ttgttatttc tagtgatgtt 21540
cttgttaaca actaaacgaa caatgtttgt ttttcttgtt ttattgccac tagtctctag 21600
tcagtgtgtt aatcttacaa ccagaactca attacccct gcatacacta attctttcac 21660
acgtggtgtt tattaccctg acaaagtttt cagatcctca gttttacatt caactcagga 21720
cttgttctta cctttctttt ccaatgttac ttggttccat gctatacatg tctctgggac 21780
caatggtact aagaggtttg ataaccctgt cctaccattt aatgatggtg tttattttgc 21840
ttccactgag aagtctaaca taataagagg ctggattttt ggtactactt tagattcgaa 21900
gacccagtcc ctacttattg ttaataacgc tactaatgtt gttattaaag tctgtgaatt 21960
tcaattttgt aatgatccat ttttgggtgt ttattaccac aaaaacaaca aaagttggat 22020
ggaaagtgag ttcagagttt attctagtgc gaataattgc acttttgaat atgtctctca 22080
gccttttctt atggaccttg aaggaaaaca gggtaatttc aaaaatctta gggaatttgt 22140
gtttaagaat attgatggtt attttaaaat atattctaag cacacgccta ttaatttagt 22200
gcgtgatctc cctcagggtt tttcggcttt agaaccattg gtagatttgc caataggtat 22260
taacatcact aggtttcaaa ctttacttgc tttacataga agttatttga ctcctggtga 22320
ttcttcttca ggttggacag ctggtgctgc agcttattat gtgggttatc ttcaacctag 22380
gacttttcta ttaaaatata atgaaaatgg aaccattaca gatgctgtag actgtgcact 22440
tgaccctctc tcagaaacaa agtgtacgtt gaaatccttc actgtagaaa aaggaatcta 22500
tcaaacttct aactttagag tccaaccaac agaatctatt gttagatttc ctaatattac 22560
aaacttgtgc ccttttggtg aagtttttaa cgccaccaga tttgcatctg tttatgcttg 22620
gaacaggaag agaatcagca actgtgttgc tgattattct gtcctatata attccgcatc 22680

-continued

```
attttccact tttaagtgtt atggagtgtc tcctactaaa ttaaatgatc tctgctttac  22740
taatgtctat gcagattcat ttgtaattag aggtgatgaa gtcagacaaa tcgctccagg  22800
gcaaactgga aagattgctg attataatta taaattacca gatgatttta caggctgcgt  22860
tatagcttgg aattctaaca atcttgattc taaggttggt ggtaattata attacctgta  22920
tagattgttt aggaagtcta atctcaaacc ttttgagaga gatatttcaa ctgaaatcta  22980
tcaggccggt agcacacctt gtaatggtgt tgaaggtttt aattgttact ttcctttaca  23040
atcatatggt ttccaaccca ctaatggtgt tggttaccaa ccatacagag tagtagtact  23100
ttcttttgaa cttctacatg caccagcaac tgtttgtgga cctaaaaagt ctactaattt  23160
ggttaaaaac aaatgtgtca atttcaactt caatggttta acaggcacag gtgttcttac  23220
tgagtctaac aaaaagtttc tgcctttcca acaatttggc agagacattg ctgacactac  23280
tgatgctgtc cgtgatccac agacacttga gattcttgac attacaccat gttcttttgg  23340
tggtgtcagt gttataacac caggaacaaa tacttctaac caggttgctg ttctttatca  23400
ggatgttaac tgcacagaag tccctgttgc tattcatgca gatcaactta ctcctacttg  23460
gcgtgtttat tctacaggtt ctaatgtttt tcaaacacgt gcaggctgtt taataggggc  23520
tgaacatgtc aacaactcat atgagtgtga catacccatt ggtgcaggta tatgcgctag  23580
ttatcagact cagactaatt ctcctcggcg ggcacgtagt gtagctagtc aatccatcat  23640
tgcctacact atgtcacttg gtgcagaaaa ttcagttgct tactctaata actctattgc  23700
catacccaca aattttacta ttagtgttac cacagaaatt ctaccagtgt ctatgaccaa  23760
gacatcagta gattgtacaa tgtacatttg tggtgattca actgaatgca gcaatctttt  23820
gttgcaatat ggcagttttt gtacacaatt aaaccgtgct ttaactggaa tagctgttga  23880
acaagacaaa aacacccaag aagtttttgc acaagtcaaa caaatttaca aaacaccacc  23940
aattaaagat tttggtggtt ttaatttttc acaaatatta ccagatccat caaaaccaag  24000
caagaggtca tttattgaag atctactttt caacaaagtg acacttgcag atgctggctt  24060
catcaaacaa tatggtgatt gccttggtga tattgctgct agagacctca tttgtgcaca  24120
aaagtttaac ggccttactg ttttgccacc tttgctcaca gatgaaatga ttgctcaata  24180
cacttctgca ctgttagcgg gtacaatcac ttctggttgg acctttggtg caggtgctgc  24240
attacaaata ccatttgcta tgcaaatggc ttataggttt aatggtattg gagttacaca  24300
gaatgttctc tatgagaacc aaaaattgat tgccaaccaa tttaatagtg ctattggcaa  24360
aattcaagac tcactttctt ccacagcaag tgcacttgga aaacttcaag atgtggtcaa  24420
ccaaaatgca caagctttaa acacgcttgt taaacaactt agctccaatt ttggtgcaat  24480
ttcaagtgtt ttaaatgata tcctttcacg tcttgacaaa gttgaggctg aagtgcaaat  24540
tgataggttg atcacaggca gacttcaaag tttgcagaca tatgtgactc aacaattaat  24600
tagagctgca gaaatcagag cttctgctaa tcttgctgct actaaaatgt cagagtgtgt  24660
acttggacaa tcaaaaagag ttgatttttg tggaaagggc tatcatctta tgtccttccc  24720
tcagtcagca cctcatggtg tagtcttctt gcatgtgact tatgtccctg cacaagaaaa  24780
gaacttcaca actgctcctg ccatttgtca tgatggaaaa gcacactttc ctcgtgaagg  24840
tgtctttgtt tcaaatggca cacactggtt tgtaacacaa aggaattttt atgaaccaca  24900
aatcattact acagacaaca catttgtgtc tggtaactgt gatgttgtaa taggaattgt  24960
caacaacaca gtttatgatc ctttgcaacc tgaattagac tcattcaagg aggagttaga  25020
taaatatttt aagaatcata catcaccaga tgttgattta ggtgacatct ctggcattaa  25080
```

tgcttcagtt gtaaacattc aaaaagaaat tgaccgcctc aatgaggttg ccaagaattt 25140
aaatgaatct ctcatcgatc tccaagaact tggaaagtat gagcagtata taaaatggcc 25200
atggtacatt tggctaggtt ttatagctgg cttgattgcc atagtaatgg tgacaattat 25260
gctttgctgt atgaccagtt gctgtagttg tctcaagggc tgttgttctt gtggatcctg 25320
ctgcaaattt gatgaagacg actctgagcc agtgctcaaa ggagtcaaat tacattacac 25380
ataaacgaac ttatggattt gtttatgaga atcttcacaa ttggaactgt aactttgaag 25440
caaggtgaaa tcaaggatgc tactccttca gattttgttc gcgctactgc aacgataccg 25500
atacaagcct cactcccttt cggatggctt attgttggcg ttgcacttct tgctgttttt 25560
cagagcgctt ccaaaatcat aaccctcaaa aagagatggc aactagcact ctccaagggt 25620
gttcactttg tttgcaactt gctgttgttg tttgtaacag tttactcaca ccttttgctc 25680
gttgctgctg gccttgaagc cccttttctc tatctttatg ctttagtcta cttcttgcag 25740
agtataaact tgtaagaat aataatgagg ctttggcttt gctggaaatg ccgttccaaa 25800
aacccattac tttatgatgc caactatttt ctttgctggc atactaattg ttacgactat 25860
tgtatacctt acaatagtgt aacttcttca attgtcatta cttcaggtga tggcacaaca 25920
agtcctattt ctgaacatga ctaccagatt ggtggttata ctgaaaaatg ggaatctgga 25980
gtaaaagact gtgttgtatt acacagttac ttcacttcag actattacca gctgtactca 26040
actcaattga gtacagacac tggtgttgaa catgttacct tcttcatcta caataaaatt 26100
gttgatgagc ctgaagaaca tgtccaaatt cacacaatcg acggttcatc cggagttgtt 26160
aatccagtaa tggaaccaat ttatgatgaa ccgacgacga ctactagcgt gcctttgtaa 26220
gcacaagctg atgagtacga acttatgtac tcattcgttt cggaagagac aggtacgtta 26280
atagttaata gcgtacttct tttcttgct ttcgtggtat tcttgctagt tacactagcc 26340
atccttactg cgcttcgatt gtgtgcgtac tgctgcaata ttgttaacgt gagtcttgta 26400
aaaccttctt tttacgttta ctctcgtgtt aaaaatctga attcttctag agttcctgat 26460
cttctggtct aaacgaacta aatattatat tagtttttct gtttggaact ttaattttag 26520
ccatggcaga ttccaacggt actattaccg ttgaagagct taaaaagctc cttgaacaat 26580
ggaacctagt aataggtttc ctattcctta catggatttg tcttctacaa tttgcctatg 26640
ccaacaggaa taggttttg tatataatta agttaatttt cctctggctg ttatggccag 26700
taactttagc ttgttttgtg cttgctgctg tttacagaat aaattggatc accggtggaa 26760
ttgctatcgc aatggcttgt cttgtaggct tgatgtggct cagctacttc attgcttctt 26820
tcagactgtt tgcgcgtacg cgttccatgt ggtcattcaa tccagaaact aacattcttc 26880
tcaacgtgcc actccatggc actattctga ccagaccgct tctagaaagt gaactcgtaa 26940
tcggagctgt gatccttcgt ggacatcttc gtattgctgg acaccatcta ggacgctgtg 27000
acatcaagga cctgcctaaa gaaatcactg ttgctacatc acgaacgctt tcttattaca 27060
aattgggagc ttcgcagcgt gtagcaggtg actcaggttt tgctgcatac agtcgctaca 27120
ggattggcaa ctataaatta aacacagacc attccagtag cagtgacaat attgctttgc 27180
ttgtacagta agtgacaaca gatgtttcat ctcgttgact ttcaggttac tatagcagag 27240
atattactaa ttattatgag gacttttaaa gtttccattt ggaatcttga ttacatcata 27300
aacctcataa ttaaaaattt atctaagtca ctaactgaga ataaatattc tcaattagat 27360
gaagagcaac caatggagat tgattaaacg aacatgaaaa ttattctttt cttggcactg 27420

-continued

```
ataacactcg ctacttgtga gctttatcac taccaagagt gtgttagagg tacaacagta  27480
cttttaaaag aaccttgctc ttctggaaca tacgagggca attcaccatt tcatcctcta  27540
gctgataaca aatttgcact gacttgcttt agcactcaat ttgcttttgc ttgtcctgac  27600
ggcgtaaaac acgtctatca gttacgtgcc agatcagttt cacctaaact gttcatcaga  27660
caagaggaag ttcaagaact ttactctcca atttttctta ttgttgcggc aatagtgttt  27720
ataacacttt gcttcacact caaaagaaag acagaatgat tgaactttca ttaattgact  27780
tctatttgtg ctttttagcc tttctgctat tccttgtttt aattatgctt attatctttt  27840
ggttctcact tgaactgcaa gatcataatg aaacttgtca cgcctaaacg aacatgaaat  27900
ttcttgtttt cttaggaatc atcacaactg tagctgcatt tcaccaagaa tgtagtttac  27960
agtcatgtac tcaacatcaa ccatatgtag ttgatgaccc gtgtcctatt cacttctatt  28020
ctaaatggta tattagagta ggagctagaa aatcagcacc tttaattgaa ttgtgcgtgg  28080
atgaggctgg ttctaaatca cccattcagt acatcgatat cggtaattat acagtttcct  28140
gtttaccttt tacaattaat tgccaggaac ctaaattggg tagtcttgta gtgcgttgtt  28200
cgttctatga agacttttta gagtatcatg acgttcgtgt tgttttagat ttcatctaaa  28260
cgaacaaact aaaatgtctg ataatggacc ccaaaatcag cgaaatgcac cccgcattac  28320
gtttggtgga ccctcagatt caactggcag taaccagaat ggagaacgca gtggggcgcg  28380
atcaaaacaa cgtcggcccc aaggtttacc caataatact gcgtcttggt tcaccgctct  28440
cactcaacat ggcaaggaag accttaaatt ccctcgagga caaggcgttc caattaacac  28500
caatagcagt ccagatgacc aaattggcta ctaccgaaga gctaccagac gaattcgtgg  28560
tggtgacggt aaaatgaaag atctcagtcc aagatggtat ttctactacc taggaactgg  28620
gccagaagct ggacttccct atggtgctaa caaagacggc atcatatggg ttgcaactga  28680
gggagccttg aatacaccaa aagatcacat tggcacccgc aatcctgcta acaatgctgc  28740
aatcgtgcta caacttcctc aaggaacaac attgccaaaa ggcttctacg cagaagggag  28800
cagaggcggc agtcaagcct cttctcgttc ctcatcacgt agtcgcaaca gttcaagaaa  28860
ttcaactcca ggcagcagta ggggaacttc tcctgctaga atggctggca atggcggtga  28920
tgctgctctt gctttgctgc tgcttgacag attgaaccag cttgagagca aaatgtctgg  28980
taaaggccaa caacaacaag gccaaactgt cactaagaaa tctgctgctg aggcttctaa  29040
gaagcctcgg caaaaacgta ctgccactaa agcatacaat gtaacacaag ctttcggcag  29100
acgtggtcca gaacaaaccc aaggaaattt tggggaccag gaactaatca gacaaggaac  29160
tgattacaaa cattggccgc aaattgcaca atttgccccc agcgcttcag cgttcttcgg  29220
aatgtcgcgc attggcatgg aagtcacacc ttcgggaacg tggttgacct acacaggtgc  29280
catcaaattg gatgacaaag atccaaattt caaagatcaa gtcattttgc tgaataagca  29340
tattgacgca tacaaaacat tcccaccaac agagcctaaa aaggacaaaa agaagaaggc  29400
tgatgaaact caagccttac cgcagagaca gaagaaacag caaactgtga ctcttcttcc  29460
tgctgcagat ttggatgatt tctccaaaca attgcaacaa tccatgagca gtgctgactc  29520
aactcaggcc taaactcatg cagaccacac aaggcagatg ggctatataa acgttttcgc  29580
ttttccgttt acgatatata gtctactctt gtgcagaatg aattctcgta actacatagc  29640
acaagtagat gtagttaact ttaatctcac atagcaatct ttaatcagtg tgtaacatta  29700
gggaggactt gaaagagcca ccacattttc accgaggcca cgcggagtac gatcgagtgt  29760
acagtgaaca atgctaggga gagctgccta tatggaagag ccctaatgtg taaaattaat  29820
```

```
tttagtagtg ctatccccat gtgattttaa tagcttctta ggagaatgac aaaaaaaaaa  29880

aaaaaaaaaa aaaaaaaaaa aaa                                          29903


<210> SEQ ID NO 2
<211> LENGTH: 1273
<212> TYPE: PRT
<213> ORGANISM: SARS-CoV-2
<220> FEATURE:
<223> OTHER INFORMATION: SARS-CoV-2 spike protein with native signal
      peptide

<400> SEQUENCE: 2

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335
```

-continued

```
Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
```

-continued

```
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170
```

```
Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270
```

<210> SEQ ID NO 3
<211> LENGTH: 3819
<212> TYPE: DNA
<213> ORGANISM: SARS-CoV-2
<220> FEATURE:
<223> OTHER INFORMATION: SARS-CoV-2 spike protein with native signal peptide

<400> SEQUENCE: 3

```
atgtttgttt ttcttgtttt attgccatta gtctctagtc agtgtgttaa tcttacaacc     60
agaactcaat taccccctgc atacactaat tctttcacac gtggtgttta ttaccctgac    120
aaagttttca gatcctcagt tttacattca actcaggact tgttcttacc tttcttttcc    180
aatgttactt ggttccatgc tatacatgtc tctgggacca atggtactaa gaggtttgat    240
aaccctgtcc taccatttaa tgatggtgtt tattttgctt ccactgagaa gtctaacata    300
ataagaggct ggatttttgg tactacttta gattcgaaga cccagtccct acttattgtt    360
aataacgcta ctaatgttgt tattaaagtc tgtgaatttc aattttgtaa tgatccattt    420
ttgggtgttt attaccacaa aaacaacaaa agttggatgg aaagtgagtt cagagtttat    480
tctagtgcga ataattgcac ttttgaatat gtctctcagc cttttcttat ggaccttgaa    540
ggaaaacagg gtaatttcaa aaatcttagg gaatttgtgt ttaagaatat tgatggttat    600
tttaaaatat attctaagca cacgcctatt aatttagtgc gtgatctccc tcagggtttt    660
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga cttttctatt aaaatataat    840
gaaaatggaa ccattacaga tgctgtagac tgtgcacttg accctctctc agaaacaaag    900
tgtacgttga aatccttcac tgtagaaaaa ggaatctatc aaacttctaa ctttagagtc    960
caaccaacag aatctattgt tagatttcct aatattacaa acttgtgccc ttttggtgaa   1020
gtttttaacg ccaccagatt tgcatctgtt tatgcttgga acaggaagag aatcagcaac   1080
tgtgttgctg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccagggc aaactggaaa gattgctgat   1260
tataattata aattaccaga tgattttaca ggctgcgtta tagcttggaa ttctaacaat   1320
cttgattcta aggttggtgg taattataat tacctgtata gattgtttag gaagtctaat   1380
```

-continued

```
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
ctacttttca acaaagtgac acttgcagat gctggcttca tcaaacaata tggtgattgc   2520
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtgctgcat tacaaatacc atttgctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acagcaagtg cacttggaaa acttcaagat gtggtcaacc aaaatgcaca agctttaaac   2880
acgcttgtta aacaacttag ctccaatttt ggtgcaattt caagtgtttt aaatgatatc   2940
ctttcacgtc ttgacaaagt tgaggctgaa gtgcaaattg ataggttgat cacaggcaga   3000
cttcaaagtt tgcagacata tgtgactcaa caattaatta gagctgcaga aatcagagct   3060
tctgctaatc ttgctgctac taaaatgtca gagtgtgtac ttggacaatc aaaaagagtt   3120
gatttttgtg gaaagggcta tcatcttatg tccttccctc agtcagcacc tcatggtgta   3180
gtcttcttgc atgtgactta tgtccctgca caagaaaaga acttcacaac tgctcctgcc   3240
atttgtcatg atggaaaagc acactttcct cgtgaaggtg tctttgtttc aaatggcaca   3300
cactggtttg taacacaaag gaatttttat gaaccacaaa tcattactac agacaacaca   3360
tttgtgtctg gtaactgtga tgttgtaata ggaattgtca acaacacagt ttatgatcct   3420
ttgcaacctg aattagactc attcaaggag gagttagata aatattttaa gaatcataca   3480
tcaccagatg ttgatttagg tgacatctct ggcattaatg cttcagttgt aaacattcaa   3540
aaagaaattg accgcctcaa tgaggttgcc aagaatttaa atgaatctct catcgatctc   3600
caagaacttg gaaagtatga gcagtatata aaatggccat ggtacatttg gctaggtttt   3660
atagctggct tgattgccat agtaatggtg acaattatgc tttgctgtat gaccagttgc   3720
tgtagttgtc tcaagggctg ttgttcttgt ggatcctgct gcaaatttga tgaagacgac   3780
```

```
tctgagccag tgctcaaagg agtcaaatta cattacaca                        3819


<210> SEQ ID NO 4
<211> LENGTH: 1198
<212> TYPE: PRT
<213> ORGANISM: SARS-CoV-2
<220> FEATURE:
<223> OTHER INFORMATION: SARS-CoV-2 spike protein ectodomain (ECD)

<400> SEQUENCE: 4

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350
```

-continued

```
Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
```

-continued

```
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                 1015                 1020

Ser Lys  Arg Val Asp Phe Cys  Gly Lys Gly Tyr His  Leu Met Ser
    1025                 1030                 1035

Phe Pro  Gln Ser Ala Pro His  Gly Val Val Phe Leu  His Val Thr
    1040                 1045                 1050

Tyr Val  Pro Ala Gln Glu Lys  Asn Phe Thr Thr Ala  Pro Ala Ile
    1055                 1060                 1065

Cys His  Asp Gly Lys Ala His  Phe Pro Arg Glu Gly  Val Phe Val
    1070                 1075                 1080

Ser Asn  Gly Thr His Trp Phe  Val Thr Gln Arg Asn  Phe Tyr Glu
    1085                 1090                 1095

Pro Gln  Ile Ile Thr Thr Asp  Asn Thr Phe Val Ser  Gly Asn Cys
    1100                 1105                 1110

Asp Val  Val Ile Gly Ile Val  Asn Asn Thr Val Tyr  Asp Pro Leu
    1115                 1120                 1125

Gln Pro  Glu Leu Asp Ser Phe  Lys Glu Glu Leu Asp  Lys Tyr Phe
    1130                 1135                 1140

Lys Asn  His Thr Ser Pro Asp  Val Asp Leu Gly Asp  Ile Ser Gly
    1145                 1150                 1155

Ile Asn  Ala Ser Val Val Asn  Ile Gln Lys Glu Ile  Asp Arg Leu
    1160                 1165                 1170

Asn Glu  Val Ala Lys Asn Leu  Asn Glu Ser Leu Ile  Asp Leu Gln
    1175                 1180                 1185
```

-continued

```
Glu Leu  Gly Lys Tyr Glu Gln  Tyr Ile Lys
    1190                 1195
```

<210> SEQ ID NO 5
<211> LENGTH: 3594
<212> TYPE: DNA
<213> ORGANISM: SARS-CoV-2
<220> FEATURE:
<223> OTHER INFORMATION: SARS-CoV-2 spike protein ECD coding sequence

<400> SEQUENCE: 5

```
cagtgtgtta atcttacaac cagaactcaa ttaccccctg catacactaa ttctttcaca     60
cgtggtgttt attaccctga caaagttttc agatcctcag ttttacattc aactcaggac    120
ttgttcttac ctttcttttc caatgttact tggttccatg ctatacatgt ctctgggacc    180
aatggtacta agaggtttga taaccctgtc ctaccattta atgatggtgt ttattttgct    240
tccactgaga agtctaacat aataagaggc tggatttttg gtactacttt agattcgaag    300
acccagtccc tacttattgt taataacgct actaatgttg ttattaaagt ctgtgaattt    360
caattttgta atgatccatt tttgggtgtt tattaccaca aaaacaacaa aagttggatg    420
gaaagtgagt tcagagttta ttctagtgcg aataattgca cttttgaata tgtctctcag    480
ccttttctta tggaccttga aggaaaacag ggtaatttca aaaatcttag ggaatttgtg    540
tttaagaata ttgatggtta ttttaaaata tattctaagc acacgcctat taatttagtg    600
cgtgatctcc ctcagggttt ttcggcttta gaaccattgg tagatttgcc aataggtatt    660
aacatcacta ggtttcaaac tttacttgct ttacatagaa gttatttgac tcctggtgat    720
tcttcttcag gttggacagc tggtgctgca gcttattatg tgggttatct tcaacctagg    780
acttttctat taaaatataa tgaaaatgga accattacag atgctgtaga ctgtgcactt    840
gaccctctct cagaaacaaa gtgtacgttg aaatccttca ctgtagaaaa aggaatctat    900
caaacttcta actttagagt ccaaccaaca gaatctattg ttagatttcc taatattaca    960
aacttgtgcc cttttggtga agtttttaac gccaccagat ttgcatctgt ttatgcttgg   1020
aacaggaaga gaatcagcaa ctgtgttgct gattattctg tcctatataa ttccgcatca   1080
ttttccactt ttaagtgtta tggagtgtct cctactaaat taaatgatct ctgctttact   1140
aatgtctatg cagattcatt tgtaattaga ggtgatgaag tcagacaaat cgctccaggg   1200
caaactggaa agattgctga ttataattat aaattaccag atgattttac aggctgcgtt   1260
atagcttgga actctaacaa tcttgattct aaggttggtg gtaattataa ttacctgtat   1320
agattgttta ggaagtctaa tctcaaacct tttgagagag atatttcaac tgaaatctat   1380
caggccggta gcacaccttg taatggtgtt gaaggtttta attgttactt tcctttacaa   1440
tcatatggtt tccaacccac taatggtgtt ggttaccaac catacagagt agtagtactt   1500
tcttttgaac ttctacatgc accagcaact gtttgtggac ctaaaaagtc tactaatttg   1560
gttaaaaaca aatgtgtcaa tttcaacttc aatggtttaa caggcacagg tgttcttact   1620
gagtctaaca aaaagtttct gcctttccaa caatttggca gagacattgc tgacactact   1680
gatgctgtcc gtgatccaca gacacttgag attcttgaca ttacaccatg ttcttttggt   1740
ggtgtcagtg ttataacacc aggaacaaat acttctaacc aggttgctgt tctttatcag   1800
gatgttaact gcacagaagt ccctgttgct attcatgcag atcaacttac tcctacttgg   1860
cgtgtttatt ctacaggttc taatgttttt caaacacgtg caggctgttt aataggggct   1920
gaacatgtca acaactcata tgagtgtgac atacccattg gtgcaggtat atgcgctagt   1980
```

```
tatcagactc agactaattc tcctcggcgg gcacgtagtg tagctagtca atccatcatt   2040
gcctacacta tgtcacttgg tgcagaaaat tcagttgctt actctaataa ctctattgcc   2100
atacccacaa attttactat tagtgttacc acagaaattc taccagtgtc tatgaccaag   2160
acatcagtag attgtacaat gtacatttgt ggtgattcaa ctgaatgcag caatcttttg   2220
ttgcaatatg gcagtttttg tacacaatta aaccgtgctt taactggaat agctgttgaa   2280
caagacaaaa acacccaaga agtttttgca caagtcaaac aaatttacaa aacaccacca   2340
attaaagatt ttggtggttt taatttttca caaatattac cagatccatc aaaaccaagc   2400
aagaggtcat ttattgaaga tctacttttc aacaaagtga cacttgcaga tgctggcttc   2460
atcaaacaat atggtgattg ccttggtgat attgctgcta gagacctcat ttgtgcacaa   2520
aagtttaacg gccttactgt tttgccacct ttgctcacag atgaaatgat tgctcaatac   2580
acttctgcac tgttagcggg tacaatcact tctggttgga cctttggtgc aggtgctgca   2640
ttacaaatac catttgctat gcaaatggct tataggttta atggtattgg agttacacag   2700
aatgttctct atgagaacca aaaattgatt gccaaccaat ttaatagtgc tattggcaaa   2760
attcaagact cactttcttc cacagcaagt gcacttggaa aacttcaaga tgtggtcaac   2820
caaaatgcac aagctttaaa cacgcttgtt aaacaactta gctccaattt tggtgcaatt   2880
tcaagtgttt taaatgatat cctttcacgt cttgacaaag ttgaggctga agtgcaaatt   2940
gataggttga tcacaggcag acttcaaagt ttgcagacat atgtgactca acaattaatt   3000
agagctgcag aaatcagagc ttctgctaat cttgctgcta ctaaaatgtc agagtgtgta   3060
cttggacaat caaaaagagt tgatttttgt ggaaagggct atcatcttat gtccttccct   3120
cagtcagcac ctcatggtgt agtcttcttg catgtgactt atgtccctgc acaagaaaag   3180
aacttcacaa ctgctcctgc catttgtcat gatggaaaag cacactttcc tcgtgaaggt   3240
gtctttgttt caaatggcac acactggttt gtaacacaaa ggaattttta tgaaccacaa   3300
atcattacta cagacaacac atttgtgtct ggtaactgtg atgttgtaat aggaattgtc   3360
aacaacacag tttatgatcc tttgcaacct gaattagact cattcaagga ggagttagat   3420
aaatatttta agaatcatac atcaccagat gttgatttag gtgacatctc tggcattaat   3480
gcttcagttg taaacattca aaaagaaatt gaccgcctca atgaggttgc caagaattta   3540
aatgaatctc tcatcgatct ccaagaactt ggaaagtatg agcagtatat aaaa         3594
```

<210> SEQ ID NO 6
<211> LENGTH: 672
<212> TYPE: PRT
<213> ORGANISM: SARS-CoV-2
<220> FEATURE:
<223> OTHER INFORMATION: SARS-CoV-2 spike protein S1 subunit

<400> SEQUENCE: 6

```
Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80
```

Ser Thr Glu Lys Ser Asn Ile Ile Arg Gly Trp Ile Phe Gly Thr Thr
85 90 95

Leu Asp Ser Lys Thr Gln Ser Leu Leu Ile Val Asn Asn Ala Thr Asn
100 105 110

Val Val Ile Lys Val Cys Glu Phe Gln Phe Cys Asn Asp Pro Phe Leu
115 120 125

Gly Val Tyr Tyr His Lys Asn Asn Lys Ser Trp Met Glu Ser Glu Phe
130 135 140

Arg Val Tyr Ser Ser Ala Asn Asn Cys Thr Phe Glu Tyr Val Ser Gln
145 150 155 160

Pro Phe Leu Met Asp Leu Glu Gly Lys Gln Gly Asn Phe Lys Asn Leu
165 170 175

Arg Glu Phe Val Phe Lys Asn Ile Asp Gly Tyr Phe Lys Ile Tyr Ser
180 185 190

Lys His Thr Pro Ile Asn Leu Val Arg Asp Leu Pro Gln Gly Phe Ser
195 200 205

Ala Leu Glu Pro Leu Val Asp Leu Pro Ile Gly Ile Asn Ile Thr Arg
210 215 220

Phe Gln Thr Leu Leu Ala Leu His Arg Ser Tyr Leu Thr Pro Gly Asp
225 230 235 240

Ser Ser Ser Gly Trp Thr Ala Gly Ala Ala Ala Tyr Tyr Val Gly Tyr
245 250 255

Leu Gln Pro Arg Thr Phe Leu Leu Lys Tyr Asn Glu Asn Gly Thr Ile
260 265 270

Thr Asp Ala Val Asp Cys Ala Leu Asp Pro Leu Ser Glu Thr Lys Cys
275 280 285

Thr Leu Lys Ser Phe Thr Val Glu Lys Gly Ile Tyr Gln Thr Ser Asn
290 295 300

Phe Arg Val Gln Pro Thr Glu Ser Ile Val Arg Phe Pro Asn Ile Thr
305 310 315 320

Asn Leu Cys Pro Phe Gly Glu Val Phe Asn Ala Thr Arg Phe Ala Ser
325 330 335

Val Tyr Ala Trp Asn Arg Lys Arg Ile Ser Asn Cys Val Ala Asp Tyr
340 345 350

Ser Val Leu Tyr Asn Ser Ala Ser Phe Ser Thr Phe Lys Cys Tyr Gly
355 360 365

Val Ser Pro Thr Lys Leu Asn Asp Leu Cys Phe Thr Asn Val Tyr Ala
370 375 380

Asp Ser Phe Val Ile Arg Gly Asp Glu Val Arg Gln Ile Ala Pro Gly
385 390 395 400

Gln Thr Gly Lys Ile Ala Asp Tyr Asn Tyr Lys Leu Pro Asp Asp Phe
405 410 415

Thr Gly Cys Val Ile Ala Trp Asn Ser Asn Asn Leu Asp Ser Lys Val
420 425 430

Gly Gly Asn Tyr Asn Tyr Leu Tyr Arg Leu Phe Arg Lys Ser Asn Leu
435 440 445

Lys Pro Phe Glu Arg Asp Ile Ser Thr Glu Ile Tyr Gln Ala Gly Ser
450 455 460

Thr Pro Cys Asn Gly Val Glu Gly Phe Asn Cys Tyr Phe Pro Leu Gln
465 470 475 480

Ser Tyr Gly Phe Gln Pro Thr Asn Gly Val Gly Tyr Gln Pro Tyr Arg
485 490 495

```
Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670


<210> SEQ ID NO 7
<211> LENGTH: 2016
<212> TYPE: DNA
<213> ORGANISM: SARS-CoV-2
<220> FEATURE:
<223> OTHER INFORMATION: SARS-CoV-2 spike protein S1 subunit coding
      sequence

<400> SEQUENCE: 7

cagtgtgtta atcttacaac cagaactcaa ttaccccctg catacactaa ttctttcaca      60

cgtggtgttt attaccctga caaagttttc agatcctcag ttttacattc aactcaggac     120

ttgttcttac ctttcttttc caatgttact tggttccatg ctatacatgt ctctgggacc     180

aatggtacta agaggtttga taaccctgtc ctaccattta atgatggtgt ttattttgct     240

tccactgaga agtctaacat aataagaggc tggatttttg gtactacttt agattcgaag     300

acccagtccc tacttattgt taataacgct actaatgttg ttattaaagt ctgtgaattt     360

caattttgta atgatccatt tttgggtgtt tattaccaca aaaacaacaa aagttggatg     420

gaaagtgagt tcagagttta ttctagtgcg aataattgca cttttgaata tgtctctcag     480

ccttttctta tggaccttga aggaaaacag ggtaatttca aaaatcttag ggaatttgtg     540

tttaagaata ttgatggtta ttttaaaata tattctaagc acacgcctat taatttagtg     600

cgtgatctcc ctcagggttt ttcggcttta gaaccattgg tagatttgcc aataggtatt     660

aacatcacta ggtttcaaac tttacttgct ttacatagaa gttatttgac tcctggtgat     720

tcttcttcag gttggacagc tggtgctgca gcttattatg tgggttatct tcaacctagg     780

acttttctat taaaatataa tgaaaatgga accattacag atgctgtaga ctgtgcactt     840

gaccctctct cagaaacaaa gtgtacgttg aaatccttca ctgtagaaaa aggaatctat     900

caaacttcta actttagagt ccaaccaaca gaatctattg ttagatttcc taatattaca     960

aacttgtgcc cttttggtga agtttttaac gccaccagat ttgcatctgt ttatgcttgg    1020

aacaggaaga gaatcagcaa ctgtgttgct gattattctg tcctatataa ttccgcatca    1080
```

```
ttttccactt ttaagtgtta tggagtgtct cctactaaat taaatgatct ctgctttact   1140

aatgtctatg cagattcatt tgtaattaga ggtgatgaag tcagacaaat cgctccaggg   1200

caaactggaa agattgctga ttataattat aaattaccag atgattttac aggctgcgtt   1260

atagcttgga attctaacaa tcttgattct aaggttggtg gtaattataa ttacctgtat   1320

agattgttta ggaagtctaa tctcaaacct tttgagagag atatttcaac tgaaatctat   1380

caggccggta gcacaccttg taatggtgtt gaaggtttta attgttactt tcctttacaa   1440

tcatatggtt tccaacccac taatggtgtt ggttaccaac catacagagt agtagtactt   1500

tcttttgaac ttctacatgc accagcaact gtttgtggac ctaaaaagtc tactaatttg   1560

gttaaaaaca aatgtgtcaa tttcaacttc aatggtttaa caggcacagg tgttcttact   1620

gagtctaaca aaaagtttct gcctttccaa caatttggca gagacattgc tgacactact   1680

gatgctgtcc gtgatccaca gacacttgag attcttgaca ttacaccatg ttcttttggt   1740

ggtgtcagtg ttataacacc aggaacaaat acttctaacc aggttgctgt tctttatcag   1800

gatgttaact gcacagaagt ccctgttgct attcatgcag atcaacttac tcctacttgg   1860

cgtgtttatt ctacaggttc taatgttttt caaacacgtg caggctgttt aataggggct   1920

gaacatgtca acaactcata tgagtgtgac atacccattg gtgcaggtat atgcgctagt   1980

tatcagactc agactaattc tcctcggcgg gcacgt                             2016
```

<210> SEQ ID NO 8
<211> LENGTH: 223
<212> TYPE: PRT
<213> ORGANISM: SARS-CoV-2
<220> FEATURE:
<223> OTHER INFORMATION: SARS-CoV-2 spike protein receptor binding domain (RBD) spanning positions 319-541 (RBD-1)

<400> SEQUENCE: 8

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190
```

```
Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220


<210> SEQ ID NO 9
<211> LENGTH: 669
<212> TYPE: DNA
<213> ORGANISM: SARS-CoV-2
<220> FEATURE:
<223> OTHER INFORMATION: SARS-CoV-2 spike protein RBD-1 coding sequence

<400> SEQUENCE: 9

agagtccaac caacagaatc tattgttaga tttcctaata ttacaaactt gtgccctttt      60

ggtgaagttt ttaacgccac cagatttgca tctgtttatg cttggaacag gaagagaatc     120

agcaactgtg ttgctgatta ttctgtccta tataattccg catcattttc cacttttaag     180

tgttatggag tgtctcctac taaattaaat gatctctgct ttactaatgt ctatgcagat     240

tcatttgtaa ttagaggtga tgaagtcaga caaatcgctc cagggcaaac tggaaagatt     300

gctgattata attataaatt accagatgat tttacaggct gcgttatagc ttggaactct     360

aacaatcttg attctaaggt tggtggtaat tataattacc tgtatagatt gtttaggaag     420

tctaatctca aaccttttga gagagatatt tcaactgaaa tctatcaggc cggtagcaca     480

ccttgtaatg gtgttgaagg ttttaattgt tactttcctt tacaatcata tggtttccaa     540

cccactaatg gtgttggtta ccaaccatac agagtagtag tactttcttt tgaacttcta     600

catgcaccag caactgtttg tggacctaaa aagtctacta atttggttaa aaacaaatgt     660

gtcaatttc                                                             669


<210> SEQ ID NO 10
<211> LENGTH: 199
<212> TYPE: PRT
<213> ORGANISM: SARS-CoV-2
<220> FEATURE:
<223> OTHER INFORMATION: SARS-CoV-2 spike protein RBD spanning positions
      331-529 (RBD-2)

<400> SEQUENCE: 10

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140
```

-continued

```
Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys
        195


<210> SEQ ID NO 11
<211> LENGTH: 597
<212> TYPE: DNA
<213> ORGANISM: SARS-CoV-2
<220> FEATURE:
<223> OTHER INFORMATION: SARS-CoV-2 spike protein RBD-2 coding sequence

<400> SEQUENCE: 11

aatattacaa acttgtgccc ttttggtgaa gtttttaacg ccaccagatt tgcatctgtt      60

tatgcttgga acaggaagag aatcagcaac tgtgttgctg attattctgt cctatataat     120

tccgcatcat tttccacttt taagtgttat ggagtgtctc ctactaaatt aaatgatctc     180

tgctttacta atgtctatgc agattcattt gtaattagag gtgatgaagt cagacaaatc     240

gctccagggc aaactggaaa gattgctgat tataattata aattaccaga tgattttaca     300

ggctgcgtta tagcttggaa ctctaacaat cttgattcta aggttggtgg taattataat     360

tacctgtata gattgtttag gaagtctaat ctcaaacctt ttgagagaga tatttcaact     420

gaaatctatc aggccggtag cacaccttgt aatggtgttg aaggttttaa ttgttacttt     480

cctttacaat catatggttt ccaacccact aatggtgttg gttaccaacc atacagagta     540

gtagtacttt cttttgaact tctacatgca ccagcaactg tttgtggacc taaaaag        597


<210> SEQ ID NO 12
<211> LENGTH: 194
<212> TYPE: PRT
<213> ORGANISM: SARS-CoV-2
<220> FEATURE:
<223> OTHER INFORMATION: SARS-CoV-2 spike protein RBD spanning positions
      331-524 (RBD-3)

<400> SEQUENCE: 12

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140
```

Ala Gly Ser Thr Pro Cys Asn Gly Val Glu Gly Phe Asn Cys Tyr Phe
145 150 155 160

Pro Leu Gln Ser Tyr Gly Phe Gln Pro Thr Asn Gly Val Gly Tyr Gln
165 170 175

Pro Tyr Arg Val Val Val Leu Ser Phe Glu Leu Leu His Ala Pro Ala
180 185 190

Thr Val

<210> SEQ ID NO 13
<211> LENGTH: 582
<212> TYPE: DNA
<213> ORGANISM: SARS-CoV-2
<220> FEATURE:
<223> OTHER INFORMATION: SARS-CoV-2 spike protein RBD-3 coding sequence

<400> SEQUENCE: 13
aatattacaa acttgtgccc ttttggtgaa gtttttaacg ccaccagatt tgcatctgtt 60
tatgcttgga acaggaagag aatcagcaac tgtgttgctg attattctgt cctatataat 120
tccgcatcat tttccacttt taagtgttat ggagtgtctc ctactaaatt aaatgatctc 180
tgctttacta atgtctatgc agattcattt gtaattagag gtgatgaagt cagacaaatc 240
gctccagggc aaactggaaa gattgctgat tataattata aattaccaga tgattttaca 300
ggctgcgtta tagcttggaa ctctaacaat cttgattcta aggttggtgg taattataat 360
tacctgtata gattgtttag gaagtctaat ctcaaacctt ttgagagaga tatttcaact 420
gaaatctatc aggccggtag cacaccttgt aatggtgttg aaggttttaa ttgttacttt 480
cctttacaat catatggttt ccaacccact aatggtgttg gttaccaacc atacagagta 540
gtagtacttt cttttgaact tctacatgca ccagcaactg tt 582

<210> SEQ ID NO 14
<211> LENGTH: 211
<212> TYPE: PRT
<213> ORGANISM: SARS-CoV-2
<220> FEATURE:
<223> OTHER INFORMATION: SARS-CoV-2 spike protein RBD spanning positions 319-529 (RBD-4)

<400> SEQUENCE: 14

Arg Val Gln Pro Thr Glu Ser Ile Val Arg Phe Pro Asn Ile Thr Asn
1 5 10 15

Leu Cys Pro Phe Gly Glu Val Phe Asn Ala Thr Arg Phe Ala Ser Val
20 25 30

Tyr Ala Trp Asn Arg Lys Arg Ile Ser Asn Cys Val Ala Asp Tyr Ser
35 40 45

Val Leu Tyr Asn Ser Ala Ser Phe Ser Thr Phe Lys Cys Tyr Gly Val
50 55 60

Ser Pro Thr Lys Leu Asn Asp Leu Cys Phe Thr Asn Val Tyr Ala Asp
65 70 75 80

Ser Phe Val Ile Arg Gly Asp Glu Val Arg Gln Ile Ala Pro Gly Gln
85 90 95

Thr Gly Lys Ile Ala Asp Tyr Asn Tyr Lys Leu Pro Asp Asp Phe Thr
100 105 110

Gly Cys Val Ile Ala Trp Asn Ser Asn Asn Leu Asp Ser Lys Val Gly
115 120 125

Gly Asn Tyr Asn Tyr Leu Tyr Arg Leu Phe Arg Lys Ser Asn Leu Lys
130 135 140

-continued

```
Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys
    210


<210> SEQ ID NO 15
<211> LENGTH: 633
<212> TYPE: DNA
<213> ORGANISM: SARS-CoV-2
<220> FEATURE:
<223> OTHER INFORMATION: SARS-CoV-2 spike protein RBD-4 coding sequence

<400> SEQUENCE: 15

agagtccaac caacagaatc tattgttaga tttcctaata ttacaaactt gtgccctttt      60

ggtgaagttt ttaacgccac cagatttgca tctgtttatg cttggaacag gaagagaatc     120

agcaactgtg ttgctgatta ttctgtccta tataattccg catcattttc cacttttaag     180

tgttatggag tgtctcctac taaattaaat gatctctgct ttactaatgt ctatgcagat     240

tcatttgtaa ttagaggtga tgaagtcaga caaatcgctc cagggcaaac tggaaagatt     300

gctgattata attataaatt accagatgat tttacaggct gcgttatagc ttggaactct     360

aacaatcttg attctaaggt tggtggtaat tataattacc tgtatagatt gtttaggaag     420

tctaatctca aaccttttga gagagatatt tcaactgaaa tctatcaggc cggtagcaca     480

ccttgtaatg gtgttgaagg ttttaattgt tactttcctt tacaatcata tggtttccaa     540

cccactaatg gtgttggtta ccaaccatac agagtagtag tactttcttt tgaacttcta     600

catgcaccag caactgtttg tggacctaaa aag                                  633


<210> SEQ ID NO 16
<211> LENGTH: 56
<212> TYPE: PRT
<213> ORGANISM: SARS-CoV-2
<220> FEATURE:
<223> OTHER INFORMATION: SARS-CoV-2 spike protein receptor binding motif
      (RBM)

<400> SEQUENCE: 16

Val Gly Gly Asn Tyr Asn Tyr Leu Tyr Arg Leu Phe Arg Lys Ser Asn
1               5                   10                  15

Leu Lys Pro Phe Glu Arg Asp Ile Ser Thr Glu Ile Tyr Gln Ala Gly
            20                  25                  30

Ser Thr Pro Cys Asn Gly Val Glu Gly Phe Asn Cys Tyr Phe Pro Leu
        35                  40                  45

Gln Ser Tyr Gly Phe Gln Pro Thr
    50                  55


<210> SEQ ID NO 17
<211> LENGTH: 168
<212> TYPE: DNA
<213> ORGANISM: SARS-CoV-2
<220> FEATURE:
<223> OTHER INFORMATION: SARS-CoV-2 spike protein RBM coding sequence
```

<400> SEQUENCE: 17

```
gttggtggta attataatta cctgtataga ttgtttagga agtctaatct caaacctttt     60

gagagagata tttcaactga aatctatcag gccggtagca caccttgtaa tggtgttgaa    120

ggttttaatt gttactttcc tttacaatca tatggtttcc aacccact                 168
```

<210> SEQ ID NO 18
<211> LENGTH: 419
<212> TYPE: PRT
<213> ORGANISM: SARS-CoV-2
<220> FEATURE:
<223> OTHER INFORMATION: SARS-CoV-2 nucleocapsid protein

<400> SEQUENCE: 18

```
Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
        35                  40                  45

Thr Ala Ser Trp Phe Thr Ala Leu Thr Gln His Gly Lys Glu Asp Leu
    50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95

Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
        115                 120                 125

Gly Ile Ile Trp Val Ala Thr Glu Gly Ala Leu Asn Thr Pro Lys Asp
    130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
        195                 200                 205

Arg Met Ala Gly Asn Gly Gly Asp Ala Ala Leu Ala Leu Leu Leu Leu
    210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
            260                 265                 270

Ala Phe Gly Arg Arg Gly Pro Glu Gln Thr Gln Gly Asn Phe Gly Asp
        275                 280                 285

Gln Glu Leu Ile Arg Gln Gly Thr Asp Tyr Lys His Trp Pro Gln Ile
    290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Ala Ala
```

```
                325                 330                 335

Ile Lys Leu Asp Asp Lys Asp Pro Asn Phe Lys Asp Gln Val Ile Leu
            340                 345                 350

Leu Asn Lys His Ile Asp Ala Tyr Lys Thr Phe Pro Pro Thr Glu Pro
        355                 360                 365

Lys Lys Asp Lys Lys Lys Lys Ala Asp Glu Thr Gln Ala Leu Pro Gln
    370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415

Thr Gln Ala
```

<210> SEQ ID NO 19
<211> LENGTH: 1257
<212> TYPE: DNA
<213> ORGANISM: SARS-CoV-2
<220> FEATURE:
<223> OTHER INFORMATION: SARS-CoV-2 nucleocapsid protein coding sequence

<400> SEQUENCE: 19

```
atgtctgata atggacccca aaatcagcga aatgcacccc gcattacgtt tggtggaccc     60

tcagattcaa ctggcagtaa ccagaatgga gaacgcagtg gggcgcgatc aaaacaacgt    120

cggccccaag gtttacccaa taatactgcg tcttggttca ccgctctcac tcaacatggc    180

aaggaagacc ttaaattccc tcgaggacaa ggcgttccaa ttaacaccaa tagcagtcca    240

gatgaccaaa ttggctacta ccgaagagct accagacgaa ttcgtggtgg tgacggtaaa    300

atgaaagatc tcagtccaag atggtatttc tactacctag gaactgggcc agaagctgga    360

cttccctatg gtgctaacaa agacggcatc atatgggttg caactgaggg agccttgaat    420

acaccaaaag atcacattgg cacccgcaat cctgctaaca atgctgcaat cgtgctacaa    480

cttcctcaag gaacaacatt gccaaaaggc ttctacgcag aagggagcag aggcggcagt    540

caagcctctt ctcgttcctc atcacgtagt cgcaacagtt caagaaattc aactccaggc    600

agcagtaggg gaacttctcc tgctagaatg gctggcaatg gcggtgatgc tgctcttgct    660

ttgctgctgc ttgacagatt gaaccagctt gagagcaaaa tgtctggtaa aggccaacaa    720

caacaaggcc aaactgtcac taagaaatct gctgctgagg cttctaagaa gcctcggcaa    780

aaacgtactg ccactaaagc atacaatgta acacaagctt tcggcagacg tggtccagaa    840

caaacccaag gaaattttgg ggaccaggaa ctaatcagac aaggaactga ttacaaacat    900

tggccgcaaa ttgcacaatt tgcccccagc gcttcagcgt tcttcggaat gtcgcgcatt    960

ggcatggaag tcacaccttc gggaacgtgg ttgacctaca cagctgccat caaattggat   1020

gacaaagatc caaatttcaa agatcaagtc attttgctga ataagcatat tgacgcatac   1080

aaaacattcc caccaacaga gcctaaaaag gacaaaaaga agaaggctga tgaaactcaa   1140

gccttaccgc agagacagaa gaaacagcaa actgtgactc ttcttcctgc tgcagatttg   1200

gatgatttct ccaaacaatt gcaacaatcc atgagcagtg ctgactcaac tcaggcc      1257
```

<210> SEQ ID NO 20
<211> LENGTH: 1273
<212> TYPE: PRT
<213> ORGANISM: Artificial Sequence
<220> FEATURE:
<223> OTHER INFORMATION: SARS-CoV-2 spike protein with native signal peptide and an N501T substitution

<400> SEQUENCE: 20

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly

-continued

```
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Thr Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830
```

```
Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230
```

```
Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270


<210> SEQ ID NO 21
<211> LENGTH: 1198
<212> TYPE: PRT
<213> ORGANISM: Artificial Sequence
<220> FEATURE:
<223> OTHER INFORMATION: SARS-CoV-2 spike protein ECD with an N501T
      substitution

<400> SEQUENCE: 21

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320
```

```
Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Thr Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735
```

```
Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                1015                1020

Ser Lys  Arg Val Asp Phe Cys  Gly Lys Gly Tyr His  Leu Met Ser
    1025                1030                1035

Phe Pro  Gln Ser Ala Pro His  Gly Val Val Phe Leu  His Val Thr
    1040                1045                1050

Tyr Val  Pro Ala Gln Glu Lys  Asn Phe Thr Thr Ala  Pro Ala Ile
    1055                1060                1065

Cys His  Asp Gly Lys Ala His  Phe Pro Arg Glu Gly  Val Phe Val
    1070                1075                1080

Ser Asn  Gly Thr His Trp Phe  Val Thr Gln Arg Asn  Phe Tyr Glu
    1085                1090                1095

Pro Gln  Ile Ile Thr Thr Asp  Asn Thr Phe Val Ser  Gly Asn Cys
    1100                1105                1110

Asp Val  Val Ile Gly Ile Val  Asn Asn Thr Val Tyr  Asp Pro Leu
    1115                1120                1125

Gln Pro  Glu Leu Asp Ser Phe  Lys Glu Glu Leu Asp  Lys Tyr Phe
    1130                1135                1140

Lys Asn  His Thr Ser Pro Asp  Val Asp Leu Gly Asp  Ile Ser Gly
```

```
    1145                1150                1155

Ile Asn  Ala Ser Val Val Asn  Ile Gln Lys Glu Ile  Asp Arg Leu
    1160                1165                1170

Asn Glu  Val Ala Lys Asn Leu  Asn Glu Ser Leu Ile  Asp Leu Gln
    1175                1180                1185

Glu Leu  Gly Lys Tyr Glu Gln  Tyr Ile Lys
    1190                1195


<210> SEQ ID NO 22
<211> LENGTH: 672
<212> TYPE: PRT
<213> ORGANISM: Artificial Sequence
<220> FEATURE:
<223> OTHER INFORMATION: SARS-CoV-2 spike protein S1 subunit with an
      N501T substitution

<400> SEQUENCE: 22

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300
```

```
Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Thr Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670
```

<210> SEQ ID NO 23
<211> LENGTH: 223
<212> TYPE: PRT
<213> ORGANISM: Artificial Sequence
<220> FEATURE:
<223> OTHER INFORMATION: SARS-CoV-2 spike protein RBD-1 with an N501T substitution

<400> SEQUENCE: 23

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Thr Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220
```

<210> SEQ ID NO 24
<211> LENGTH: 198
<212> TYPE: PRT
<213> ORGANISM: Artificial Sequence
<220> FEATURE:
<223> OTHER INFORMATION: SARS-CoV-2 spike protein RBD-2 with an N501T substitution (RBD-6)

<400> SEQUENCE: 24

```
Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
        115                 120                 125

Asn Leu Lys Pro Phe Glu Arg Asp Ile Ser Thr Glu Ile Tyr Gln Ala
```

```
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Thr Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys
        195


<210> SEQ ID NO 25
<211> LENGTH: 194
<212> TYPE: PRT
<213> ORGANISM: Artificial Sequence
<220> FEATURE:
<223> OTHER INFORMATION: SARS-CoV-2 spike protein RBD-3 with an N501T
      substitution (RBD-7)

<400> SEQUENCE: 25

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Thr Gly Val Gly Tyr Gln
                165                 170                 175

Pro Tyr Arg Val Val Val Leu Ser Phe Glu Leu Leu His Ala Pro Ala
            180                 185                 190

Thr Val


<210> SEQ ID NO 26
<211> LENGTH: 211
<212> TYPE: PRT
<213> ORGANISM: Artificial Sequence
<220> FEATURE:
<223> OTHER INFORMATION: SARS-CoV-2 spike protein RBD-4 with an N501T
      substitution (RBD-8)

<400> SEQUENCE: 26

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30
```

-continued

```
Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Thr Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys
    210
```

<210> SEQ ID NO 27
<211> LENGTH: 633
<212> TYPE: DNA
<213> ORGANISM: Artificial Sequence
<220> FEATURE:
<223> OTHER INFORMATION: SARS-CoV-2 spike protein RBD-8 coding sequence

<400> SEQUENCE: 27

```
agagtccaac caacagaatc tattgttaga tttcctaata ttacaaactt gtgccctttt      60

ggtgaagttt ttaacgccac cagatttgca tctgtttatg cttggaacag gaagagaatc     120

agcaactgtg ttgctgatta ttctgtccta tataattccg catcattttc cacttttaag     180

tgttatggag tgtctcctac taaattaaat gatctctgct ttactaatgt ctatgcagat     240

tcatttgtaa ttagaggtga tgaagtcaga caaatcgctc cagggcaaac tggaaagatt     300

gctgattata attataaatt accagatgat tttacaggct gcgttatagc ttggaactct     360

aacaatcttg attctaaggt tggtggtaat tataattacc tgtatagatt gtttaggaag     420

tctaatctca aacctttga gagagatatt tcaactgaaa tctatcaggc cggtagcaca      480

ccttgtaatg gtgttgaagg ttttaattgt tactttcctt tacaatcata tggtttccaa     540

cccactactg gtgttggtta ccaaccatac agagtagtag tactttcttt tgaacttcta     600

catgcaccag caactgtttg tggacctaaa aag                                  633
```

<210> SEQ ID NO 28
<211> LENGTH: 8
<212> TYPE: PRT
<213> ORGANISM: Artificial Sequence
<220> FEATURE:
<223> OTHER INFORMATION: (G3S)2 linker peptide

<400> SEQUENCE: 28

-continued

Gly Gly Gly Ser Gly Gly Gly Ser
1 5

<210> SEQ ID NO 29
<211> LENGTH: 24
<212> TYPE: DNA
<213> ORGANISM: Artificial Sequence
<220> FEATURE:
<223> OTHER INFORMATION: (G3S)2 linker peptide coding sequence

<400> SEQUENCE: 29
ggaggaggaa gtggaggagg aagt 24

<210> SEQ ID NO 30
<211> LENGTH: 28
<212> TYPE: PRT
<213> ORGANISM: Artificial Sequence
<220> FEATURE:
<223> OTHER INFORMATION: Trimmerization peptide

<400> SEQUENCE: 30

Gly Tyr Ile Pro Glu Ala Pro Arg Asp Gly Gln Ala Tyr Val Arg Lys
1 5 10 15

Asp Gly Glu Trp Val Leu Leu Ser Thr Phe Leu Gly
20 25

<210> SEQ ID NO 31
<211> LENGTH: 84
<212> TYPE: DNA
<213> ORGANISM: Artificial Sequence
<220> FEATURE:
<223> OTHER INFORMATION: Trimmerization peptide coding sequence

<400> SEQUENCE: 31
ggctatattc cggaagcgcc gcgcgatggc caggcgtatg tgcgcaaaga tggcgaatgg 60
gtgctgctga gcacctttct gggc 84

<210> SEQ ID NO 32
<211> LENGTH: 1234
<212> TYPE: PRT
<213> ORGANISM: Artificial Sequence
<220> FEATURE:
<223> OTHER INFORMATION: SARS-CoV-2 spike protein ECD with C terminal
fusion of a (G3S)2 linker and a trimmerization peptide

<400> SEQUENCE: 32

Gln Cys Val Asn Leu Thr Thr Arg Thr Gln Leu Pro Pro Ala Tyr Thr
1 5 10 15

Asn Ser Phe Thr Arg Gly Val Tyr Tyr Pro Asp Lys Val Phe Arg Ser
20 25 30

Ser Val Leu His Ser Thr Gln Asp Leu Phe Leu Pro Phe Phe Ser Asn
35 40 45

Val Thr Trp Phe His Ala Ile His Val Ser Gly Thr Asn Gly Thr Lys
50 55 60

Arg Phe Asp Asn Pro Val Leu Pro Phe Asn Asp Gly Val Tyr Phe Ala
65 70 75 80

Ser Thr Glu Lys Ser Asn Ile Ile Arg Gly Trp Ile Phe Gly Thr Thr
85 90 95

Leu Asp Ser Lys Thr Gln Ser Leu Leu Ile Val Asn Asn Ala Thr Asn
100 105 110

Val Val Ile Lys Val Cys Glu Phe Gln Phe Cys Asn Asp Pro Phe Leu
115 120 125

-continued

```
Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540
```

```
Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
```

```
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                 1015                1020

Ser Lys  Arg Val Asp Phe Cys  Gly Lys Gly Tyr His  Leu Met Ser
    1025                 1030                1035

Phe Pro  Gln Ser Ala Pro His  Gly Val Val Phe Leu  His Val Thr
    1040                 1045                1050

Tyr Val  Pro Ala Gln Glu Lys  Asn Phe Thr Thr Ala  Pro Ala Ile
    1055                 1060                1065

Cys His  Asp Gly Lys Ala His  Phe Pro Arg Glu Gly  Val Phe Val
    1070                 1075                1080

Ser Asn  Gly Thr His Trp Phe  Val Thr Gln Arg Asn  Phe Tyr Glu
    1085                 1090                1095

Pro Gln  Ile Ile Thr Thr Asp  Asn Thr Phe Val Ser  Gly Asn Cys
    1100                 1105                1110

Asp Val  Val Ile Gly Ile Val  Asn Asn Thr Val Tyr  Asp Pro Leu
    1115                 1120                1125

Gln Pro  Glu Leu Asp Ser Phe  Lys Glu Glu Leu Asp  Lys Tyr Phe
    1130                 1135                1140

Lys Asn  His Thr Ser Pro Asp  Val Asp Leu Gly Asp  Ile Ser Gly
    1145                 1150                1155

Ile Asn  Ala Ser Val Val Asn  Ile Gln Lys Glu Ile  Asp Arg Leu
    1160                 1165                1170

Asn Glu  Val Ala Lys Asn Leu  Asn Glu Ser Leu Ile  Asp Leu Gln
    1175                 1180                1185

Glu Leu  Gly Lys Tyr Glu Gln  Tyr Ile Lys Gly Gly  Gly Ser Gly
    1190                 1195                1200

Gly Gly  Ser Gly Tyr Ile Pro  Glu Ala Pro Arg Asp  Gly Gln Ala
    1205                 1210                1215

Tyr Val  Arg Lys Asp Gly Glu  Trp Val Leu Leu Ser  Thr Phe Leu
    1220                 1225                1230

Gly
```

<210> SEQ ID NO 33
<211> LENGTH: 3702
<212> TYPE: DNA
<213> ORGANISM: Artificial Sequence
<220> FEATURE:
<223> OTHER INFORMATION: SARS-CoV-2 spike protein ECD with C terminal fusion of a (G3S)2 linker and a trimmerization peptide coding sequence

<400> SEQUENCE: 33

```
cagtgtgtta atcttacaac cagaactcaa ttaccccctg catacactaa ttctttcaca     60

cgtggtgttt attaccctga caaagttttc agatcctcag ttttacattc aactcaggac    120

ttgttcttac ctttcttttc caatgttact tggttccatg ctatacatgt ctctgggacc    180

aatggtacta agaggtttga taaccctgtc ctaccattta atgatggtgt ttattttgct    240

tccactgaga agtctaacat aataagaggc tggatttttg gtactacttt agattcgaag    300

acccagtccc tacttattgt taataacgct actaatgttg ttattaaagt ctgtgaattt    360
```

-continued

```
caattttgta atgatccatt tttgggtgtt tattaccaca aaaacaacaa aagttggatg    420
gaaagtgagt tcagagttta ttctagtgcg aataattgca cttttgaata tgtctctcag    480
ccttttctta tggaccttga aggaaaacag ggtaatttca aaaatcttag ggaatttgtg    540
tttaagaata ttgatggtta ttttaaaata tattctaagc acacgcctat taatttagtg    600
cgtgatctcc ctcagggttt ttcggcttta gaaccattgg tagatttgcc aataggtatt    660
aacatcacta ggtttcaaac tttacttgct ttacatagaa gttatttgac tcctggtgat    720
tcttcttcag gttggacagc tggtgctgca gcttattatg tgggttatct tcaacctagg    780
acttttctat taaaatataa tgaaaatgga accattacag atgctgtaga ctgtgcactt    840
gaccctctct cagaaacaaa gtgtacgttg aaatccttca ctgtagaaaa aggaatctat    900
caaacttcta actttagagt ccaaccaaca gaatctattg ttagatttcc taatattaca    960
aacttgtgcc cttttggtga agtttttaac gccaccagat ttgcatctgt ttatgcttgg   1020
aacaggaaga gaatcagcaa ctgtgttgct gattattctg tcctatataa ttccgcatca   1080
ttttccactt ttaagtgtta tggagtgtct cctactaaat taaatgatct ctgctttact   1140
aatgtctatg cagattcatt tgtaattaga ggtgatgaag tcagacaaat cgctccaggg   1200
caaactggaa agattgctga ttataattat aaattaccag atgattttac aggctgcgtt   1260
atagcttgga actctaacaa tcttgattct aaggttggtg gtaattataa ttacctgtat   1320
agattgttta ggaagtctaa tctcaaacct tttgagagag atatttcaac tgaaatctat   1380
caggccggta gcacaccttg taatggtgtt gaaggtttta attgttactt tcctttacaa   1440
tcatatggtt tccaacccac taatggtgtt ggttaccaac catacagagt agtagtactt   1500
tcttttgaac ttctacatgc accagcaact gtttgtggac ctaaaaagtc tactaatttg   1560
gttaaaaaca aatgtgtcaa tttcaacttc aatggtttaa caggcacagg tgttcttact   1620
gagtctaaca aaaagtttct gcctttccaa caatttggca gagacattgc tgacactact   1680
gatgctgtcc gtgatccaca gacacttgag attcttgaca ttacaccatg ttcttttggt   1740
ggtgtcagtg ttataacacc aggaacaaat acttctaacc aggttgctgt tctttatcag   1800
gatgttaact gcacagaagt ccctgttgct attcatgcag atcaacttac tcctacttgg   1860
cgtgtttatt ctacaggttc taatgttttt caaacacgtg caggctgttt aataggggct   1920
gaacatgtca acaactcata tgagtgtgac atacccattg gtgcaggtat atgcgctagt   1980
tatcagactc agactaattc tcctcggcgg gcacgtagtg tagctagtca atccatcatt   2040
gcctacacta tgtcacttgg tgcagaaaat tcagttgctt actctaataa ctctattgcc   2100
atacccacaa attttactat tagtgttacc acagaaattc taccagtgtc tatgaccaag   2160
acatcagtag attgtacaat gtacatttgt ggtgattcaa ctgaatgcag caatcttttg   2220
ttgcaatatg gcagtttttg tacacaatta aaccgtgctt taactggaat agctgttgaa   2280
caagacaaaa acacccaaga agtttttgca caagtcaaac aaatttacaa aacaccacca   2340
attaaagatt ttggtggttt taatttttca caaatattac cagatccatc aaaaccaagc   2400
aagaggtcat ttattgaaga tctacttttc aacaaagtga cacttgcaga tgctggcttc   2460
atcaaacaat atggtgattg ccttggtgat attgctgcta gagacctcat ttgtgcacaa   2520
aagtttaacg gccttactgt tttgccacct ttgctcacag atgaaatgat tgctcaatac   2580
acttctgcac tgttagcggg tacaatcact tctggttgga cctttggtgc aggtgctgca   2640
ttacaaatac catttgctat gcaaatggct tataggttta atggtattgg agttacacag   2700
aatgttctct atgagaacca aaaattgatt gccaaccaat ttaatagtgc tattggcaaa   2760
```

-continued

```
attcaagact cactttcttc cacagcaagt gcacttggaa aacttcaaga tgtggtcaac   2820

caaaatgcac aagctttaaa cacgcttgtt aaacaactta gctccaattt tggtgcaatt   2880

tcaagtgttt taaatgatat cctttcacgt cttgacaaag ttgaggctga agtgcaaatt   2940

gataggttga tcacaggcag acttcaaagt ttgcagacat atgtgactca acaattaatt   3000

agagctgcag aaatcagagc ttctgctaat cttgctgcta ctaaaatgtc agagtgtgta   3060

cttggacaat caaaaagagt tgatttttgt ggaaagggct atcatcttat gtccttccct   3120

cagtcagcac ctcatggtgt agtcttcttg catgtgactt atgtccctgc acaagaaaag   3180

aacttcacaa ctgctcctgc catttgtcat gatggaaaag cacactttcc tcgtgaaggt   3240

gtctttgttt caaatggcac acactggttt gtaacacaaa ggaattttta tgaaccacaa   3300

atcattacta cagacaacac atttgtgtct ggtaactgtg atgttgtaat aggaattgtc   3360

aacaacacag tttatgatcc tttgcaacct gaattagact cattcaagga ggagttagat   3420

aaatatttta agaatcatac atcaccagat gttgatttag gtgacatctc tggcattaat   3480

gcttcagttg taaacattca aaaagaaatt gaccgcctca atgaggttgc caagaattta   3540

aatgaatctc tcatcgatct ccaagaactt ggaaagtatg agcagtatat aaaaggagga   3600

ggaagtggag gaggaagtgg ctatattccg gaagcgccgc gcgatggcca ggcgtatgtg   3660

cgcaaagatg gcgaatgggt gctgctgagc acctttctgg gc                      3702
```

<210> SEQ ID NO 34
<211> LENGTH: 235
<212> TYPE: PRT
<213> ORGANISM: Artificial Sequence
<220> FEATURE:
<223> OTHER INFORMATION: SARS-CoV-2 spike protein RBD-2 with C-terminal fusion of a (G3S)2 linker and a trimmerization peptide

<400> SEQUENCE: 34

```
Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190
```

-continued

```
Thr Val Cys Gly Pro Lys Lys Gly Gly Gly Ser Gly Gly Gly Ser Gly
        195                 200                 205

Tyr Ile Pro Glu Ala Pro Arg Asp Gly Gln Ala Tyr Val Arg Lys Asp
    210                 215                 220

Gly Glu Trp Val Leu Leu Ser Thr Phe Leu Gly
225                 230                 235
```

```
<210> SEQ ID NO 35
<211> LENGTH: 705
<212> TYPE: DNA
<213> ORGANISM: Artificial Sequence
<220> FEATURE:
<223> OTHER INFORMATION: SARS-CoV-2 spike protein RBD-2 with C-terminal
      fusion of a (G3S)2 linker and a trimmerization peptide coding
      sequence

<400> SEQUENCE: 35

aatattacaa acttgtgccc ttttggtgaa gtttttaacg ccaccagatt tgcatctgtt     60

tatgcttgga acaggaagag aatcagcaac tgtgttgctg attattctgt cctatataat    120

tccgcatcat tttccacttt taagtgttat ggagtgtctc ctactaaatt aaatgatctc    180

tgctttacta atgtctatgc agattcattt gtaattagag gtgatgaagt cagacaaatc    240

gctccagggc aaactggaaa gattgctgat tataattata aattaccaga tgattttaca    300

ggctgcgtta tagcttggaa ctctaacaat cttgattcta aggttggtgg taattataat    360

tacctgtata gattgtttag gaagtctaat ctcaaacctt ttgagagaga tatttcaact    420

gaaatctatc aggccggtag cacaccttgt aatggtgttg aaggttttaa ttgttacttt    480

cctttacaat catatggttt ccaacccact aatggtgttg gttaccaacc atacagagta    540

gtagtacttt cttttgaact tctacatgca ccagcaactg tttgtggacc taaaaaggga    600

ggaggaagtg gaggaggaag tggctatatt ccggaagcgc cgcgcgatgg ccaggcgtat    660

gtgcgcaaag atggcgaatg ggtgctgctg agcacctttc tgggc                    705


<210> SEQ ID NO 36
<211> LENGTH: 13
<212> TYPE: PRT
<213> ORGANISM: Artificial Sequence
<220> FEATURE:
<223> OTHER INFORMATION: SARS-CoV-2 spike protein native signal peptide

<400> SEQUENCE: 36

Met Phe Val Phe Leu Val Leu Leu Pro Leu Val Ser Ser
1               5                   10


<210> SEQ ID NO 37
<211> LENGTH: 39
<212> TYPE: DNA
<213> ORGANISM: SARS-CoV-2
<220> FEATURE:
<223> OTHER INFORMATION: SARS-CoV-2 spike protein native signal peptide
      coding sequence

<400> SEQUENCE: 37

atgtttgttt ttcttgtttt attgccatta gtctctagt                           39


<210> SEQ ID NO 38
<211> LENGTH: 18
<212> TYPE: PRT
<213> ORGANISM: SARS-CoV-2
<220> FEATURE:
<223> OTHER INFORMATION: SARS-CoV-2 spike protein native signal peptide
```

coding sequence

<400> SEQUENCE: 38

Met Asp Trp Thr Trp Ile Leu Phe Leu Val Ala Ala Ala Thr Arg Val
1 5 10 15

His Ser

<210> SEQ ID NO 39
<211> LENGTH: 54
<212> TYPE: DNA
<213> ORGANISM: Artificial Sequence
<220> FEATURE:
<223> OTHER INFORMATION: Human IgE signal peptide amino acid sequence

<400> SEQUENCE: 39
atggactgga cctggattct cttcttggtg gcagcagcca cgcgagtcca ctcc 54

<210> SEQ ID NO 40
<211> LENGTH: 1260
<212> TYPE: PRT
<213> ORGANISM: Artificial Sequence
<220> FEATURE:
<223> OTHER INFORMATION: SARS-CoV-2 spike protein without native signal peptide

<400> SEQUENCE: 40

Gln Cys Val Asn Leu Thr Thr Arg Thr Gln Leu Pro Pro Ala Tyr Thr
1 5 10 15

Asn Ser Phe Thr Arg Gly Val Tyr Tyr Pro Asp Lys Val Phe Arg Ser
20 25 30

Ser Val Leu His Ser Thr Gln Asp Leu Phe Leu Pro Phe Phe Ser Asn
35 40 45

Val Thr Trp Phe His Ala Ile His Val Ser Gly Thr Asn Gly Thr Lys
50 55 60

Arg Phe Asp Asn Pro Val Leu Pro Phe Asn Asp Gly Val Tyr Phe Ala
65 70 75 80

Ser Thr Glu Lys Ser Asn Ile Ile Arg Gly Trp Ile Phe Gly Thr Thr
85 90 95

Leu Asp Ser Lys Thr Gln Ser Leu Leu Ile Val Asn Asn Ala Thr Asn
100 105 110

Val Val Ile Lys Val Cys Glu Phe Gln Phe Cys Asn Asp Pro Phe Leu
115 120 125

Gly Val Tyr Tyr His Lys Asn Asn Lys Ser Trp Met Glu Ser Glu Phe
130 135 140

Arg Val Tyr Ser Ser Ala Asn Asn Cys Thr Phe Glu Tyr Val Ser Gln
145 150 155 160

Pro Phe Leu Met Asp Leu Glu Gly Lys Gln Gly Asn Phe Lys Asn Leu
165 170 175

Arg Glu Phe Val Phe Lys Asn Ile Asp Gly Tyr Phe Lys Ile Tyr Ser
180 185 190

Lys His Thr Pro Ile Asn Leu Val Arg Asp Leu Pro Gln Gly Phe Ser
195 200 205

Ala Leu Glu Pro Leu Val Asp Leu Pro Ile Gly Ile Asn Ile Thr Arg
210 215 220

Phe Gln Thr Leu Leu Ala Leu His Arg Ser Tyr Leu Thr Pro Gly Asp
225 230 235 240

Ser Ser Ser Gly Trp Thr Ala Gly Ala Ala Ala Tyr Tyr Val Gly Tyr
245 250 255

-continued

```
Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670
```

-continued

```
Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                1015                1020

Ser Lys  Arg Val Asp Phe Cys  Gly Lys Gly Tyr His  Leu Met Ser
    1025                1030                1035

Phe Pro  Gln Ser Ala Pro His  Gly Val Val Phe Leu  His Val Thr
    1040                1045                1050

Tyr Val  Pro Ala Gln Glu Lys  Asn Phe Thr Thr Ala  Pro Ala Ile
    1055                1060                1065

Cys His  Asp Gly Lys Ala His  Phe Pro Arg Glu Gly  Val Phe Val
    1070                1075                1080

Ser Asn  Gly Thr His Trp Phe  Val Thr Gln Arg Asn  Phe Tyr Glu
```

```
    1085                1090                1095

Pro Gln  Ile Ile Thr Thr Asp  Asn Thr Phe Val Ser  Gly Asn Cys
    1100                1105                1110

Asp Val  Val Ile Gly Ile Val  Asn Asn Thr Val Tyr  Asp Pro Leu
    1115                1120                1125

Gln Pro  Glu Leu Asp Ser Phe  Lys Glu Glu Leu Asp  Lys Tyr Phe
    1130                1135                1140

Lys Asn  His Thr Ser Pro Asp  Val Asp Leu Gly Asp  Ile Ser Gly
    1145                1150                1155

Ile Asn  Ala Ser Val Val Asn  Ile Gln Lys Glu Ile  Asp Arg Leu
    1160                1165                1170

Asn Glu  Val Ala Lys Asn Leu  Asn Glu Ser Leu Ile  Asp Leu Gln
    1175                1180                1185

Glu Leu  Gly Lys Tyr Glu Gln  Tyr Ile Lys Trp Pro  Trp Tyr Ile
    1190                1195                1200

Trp Leu  Gly Phe Ile Ala Gly  Leu Ile Ala Ile Val  Met Val Thr
    1205                1210                1215

Ile Met  Leu Cys Cys Met Thr  Ser Cys Cys Ser Cys  Leu Lys Gly
    1220                1225                1230

Cys Cys  Ser Cys Gly Ser Cys  Cys Lys Phe Asp Glu  Asp Asp Ser
    1235                1240                1245

Glu Pro  Val Leu Lys Gly Val  Lys Leu His Tyr Thr
    1250                1255                1260


<210> SEQ ID NO 41
<211> LENGTH: 3633
<212> TYPE: DNA
<213> ORGANISM: Artificial Sequence
<220> FEATURE:
<223> OTHER INFORMATION: SARS-CoV-2 spike protein without native signal
      peptide coding sequence

<400> SEQUENCE: 41

atgtttgttt ttcttgtttt attgccatta gtctctagtc agtgtgttaa tcttacaacc     60

agaactcaat taccccctgc atacactaat tctttcacac gtggtgttta ttaccctgac    120

aaagttttca gatcctcagt tttacattca actcaggact tgttcttacc tttcttttcc    180

aatgttactt ggttccatgc tatacatgtc tctgggacca atggtactaa gaggtttgat    240

aaccctgtcc taccatttaa tgatggtgtt tattttgctt ccactgagaa gtctaacata    300

ataagaggct ggatttttgg tactacttta gattcgaaga cccagtccct acttattgtt    360

aataacgcta ctaatgttgt tattaaagtc tgtgaatttc aattttgtaa tgatccattt    420

ttgggtgttt attaccacaa aaacaacaaa agttggatgg aaagtgagtt cagagtttat    480

tctagtgcga ataattgcac ttttgaatat gtctctcagc cttttcttat ggaccttgaa    540

ggaaaacagg gtaatttcaa aaatcttagg gaatttgtgt ttaagaatat tgatggttat    600

tttaaaatat attctaagca cacgcctatt aatttagtgc gtgatctccc tcagggtttt    660

tcggctttag aaccattggt agatttgcca ataggtatta acatcactag gtttcaaact    720

ttacttgctt tacatagaag ttatttgact cctggtgatt cttcttcagg ttggacagct    780

ggtgctgcag cttattatgt gggttatctt caacctagga cttttctatt aaaatataat    840

gaaaatggaa ccattacaga tgctgtagac tgtgcacttg accctctctc agaaacaaag    900

tgtacgttga aatccttcac tgtagaaaaa ggaatctatc aaacttctaa ctttagagtc    960

caaccaacag aatctattgt tagatttcct aatattacaa acttgtgccc ttttggtgaa   1020
```

gtttttaacg ccaccagatt tgcatctgtt tatgcttgga acaggaagag aatcagcaac 1080
tgtgttgctg attattctgt cctatataat tccgcatcat tttccacttt taagtgttat 1140
ggagtgtctc ctactaaatt aaatgatctc tgctttacta atgtctatgc agattcattt 1200
gtaattagag gtgatgaagt cagacaaatc gctccagggc aaactggaaa gattgctgat 1260
tataattata aattaccaga tgattttaca ggctgcgtta tagcttggaa ctctaacaat 1320
cttgattcta aggttggtgg taattataat tacctgtata gattgtttag gaagtctaat 1380
ctcaaacctt ttgagagaga tatttcaact gaaatctatc aggccggtag cacaccttgt 1440
aatggtgttg aaggttttaa ttgttacttt cctttacaat catatggttt ccaacccact 1500
aatggtgttg gttaccaacc atacagagta gtagtacttt cttttgaact tctacatgca 1560
ccagcaactg tttgtggacc taaaaagtct actaatttgg ttaaaaacaa atgtgtcaat 1620
ttcaacttca atggtttaac aggcacaggt gttcttactg agtctaacaa aaagtttctg 1680
cctttccaac aatttggcag agacattgct gacactactg atgctgtccg tgatccacag 1740
acacttgaga ttcttgacat tacaccatgt tcttttggtg gtgtcagtgt tataacacca 1800
ggaacaaata cttctaacca ggttgctgtt ctttatcagg atgttaactg cacagaagtc 1860
cctgttgcta ttcatgcaga tcaacttact cctacttggc gtgtttattc tacaggttct 1920
aatgtttttc aaacacgtgc aggctgttta ataggggctg aacatgtcaa caactcatat 1980
gagtgtgaca tacccattgg tgcaggtata tgcgctagtt atcagactca gactaattct 2040
cctcggcggg cacgtagtgt agctagtcaa tccatcattg cctacactat gtcacttggt 2100
gcagaaaatt cagttgctta ctctaataac tctattgcca tacccacaaa ttttactatt 2160
agtgttacca cagaaattct accagtgtct atgaccaaga catcagtaga ttgtacaatg 2220
tacatttgtg gtgattcaac tgaatgcagc aatcttttgt tgcaatatgg cagtttttgt 2280
acacaattaa accgtgcttt aactggaata gctgttgaac aagacaaaaa cacccaagaa 2340
gtttttgcac aagtcaaaca aatttacaaa acaccaccaa ttaaagattt tggtggtttt 2400
aatttttcac aaatattacc agatccatca aaaccaagca agaggtcatt tattgaagat 2460
ctacttttca acaaagtgac acttgcagat gctggcttca tcaaacaata tggtgattgc 2520
cttggtgata ttgctgctag agacctcatt tgtgcacaaa agtttaacgg ccttactgtt 2580
ttgccacctt tgctcacaga tgaaatgatt gctcaataca cttctgcact gttagcgggt 2640
acaatcactt ctggttggac ctttggtgca ggtgctgcat tacaaatacc atttgctatg 2700
caaatggctt ataggtttaa tggtattgga gttacacaga atgttctcta tgagaaccaa 2760
aaattgattg ccaaccaatt taatagtgct attggcaaaa ttcaagactc actttcttcc 2820
acagcaagtg cacttggaaa acttcaagat gtggtcaacc aaaatgcaca agctttaaac 2880
acgcttgtta aacaacttag ctccaatttt ggtgcaattt caagtgtttt aaatgatatc 2940
ctttcacgtc ttgacaaagt tgaggctgaa gtgcaaattg ataggttgat cacaggcaga 3000
cttcaaagtt tgcagacata tgtgactcaa caattaatta gagctgcaga aatcagagct 3060
tctgctaatc ttgctgctac taaaatgtca gagtgtgtac ttggacaatc aaaaagagtt 3120
gatttttgtg gaaagggcta tcatcttatg tccttccctc agtcagcacc tcatggtgta 3180
gtcttcttgc atgtgactta tgtccctgca caagaaaaga acttcacaac tgctcctgcc 3240
atttgtcatg atggaaaagc acactttcct cgtgaaggtg tctttgtttc aaatggcaca 3300
cactggtttg taacacaaag gaatttttat gaaccacaaa tcattactac agacaacaca 3360

```
tttgtgtctg gtaactgtga tgttgtaata ggaattgtca acaacacagt ttatgatcct   3420

ttgcaacctg aattagactc attcaaggag gagttagata aatattttaa gaatcataca   3480

tcaccagatg ttgatttagg tgacatctct ggcattaatg cttcagttgt aaacattcaa   3540

aaagaaattg accgcctcaa tgaggttgcc aagaatttaa atgaatctct catcgatctc   3600

caagaacttg gaaagtatga gcagtatata aaa                                3633


<210> SEQ ID NO 42
<211> LENGTH: 1211
<212> TYPE: PRT
<213> ORGANISM: SARS-CoV-2
<220> FEATURE:
<223> OTHER INFORMATION: SARS-CoV-2 spike protein ectodomain (ECD) with
      native signal peptide

<400> SEQUENCE: 42

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
```

```
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735
```

```
Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140
```

| | | | | | | | | | | |
|---|---|---|---|---|---|---|---|---|---|---|
| Glu | Leu | Asp | Ser | Phe | Lys | Glu | Glu | Leu | Asp | Lys | Tyr | Phe | Lys | Asn |
| | 1145 | | | | | 1150 | | | | | 1155 | | | |
| His | Thr | Ser | Pro | Asp | Val | Asp | Leu | Gly | Asp | Ile | Ser | Gly | Ile | Asn |
| | 1160 | | | | | 1165 | | | | | 1170 | | | |
| Ala | Ser | Val | Val | Asn | Ile | Gln | Lys | Glu | Ile | Asp | Arg | Leu | Asn | Glu |
| | 1175 | | | | | 1180 | | | | | 1185 | | | |
| Val | Ala | Lys | Asn | Leu | Asn | Glu | Ser | Leu | Ile | Asp | Leu | Gln | Glu | Leu |
| | 1190 | | | | | 1195 | | | | | 1200 | | | |
| Gly | Lys | Tyr | Glu | Gln | Tyr | Ile | Lys |
| | 1205 | | | | | 1210 | |

<210> SEQ ID NO 43
<211> LENGTH: 3633
<212> TYPE: DNA
<213> ORGANISM: SARS-CoV-2
<220> FEATURE:
<223> OTHER INFORMATION: SARS-CoV-2 spike protein ectodomain (ECD) with native signal peptide coding sequence

<400> SEQUENCE: 43

```
atgtttgttt ttcttgtttt attgccatta gtctctagtc agtgtgttaa tcttacaacc     60
agaactcaat taccccctgc atacactaat tctttcacac gtggtgttta ttaccctgac    120
aaagttttca gatcctcagt tttacattca actcaggact tgttcttacc tttcttttcc    180
aatgttactt ggttccatgc tatacatgtc tctgggacca atggtactaa gaggtttgat    240
aaccctgtcc taccatttaa tgatggtgtt tattttgctt ccactgagaa gtctaacata    300
ataagaggct ggatttttgg tactacttta gattcgaaga cccagtccct acttattgtt    360
aataacgcta ctaatgttgt tattaaagtc tgtgaatttc aattttgtaa tgatccattt    420
ttgggtgttt attaccacaa aaacaacaaa agttggatgg aaagtgagtt cagagtttat    480
tctagtgcga ataattgcac ttttgaatat gtctctcagc cttttcttat ggaccttgaa    540
ggaaaacagg gtaatttcaa aaatcttagg gaatttgtgt ttaagaatat tgatggttat    600
tttaaaatat attctaagca cacgcctatt aatttagtgc gtgatctccc tcagggtttt    660
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga cttttctatt aaaatataat    840
gaaaatggaa ccattacaga tgctgtagac tgtgcacttg accctctctc agaaacaaag    900
tgtacgttga aatccttcac tgtagaaaaa ggaatctatc aaacttctaa ctttagagtc    960
caaccaacag aatctattgt tagatttcct aatattacaa acttgtgccc ttttggtgaa   1020
gtttttaacg ccaccagatt tgcatctgtt tatgcttgga acaggaagag aatcagcaac   1080
tgtgttgctg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccagggc aaactggaaa gattgctgat   1260
tataattata aattaccaga tgattttaca ggctgcgtta tagcttggaa ctctaacaat   1320
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
```

```
ttcaacttca atggtttaac aggcacaggt gttcttactg agtctaacaa aaagtttctg   1680

cctttccaac aatttggcag agacattgct gacactactg atgctgtccg tgatccacag   1740

acacttgaga ttcttgacat tacaccatgt tcttttggtg gtgtcagtgt tataacacca   1800

ggaacaaata cttctaacca ggttgctgtt ctttatcagg atgttaactg cacagaagtc   1860

cctgttgcta ttcatgcaga tcaacttact cctacttggc gtgtttattc tacaggttct   1920

aatgtttttc aaacacgtgc aggctgttta ataggggctg aacatgtcaa caactcatat   1980

gagtgtgaca tacccattgg tgcaggtata tgcgctagtt atcagactca gactaattct   2040

cctcggcggg cacgtagtgt agctagtcaa tccatcattg cctacactat gtcacttggt   2100

gcagaaaatt cagttgctta ctctaataac tctattgcca tacccacaaa ttttactatt   2160

agtgttacca cagaaattct accagtgtct atgaccaaga catcagtaga ttgtacaatg   2220

tacatttgtg gtgattcaac tgaatgcagc aatcttttgt tgcaatatgg cagtttttgt   2280

acacaattaa accgtgcttt aactggaata gctgttgaac aagacaaaaa cacccaagaa   2340

gtttttgcac aagtcaaaca aatttacaaa acaccaccaa ttaaagattt tggtggtttt   2400

aatttttcac aaatattacc agatccatca aaaccaagca agaggtcatt tattgaagat   2460

ctacttttca acaaagtgac acttgcagat gctggcttca tcaaacaata tggtgattgc   2520

cttggtgata ttgctgctag agacctcatt tgtgcacaaa agtttaacgg ccttactgtt   2580

ttgccacctt tgctcacaga tgaaatgatt gctcaataca cttctgcact gttagcgggt   2640

acaatcactt ctggttggac ctttggtgca ggtgctgcat tacaaatacc atttgctatg   2700

caaatggctt ataggtttaa tggtattgga gttacacaga atgttctcta tgagaaccaa   2760

aaattgattg ccaaccaatt taatagtgct attggcaaaa ttcaagactc actttcttcc   2820

acagcaagtg cacttggaaa acttcaagat gtggtcaacc aaaatgcaca agctttaaac   2880

acgcttgtta aacaacttag ctccaatttt ggtgcaattt caagtgtttt aaatgatatc   2940

ctttcacgtc ttgacaaagt tgaggctgaa gtgcaaattg ataggttgat cacaggcaga   3000

cttcaaagtt tgcagacata tgtgactcaa caattaatta gagctgcaga aatcagagct   3060

tctgctaatc ttgctgctac taaaatgtca gagtgtgtac ttggacaatc aaaaagagtt   3120

gatttttgtg gaaagggcta tcatcttatg tccttccctc agtcagcacc tcatggtgta   3180

gtcttcttgc atgtgactta tgtccctgca caagaaaaga acttcacaac tgctcctgcc   3240

atttgtcatg atggaaaagc acactttcct cgtgaaggtg tctttgtttc aaatggcaca   3300

cactggtttg taacacaaag gaatttttat gaaccacaaa tcattactac agacaacaca   3360

tttgtgtctg gtaactgtga tgttgtaata ggaattgtca acaacacagt ttatgatcct   3420

ttgcaacctg aattagactc attcaaggag gagttagata aatattttaa gaatcataca   3480

tcaccagatg ttgatttagg tgacatctct ggcattaatg cttcagttgt aaacattcaa   3540

aaagaaattg accgcctcaa tgaggttgcc aagaatttaa atgaatctct catcgatctc   3600

caagaacttg gaaagtatga gcagtatata aaa                                3633
```

<210> SEQ ID NO 44
<211> LENGTH: 685
<212> TYPE: PRT
<213> ORGANISM: SARS-CoV-2
<220> FEATURE:
<223> OTHER INFORMATION: SARS-CoV-2 spike protein S1 subunit with native signal peptide

<400> SEQUENCE: 44

-continued

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415
```

```
Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg
        675                 680                 685
```

<210> SEQ ID NO 45
<211> LENGTH: 2055
<212> TYPE: DNA
<213> ORGANISM: SARS-CoV-2
<220> FEATURE:
<223> OTHER INFORMATION: SARS-CoV-2 spike protein S1 subunit with native signal peptide coding sequence

<400> SEQUENCE: 45

```
atgtttgttt ttcttgtttt attgccatta gtctctagtc agtgtgttaa tcttacaacc      60

agaactcaat taccccctgc atacactaat tctttcacac gtggtgttta ttaccctgac     120

aaagttttca gatcctcagt tttacattca actcaggact tgttcttacc tttcttttcc     180

aatgttactt ggttccatgc tatacatgtc tctgggacca atggtactaa gaggtttgat     240

aaccctgtcc taccatttaa tgatggtgtt tattttgctt ccactgagaa gtctaacata     300

ataagaggct ggatttttgg tactacttta gattcgaaga cccagtccct acttattgtt     360

aataacgcta ctaatgttgt tattaaagtc tgtgaatttc aattttgtaa tgatccattt     420

ttgggtgttt attaccacaa aaacaacaaa agttggatgg aaagtgagtt cagagtttat     480

tctagtgcga ataattgcac ttttgaatat gtctctcagc cttttcttat ggaccttgaa     540
```

-continued

```
ggaaaacagg gtaatttcaa aaatcttagg gaatttgtgt ttaagaatat tgatggttat    600

tttaaaatat attctaagca cacgcctatt aatttagtgc gtgatctccc tcagggtttt    660

tcggctttag aaccattggt agatttgcca ataggtatta acatcactag gtttcaaact    720

ttacttgctt tacatagaag ttatttgact cctggtgatt cttcttcagg ttggacagct    780

ggtgctgcag cttattatgt gggttatctt caacctagga cttttctatt aaaatataat    840

gaaaatggaa ccattacaga tgctgtagac tgtgcacttg accctctctc agaaacaaag    900

tgtacgttga aatccttcac tgtagaaaaa ggaatctatc aaacttctaa ctttagagtc    960

caaccaacag aatctattgt tagatttcct aatattacaa acttgtgccc ttttggtgaa   1020

gtttttaacg ccaccagatt tgcatctgtt tatgcttgga acaggaagag aatcagcaac   1080

tgtgttgctg attattctgt cctatataat tccgcatcat tttccacttt taagtgttat   1140

ggagtgtctc ctactaaatt aaatgatctc tgctttacta atgtctatgc agattcattt   1200

gtaattagag gtgatgaagt cagacaaatc gctccagggc aaactggaaa gattgctgat   1260

tataattata aattaccaga tgattttaca ggctgcgtta tagcttggaa ttctaacaat   1320

cttgattcta aggttggtgg taattataat tacctgtata gattgtttag gaagtctaat   1380

ctcaaacctt ttgagagaga tatttcaact gaaatctatc aggccggtag cacaccttgt   1440

aatggtgttg aaggttttaa ttgttacttt cctttacaat catatggttt ccaacccact   1500

aatggtgttg gttaccaacc atacagagta gtagtacttt cttttgaact tctacatgca   1560

ccagcaactg tttgtggacc taaaaagtct actaatttgg ttaaaaacaa atgtgtcaat   1620

ttcaacttca atggtttaac aggcacaggt gttcttactg agtctaacaa aaagtttctg   1680

cctttccaac aatttggcag agacattgct gacactactg atgctgtccg tgatccacag   1740

acacttgaga ttcttgacat tacaccatgt tcttttggtg gtgtcagtgt tataacacca   1800

ggaacaaata cttctaacca ggttgctgtt ctttatcagg atgttaactg cacagaagtc   1860

cctgttgcta ttcatgcaga tcaacttact cctacttggc gtgtttattc tacaggttct   1920

aatgtttttc aaacacgtgc aggctgttta ataggggctg aacatgtcaa caactcatat   1980

gagtgtgaca tacccattgg tgcaggtata tgcgctagtt atcagactca gactaattct   2040

cctcggcggg cacgt                                                    2055
```

<210> SEQ ID NO 46
<211> LENGTH: 39
<212> TYPE: DNA
<213> ORGANISM: Artificial Sequence
<220> FEATURE:
<223> OTHER INFORMATION: Exemplary 5-Prime-UTR DNA Sequence

<400> SEQUENCE: 46

```
gaaataagag agaaaagaag agtaagaaga aatataaga                            39
```

<210> SEQ ID NO 47
<211> LENGTH: 39
<212> TYPE: RNA
<213> ORGANISM: Artificial Sequence
<220> FEATURE:
<223> OTHER INFORMATION: Exemplary 5-Prime-UTR RNA Sequence

<400> SEQUENCE: 47

```
gaaauaagag agaaaagaag aguaagaaga aauauaaga                            39
```

<210> SEQ ID NO 48

<211> LENGTH: 43
<212> TYPE: DNA
<213> ORGANISM: Artificial Sequence
<220> FEATURE:
<223> OTHER INFORMATION: Exemplary 5-Prime-UTR DNA Sequence

<400> SEQUENCE: 48
cttgttcttt ttgcagaagc tcagaataaa cgctcaactt tgg 43

<210> SEQ ID NO 49
<211> LENGTH: 43
<212> TYPE: RNA
<213> ORGANISM: Artificial Sequence
<220> FEATURE:
<223> OTHER INFORMATION: Exemplary 5-Prime-UTR RNA Sequence

<400> SEQUENCE: 49
cuuguucuuu uugcagaagc ucagaauaaa cgcucaacuu ugg 43

<210> SEQ ID NO 50
<211> LENGTH: 100
<212> TYPE: DNA
<213> ORGANISM: Artificial Sequence
<220> FEATURE:
<223> OTHER INFORMATION: Exemplary 5-Prime-UTR DNA Sequence

<400> SEQUENCE: 50
gcaggagcca gggctgggca taaaagtcag ggcagagcca tctattgctt acatttgctt 60
ctgacacaac tgtgttcact agcaacctca aacagacacc 100

<210> SEQ ID NO 51
<211> LENGTH: 100
<212> TYPE: RNA
<213> ORGANISM: Artificial Sequence
<220> FEATURE:
<223> OTHER INFORMATION: Exemplary 5-Prime-UTR RNA Sequence

<400> SEQUENCE: 51
gcaggagcca gggcugggca uaaaagucag ggcagagcca ucuauugcuu acauuugcuu 60
cugacacaac uguguucacu agcaaccuca aacagacacc 100

<210> SEQ ID NO 52
<211> LENGTH: 113
<212> TYPE: DNA
<213> ORGANISM: Artificial Sequence
<220> FEATURE:
<223> OTHER INFORMATION: Exemplary 3-Prime-UTR DNA Sequence

<400> SEQUENCE: 52
taggctggag cctcggtggc catgcttctt gccccttggg cctcccccca gcccctcctc 60
cccttcctgc acccgtaccc ccgtggtctt tgaataaagt ctgagtgggc ggc 113

<210> SEQ ID NO 53
<211> LENGTH: 113
<212> TYPE: RNA
<213> ORGANISM: Artificial Sequence
<220> FEATURE:
<223> OTHER INFORMATION: Exemplary 3-Prime-UTR RNA Sequence

<400> SEQUENCE: 53
uaggcuggag ccucgguggc caugcuucuu gccccuuggg ccucccccca gccccuccuc 60
cccuuccugc acccguaccc ccguggucuu ugaauaaagu cugagugggc ggc 113

<210> SEQ ID NO 54
<211> LENGTH: 132
<212> TYPE: DNA
<213> ORGANISM: Artificial Sequence
<220> FEATURE:
<223> OTHER INFORMATION: Exemplary 3-Prime-UTR DNA Sequence

<400> SEQUENCE: 54
gctcgctttc ttgctgtcca atttctatta aaggttcctt tgttccctaa gtccaactac 60
taaactgggg gatattatga agggccttga gcatctggat tctgcctaat aaaaaacatt 120
tattttcatt gc 132

<210> SEQ ID NO 55
<211> LENGTH: 132
<212> TYPE: RNA
<213> ORGANISM: Artificial Sequence
<220> FEATURE:
<223> OTHER INFORMATION: Exemplary 3-Prime-UTR RNA Sequence

<400> SEQUENCE: 55
gcucgcuuuc uugcugucca auuucuauua aagguuccuu uguucccuaa guccaacuac 60
uaaacugggg gauauuauga agggccuuga gcaucuggau ucugccuaau aaaaaacauu 120
uauuuucauu gc 132

<210> SEQ ID NO 56
<211> LENGTH: 278
<212> TYPE: DNA
<213> ORGANISM: Artificial Sequence
<220> FEATURE:
<223> OTHER INFORMATION: Exemplary 3-Prime-UTR DNA Sequence

<400> SEQUENCE: 56
ctggtactgc atgcacgcaa tgctagctgc ccctttcccg tcctgggtac cccgagtctc 60
ccccgacctc gggtcccagg tatgctccca cctccacctg ccccactcac cacctctgct 120
agttccagac acctcccaag cacgcagcaa tgcagctcaa aacgcttagc ctagccacac 180
ccccacggga aacagcagtg attaaccttt agcaataaac gaaagtttaa ctaagctata 240
ctaaccccag ggttggtcaa tttcgtgcca gccacacc 278

<210> SEQ ID NO 57
<211> LENGTH: 278
<212> TYPE: RNA
<213> ORGANISM: Artificial Sequence
<220> FEATURE:
<223> OTHER INFORMATION: Exemplary 3-Prime-UTR RNA Sequence

<400> SEQUENCE: 57
cugguacugc augcacgcaa ugcuagcugc cccuuucccg uccuggguac cccgagucuc 60
ccccgaccuc gggucccagg uaugcuccca ccuccaccug ccccacucac caccucugcu 120
aguuccagac accucccaag cacgcagcaa ugcagcucaa aacgcuuagc cuagccacac 180
ccccacggga aacagcagug auuaaccuuu agcaauaaac gaaaguuuaa cuaagcuaua 240
cuaaccccag gguuggucaa uuucgugcca gccacacc 278

<210> SEQ ID NO 58
<211> LENGTH: 24
<212> TYPE: DNA
<213> ORGANISM: Artificial Sequence
<220> FEATURE:
<223> OTHER INFORMATION: stem-loop sequence -continued

```
<400> SEQUENCE: 58

caaaggctct tttcagagcc acca                                          24


<210> SEQ ID NO 59
<211> LENGTH: 24
<212> TYPE: RNA
<213> ORGANISM: Artificial Sequence
<220> FEATURE:
<223> OTHER INFORMATION: stem-loop sequence

<400> SEQUENCE: 59

caaaggcucu uuucagagcc acca                                          24
```

NUCLEIC ACID VACCINES FOR CORONAVIRUS

1. CROSS-REFERENCE TO RELATED APPLICATION

This application is a continuation of International Application No.: PCT/CN2021/085883 filed Apr. 8, 2021, which claims the benefit of priority to Chinese Patent Application No.: 202010276288.0 filed on Apr. 9, 2020, U.S. Provisional Application No. 63/011,116 filed on Apr. 16, 2020, and Chinese Patent Application No.: 202110293284.8 filed on Mar. 19, 2021, the contents of each of which is incorporated by reference in its entirety.

2. FIELD

The present disclosure generally relates to nucleic acid molecules that can be used for the management, prevention, and treatment of coronavirus infection. The present disclosure also relates to lipid-containing compositions, including vaccines, of the nucleic acid molecules, and related methods of delivery.

3. BACKGROUND

Coronaviruses pose serious health threats to humans and other animals. From 2002 to 2003, severe acute respiratory syndrome coronavirus (SARS-CoV) infected 8,000 people, with a fatality rate of ~9%. Since 2012, Middle East respiratory syndrome coronavirus (MERS-CoV) has infected more than 1,700 people, with a fatality rate of ~36%. Since 2013, porcine epidemic diarrhea coronavirus (PEDV) has swept throughout the United States, causing an almost 100% fatality rate in piglets and wiping out more than 10% of America's pig population in less than a year. In March 2020, the World Health Organization (WHO) announced a pandemic caused by the outbreak of Coronavirus Disease 2019 (COVID-19), which swept into more than 180 countries and killed more than 80,000 people in the first few months of the outbreak. In general, the disease is caused by a newly discovered coronavirus, SARS-CoV-2, which shows symptoms of widespread respiratory, gastrointestinal, and central nervous system diseases in humans and other animals, threatening human health and causing economic loss. Therefore, there exist an urgent need for effective therapeutics, including vaccines for curbing coronavirus infections. The present disclosure meets this need.

4. SUMMARY

In one aspect, provided herein are non-naturally occurring nucleic acid molecules that can be used for the prevention, management and treatment of infectious diseases. In some embodiments, the non-naturally occurring nucleic acids encode a viral peptide or protein derived from coronavirus SARS-CoV-2. In some embodiments, the non-naturally occurring nucleic acid encode a viral peptide or protein derived from a coronavirus comprising a genome, wherein the genome comprises the nucleic acid sequence set forth in SEQ ID NO:1.

In some embodiments, the non-naturally occurring nucleic acid molecule comprises a coding region, wherein the coding region comprises one or more open reading frames (ORFs), and wherein at least one ORFs encodes the viral peptide or protein. In some embodiments, at least one ORFs encodes a heterologous peptide or polypeptide. In some embodiments, the heterologous peptide or polypeptide is an immuno-stimulating peptide or protein. In some embodiments, the ORF encodes a fusion protein comprising the viral peptide or protein fused to a heterologous peptide or polypeptide. In some embodiments, the heterologous peptide or polypeptide is selected from a Fc region of human immunoglobulin, a signal peptide, and a peptide facilitating multimerization of the fusion protein.

In some embodiments, the one or more ORFs consists a coding sequence as set forth in Tables 1 to 4. In some embodiments, the one or more ORFs consists a coding sequence selected from SEQ ID NOS:3, 5, 7, 9, 11, 13, 15, 17, 19, 27, 29, 31, 33, 35, 37, 39, 41, 43, and 45, or a transcribed RNA sequence thereof. In some embodiments, the one or more ORFs encodes a peptide or protein selected from SEQ ID NOS:2, 4, 6, 8, 10, 12, 14, 16 18, 20-26, 28, 30, 32, 34, 36, 38, 40, 42, and 44.

In some embodiments, the non-naturally occurring nucleic acid molecule further comprises a 5' untranslated region (5'-UTR), wherein the 5'-UTR comprises the sequence set forth in SEQ ID NOS: 46-51. In some embodiments, the non-naturally occurring nucleic acid molecule further comprises a 3' untranslated region (3'-UTR), wherein the 3'-UTR comprises the sequence set forth in SEQ ID NOS: 52-57. In some embodiments, the 3'-UTR further comprises a poly-A tail or a polyadenylation signal.

In some embodiments, the non-naturally occurring nucleic acid molecule further comprises one or more functional nucleotide analogs that are selected from pseudouridine, 1-methyl-pseudouridine and 5-methylcytosine. In some embodiments, the non-naturally occurring nucleic acid molecule further comprises the nucleic acid is DNA or mRNA.

In some embodiments, disclosed herein are vectors or cells comprising the naturally occurring nucleic acid molecule as described herein. In some embodiments, disclosed herein are compositions comprising the naturally occurring nucleic acid molecule as described herein. In some embodiments, the composition is formulated as lipid nanoparticles encapsulating the nucleic acid in a lipid shell. In some embodiments, the composition is a pharmaceutical composition.

In one aspect, provided herein are pharmaceutical compositions comprising at least one nucleic acid encoding a viral peptide or protein derived from coronavirus SARS-CoV-2. In some embodiments, provided herein are pharmaceutical compositions comprising at least one nucleic acid encoding a viral peptide or protein derived from a coronavirus comprising a genome, wherein the genome comprises the nucleic acid sequence set forth in SEQ ID NO:1.

In some embodiments of the pharmaceutical composition described herein, the viral peptide or protein is selected from: (a) a spike (S) protein of the coronavirus, (b) a matrix (M) protein of the coronavirus, (c) a nucleocapsid (N) protein of the coronavirus, (d) an envelope (E) protein of the coronavirus, (e) a hemagglutinin-esterase (HE) protein, (f) an immunogenic fragment of any one of (a) to (e); and (g) a functional derivative of any one of (a) to (f).

In some embodiments, the viral peptide or protein is the S protein, an immunogenic fragment of the S protein, or a functional derivative of the S protein or the immunogenic fragment thereof. In some embodiments, the immunogenic fragment of the S protein is selected from an ectodomain (ECD), an S1 subunit, a receptor binding domain (RBD), and a receptor-binding motif (RBM).

In some embodiments of the pharmaceutical composition described herein, the viral peptide or protein is a functional derivative of RBD. In some embodiments, the functional derivative of RBD comprises one or more amino acid substitutions in the RBD that are capable of increasing binding affinity of the RBD to receptor in a host cell. In some embodiments, the receptor is ACE2. In some embodiments, the amino acid substitution comprises N501T.

In some embodiments of the pharmaceutical composition described herein, the viral peptide or protein comprises the amino acid sequence set forth in SEQ ID NOS: 2, 4, 6, 8, 10, 12, 14, 16 18, 20-26, 32, 34, 40, 42, and 44. In some embodiments, the nucleic acid comprises the sequence as set forth in SEQ ID NOS: 3, 5, 7, 9, 11, 13, 15, 17, 19, 27, 29, 31, 33, 35, 37, 39, 41, 43, 45, 46, 48, 50, 52, 54, 56 or a transcribed RNA sequence thereof.

In some embodiments of the pharmaceutical composition described herein, the functional derivative of the RBD comprises the RBD fused to an Fc region of human immunoglobulin. In some embodiments, the immunoglobulin is IgG1.

In some embodiments of the pharmaceutical composition described herein, the functional derivative of RBD comprises the RBD fused to a peptide facilitating multimerization of the fusion protein. In some embodiments, the functional derivative of S-RBD is configured to form a trimeric complex.

In some embodiments of the pharmaceutical composition described herein, the viral peptide or protein is the N protein. In some embodiments, the N protein comprises the amino acid sequence set forth in SEQ ID NO: 18. In some embodiments, the nucleic acid comprises the sequence set forth in SEQ ID NO: 19 or a RNA sequence transcribed therefrom.

In some embodiments of the pharmaceutical composition described herein, the nucleic acid further comprises a 5' untranslated region and/or a 3' untranslated region. In some embodiments, the 5' untranslated region comprises a sequence selected from SEQ ID NOS: 46-51. In some embodiments, the 3' untranslated region comprises a poly-A tail or a polyadenylation signal. In some embodiments, the 3' untranslated region comprises a sequence selected from SEQ ID NOS: 52-57.

In some embodiments of the pharmaceutical composition described herein, the nucleic acid comprises one or more functional nucleotide analogs selected from pseudouridine, 1-methyl-pseudouridine and 5-methylcytosine.

In some embodiments of the pharmaceutical composition described herein, the composition further comprises at least one lipid. In some embodiments, the lipid is a compound according to Formula (I) to (IV). In some embodiments, the lipid is a compound according to Formula (I-A), (I-B), (IB'), (I-B"), (I-C), (I-D), (I-E), (I-F), (I-F'), (I-F"), (I-G), (I-H), (I-I), (I-J), (I-J'), (I-J"), (I-K), (I-L), (I-M), (I-N), (I-N'), (I-O), (LP), (I-Q), (I-R), (I-R'), (I-R"), (I-S), (I-T), (I-U), (II-A), (II-B), (II-B'), (II-B"), (II-C), (II-D), (II-E), (II-F), (II-F'), (II-F"), (II-G), (II-H), (II-I), (II-J), (II-J'), (II-J"), (II-K), (II-L), (II-M), (II-N), (II-N'), (II-N"), (II-O), (II-P), (II-Q), (II-R), (II-R'), (II-R"), (II-S), (II-T), (II-U), (III-A), (III-B), (III-B'), (III-B"), (III-C), (II-D), (III-E), (III-F), (III-F'), (III-F"), (III-G), (III-H), (III-I), (III-J), (III-J'), (III-J"), (III-K), (III-L), (III-M), (III-N), (III-N'), (III-N"), (III-O), (III-P), (III-Q), (III-R), (III-R'), (III-R"), (III-S), (III-T), (III-U), (IV-A), (IV-B), (IV-B'), (IV-B"), (IV-C), (IV-D), (IV-E), (IV-F), (IV-F'), (IV-F"), (IV-G), (IV-H), (IV-I), (IV-J), (IV-J'), (IV-J"), (IV-K), (IV-L), (IV-M), (IV-N), (IV-N'), (IV-N"), (IV-O), (IV-P), (IV-Q), (IV-R), (IV-R'), (IV-R"), (IV-S), (IV-T) or (IV-U). In some embodiments, the lipid is a compound listed in Table 1. In some embodiments, the composition is formulated as lipid nanoparticles encapsulating the nucleic acid in a lipid shell. In some embodiments, the composition is a vaccine.

In one aspect, provided herein are methods for managing, preventing or treating an infectious disease caused by coronavirus in a subject, comprising administering to the subject a therapeutically effective amount of the non-naturally occurring nucleic acid described herein, or a therapeutically effective amount of the pharmaceutical composition as described herein.

In some embodiments of the method described herein, the subject is a human or a non-human mammal. In some embodiments, the subject is a human adult, a human child or a human toddler. In some embodiments, the subject has the infectious disease. In some embodiments, the subject is at risk of, or is susceptible to, infection by the coronavirus. In some embodiments, the subject is an elderly human. In some embodiments, subject has been diagnosed positive for infection by the coronavirus. In some embodiments, the subject is asymptomatic.

In some embodiments of the method described herein, the method comprises administering lipid nanoparticles encapsulating the nucleic acid to the subject, and wherein the lipid nanoparticles are endocytosed by the cells in the subject. In some embodiments, the nucleic acid is expressed by the cells in the subject.

In some embodiments of the method described herein, an immune response against the coronavirus is elicited in the subject. In some embodiments, the immune response comprises production of an antibody specifically binds to the viral peptide or protein encoded by the nucleic acid. In some embodiments, the antibody is a neutralizing antibody against the coronavirus or cells infected by the coronavirus. In some embodiments, the serum titer of the antibody is increased in the subject.

In some embodiments, the antibody specifically binds to one or more epitopes of the S protein. In some embodiments of the method described herein, one or more function or activity of the S protein is attenuated. In some embodiments, the attenuation of the S protein function or activity is measured by (a) reduction of binding of the S protein to host cell receptor; (b) reduction of attachment of the coronavirus to a host cell; (c) reduction of host cell membrane fusion induced by the coronavirus; or (d) reduction of the number of cells infected by the coronavirus in the subject. In some embodiments, the host receptor is selected from angiotensin-converting enzyme 2 (ACE2), aminopeptidase N (APN), dipeptidyl peptidase 4 (DPP4), carcinoembryonic antigen-related cell adhesion molecule 1 (CEACAM1) and sugar. In some embodiments, the S protein function or activity is reduced by 10%, 20%, 30%, 40%, 50%, 60%, 70%, 80%, 90%, 95% or 100%.

In some embodiments of the method described herein, the antibody specifically bind to one or more epitopes of the N protein. In some embodiments, one or more function or activity of the N protein is attenuated. In some embodiments, the attenuation of the N protein function or activity is measured by (a) reduction of binding of the N protein to replicated genomic sequence of the coronavirus; (b) reduction of packaging of replicated genomic sequence of the coronavirus into a functional viral capsid; or (c) reduction of the number of replicated viral particles in the subject. In some embodiments, the N protein function or activity is reduced by 10%, 20%, 30%, 40%, 50%, 60%, 70%, 80%, 90%, 95% or 100%.

In some embodiments of the method described herein, antibody binds to a viral particle or an infected cell and mark the viral particle of infected cell for destruction by the immune system of the subject. In some embodiments, endocytosis of viral particles bound by the antibody is induced or enhanced. In some embodiments, antibody-dependent cell-mediated cytotoxicity (ADCC) against infected cells in the subject is induced or enhanced. In some embodiments, antibody-dependent cellular phagocytosis (ADCP) against infected cells in the subject is induced or enhanced. In some embodiments, complement dependent cytotoxicity (CDC) against infected cells in the subject is induced or enhanced.

In some embodiments of the method described herein, the infectious disease is respiratory tract infection, lung infection, renal infection, liver infection, enteric infection, neurologic infections, respiratory syndrome, bronchitis, pneumonia, gastroenteritis, encephalomyelitis, encephalitis, sarcoidosis, diarrhea, hepatitis, and demyelinating disease. In some embodiments, the infectious disease is respiratory tract infection. In some embodiments, the infectious disease is lung infection. In some embodiments, the infectious disease is respiratory syndrome. In some embodiments, the infectious disease is pneumonia.

5. BRIEF DESCRIPTION OF THE FIGURES

FIG. 1 shows an exemplary HPLC analysis and purification of in vitro transcribed mRNA constructs according to the present disclosure. The main peak (b) represents in vitro transcribed mRNA molecules, and the minor peak (a) represents an entity of impurity.

FIG. 2 shows confocal fluorescence microscopy images of Hela cells transfected with mRNA constructs according to the present disclosure. The RBD-FITC channel shows staining of the cells using 3 different monoclonal antibodies (H014, mh001 and mh219) recognizing SARS-CoV-2 S protein RBD, respectively. The DAPI channel shows staining of the cells with the blue-fluorescent DNA stain DAPI (4',6-diamidino-2-phenylindole). The Bright channel shows bright field images of the cells. Non-transfected Hela cells (Mock) was included as a negative control. Scale bar is 50 mm.

FIG. 3 shows Western blot analysis of culture supernatant of HeLa cells transfected with mRNA constructs encoding SARS-CoV-2 S protein antigens according to the present disclosure. Particularly, three different mRNA constructs encoding different antigenic fragments of the SARS-CoV-2 S protein RBD (RBD sample-1, RBD sample-2 and rRBD-His) were included in the analysis. An irrelevant mRNA control was also included. Monomers and dimmers of the encoded RBD fragments are shown on the blot.

6. DETAILED DESCRIPTION

Figure 1:
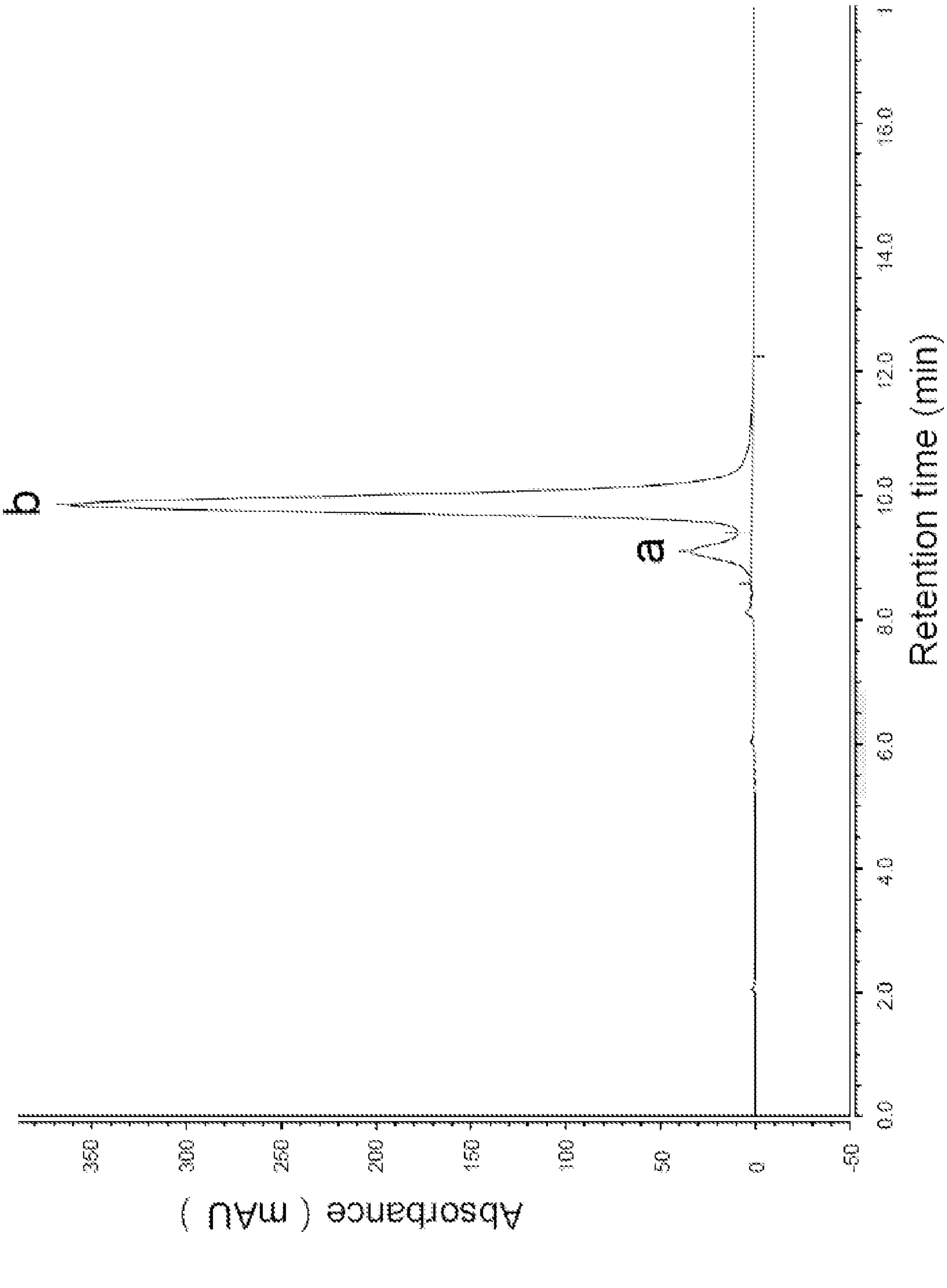

Provided herein are therapeutic nucleic acid molecules useful for the prevention, management and treatment of infectious disease or condition caused by coronaviruses. Also provided herein are pharmaceutical composition comprising the therapeutic nucleic acid molecules, including pharmaceutical composition formulated as lipid nanoparticles and related therapeutic methods and uses for preventing, managing and treating of infectious disease or condition caused by coronaviruses, including the pathogen causing the pandemic known as the COVID-19. Additional features of the present disclosure will become apparent to those skilled in the art upon consideration of the following detailed description of particular embodiments.

6.1 General Techniques

Techniques and procedures described or referenced herein include those that are generally well understood and/or commonly employed using conventional methodology by those skilled in the art, such as, for example, the widely utilized methodologies described in Sambrook et al., *Molecular Cloning: A Laboratory Manual* (3d ed. 2001); *Current Protocols in Molecular Biology* (Ausubel et al. eds., 2003).

6.2 Terminology

Unless described otherwise, all technical and scientific terms used herein have the same meaning as is commonly understood by one of ordinary skill in the art. For purposes of interpreting this specification, the following description of terms will apply and whenever appropriate, terms used in the singular will also include the plural and vice versa. All patents, applications, published applications, and other publications are incorporated by reference in their entirety. In the event that any description of terms set forth conflicts with any document incorporated herein by reference, the description of term set forth below shall control.

As used herein and unless otherwise specified, the term "lipid" refers to a group of organic compounds that include, but are not limited to, esters of fatty acids and are generally characterized by being poorly soluble in water, but soluble in many nonpolar organic solvents. While lipids generally have poor solubility in water, there are certain categories of lipids (e.g., lipids modified by polar groups, e.g., DMG-PEG2000) that have limited aqueous solubility and can dissolve in water under certain conditions. Known types of lipids include biological molecules such as fatty acids, waxes, sterols, fat-soluble vitamins, monoglycerides, diglycerides, triglycerides, and phospholipids. Lipids can be divided into at least three classes: (1) "simple lipids," which include fats and oils as well as waxes; (2) "compound lipids," which include phospholipids and glycolipids (e.g., DMPE-PEG2000); and (3) "derived lipids" such as steroids. Further, as used herein, lipids also encompass lipidoid compounds. The term "lipidoid compound," also simply "lipidoid", refers to a lipid-like compound (e.g. an amphiphilic compound with lipid-like physical properties).

The term "lipid nanoparticle" or "LNP" refers to a particle having at least one dimension on the order of nanometers (nm) (e.g., 1 to 1,000 nm), which contains one or more types of lipid molecules. The LNP provided herein can further contain at least one non-lipid payload molecule (e.g., one or more nucleic acid molecules). In some embodiments, the LNP comprises a non-lipid payload molecule either partially or completely encapsulated inside a lipid shell. Particularly, in some embodiments, wherein the payload is a negatively charged molecule (e.g., mRNA encoding a viral protein), and the lipid components of the LNP comprise at least one cationic lipid. Without being bound by the theory, it is contemplated that the cationic lipids can interact with the negatively charged payload molecules and facilitates incorporation and/or encapsulation of the payload into the LNP during LNP formation. Other lipids that can form part of a LNP as provided herein include but are not limited to neutral lipids and charged lipids, such as steroids, polymer conjugated lipids, and various zwitterionic lipids. In certain embodiments, a LNP according to the present disclosure comprises one or more lipids of Formula (I) to (IV) (and sub-formulas thereof) as described herein.

The term "cationic lipid" refers to a lipid that is either positively charged at any pH value or hydrogen ion activity of its environment, or capable of being positively charged in response to the pH value or hydrogen ion activity of its environment (e.g., the environment of its intended use). Thus, the term "cationic" encompasses both "permanently cationic" and "cationisable." In certain embodiments, the positive charge in a cationic lipid results from the presence of a quaternary nitrogen atom. In certain embodiments, the cationic lipid comprises a zwitterionic lipid that assumes a positive charge in the environment of its intended use (e.g., at physiological pH). In certain embodiments, the cationic lipid is one or more lipids of Formula (I) to (IV) (and sub-formulas thereof) as described herein.

The term "polymer conjugated lipid" refers to a molecule comprising both a lipid portion and a polymer portion. An example of a polymer conjugated lipid is a pegylated lipid (PEG-lipid), in which the polymer portion comprises a polyethylene glycol.

The term "neutral lipid" encompasses any lipid molecules existing in uncharged forms or neutral zwitterionic forms at a selected pH value or within a selected pH range. In some embodiments, the selected useful pH value or range corresponds to the pH condition in an environment of the intended uses of the lipids, such as the physiological pH. As non-limiting examples, neutral lipids that can be used in connection with the present disclosure include, but are not limited to, phosphotidylcholines such as 1,2-distearoyl-sn-glycero-3-phosphocholine (DSPC), 1,2-dipalmitoyl-sn-glycero-3-phosphocholine (DPPC), 1,2-dimyristoyl-sn-glycero-3-phosphocholine (DMPC), 1-palmitoyl-2-oleoyl-sn-glycero-3-phosphocholine (POPC), 1,2-dioleoyl-sn-glycero-3-phosphocholine (DOPC), phophatidylethanolamines such as 1,2-dioleoyl-sn-glycero-3-phosphoethanolamine (DOPE), 2-((2,3-bis(oleoyloxy) propyl)dimethylammonio)ethyl hydrogen phosphate (DOCP), sphingomyelins (SM), ceramides, steroids such as sterols and their derivatives. Neutral lipids as provided herein may be synthetic or derived (isolated or modified) from a natural source or compound.

The term "charged lipid" encompasses any lipid molecules that exist in either positively charged or negatively charged forms at a selected pH or within a selected pH range. In some embodiments, the selected pH value or range corresponds to the pH condition in an environment of the intended uses of the lipids, such as the physiological pH. As non-limiting examples, neutral lipids that can be used in connection with the present disclosure include, but are not limited to, phosphatidylserines, phosphatidic acids, phosphatidylglycerols, phosphatidylinositols, sterol hemisuccinates, dialkyl trimethylammonium-propanes, (e.g., DOTAP, DOTMA), dialkyl dimethylaminopropanes, ethyl phosphocholines, dimethylaminoethane carbamoyl sterols (e.g., DC-Chol), 1,2-dioleoyl-sn-glycero-3-phospho-L-serine sodium salt (DOPS-Na), 1,2-dioleoyl-sn-glycero-3-phospho-(1'-rac-glycerol) sodium salt (DOPG-Na), and 1,2-dioleoyl-sn-glycero-3-phosphate sodium salt (DOPA-Na). Charged lipids as provided herein may be synthetic or derived (isolated or modified) from a natural source or compound.

As used herein, and unless otherwise specified, the term "alkyl" refers to a straight or branched hydrocarbon chain radical consisting solely of carbon and hydrogen atoms, which is saturated. In one embodiment, the alkyl group has, for example, from one to twenty-four carbon atoms ($C_1$-$C_{24}$ alkyl), four to twenty carbon atoms ($C_4$-$C_{20}$ alkyl), six to sixteen carbon atoms ($C_6$-$C_{16}$ alkyl), six to nine carbon atoms ($C_6$-$C_9$ alkyl), one to fifteen carbon atoms ($C_1$-$C_{15}$ alkyl), one to twelve carbon atoms ($C_1$-$C_{12}$ alkyl), one to eight carbon atoms ($C_1$-$C_8$ alkyl) or one to six carbon atoms ($C_1$-$C_6$ alkyl) and which is attached to the rest of the molecule by a single bond. Examples of alkyl groups include, but are not limited to, methyl, ethyl, n-propyl, 1-methylethyl (isopropyl), n-butyl, n-pentyl, 1,1-dimethylethyl (t-butyl), 3-methylhexyl, 2-methylhexyl, and the like. Unless otherwise specified, an alkyl group is optionally substituted.

As used herein, and unless otherwise specified, the term "alkenyl" refers to a straight or branched hydrocarbon chain radical consisting solely of carbon and hydrogen atoms, which contains one or more carbon-carbon double bonds. The term "alkenyl" also embraces radicals having "cis" and "trans" configurations, or alternatively, "E" and "Z" configurations, as appreciated by those of ordinary skill in the art. In one embodiment, the alkenyl group has, for example, from two to twenty-four carbon atoms ($C_2$-$C_{24}$ alkenyl), four to twenty carbon atoms ($C_4$-$C_{20}$ alkenyl), six to sixteen carbon atoms ($C_6$-$C_{16}$ alkenyl), six to nine carbon atoms ($C_6$-$C_9$ alkenyl), two to fifteen carbon atoms ($C_2$-$C_{15}$ alkenyl), two to twelve carbon atoms ($C_2$-$C_{12}$ alkenyl), two to eight carbon atoms ($C_2$-$C_8$ alkenyl) or two to six carbon atoms ($C_2$-$C_6$ alkenyl) and which is attached to the rest of the molecule by a single bond. Examples of alkenyl groups include, but are not limited to, ethenyl, prop-1-enyl, but-1-enyl, pent-1-enyl, penta-1,4-dienyl, and the like. Unless otherwise specified, an alkenyl group is optionally substituted.

As used herein, and unless otherwise specified, the term "alkynyl" refers to a straight or branched hydrocarbon chain radical consisting solely of carbon and hydrogen atoms, which contains one or more carbon-carbon triple bonds. In one embodiment, the alkynyl group has, for example, from two to twenty-four carbon atoms ($C_2$-$C_{24}$ alkynyl), four to twenty carbon atoms ($C_4$-$C_{20}$ alkynyl), six to sixteen carbon atoms ($C_6$-$C_{16}$ alkynyl), six to nine carbon atoms ($C_6$-$C_9$ alkynyl), two to fifteen carbon atoms ($C_2$-$C_{15}$ alkynyl), two to twelve carbon atoms ($C_2$-$C_{12}$ alkynyl), two to eight carbon atoms ($C_2$-$C_8$ alkynyl) or two to six carbon atoms ($C_2$-$C_6$ alkynyl) and which is attached to the rest of the molecule by a single bond. Examples of alkynyl groups include, but are not limited to, ethynyl, propynyl, butynyl, pentynyl, and the like. Unless otherwise specified, an alkynyl group is optionally substituted.

As used herein, and unless otherwise specified, the term "alkylene" or "alkylene chain" refers to a straight or branched divalent hydrocarbon chain linking the rest of the molecule to a radical group, consisting solely of carbon and hydrogen, which is saturated. In one embodiment, the alkylene has, for example, from one to twenty-four carbon atoms ($C_1$-$C_{24}$ alkylene), one to fifteen carbon atoms ($C_1$-$C_{15}$ alkylene), one to twelve carbon atoms ($C_1$-$C_{12}$ alkylene), one to eight carbon atoms ($C_1$-$C_8$ alkylene), one to six carbon atoms ($C_1$-$C_6$ alkylene), two to four carbon atoms ($C_2$-$C_4$ alkylene), one to two carbon atoms ($C_1$-$C_2$ alkylene). Examples of alkylene groups include, but are not limited to, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless otherwise specified, an alkylene chain is optionally substituted.

As used herein, and unless otherwise specified, the term "alkenylene" refers to a straight or branched divalent hydrocarbon chain linking the rest of the molecule to a radical group, consisting solely of carbon and hydrogen, which contains one or more carbon-carbon double bonds. In one embodiment, the alkenylene has, for example, from two to twenty-four carbon atoms ($C_2$-$C_{24}$ alkenylene), two to fifteen carbon atoms ($C_2$-$C_{15}$ alkenylene), two to twelve carbon atoms ($C_2$-$C_{12}$ alkenylene), two to eight carbon atoms ($C_2$-$C_8$ alkenylene), two to six carbon atoms ($C_2$-$C_6$ alkenylene) or two to four carbon atoms ($C_2$-$C_4$ alkenylene). Examples of alkenylene include, but are not limited to, ethenylene, propenylene, n-butenylene, and the like. The alkenylene is attached to the rest of the molecule through a single or double bond and to the radical group through a single or double bond. The points of attachment of the alkenylene to the rest of the molecule and to the radical group can be through one carbon or any two carbons within the chain. Unless otherwise specified, an alkenylene is optionally substituted.

As used herein, and unless otherwise specified, the term "cycloalkyl" refers to a non-aromatic monocyclic or polycyclic hydrocarbon radical consisting solely of carbon and hydrogen atoms, and which is saturated. Cycloalkyl group may include fused or bridged ring systems. In one embodiment, the cycloalkyl has, for example, from 3 to 15 ring carbon atoms ($C_3$-$C_{15}$ cycloalkyl), from 3 to 10 ring carbon atoms ($C_3$-$C_{10}$ cycloalkyl), or from 3 to 8 ring carbon atoms ($C_3$-$C_8$ cycloalkyl). The cycloalkyl is attached to the rest of the molecule by a single bond. Examples of monocyclic cycloalkyl radicals include, but are not limited to, cyclopropyl, cyclobutyl, cyclopentyl, cyclohexyl, cycloheptyl, and cyclooctyl. Examples of polycyclic cycloalkyl radicals include, but are not limited to, adamantyl, norbornyl, decalinyl, 7,7-dimethyl-bicyclo[2.2.1]heptanyl, and the like. Unless otherwise specified, a cycloalkyl group is optionally substituted.

As used herein, and unless otherwise specified, the term "cycloalkylene" is a divalent cycloalkyl group. Unless otherwise specified, a cycloalkylene group isoptionally substituted.

As used herein, and unless otherwise specified, the term "cycloalkenyl" refers to a non-aromatic monocyclic or polycyclic hydrocarbon radical consisting solely of carbon and hydrogen atoms, and which includes one or more carbon-carbon double bonds. Cycloalkenyl may include fused or bridged ring systems. In one embodiment, the cycloalkenyl has, for example, from 3 to 15 ring carbon atoms ($C_3$-$C_{15}$ cycloalkenyl), from 3 to 10 ring carbon atoms ($C_3$-$C_{10}$ cycloalkenyl), or from 3 to 8 ring carbon atoms ($C_3$-$C_8$ cycloalkenyl). The cycloalkenyl is attached to the rest of the molecule by a single bond. Examples of monocyclic cycloalkenyl radicals include, but are not limited to, cyclopropenyl, cyclobutenyl, cyclopentenyl, cyclohexenyl, cycloheptenyl, cyclooctenyl, and the like. Unless otherwise specified, a cycloalkenyl group is optionally substituted.

As used herein, and unless otherwise specified, the term "cycloalkenylene" is a divalent cycloalkenyl group. Unless otherwise specified, a cycloalkenylene group is optionally substituted.

As used herein, and unless otherwise specified, the term "heterocyclyl" refers to a non-aromatic radical monocyclic or polycyclic moiety that contains one or more (e.g., one, one or two, one to three, or one to four) heteroatoms independently selected from nitrogen, oxygen, phosphorous, and sulfur. The heterocyclyl may be attached to the main structure at any heteroatom or carbon atom. A heterocyclyl group can be a monocyclic, bicyclic, tricyclic, tetracyclic, or other polycyclic ring system, wherein the polycyclic ring systems can be a fused, bridged or spiro ring system. Heterocyclyl polycyclic ring systems can include one or more heteroatoms in one or more rings. A heterocyclyl group can be saturated or partially unsaturated. Saturated heterocycloalkyl groups can be termed "heterocycloalkyl". Partially unsaturated heterocycloalkyl groups can be termed "heterocycloalkenyl" if the heterocyclyl contains at least one double bond, or "heterocycloalkynyl" if the heterocyclyl contains at least one triple bond. In one embodiment, the heterocyclyl has, for example, 3 to 18 ring atoms (3- to 18-membered heterocyclyl), 4 to 18 ring atoms (4- to 18-membered heterocyclyl), 5 to 18 ring atoms (3- to 18-membered heterocyclyl), 4 to 8 ring atoms (4- to 8-membered heterocyclyl), or 5 to 8 ring atoms (5- to 8-membered heterocyclyl). Whenever it appears herein, a numerical range such as "3 to 18" refers to each integer in the given range; e.g., "3 to 18 ring atoms" means that the heterocyclyl group can consist of 3 ring atoms, 4 ring atoms, 5 ring atoms, 6 ring atoms, 7 ring atoms, 8 ring atoms, 9 ring atoms, 10 ring atoms, etc., up to and including 18 ring atoms. Examples of heterocyclyl groups include, but are not limited to, imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl. Unless otherwise specified, a heterocyclyl group is optionally substituted.

As used herein, and unless otherwise specified, the term "heterocyclylene" is a divalent heterocyclyl group. Unless otherwise specified, a heterocyclylene group is optionally substituted As used herein, and unless otherwise specified, the term "aryl" refers to a monocyclic aromatic group and/or multicyclic monovalent aromatic group that contain at least one aromatic hydrocarbon ring. In certain embodiments, the aryl has from 6 to 18 ring carbon atoms ($C_6$-$C_{18}$ aryl), from 6 to 14 ring carbon atoms ($C_6$-$C_{14}$ aryl), or from 6 to 10 ring carbon atoms ($C_6$-$C_{10}$ aryl). Examples of aryl groups include, but are not limited to, phenyl, naphthyl, fluorenyl, azulenyl, anthryl, phenanthryl, pyrenyl, biphenyl, and terphenyl. The term "aryl" also refers to bicyclic, tricyclic, or other multicyclic hydrocarbon rings, where at least one of the rings is aromatic and the others of which may be saturated, partially unsaturated, or aromatic, for example, dihydronaphthyl, indenyl, indanyl, or tetrahydronaphthyl (tetralinyl). Unless otherwise specified, an aryl group is optionally substituted.

As used herein, and unless otherwise specified, the term "arylene" is a divalent aryl group. Unless otherwise specified, an arylene group is optionally substituted.

As used herein, and unless otherwise specified, the term "heteroaryl" refers to a monocyclic aromatic group and/or multicyclic aromatic group that contains at least one aromatic ring, wherein at least one aromatic ring contains one or more (e.g., one, one or two, one to three, or one to four) heteroatoms independently selected from O, S, and N. The heteroaryl may be attached to the main structure at any heteroatom or carbon atom. In certain embodiments, the heteroaryl has from 5 to 20, from 5 to 15, or from 5 to 10 ring atoms. The term "heteroaryl" also refers to bicyclic, tricyclic, or other multicyclic rings, where at least one of the rings is aromatic and the others of which may be saturated, partially unsaturated, or aromatic, wherein at least one aromatic ring contains one or more heteroatoms independently selected from O, S, and N. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrollinyl, acridinyl, phenanthridinyl, and xanthenyl. Unless otherwise specified, a heteroaryl group is optionally substituted.

As used herein, and unless otherwise specified, the term "heteroarylene" is a divalent heteroaryl group. Unless otherwise specified, a heteroarylene group is optionally substituted.

When the groups described herein are said to be "substituted," they may be substituted with any appropriate substituent or substituents. Illustrative examples of substituents include, but are not limited to, those found in the exemplary compounds and embodiments provided herein, as well as: a halogen atom such as F, CI, Br, or I; cyano; oxo (═O); hydroxyl (—OH); alkyl; alkenyl; alkynyl; cycloalkyl; aryl; —(C═O)OR'; —O(C═O)R'; —C(═O)R'; —OR'; —S(O)$_x$R'; —S—SR'; —C(═O)SR'; —SC(═O)R'; —NR'R'; —NR'C(═O)R'; —C(═O)NR'R'; —NR'C(═O)NR'R'; —OC(═O)NR'; —NR'C(═O)OR'; —NR'S(O)$_x$NR'R'; —NR'S(O)$_x$R'; and —S(O)$_x$NR'R', wherein: R' is, at each occurrence, independently H, $C_1$-$C_{15}$ alkyl or cycloalkyl, and x is 0, 1 or 2. In some embodiments the substituent is a $C_1$-$C_{12}$ alkyl group. In other embodiments, the substituent is a cycloalkyl group. In other embodiments, the substituent is a halo group, such as fluoro. In other embodiments, the substituent is an oxo group. In other embodiments, the substituent is a hydroxyl group. In other embodiments, the substituent is an alkoxy group (—OR'). In other embodiments, the substituent is a carboxyl group. In other embodiments, the substituent is an amino group (—NR'R').

As used herein, and unless otherwise specified, the term "optional" or "optionally" (e.g., optionally substituted) means that the subsequently described event of circumstances may or may not occur, and that the description includes instances where said event or circumstance occurs and instances in which it does not. For example, "optionally substituted alkyl" means that the alkyl radical may or may not be substituted and that the description includes both substituted alkyl radicals and alkyl radicals having no substitution.

As used herein, and unless otherwise specified, the term "prodrug" of a biologically active compound refers to a compound that may be converted under physiological conditions or by solvolysis to the biologically active compound. In one embodiment, the term "prodrug" refers to a metabolic precursor of the biologically active compound that is pharmaceutically acceptable. A prodrug may be inactive when administered to a subject in need thereof, but is converted in vivo to the biologically active compound. Prodrugs are typically rapidly transformed in vivo to yield the parent biologically active compound, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

In one embodiment, the term "prodrug" is also meant to include any covalently bonded carriers, which release the active compound in vivo when such prodrug is administered to a mammalian subject. Prodrugs of a compound may be prepared by modifying functional groups present in the compound in such a way that the modifications are cleaved, either in routine manipulation or in vivo, to the parent compound. Prodrugs include compounds wherein a hydroxyl, amino or mercapto group is bonded to any group that, when the prodrug of the compound is administered to a mammalian subject, cleaves to form a free hydroxyl, free amino or free mercapto group, respectively.

Examples of prodrugs include, but are not limited to, acetate, formate and benzoate derivatives of alcohol or amide derivatives of amine functional groups in the compounds provided herein.

As used herein, and unless otherwise specified, the term "pharmaceutically acceptable salt" includes both acid and base addition salts.

Examples of pharmaceutically acceptable acid addition salts include, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

Examples of pharmaceutically acceptable base addition salt include, but are not limited to, salts prepared from addition of an inorganic base or an organic base to a free acid compound. Salts derived from inorganic bases include, but are not limited to, the sodium, potassium, lithium, ammonium, calcium, magnesium, iron, zinc, copper, manganese, aluminum salts and the like. In one embodiment, the inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. In one embodiment, the organic bases are isopropylamine, diethylamine, ethanolamine, trimethylamine, dicyclohexylamine, choline and caffeine.

A compound provided herein may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. Unless otherwise specified, a compound provided herein is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, and unless otherwise specified, the term "isomer" refers to different compounds that have the same molecular formula. "Stereoisomers" are isomers that differ only in the way the atoms are arranged in space. "Atropisomers" are stereoisomers from hindered rotation about single bonds. "Enantiomers" are a pair of stereoisomers that are non-superimposable mirror images of each other. A mixture of a pair of enantiomers in any proportion can be known as a "racemic" mixture. "Diastereoisomers" are stereoisomers that have at least two asymmetric atoms, but which are not mirror-images of each other.

"Stereoisomers" can also include E and Z isomers, or a mixture thereof, and cis and trans isomers or a mixture thereof. In certain embodiments, a compound described herein is isolated as either the E or Z isomer. In other embodiments, a compound described herein is a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

It should also be noted a compound described herein can contain unnatural proportions of atomic isotopes at one or more of the atoms. For example, the compounds may be radiolabeled with radioactive isotopes, such as for example tritium ($^{3}H$), iodine-125 ($^{125}I$) sulfur-35 ($^{35}S$), or carbon-14 ($^{14}C$), or may be isotopically enriched, such as with deuterium ($^{2}H$), carbon-13 ($^{13}C$), or nitrogen-15 ($^{15}N$). As used herein, an "isotopolog" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of a compound described herein, whether radioactive or not, are intended to be encompassed within the scope of the embodiments provided herein. In some embodiments, there are provided isotopologs of a compound described herein, for example, the isotopologs are deuterium, carbon-13, and/or nitrogen-15 enriched. As used herein, "deuterated", means a compound wherein at least one hydrogen (H) has been replaced by deuterium (indicated by D or $^{2}H$), that is, the compound is enriched in deuterium in at least one position.

It should be noted that if there is a discrepancy between a depicted structure and a name for that structure, the depicted structure is to be accorded more weight.

As used herein, and unless otherwise specified, the term "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The term "composition" is intended to encompass a product containing the specified ingredients (e.g., a mRNA molecule provided herein) in, optionally, the specified amounts.

The term "polynucleotide" or "nucleic acid," as used interchangeably herein, refers to polymers of nucleotides of any length and includes, e.g., DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. Nucleic acid can be in either single- or double-stranded forms. As used herein and unless otherwise specified, "nucleic acid" also includes nucleic acid mimics such as locked nucleic acids (LNAs), peptide nucleic acids (PNAs), and morpholinos. "Oligonucleotide," as used herein, refers to short synthetic polynucleotides that are generally, but not necessarily, fewer than about 200 nucleotides in length. The terms "oligonucleotide" and "polynucleotide" are not mutually exclusive. The description above for polynucleotides is equally and fully applicable to oligonucleotides. Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences."

As used herein, the term "non-naturally occurring" when used in reference to a nucleic acid molecule as described herein is intended to mean that the nucleic acid molecule is not found in nature. A non-naturally occurring nucleic acid encoding a viral peptide or protein contains at least one genetic alternation or chemical modification not normally found in a naturally occurring strain of the virus, including wild-type strains of the virus. Genetic alterations include, for example, modifications introducing expressible nucleic acid sequences encoding peptides or polypeptides heterologous to the virus, other nucleic acid additions, nucleic acid deletions, nucleic acid substitution, and/or other functional disruption of the virus' genetic material. Such modifications include, for example, modifications in the coding regions and functional fragments thereof, for heterologous, homologous or both heterologous and homologous polypeptides for the viral species. Additional modifications include, for example, modifications in non-coding regulatory regions in which the modifications alter expression of a gene or operon. Additional modifications also include, for example, incorporation of a nucleic acid sequence into a vector, such as a plasmid or an artificial chromosome. Chemical modifications include, for example, one or more functional nucleotide analog as described herein.

An "isolated nucleic acid" is a nucleic acid, for example, an RNA, DNA, or a mixed nucleic acids, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as an mRNA molecule, can be substantially free of other cellular material, or culture medium when produced by recombinant techniques, or substantially free of chemical precursors or other chemicals when chemically synthesized. In a specific embodiment, one or more nucleic acid molecules encoding an antigen as described herein are isolated or purified. The term embraces nucleic acid sequences that have been removed from their naturally occurring environment, and includes recombinant or cloned DNA or RNA isolates and chemically synthesized analogues or analogues biologically synthesized by heterologous systems. A substantially pure molecule may include isolated forms of the molecule.

The term "encoding nucleic acid" or grammatical equivalents thereof as it is used in reference to nucleic acid molecule encompasses (a) a nucleic acid molecule in its native state or when manipulated by methods well known to those skilled in the art that can be transcribed to produce mRNA which is then translated into a peptide and/or polypeptide, and (b) the mRNA molecule itself. The antisense strand is the complement of such a nucleic acid molecule, and the encoding sequence can be deduced therefrom. The term "coding region" refers to a portion in an encoding nucleic acid sequence that is translated into a peptide or polypeptide. The term "untranslated region" or "UTR" refers to the portion of an encoding nucleic acid that is not translated into a peptide or polypeptide. Depending on the orientation of a UTR with respect to the coding region of a nucleic acid molecule, a UTR is referred to as the 5'-UTR if located to the 5'-end of a coding region, and a UTR is referred to as the 3'-UTR if located to the 3'-end of a coding region.

The term "mRNA" as used herein refers to a message RNA molecule comprising one or more open reading frame (ORF) that can be translated by a cell or an organism provided with the mRNA to produce one or more peptide or protein product. The region containing the one or more ORFs is referred to as the coding region of the mRNA molecule. In certain embodiments, the mRNA molecule further comprises one or more untranslated regions (UTRs).

In certain embodiments, the mRNA is a monocistronic mRNA that comprises only one ORF. In certain embodiments, the monocistronic mRNA encodes a peptide or protein comprising at least one epitope of a selected antigen (e.g., a pathogenic antigen or a tumor associated antigen). In other embodiments, the mRNA is a multicistronic mRNA that comprises two or more ORFs. In certain embodiments, the multiecistronic mRNA encodes two or more peptides or proteins that can be the same or different from each other. In certain embodiments, each peptide or protein encoded by a multicistronic mRNA comprises at least one epitope of a selected antigen. In certain embodiments, different peptide or protein encoded by a multicistronic mRNA each comprises at least one epitope of different antigens. In any of the embodiments described herein, the at least one epitope can be at least 2, at least 3, at least 4, at least 5, at least 6, at least 7, at least 8, at least 9, or at least 10 epitopes of an antigen.

The term "nucleobases" encompasses purines and pyrimidines, including natural compounds adenine, thymine, guanine, cytosine, uracil, inosine, and natural or synthetic analogs or derivatives thereof.

The term "functional nucleotide analog" as used herein refers to a modified version of a canonical nucleotide A, G, C, U or T that (a) retains the base-pairing properties of the corresponding canonical nucleotide, and (b) contains at least one chemical modification to (i) the nucleobase, (ii) the sugar group, (iii) the phosphate group, or (iv) any combinations of (i) to (iii), of the corresponding natural nucleotide. As used herein, base pairing encompasses not only the canonical Watson-Crick adenine-thymine, adenine-uracil, or guanine-cytosine base pairs, but also base pairs formed between canonical nucleotides and functional nucleotide analogs or between a pair of functional nucleotide analogs, wherein the arrangement of hydrogen bond donors and hydrogen bond acceptors permits hydrogen bonding between a modified nucleobase and a canonical nucleobase or between two complementary modified nucleobase structures. For example, a functional analog of guanosine (G) retains the ability to base-pair with cytosine (C) or a functional analog of cytosine. One example of such non-canonical base pairing is the base pairing between the modified nucleotide inosine and adenine, cytosine, or uracil. As described herein, a functional nucleotide analog can be either naturally occurring or non-naturally occurring. Accordingly, a nucleic acid molecule containing a functional nucleotide analog can have at least one modified nucleobase, sugar group and/or internucleoside linkage. Exemplary chemical modifications to the nucleobases, sugar groups, or internucleoside linkages of a nucleic acid molecule are provided herein.

The terms "translational enhancer element," "TEE" and "translational enhancers" as used herein refers to an region in a nucleic acid molecule that functions to promotes translation of a coding sequence of the nucleic acid into a protein or peptide product, such as via cap-dependent or cap-independent translation. A TEE typically locates in the UTR region of a nucleic acid molecule (e.g., mRNA) and enhance the translational level of a coding sequence located either upstream or downstream. For example, a TEE in a 5'-UTR of a nucleic acid molecule can locate between the promoter and the starting codon of the nucleic acid molecule. Various TEE sequences are known in the art (Wellensiek et al. Genome-wide profiling of human cap-independent translation-enhancing elements, *Nature Methods,* 2013 August;

10(8): 747-750; Chappell et al. PNAS Jun. 29, 2004 101 (26) 9590-9594). Some TEEs are known to be conserved across multiple species (Pánek et al. *Nucleic Acids Research*, Volume 41, Issue 16, 1 Sep. 2013, Pages 7625-7634).

As used herein, the term "stem-loop sequence" refers to a single-stranded polynucleotide sequence having at least two regions that are complementary or substantially complementary to each other when read in opposite directions, and thus capable of base-pairing with each other to form at least one double helix and an unpaired loop. The resulting structure is known as a stem-loop structure, a hairpin, or a hairpin loop, which is a secondary structure found in many RNA molecules.

The term "peptide" as used herein refers to a polymer containing between two and fifty (2-50) amino acid residues linked by one or more covalent peptide bond(s). The terms apply to naturally occurring amino acid polymers as well as amino acid polymers in which one or more amino acid residues is a non-naturally occurring amino acid (e.g., an amino acid analog or non-natural amino acid).

The terms "polypeptide" and "protein" are used interchangeably herein to refer to a polymer of greater than fifty (50) amino acid residues linked by covalent peptide bonds. That is, a description directed to a polypeptide applies equally to a description of a protein, and vice versa. The terms apply to naturally occurring amino acid polymers as well as amino acid polymers in which one or more amino acid residues is a non-naturally occurring amino acid (e.g., an amino acid analog). As used herein, the terms encompass amino acid chains of any length, including full length proteins (e.g., antigens).

In the context of a peptide or polypeptide, the term "derivative" as used herein refers to a peptide or polypeptide that comprises an amino acid sequence of the viral peptide or protein, or a fragment of a viral peptide or protein, which has been altered by the introduction of amino acid residue substitutions, deletions, or additions. The term "derivative" as used herein also refers to a viral peptide or protein, or a fragment of a viral peptide or protein, which has been chemically modified, e.g., by the covalent attachment of any type of molecule to the polypeptide. For example, but not by way of limitation, a viral peptide or protein or a fragment of the viral peptide or protein may be chemically modified, e.g., by glycosylation, acetylation, pegylation, phosphorylation, amidation, derivatization by known protecting/blocking groups, proteolytic cleavage, chemical cleavage, formulation, metabolic synthesis of tunicamycin, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the viral peptide or protein. Further, a derivative of a viral peptide or protein or a fragment of a viral peptide or protein may contain one or more non-classical amino acids. In specific embodiments, a derivative is a functional derivative of the native or unmodified peptide or polypeptide from which it was derived.

The term "functional derivative" refers to a derivative that retains one or more functions or activities of the naturally occurring or starting peptide or polypeptide from which it was derived. For example, a functional derivative of a coronavirus S protein may retain the ability to bind one or more of its receptors on a host cell. For example, a functional derivative of a coronavirus N protein may retain the ability to bind RNA or the package viral genome.

The term "identity" refers to a relationship between the sequences of two or more polypeptide molecules or two or more nucleic acid molecules, as determined by aligning and comparing the sequences. "Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or MEGALIGN (DNAStar, Inc.) software. Those skilled in the art can determine appropriate parameters for aligning sequences, including any algorithms needed to achieve maximal alignment over the full length of the sequences being compared.

A "modification" of an amino acid residue/position refers to a change of a primary amino acid sequence as compared to a starting amino acid sequence, wherein the change results from a sequence alteration involving said amino acid residue/position. For example, typical modifications include substitution of the residue with another amino acid (e.g., a conservative or non-conservative substitution), insertion of one or more (e.g., generally fewer than 5, 4, or 3) amino acids adjacent to said residue/position, and/or deletion of said residue/position.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, fragments refers to polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, at least 250, at least 300, at least 350, at least 400, at least 450, at least 500, at least 550, at least 600, at least 650, at least 700, at least 750, at least 800, at least 850, at least 900, or at least 950 contiguous amino acid residues of the amino acid sequence of a polypeptide. In a specific embodiment, a fragment of a polypeptide retains at least 1, at least 2, at least 3, or more functions of the polypeptide.

The term "immunogenic fragment" as used herein in the context of a peptide or polypeptide (e.g., a protein), refers to a fragment of a peptide or polypeptide that retains the ability of the peptide or polypeptide in eliciting an immune response upon contacting the immune system of a mammal, including innate immune responses and/or adaptive immune responses. In some embodiments, an immunogenic fragment of a peptide or polypeptide can be an epitope.

The term “antigen” refers to a substance that can be recognized by the immune system of a subject (including by the adaptive immune system), and is capable of triggering an immune response after the subject is contacted with the antigen (including an antigen-specific immune response). In certain embodiments, the antigen is a protein associated with a diseased cell, such as a cell infected by a pathogen or a neoplastic cell (e.g., tumor associated antigen (TAA)).

An “epitope” is the site on the surface of an antigen molecule to which a single antibody molecule binds, such as a localized region on the surface of an antigen that is capable of being bound to one or more antigen binding regions of an antibody, and that has antigenic or immunogenic activity in an animal, such as a mammal (e.g., a human), that is capable of eliciting an immune response. An epitope having immunogenic activity is a portion of a polypeptide that elicits an antibody response in an animal. An epitope having antigenic activity is a portion of a polypeptide to which an antibody binds as determined by any method well known in the art, including, for example, by an immunoassay. Antigenic epitopes need not necessarily be immunogenic. Epitopes often consist of chemically active surface groupings of molecules such as amino acids or sugar side chains and have specific three dimensional structural characteristics as well as specific charge characteristics. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure. Induced epitopes are formed when the three dimensional structure of the protein is in an altered conformation, such as following activation or binding of another protein or ligand. In certain embodiments, an epitope is a three-dimensional surface feature of a polypeptide. In other embodiments, an epitope is linear feature of a polypeptide. Generally an antigen has several or many different epitopes and may react with many different antibodies.

The terms “severe acute respiratory syndrome coronavirus 2” or “SARS-CoV-2” or “2019-nCoV” are used interchangeably herein to refer to the coronavirus that caused the pandemic of infectious diseases in 2019. GenBank™ accession number MN908947 provides exemplary genome sequence of SARS-CoV-2 (SEQ ID NO:1).

The term “heterologous” refers an entity not found in nature to be associated with (e.g., encoded by and/or expressed by the genome of) a naturally occurring coronavirus. The term “homologous” refers an entity found in nature to be associated with (e.g., encoded by and/or expressed by the genome of) a naturally occurring coronavirus.

The term “genetic vaccine” as used herein refers to a therapeutic or prophylactic composition comprising at least one nucleic acid molecule encoding an antigen associated with a target disease (e.g., an infectious disease or a neoplastic disease). Administration of the vaccine to a subject (“vaccination”) allows for the production of the encoded peptide or protein, thereby eliciting an immune response against the target disease in the subject. In certain embodiments, the immune response comprises adaptive immune response, such as the production of antibodies against the encoded antigen, and/or activation and proliferations of immune cells capable of specifically eliminating diseased cells expressing the antigen. In certain embodiments, the immune response further comprises innate immune response. According to the present disclosure, a vaccine can be administered to a subject either before or after the onset of clinical symptoms of the target disease. In some embodiments, vaccination of a healthy or asymptomatic subject renders the vaccinated subject immune or less susceptible to the development of the target disease. In some embodiments, vaccination of a subject showing symptoms of the disease improves the condition of, or treats, the disease in the vaccinated subject.

The term “vector” refers to a substance that is used to carry or include a nucleic acid sequence, including for example, a nucleic acid sequence encoding a viral peptide or protein as described herein, in order to introduce a nucleic acid sequence into a host cell, or serve as a transcription template to carry out in vitro transcription reaction in a cell-free system to produce mRNA. Vectors applicable for use include, for example, expression vectors, plasmids, phage vectors, viral vectors, episomes, and artificial chromosomes, which can include selection sequences or markers operable for stable integration into a host cell's chromosome. Additionally, the vectors can include one or more selectable marker genes and appropriate transcription or translation control sequences. Selectable marker genes that can be included, for example, provide resistance to antibiotics or toxins, complement auxotrophic deficiencies, or supply critical nutrients not in the culture media. Transcription or translation control sequences can include constitutive and inducible promoters, transcription enhancers, transcription terminators, and the like, which are well known in the art. When two or more nucleic acid molecules are to be co-transcribed or co-translated (e.g., nucleic acid molecules encoding two or more different viral peptides or proteins), both nucleic acid molecules can be inserted, for example, into a single expression vector or in separate expression vectors. For single vector transcription and/or translation, the encoding nucleic acids can be operationally linked to one common transcription or translation control sequence or linked to different transcription or translation control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product (e.g., a mRNA transcript of the nucleic acid as described herein), and it is further understood that expression levels can be optimized to obtain sufficient expression using methods well known in the art.

The terms “innate immune response” and “innate immunity” are recognized in the art, and refer to non-specific defense mechanism a body's immune system initiates upon recognition of pathogen-associated molecular patterns, which involves different forms of cellular activities, including cytokine production and cell death through various pathways. As used herein, innate immune responses include, without limitation, increased production of inflammation cytokines (e.g., type I interferon or IL-10 production), activation of the NFκB pathway, increased proliferation, maturation, differentiation and/or survival of immune cells, and in some cases, induction of cell apoptosis. Activation of the innate immunity can be detected using methods known in the art, such as measuring the (NF)-κB activation.

The terms "adaptive immune response" and "adaptive immunity" are recognized in the art, and refer to antigen-specific defense mechanism a body's immune system initiates upon recognition of a specific antigen, which include both humoral response and cell-mediated responses. As used herein, adaptive immune responses include cellular responses that is triggered and/or augmented by a vaccine composition, such as a genetic composition described herein. In some embodiments, the vaccine composition comprises an antigen that is the target of the antigen-specific adaptive immune response. In other embodiments, the vaccine composition, upon administration, allows the production in an immunized subject of an antigen that is the target of the antigen-specific adaptive immune response. Activation of an adaptive immune response can be detected using methods known in the art, such as measuring the antigen-specific antibody production, or the level of antigen-specific cell-mediated cytotoxicity.

"Antibody-dependent cell-mediated cytotoxicity" or "ADCC" refers to a form of cytotoxicity in which secreted immunoglobulin bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. NK cells, the primary cells for mediating ADCC, express FcγRIII only, whereas monocytes express FcγRI, FcγRII, and FcγRIII. FcR expression on hematopoietic cells is known (see, e.g., Ravetch and Kinet, 1991, Annu. Rev. Immunol. 9:457-92). To assess ADCC activity of a molecule of interest, an in vitro ADCC assay (see, e.g., U.S. Pat. Nos. 5,500,362 and 5,821,337) can be performed. Useful effector cells for such assays include peripheral blood mononuclear cells (PBMC) and Natural Killer (NK) cells. Alternatively or additionally, ADCC activity of the molecule of interest may be assessed in vivo, for example, in an animal model (see, e.g., Clynes et al., 1998, Proc. Natl. Acad. Sci. USA 95:652-56). Antibodies with little or no ADCC activity may be selected for use.

"Antibody-dependent cellular phagocytosis" or "ADCP" refers to the destruction of target cells via monocyte or macrophage-mediated phagocytosis when immunoglobulin bound onto Fc receptors (FcRs) present on certain phagocytotic cells (e.g., neutrophils, monocytes, and macrophages) enable these phagocytotic cells to bind specifically to an antigen-bearing target cell and subsequently kill the target cell. To assess ADCP activity of a molecule of interest, an in vitro ADCP assay (see, e.g., Bracher et al., 2007, J. Immunol. Methods 323:160-71) can be performed. Useful phagocytotic cells for such assays include peripheral blood mononuclear cells (PBMC), purified monocytes from PBMC, or U937 cells differentiated to the mononuclear type. Alternatively or additionally, ADCP activity of the molecule of interest may be assessed in vivo, for example, in an animal model (see, e.g., Wallace et al., 2001, J. Immunol. Methods 248:167-82). Antibodies with little or no ADCP activity may be selected for use.

"Fc receptor" or "FcR" describes a receptor that binds to the Fc region of an antibody. An exemplary FcR is a native sequence human FcR. Moreover, an exemplary FcR is one that binds an IgG antibody (e.g., a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof (see, e.g., Daëron, 1997, Annu. Rev. Immunol. 15:203-34). Various FcRs are known (see, e.g., Ravetch and Kinet, 1991, Annu. Rev. Immunol. 9:457-92; Capel et al., 1994, Immunomethods 4:25-34; and de Haas et al., 1995, J. Lab. Clin. Med. 126:330-41). Other FcRs, including those to be identified in the future, are encompassed by the term "FcR" herein. The term also includes the neonatal receptor, FcRn, which is responsible for the transfer of maternal IgGs to the fetus (see, e.g., Guyer et al., 1976, J. Immunol. 117:587-93; and Kim et al., 1994, Eu. J. Immunol. 24:2429-34). Antibody variants with improved or diminished binding to FcRs have been described (see, e.g., WO 2000/42072; U.S. Pat. Nos. 7,183,387; 7,332,581; and 7,335,742; Shields et al. 2001, J. Biol. Chem. 9(2):6591-604).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay (see, e.g., Gazzano-Santoro et al., 1996, J. Immunol. Methods 202:163) may be performed. Polypeptide variants with altered Fc region amino acid sequences (polypeptides with a variant Fc region) and increased or decreased C1q binding capability have been described (see, e.g., U.S. Pat. No. 6,194,551; WO 1999/51642; Idusogie et al., 2000, J. Immunol. 164: 4178-84). Antibodies with little or no CDC activity may be selected for use.

The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa), each amino-terminal portion of each chain includes a variable region of about 100 to about 130 or more amino acids, and each carboxy-terminal portion of each chain includes a constant region. See, e.g., *Antibody Engineering* (Borrebaeck ed., 2d ed. 1995); and Kuby, *Immunology* (3d ed. 1997). In specific embodiments, the specific molecular antigen can be bound by an antibody provided herein, including a polypeptide, a fragment or an epitope thereof. Antibodies also include, but are not limited to, synthetic antibodies, recombinantly produced antibodies, camelized antibodies, intrabodies, anti-idiotypic (anti-Id) antibodies, and functional fragments of any of the above, which refers to a portion of an antibody heavy or light chain polypeptide that retains some or all of the binding activity of the antibody from which the fragment was derived. Non-limiting examples of functional fragments include single-chain Fvs (scFv) (e.g., including monospecific, bispecific, etc.), Fab fragments, F(ab') fragments, F(ab)$_2$ fragments, F(ab')$_2$ fragments, disulfide-linked Fvs (dsFv), Fd fragments, Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site (e.g., one or more CDRs of an antibody). Such antibody fragments can be found in, for example, Harlow and Lane, *Antibodies: A Laboratory Manual* (1989); *Mol. Biology and Biotechnology: A Comprehensive Desk Reference* (Myers ed., 1995); Huston et al., 1993, Cell Biophysics 22:189-224;

Plückthun and Skerra, 1989, Meth. Enzymol. 178:497-515; and Day, Advanced Immunochemistry (2d ed. 1990). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule.

The term "administer" or "administration" refers to the act of injecting or otherwise physically delivering a substance as it exists outside the body (e.g., a lipid nanoparticle composition as described herein) into a patient, such as by mucosal, intradermal, intravenous, intramuscular delivery, and/or any other method of physical delivery described herein or known in the art. When a disease, disorder, condition, or a symptom thereof, is being treated, administration of the substance typically occurs after the onset of the disease, disorder, condition, or symptoms thereof. When a disease, disorder, condition, or symptoms thereof, are being prevented, administration of the substance typically occurs before the onset of the disease, disorder, condition, or symptoms thereof.

"Chronic" administration refers to administration of the agent(s) in a continuous mode (e.g., for a period of time such as days, weeks, months, or years) as opposed to an acute mode, so as to maintain the initial therapeutic effect (activity) for an extended period of time. "Intermittent" administration is treatment that is not consecutively done without interruption, but rather is cyclic in nature.

The term "targeted delivery" or the verb form "target" as used herein refers to the process that promotes the arrival of a delivered agent (such as a therapeutic payload molecule in a lipid nanoparticle composition as described herein) at a specific organ, tissue, cell and/or intracellular compartment (referred to as the targeted location) more than any other organ, tissue, cell or intracellular compartment (referred to as the non-target location). Targeted delivery can be detected using methods known in the art, for example, by comparing the concentration of the delivered agent in a targeted cell population with the concentration of the delivered agent at a non-target cell population after systemic administration. In certain embodiments, targeted delivery results in at least 2 fold higher concentration at a targeted location as compared to a non-target location.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with a disease, disorder, or condition, including, for example, infection and neoplasia. In some embodiments, the effective amount is a therapeutically effective amount or a prophylactically effective amount.

The term "therapeutically effective amount" as used herein refers to the amount of an agent (e.g., a vaccine composition) that is sufficient to reduce and/or ameliorate the severity and/or duration of a given disease, disorder, or condition, and/or a symptom related thereto (e.g., an infectious disease such as caused by viral infection, or a neoplastic disease such as cancer). A "therapeutically effective amount" of a substance/molecule/agent of the present disclosure (e.g., the lipid nanoparticle composition as described herein) may vary according to factors such as the disease state, age, sex, and weight of the individual, and the ability of the substance/molecule/agent to elicit a desired response in the individual. A therapeutically effective amount encompasses an amount in which any toxic or detrimental effects of the substance/molecule/agent are outweighed by the therapeutically beneficial effects. In certain embodiments, the term "therapeutically effective amount" refers to an amount of a lipid nanoparticle composition as described herein or a therapeutic or prophylactic agent contained therein (e.g., a therapeutic mRNA) effective to "treat" a disease, disorder, or condition, in a subject or mammal.

A "prophylactically effective amount" is an amount of a pharmaceutical composition that, when administered to a subject, will have the intended prophylactic effect, e.g., preventing, delaying, or reducing the likelihood of the onset (or reoccurrence) of a disease, disorder, condition, or associated symptom(s) (e.g., an infectious disease such as caused by viral infection, or a neoplastic disease such as cancer). Typically, but not necessarily, since a prophylactic dose is used in subjects prior to or at an earlier stage of a disease, disorder, or condition, a prophylactically effective amount may be less than a therapeutically effective amount. The full therapeutic or prophylactic effect does not necessarily occur by administration of one dose, and may occur only after administration of a series of doses. Thus, a therapeutically or prophylactically effective amount may be administered in one or more administrations.

The terms "prevent," "preventing," and "prevention" refer to reducing the likelihood of the onset (or recurrence) of a disease, disorder, condition, or associated symptom(s) (e.g., an infectious disease such as caused by viral infection, or a neoplastic disease such as cancer).

The terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., prophylactic or therapeutic agents, such as a lipid nanoparticle composition as described herein) to "manage" an infectious or neoplastic disease, one or more symptoms thereof, so as to prevent the progression or worsening of the disease.

The term "prophylactic agent" refers to any agent that can totally or partially inhibit the development, recurrence, onset, or spread of disease and/or symptom related thereto in a subject.

The term "therapeutic agent" refers to any agent that can be used in treating, preventing, or alleviating a disease, disorder, or condition, including in the treatment, prevention, or alleviation of one or more symptoms of a disease, disorder, or condition and/or a symptom related thereto.

The term "therapy" refers to any protocol, method, and/or agent that can be used in the prevention, management, treatment, and/or amelioration of a disease, disorder, or condition. In certain embodiments, the terms "therapies" and "therapy" refer to a biological therapy, supportive therapy, and/or other therapies useful in the prevention, management, treatment, and/or amelioration of a disease, disorder, or condition, known to one of skill in the art such as medical personnel.

As used herein, a "prophylactically effective serum titer" is the serum titer of an antibody in a subject (e.g., a human), that totally or partially inhibits the development, recurrence, onset, or spread of a disease, disorder, or condition, and/or symptom related thereto in the subject.

In certain embodiments, a "therapeutically effective serum titer" is the serum titer of an antibody in a subject (e.g., a human), that reduces the severity, the duration, and/or the symptoms associated with a disease, disorder, or condition, in the subject.

The term "serum titer" refers to an average serum titer in a subject from multiple samples (e.g., at multiple time points) or in a population of at least 10, at least 20, at least 40 subjects, up to about 100, 1000, or more.

The term "side effects" encompasses unwanted and/or adverse effects of a therapy (e.g., a prophylactic or therapeutic agent). Unwanted effects are not necessarily adverse. An adverse effect from a therapy (e.g., a prophylactic or therapeutic agent) might be harmful, uncomfortable, or risky. Examples of side effects include, diarrhea, cough, gastroenteritis, wheezing, nausea, vomiting, anorexia, abdominal cramping, fever, pain, loss of body weight, dehydration, alopecia, dyspenea, insomnia, dizziness, mucositis, nerve and muscle effects, fatigue, dry mouth, loss of appetite, rashes or swellings at the site of administration, flu-like symptoms such as fever, chills, and fatigue, digestive tract problems, and allergic reactions. Additional undesired effects experienced by patients are numerous and known in the art. Many are described in *Physician's Desk Reference* (68th ed. 2014).

The terms "subject" and "patient" may be used interchangeably. As used herein, in certain embodiments, a subject is a mammal, such as a non-primate (e.g., cow, pig, horse, cat, dog, rat, etc.) or a primate (e.g., monkey and human). In specific embodiments, the subject is a human. In one embodiment, the subject is a mammal (e.g., a human) having an infectious disease or neoplastic disease. In another embodiment, the subject is a mammal (e.g., a human) at risk of developing an infectious disease or neoplastic disease.

The term "elderly human" refers to a human 65 years or older. The term "human adult" refers to a human that is 18 years or older. The term "human child" refers to a human that is 1 year to 18 years old. The term "human toddler" refers to a human that is 1 year to 3 years old. The term "human infant" refers to a newborn to 1 year old year human.

The term "detectable probe" refers to a composition that provides a detectable signal. The term includes, without limitation, any fluorophore, chromophore, radiolabel, enzyme, antibody or antibody fragment, and the like, that provide a detectable signal via its activity.

The term "detectable agent" refers to a substance that can be used to ascertain the existence or presence of a desired molecule, such as an antigen encoded by an mRNA molecule as described herein, in a sample or subject. A detectable agent can be a substance that is capable of being visualized or a substance that is otherwise able to be determined and/or measured (e.g., by quantitation).

"Substantially all" refers to at least about 60%, at least about 65%, at least about 70%, at least about 75%, at least about 80%, at least about 85%, at least about 90%, at least about 95%, at least about 98%, at least about 99%, or about 100%.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 20%, 15%, 10%, 9%, 8%, 7%, 6%, 5%, 4%, 3%, 2%, 1%, 0.5%, 0.05%, or less of a given value or range.

The singular terms "a," "an," and "the" as used herein include the plural reference unless the context clearly indicates otherwise.

All publications, patent applications, accession numbers, and other references cited in this specification are herein incorporated by reference in their entirety as if each individual publication or patent application were specifically and individually indicated to be incorporated by reference. The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates which can need to be independently confirmed.

A number of embodiments of the invention have been described. Nevertheless, it will be understood that various modifications may be made without departing from the spirit and scope of the invention. Accordingly, the descriptions in the Experimental section and examples are intended to illustrate but not limit the scope of invention described in the claims.

6.3 Therapeutic Nucleic Acids

In one aspect, provided herein are therapeutic nucleic acid molecules for the management, prevention and treatment of coronavirus infection. In some embodiments, the therapeutic nucleic acid encodes a peptide or polypeptide, which upon administration into a subject in need thereof, is expressed by the cells in the subject to produce the encoded peptide or polypeptide. In some embodiments, the therapeutic nucleic acid molecules are DNA molecules. In other embodiments, the therapeutic nucleic acid molecules are RNA molecules. In particular embodiments, the therapeutic nucleic acid molecules are mRNA molecules.

In some embodiments, the therapeutic nucleic acid molecule is formulated in a vaccine composition. In some embodiments, the vaccine composition is a genetic vaccine as described herein. In some embodiments, the vaccine composition comprises an mRNA molecule as described herein.

In some embodiments, the mRNA molecule of the present disclosure encodes a peptide or polypeptide of interest, including any naturally or non-naturally occurring or otherwise modified polypeptide. A peptide or polypeptide encoded by an mRNA may be of any size and may have any secondary structure or activity. In some embodiments, the polypeptide encoded by an mRNA payload can have a therapeutic effect when expressed in a cell.

In some embodiment, the mRNA molecule of the present disclosure comprises at least one coding region encoding a peptide or polypeptide of interest (e.g., an open reading frame (ORF)). In some embodiments, the nucleic acid molecule further comprises at least one untranslated region (UTR). In particular embodiments, the untranslated region (UTR) is located upstream (to the 5'-end) of the coding region, and is referred to herein as the 5'-UTR. In particular embodiments, the untranslated region (UTR) is located downstream (to the 3'-end) of the coding region, and is referred to herein as the 3'-UTR. In particular embodiments, the nucleic acid molecule comprises both a 5'-UTR and a 3'-UTR. In some embodiments, the 5'-UTR comprises a 5'-Cap structure. In some embodiments, the nucleic acid molecule comprises a Kozak sequence (e.g., in the 5'-UTR). In some embodiments, the nucleic acid molecule comprises a poly-A region (e.g., in the 3'-UTR). In some embodiments, the nucleic acid molecule comprises a polyadenylation signal (e.g., in the 3'-UTR). In some embodiments, the nucleic acid molecule comprises stabilizing region (e.g., in the 3'-UTR). In some embodiments, the nucleic acid molecule comprises a secondary structure. In some embodiments, the secondary structure is a stem-loop. In some embodiments, the nucleic acid molecule comprises a stem-loop sequence (e.g., in the 5'-UTR and/or the 3'-UTR). In some embodiments, the nucleic acid molecule comprises one or more intronic regions capable of being excised during splicing. In a specific embodiment, the nucleic acid molecule comprises one or more region selected from a 5'-UTR, and a coding region. In a specific embodiment, the nucleic acid molecule comprises one or more region selected from a coding region and a 3'-UTR. In a specific embodiment, the nucleic acid molecule comprises one or more region selected from a 5'-UTR, a coding region, and a 3'-UTR.

6.3.1 Coding Region

In some embodiments, the nucleic acid molecule of the present disclosure comprises at least one coding region. In some embodiments, the coding region is an open reading frame (ORF) that encodes for a single peptide or protein. In some embodiments, the coding region comprises at least two ORFs, each encoding a peptide or protein. In those embodiments where the coding region comprises more than one ORFs, the encoded peptides and/or proteins can be the same as or different from each other. In some embodiments, the multiple ORFs in a coding region are separated by non-coding sequences. In specific embodiments, a non-coding sequence separating two ORFs comprises an internal ribosome entry sites (IRES).

Without being bound by the theory, it is contemplated that an internal ribosome entry sites (IRES) can act as the sole ribosome binding site, or serve as one of multiple ribosome binding sites of an mRNA. An mRNA molecule containing more than one functional ribosome binding site can encode several peptides or proteins that are translated independently by the ribosomes (e.g., multicistronic mRNA). Accordingly, in some embodiments, the nucleic acid molecule of the present disclosure (e.g., mRNA) comprises one or more internal ribosome entry sites (IRES). Examples of IRES sequences that can be used in connection with the present disclosure include, without limitation, those from picomaviruses (e.g., FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

In various embodiments, the nucleic acid molecule of the present disclosure encodes for at least 1, 2, 3, 4, 5, 6, 7, 8, 9, 10 or more than 10 peptides or proteins. Peptides and proteins encoded by a nucleic acid molecule can be the same or different. In some embodiments, the nucleic acid molecule of the present disclosure encodes a dipeptide (e.g., camosine and anserine). In some embodiments, the nucleic acid molecule encodes a tripeptide. In some embodiments, the nucleic acid molecule encodes a tetrapeptide. In some embodiments, the nucleic acid molecule encodes a pentapeptide. In some embodiments, the nucleic acid molecule encodes a hexapeptide. In some embodiments, the nucleic acid molecule encodes a heptapeptide. In some embodiments, the nucleic acid molecule encodes an octapeptide. In some embodiments, the nucleic acid molecule encodes a nonapeptide. In some embodiments, the nucleic acid molecule encodes a decapeptide. In some embodiments, the nucleic acid molecule encodes a peptide or polypeptide that has at least about 15 amino acids. In some embodiments, the nucleic acid molecule encodes a peptide or polypeptide that has at least about 50 amino acids. In some embodiments, the nucleic acid molecule encodes a peptide or polypeptide that has at least about 100 amino acids. In some embodiments, the nucleic acid molecule encodes a peptide or polypeptide that has at least about 150 amino acids. In some embodiments, the nucleic acid molecule encodes a peptide or polypeptide that has at least about 300 amino acids. In some embodiments, the nucleic acid molecule encodes a peptide or polypeptide that has at least about 500 amino acids. In some embodiments, the nucleic acid molecule encodes a peptide or polypeptide that has at least about 1000 amino acids.

In some embodiments, the nucleic acid molecule of the present disclosure is at least about 30 nucleotides (nt) in length. In some embodiments, the nucleic acid molecule is at least about 35 nt in length. In some embodiments, the nucleic acid molecule is at least about 40 nt in length. In some embodiments, the nucleic acid molecule is at least about 45 nt in length. In some embodiments the nucleic acid molecule is at least about 50 nt in length. In some embodiments, the nucleic acid molecule is at least about 55 nt in length. In some embodiments, the nucleic acid molecule is at least about 60 nt in length. In some embodiments, the nucleic acid molecule is at least about 65 nt in length. In some embodiments, the nucleic acid molecule is at least about 70 nt in length. In some embodiments, the nucleic acid molecule is at least about 75 nt in length. In some embodiments, the nucleic acid molecule is at least about 80 nt in length. In some embodiments the nucleic acid molecule is at least about 85 nt in length. In some embodiments, the nucleic acid molecule is at least about 90 nt in length. In some embodiments, the nucleic acid molecule is at least about 95 nt in length. In some embodiments, the nucleic acid molecule is at least about 100 nt in length. In some embodiments, the nucleic acid molecule is at least about 120 nt in length. In some embodiments, the nucleic acid molecule is at least about 140 nt in length. In some embodiments, the nucleic acid molecule is at least about 160 nt in length. In some embodiments, the nucleic acid molecule is at least about 180 nt in length. In some embodiments, the nucleic acid molecule is at least about 200 nt in length. In some embodiments, the nucleic acid molecule is at least about 250 nt in length. In some embodiments, the nucleic acid molecule is at least about 300 nt in length. In some embodiments, the nucleic acid molecule is at least about 400 nt in length. In some embodiments, the nucleic acid molecule is at least about 500 nt in length. In some embodiments, the nucleic acid molecule is at least about 600 nt in length. In some embodiments, the nucleic acid molecule is at least about 700 nt in length. In some embodiments, the nucleic acid molecule is at least about 800 nt in length. In some embodiments, the nucleic acid molecule is at least about 900 nt in length. In some embodiments, the nucleic acid molecule is at least about 1000 nt in length. In some embodiments, the nucleic acid molecule is at least about 1100 nt in length. In some embodiments, the nucleic acid molecule is at least about 1200 nt in length. In some embodiments, the nucleic acid molecule is at least about 1300 nt in length. In some embodiments, the nucleic acid molecule is at least about 1400 nt in length. In some embodiments, the nucleic acid molecule is at least about 1500 nt in length. In some embodiments, the nucleic acid molecule is at least about 1600 nt in length. In some embodiments, the nucleic acid molecule is at least about 1700 nt in length. In some embodiments, the nucleic acid molecule is at least about 1800 nt in length. In some embodiments, the nucleic acid molecule is at least about 1900 nt in length. In some embodiments, the nucleic acid molecule is at least about 2000 nt in length. In some embodiments, the nucleic acid molecule is at least about 2500 nt in length. In some embodiments, the nucleic acid molecule is at least about 3000 nt in length. In some embodiments, the nucleic acid molecule is at least about 3500 nt in length. In some embodiments, the nucleic acid molecule is at least about 4000 nt in length. In some embodiments, the nucleic acid molecule is at least about 4500 nt in length. In some embodiments, the nucleic acid molecule is at least about 5000 nt in length.

In specific embodiments, the therapeutic nucleic acid of the present disclosure are formulated as a vaccine composition (e.g., a genetic vaccine) as described herein. In some embodiments, the therapeutic nucleic acid encodes a peptide or protein capable of eliciting immunity against one or more target conditions or disease. In some embodiments, the target condition is related to or caused by infection by a pathogen, such as a coronavirus (e.g. COVID-19), influenza, measles, human papillomavirus (HPV), rabies, meningitis, whooping cough, tetanus, plague, hepatitis, and tuberculosis. In some embodiments, the therapeutic nucleic acid sequence (e.g., mRNA) encoding a pathogenic protein characteristic for the pathogen, or an immunogenic fragment (e.g., epitope) or derivative thereof. The vaccine, upon administration to a vaccinated subject, allows for expression of the encoded pathogenic protein (or the immunogenic fragment or derivative thereof), thereby eliciting immunity in the subject against the pathogen.

In specific embodiments, provided herein are therapeutic compositions (e.g., vaccine compositions) for the management, prevention and treatment of infectious diseases or conditions caused by coronaviruses. Coronaviruses belong to the family Coronaviridae in the order Nidoviralesn and are classified into four genera: Alphacoronavirus, Betacoronavirus, Gammacoronavirus, and Deltacoronavirus. Among them, alpha-and betacoronaviruses infect mammals, gammacoronaviruses infect avian species, and deltacoronaviruses infect both mammalian and avian species. Representative alphacoronaviruses include human coronavirus NL63 (HCoV-NL63), porcine transmissible gastroenteritis coronavirus (TGEV), PEDV, and porcine respiratory coronavirus (PRCV). Representative betacoronaviruses include SARS-CoV, MERS-CoV, bat coronavirus HKU4, mouse hepatitis coronavirus (MEV), bovine coronavirus (BCoV), and human coronavirus OC43. Representative gamma-and deltacoronaviruses include avian infectious bronchitis coronavirus (IBV) and porcine deltacoronavirus (PdCV), respectively. Li et al. Annu Rev Virol. 2016 3(1):237-261.

Without being bound by the theory, it is contemplated that coronaviruses are enveloped, positive-stranded RNA viruses. They have large genomes, typically ranging from 27 to 32 kb. The genome is packed inside a helical capsid formed by the nucleocapsid (N) protein and further surrounded by an envelope. Associated with the viral envelope are at least three structural proteins: the membrane (M) protein and the envelope (E) protein are involved in virus assembly, whereas the spike (S) protein mediates virus entry into host cells. Some coronaviruses also encode an envelope-associated hemagglutinin-esterase (HE) protein. Among these structural proteins, the spike forms large protrusions from the virus surface, giving coronaviruses the appearance of having crowns. It is further contemplated that in addition to mediating virus entry, the spike protein may play a role in determining the viral host range and tissue tropism and a major inducer of host immune responses. Li et al. Annu Rev Virol. 2016 3(1):237-261.

Accordingly, in some embodiments, provided herein are therapeutic nucleic acids encoding a viral peptide or protein derived from a coronavirus. In some embodiments, the nucleic acid encodes a viral peptide or protein derived from a coronavirus, where the viral peptide or protein is one or more selected from (a) the N protein, (b) the M protein, (c) the E protein, (d) the S protein, (e) the HE protein, (f) an immunogenic fragment of any one of (a) to (e), and (g) a functional derivative of any one of (a) to (f).

Without being bound by the theory, it is contemplated that the coronavirus S protein contains three segments: an ectodomain, a single-pass transmembrane anchor, and an intracellular tail. It is further contemplated that the ectodomain comprises a receptor-binding subunit 51 and a membrane-fusion subunit S2. The 51 subunit further comprises two major domains: the N-terminal domain (S1-NTD) and C-terminal domain (S1-CTD). It is further contemplated that one or both of these domains in the 51 subunit may bind to receptors on a host cell, and function as the receptor binding domain (RBD). Particularly, it is further contemplated that host receptors recognized by either domains in the 51 subunit include angiotensin-converting enzyme 2 (ACE2), aminopeptidase N (APN), dipeptidyl peptidase 4 (DPP4), carcinoembryonic antigen-related cell adhesion molecule 1 (CEACAM1) and sugar. It is further contemplated that S1-CTD contains two subdomains: a core structure and a receptor-binding motif (RBM). The RBM binds to ACE2 receptors on host cells.

Accordingly, in some embodiments, the therapeutic nucleic acid of the present disclosure encodes the coronavirus S protein, or an immunogenic fragment of the S protein, or a functional derivative of the S protein or the immunogenic fragment thereof. In specific embodiments, the immunogenic fragment of the S protein is selected from the ectodomain, the S1 subunit, the receptor binding domain (RBD), and the receptor binding motif (RBM). In other embodiments, the immunogenic fragment of the S protein is selected from the transmembrane domain, the intracellular tail, the S2 subunit, the S1-NTD domain, and the S1-CTD domain. Table 1 shows exemplary SARS-CoV-2 native antigen sequences.

TABLE 1

Exemplary native sequences of SARS-CoV-2 antigens.

| SEQUENCE NAME (SEQ ID NO:) | AMINO ACID OR NUCLEIC ACID SEQUENCE |
|---|---|
| SARS-CoV-2 spike protein with native signal peptide amino acid sequence (SEQ ID NO: 2) | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVY<br>FASTEKSNIIRGWIFGTTLDSKTQSLLIVNNATNVVIKVCEFQFCND<br>PFLGVYYHKNNKSWMESEFRVYSSANNCTFEYVSQPFLMDLEGK<br>QGNFKNLREFVFKNIDGYFKIYSKHTPINLVRDLPQGFSALEPLVDL<br>PIGINITRFQTLLALHRSYLTPGDSSSGWTAGAAAYYVGYLQPRTFL<br>LKYNENGTITDAVDCALDPLSETKCTLKSFTVEKGIYQTSNFRVQP<br>TESIVRFPNITNLCPFGEVFNATRFASVYAWNRKRISNCVADYSVLY<br>NSASFSTFKCYGVSPTKLNDLCFTNVYADSFVIRGDEVRQIAPGQT<br>GKIADYNYKLPDDFTGCVIAWNSNNLDSKVGGNYNYLYRLFRKS<br>NLKPFERDISTEIYQAGSTPCNGVEGFNCYFPLQSYGFQPTNGVGY |

TABLE 1-continued

Exemplary native sequences of SARS-CoV-2 antigens.

| SEQUENCE NAME (SEQ ID NO:) | AMINO ACID OR NUCLEIC ACID SEQUENCE |
|---|---|
| | QPYRVVVLSFELLHAPATVCGPKKSTNLVKNKCVNFNFNGLTGTG<br>VLTESNKKFLPFQQFGRDIADTTDAVRDPQTLEILDITPCSFGGVSVI<br>TPGTNTSNQVAVLYQDVNCTEVPVAIHADQLTPTWRVYSTGSNVF<br>QTRAGCLIGAEHVNNSYECDIPIGAGICASYQTQTNSPRRARSVAS<br>QSIIAYTMSLGAENSVAYSNNSIAIPTNFTISVTTEILPVSMTKTSVD<br>CTMYICGDSTECSNLLLQYGSFCTQLNRALTGIAVEQDKNTQEVFA<br>QVKQIYKTPPIKDFGGFNFSQILPDPSKPSKRSFIEDLLFNKVTLAD<br>AGFIKQYGDCLGDIAARDLICAQKFNGLTVLPPLLTDEMIAQYTSA<br>LLAGTITSGWTFGAGAALQIPFAMQMAYRFNGIGVTQNVLYENQK<br>LIANQFNSAIGKIQDSLSSTASALGKLQDVVNQNAQALNTLVKQLS<br>SNFGAISSVLNDILSRLDKVEAEVQIDRLITGRLQSLQTYVTQQLIR<br>AAEIRASANLAATKMSECVLGQSKRVDFCGKGYHLMSFPQSAPH<br>GVVFLHVTYVPAQEKNFTTAPAICHDGKAHFPREGVFVSNGTHWF<br>VTQRNFYEPQIITTDNTFVSGNCDVVIGIVNNTVYDPLQPELDSFKE<br>ELDKYFKNHTSPDVDLGDISGINASVVNIQKEIDRLNEVAKNLNES<br>LIDLQELGKYEQYIKWPWYIWLGFIAGLIAIVMVTIMLCCMTSCCS<br>CLKGCCSCGSCCKFDEDDSEPVLKGVKLHYT |
| SARS-CoV-2 spike protein with native signal peptide coding sequence (SEQ ID NO: 3) | ATGTTTGTTTTTCTTGTTTTATTGCCATTAGTCTCTAGTCAGTGT<br>GTTAATCTTACAACCAGAACTCAATTACCCCCTGCATACACTAA<br>TTCTTTCACACGTGGTGTTTATTACCCTGACAAAGTTTTCAGAT<br>CCTCAGTTTTACATTCAACTCAGGACTTGTTCTTACCTTTCTTTT<br>CCAATGTTACTTGGTTCCATGCTATACATGTCTCTGGGACCAAT<br>GGTACTAAGAGGTTTGATAACCCTGTCCTACCATTTAATGATGG<br>TGTTTATTTTGCTTCCACTGAGAAGTCTAACATAATAAGAGGCT<br>GGATTTTTGGTACTACTTTAGATTCGAAGACCCAGTCCCTACTT<br>ATTGTTAATAACGCTACTAATGTTGTTATTAAAGTCTGTGAATT<br>TCAATTTTGTAATGATCCATTTTTGGGTGTTTATTACCACAAAA<br>ACAACAAAAGTTGGATGGAAAGTGAGTTCAGAGTTTATTCTAG<br>TGCGAATAATTGCACTTTTGAATATGTCTCTCAGCCTTTTCTTAT<br>GGACCTTGAAGGAAAACAGGGTAATTTCAAAAATCTTAGGGAA<br>TTTGTGTTTAAGAATATTGATGGTTATTTTAAAATATATTCTAA<br>GCACACGCCTATTAATTTAGTGCGTGATCTCCCTCAGGGTTTTT<br>CGGCTTTAGAACCATTGGTAGATTTGCCAATAGGTATTAACATC<br>ACTAGGTTTCAAACTTTACTTGCTTTACATAGAAGTTATTTGAC<br>TCCTGGTGATTCTTCTTCAGGTTGGACAGCTGGTGCTGCAGCTT<br>ATTATGTGGGTTATCTTCAACCTAGGACTTTTCTATTAAAATAT<br>AATGAAAATGGAACCATTACAGATGCTGTAGACTGTGCACTTG<br>ACCCTCTCTCAGAAACAAAGTGTACGTTGAAATCCTTCACTGTA<br>GAAAAAGGAATCTATCAAACTTCTAACTTTAGAGTCCAACCAA<br>CAGAATCTATTGTTAGATTTCCTAATATTACAAACTTGTGCCCT<br>TTTGGTGAAGTTTTTAACGCCACCAGATTTGCATCTGTTTATGC<br>TTGGAACAGGAAGAGAATCAGCAACTGTGTTGCTGATTATTCT<br>GTCCTATATAATTCCGCATCATTTTCCACTTTTAAGTGTTATGG<br>AGTGTCTCCTACTAAATTAAATGATCTCTGCTTTACTAATGTCT<br>ATGCAGATTCATTTGTAATTAGAGGTGATGAAGTCAGACAAAT<br>CGCTCCAGGGCAAACTGGAAAGATTGCTGATTATAATTATAAA<br>TTACCAGATGATTTTACAGGCTGCGTTATAGCTTGGAATTCTAA<br>CAATCTTGATTCTAAGGTTGGTGGTAATTATAATTACCTGTATA<br>GATTGTTTAGGAAGTCTAATCTCAAACCTTTTGAGAGAGATATT<br>TCAACTGAAATCTATCAGGCCGGTAGCACACCTTGTAATGGTG<br>TTGAAGGTTTTAATTGTTACTTTCCTTTACAATCATATGGTTTCC<br>AACCCACTAATGGTGTTGGTTACCAACCATACAGAGTAGTAGT<br>ACTTTCTTTTGAACTTCTACATGCACCAGCAACTGTTTGTGGAC<br>CTAAAAAGTCTACTAATTTGGTTAAAAACAAATGTGTCAATTTC<br>AACTTCAATGGTTTAACAGGCACAGGTGTTCTTACTGAGTCTAA<br>CAAAAAGTTTCTGCCTTTCCAACAATTTGGCAGAGACATTGCTG<br>ACACTACTGATGCTGTCCGTGATCCACAGACACTTGAGATTCTT<br>GACATTACACCATGTTCTTTTGGTGGTGTCAGTGTTATAACACC<br>AGGAACAAATACTTCTAACCAGGTTGCTGTTCTTTATCAGGATG<br>TTAACTGCACAGAAGTCCCTGTTGCTATTCATGCAGATCAACTT<br>ACTCCTACTTGGCGTGTTTATTCTACAGGTTCTAATGTTTTTCAA<br>ACACGTGCAGGCTGTTTAATAGGGGCTGAACATGTCAACAACT<br>CATATGAGTGTGACATACCCATTGGTGCAGGTATATGCGCTAG<br>TTATCAGACTCAGACTAATTCTCCTCGGCGGGCACGTAGTGTAG<br>CTAGTCAATCCATCATTGCCTACACTATGTCACTTGGTGCAGAA<br>AATTCAGTTGCTTACTCTAATAACTCTATTGCCATACCCACAAA<br>TTTTACTATTAGTGTTACCACAGAAATTCTACCAGTGTCTATGA<br>CCAAGACATCAGTAGATTGTACAATGTACATTTGTGGTGATTCA<br>ACTGAATGCAGCAATCTTTTGTTGCAATATGGCAGTTTTTGTAC<br>ACAATTAAACCGTGCTTTAACTGGAATAGCTGTTGAACAAGAC<br>AAAAACACCCAAGAAGTTTTTGCACAAGTCAAACAAATTTACA<br>AAACACCACCAATTAAAGATTTTGGTGGTTTTAATTTTTCACAA<br>ATATTACCAGATCCATCAAAACCAAGCAAGAGGTCATTTATTG<br>AAGATCTACTTTTCAACAAAGTGACACTTGCAGATGCTGGCTTC |

TABLE 1-continued

Exemplary native sequences of SARS-CoV-2 antigens.

| SEQUENCE NAME (SEQ ID NO:) | AMINO ACID OR NUCLEIC ACID SEQUENCE |
|---|---|
| | ATCAAACAATATGGTGATTGCCTTGGTGATATTGCTGCTAGAG<br>ACCTCATTTGTGCACAAAAGTTTAACGGCCTTACTGTTTTGCCA<br>CCTTTGCTCACAGATGAAATGATTGCTCAATACACTTCTGCACT<br>GTTAGCGGGTACAATCACTTCTGGTTGGACCTTTGGTGCAGGTG<br>CTGCATTACAAATACCATTTGCTATGCAAATGGCTTATAGGTTT<br>AATGGTATTGGAGTTACACAGAATGTTCTCTATGAGAACCAAA<br>AATTGATTGCCAACCAATTTAATAGTGCTATTGGCAAAATTCAA<br>GACTCACTTTCTTCCACAGCAAGTGCACTTGGAAAACTTCAAG<br>ATGTGGTCAACCAAAATGCACAAGCTTTAAACACGCTTGTTAA<br>ACAACTTAGCTCCAATTTTGGTGCAATTTCAAGTGTTTTAAATG<br>ATATCCTTTCACGTCTTGACAAAGTTGAGGCTGAAGTGCAAATT<br>GATAGGTTGATCACAGGCAGACTTCAAAGTTTGCAGACATATG<br>TGACTCAACAATTAATTAGAGCTGCAGAAATCAGAGCTTCTGC<br>TAATCTTGCTGCTACTAAAATGTCAGAGTGTGTACTTGGACAAT<br>CAAAAAGAGTTGATTTTTGTGGAAAGGGCTATCATCTTATGTCC<br>TTCCCTCAGTCAGCACCTCATGGTGTAGTCTTCTTGCATGTGAC<br>TTATGTCCCTGCACAAGAAAAGAACTTCACAACTGCTCCTGCC<br>ATTTGTCATGATGGAAAAGCACACTTTCCTCGTGAAGGTGTCTT<br>TGTTTCAAATGGCACACACTGGTTTGTAACACAAAGGAATTTTT<br>ATGAACCACAAATCATTACTACAGACAACACATTTGTGTCTGG<br>TAACTGTGATGTTGTAATAGGAATTGTCAACAACACAGTTTATG<br>ATCCTTTGCAACCTGAATTAGACTCATTCAAGGAGGAGTTAGA<br>TAAATATTTTAAGAATCATACATCACCAGATGTTGATTTAGGTG<br>ACATCTCTGGCATTAATGCTTCAGTTGTAAACATTCAAAAAGA<br>AATTGACCGCCTCAATGAGGTTGCCAAGAATTTAAATGAATCT<br>CTCATCGATCTCCAAGAACTTGGAAAGTATGAGCAGTATATAA<br>AATGGCCATGGTACATTTGGCTAGGTTTTATAGCTGGCTTGATT<br>GCCATAGTAATGGTGACAATTATGCTTTGCTGTATGACCAGTTG<br>CTGTAGTTGTCTCAAGGGCTGTTGTTCTTGTGGATCCTGCTGCA<br>AATTTGATGAAGACGACTCTGAGCCAGTGCTCAAAGGAGTCAA<br>ATTACATTACACA |
| SARS-CoV-2 spike protein ectodomain (ECD) amino acid sequence (SEQ ID NO: 4) | QCVNLTTRTQLPPAYTNSFTRGVYYPDKVFRSSVLHSTQDLFLPFF<br>SNVTWFHAIHVSGTNGTKRFDNPVLPFNDGVYFASTEKSNIIRGWI<br>FGTTLDSKTQSLLIVNNATNVVIKVCEFQFCNDPFLGVYYHKNNK<br>SWMESEFRVYSSANNCTFEYVSQPFLMDLEGKQGNFKNLREFVF<br>KNIDGYFKIYSKHTPINLVRDLPQGFSALEPLVDLPIGINITRFQTLL<br>ALHRSYLTPGDSSSGWTAGAAAYYVGYLQPRTFLLKYNENGTITD<br>AVDCALDPLSETKCTLKSFTVEKGIYQTSNFRVQPTESIVRFPNITN<br>LCPFGEVFNATRFASVYAWNRKRISNCVADYSVLYNSASFSTFKC<br>YGVSPTKLNDLCFTNVYADSFVIRGDEVRQIAPGQTGKIADYNYK<br>LPDDFTGCVIAWNSNNLDSKVGGNYNYLYRLFRKSNLKPFERDIS<br>TEIYQAGSTPCNGVEGFNCYFPLQSYGFQPTNGVGYQPYRVVVLS<br>FELLHAPATVCGPKKSTNLVKNKCVNFNFNGLTGTGVLTESNKKF<br>LPFQQFGRDIADTTDAVRDPQTLEILDITPCSFGGVSVITPGTNTSN<br>QVAVLYQDVNCTEVPVAIHADQLTPTWRVYSTGSNVFQTRAGCL<br>IGAEHVNNSYECDIPIGAGICASYQTQTNSPRRARSVASQSIIAYTM<br>SLGAENSVAYSNNSIAIPTNFTISVTTEILPVSMTKTSVDCTMYICG<br>DSTECSNLLLQYGSFCTQLNRALTGIAVEQDKNTQEVFAQVKQIY<br>KTPPIKDFGGFNFSQILPDPSKPSKRSFIEDLLFNKVTLADAGFIKQY<br>GDCLGDIAARDLICAQKFNGLTVLPPLLTDEMIAQYTSALLAGTIT<br>SGWTFGAGAALQIPFAMQMAYRFNGIGVTQNVLYENQKLIANQF<br>NSAIGKIQDSLSSTASALGKLQDVVNQNAQALNTLVKQLSSNFGAI<br>SSVLNDILSRLDKVEAEVQIDRLITGRLQSLQTYVTQQLIRAAEIRA<br>SANLAATKMSECVLGQSKRVDFCGKGYHLMSFPQSAPHGVVFLH<br>VTYVPAQEKNFTTAPAICHDGKAHFPREGVFVSNGTHWFVTQRN<br>FYEPQIITTDNTFVSGNCDVVIGIVNNTVYDPLQPELDSFKEELDKY<br>FKNHTSPDVDLGDISGINASVVNIQKEIDRLNEVAKNLNESLIDLQE<br>LGKYEQYIK |
| SARS-CoV-2 spike protein ECD coding sequence (SEQ ID NO: 5) | CAGTGTGTTAATCTTACAACCAGAACTCAATTACCCCCTGCATA<br>CACTAATTCTTTCACACGTGGTGTTTATTACCCTGACAAAGTTT<br>TCAGATCCTCAGTTTTACATTCAACTCAGGACTTGTTCTTACCTT<br>TCTTTTCCAATGTTACTTGGTTCCATGCTATACATGTCTCTGGGA<br>CCAATGGTACTAAGAGGTTTGATAACCCTGTCCTACCATTTAAT<br>GATGGTGTTTATTTTGCTTCCACTGAGAAGTCTAACATAATAAG<br>AGGCTGGATTTTTGGTACTACTTTAGATTCGAAGACCCAGTCCC<br>TACTTATTGTTAATAACGCTACTAATGTTGTTATTAAAGTCTGT<br>GAATTTCAATTTTGTAATGATCCATTTTTGGGTGTTTATTACCAC<br>AAAAACAACAAAAGTTGGATGGAAAGTGAGTTCAGAGTTTATT<br>CTAGTGCGAATAATTGCACTTTTGAATATGTCTCTCAGCCTTTT<br>CTTATGGACCTTGAAGGAAAACAGGGTAATTTCAAAAATCTTA<br>GGGAATTTGTGTTTAAGAATATTGATGGTTATTTTAAAATATAT<br>TCTAAGCACACGCCTATTAATTTAGTGCGTGATCTCCCTCAGGG<br>TTTTTCGGCTTTAGAACCATTGGTAGATTTGCCAATAGGTATTA |

TABLE 1-continued

Exemplary native sequences of SARS-CoV-2 antigens.

| SEQUENCE NAME (SEQ ID NO:) | AMINO ACID OR NUCLEIC ACID SEQUENCE |
|---|---|
| | ACATCACTAGGTTTCAAACTTTACTTGCTTTACATAGAAGTTAT<br>TTGACTCCTGGTGATTCTTCTTCAGGTTGGACAGCTGGTGCTGC<br>AGCTTATTATGTGGGTTATCTTCAACCTAGGACTTTTCTATTAA<br>AATATAATGAAAATGGAACCATTACAGATGCTGTAGACTGTGC<br>ACTTGACCCTCTCTCAGAAACAAAGTGTACGTTGAAATCCTTCA<br>CTGTAGAAAAAGGAATCTATCAAACTTCTAACTTTAGAGTCCA<br>ACCAACAGAATCTATTGTTAGATTTCCTAATATTACAAACTTGT<br>GCCCTTTTGGTGAAGTTTTTAACGCCACCAGATTTGCATCTGTT<br>TATGCTTGGAACAGGAAGAGAATCAGCAACTGTGTTGCTGATT<br>ATTCTGTCCTATATAATTCCGCATCATTTTCCACTTTTAAGTGTT<br>ATGGAGTGTCTCCTACTAAATTAAATGATCTCTGCTTTACTAAT<br>GTCTATGCAGATTCATTTGTAATTAGAGGTGATGAAGTCAGAC<br>AAATCGCTCCAGGGCAAACTGGAAAGATTGCTGATTATAATTA<br>TAAATTACCAGATGATTTTACAGGCTGCGTTATAGCTTGGAACT<br>CTAACAATCTTGATTCTAAGGTTGGTGGTAATTATAATTACCTG<br>TATAGATTGTTTAGGAAGTCTAATCTCAAACCTTTTGAGAGAGA<br>TATTTCAACTGAAATCTATCAGGCCGGTAGCACACCTTGTAATG<br>GTGTTGAAGGTTTTAATTGTTACTTTCCTTTACAATCATATGGTT<br>TCCAACCCACTAATGGTGTTGGTTACCAACCATACAGAGTAGT<br>AGTACTTTCTTTTGAACTTCTACATGCACCAGCAACTGTTTGTG<br>GACCTAAAAAGTCTACTAATTTGGTTAAAAACAAATGTGTCAA<br>TTTCAACTTCAATGGTTTAACAGGCACAGGTGTTCTTACTGAGT<br>CTAACAAAAAGTTTCTGCCTTTCCAACAATTTGGCAGAGACATT<br>GCTGACACTACTGATGCTGTCCGTGATCCACAGACACTTGAGA<br>TTCTTGACATTACACCATGTTCTTTTGGTGGTGTCAGTGTTATA<br>ACACCAGGAACAAATACTTCTAACCAGGTTGCTGTTCTTTATCA<br>GGATGTTAACTGCACAGAAGTCCCTGTTGCTATTCATGCAGATC<br>AACTTACTCCTACTTGGCGTGTTTATTCTACAGGTTCTAATGTTT<br>TTCAAACACGTGCAGGCTGTTTAATAGGGGCTGAACATGTCAA<br>CAACTCATATGAGTGTGACATACCCATTGGTGCAGGTATATGC<br>GCTAGTTATCAGACTCAGACTAATTCTCCTCGGCGGGCACGTA<br>GTGTAGCTAGTCAATCCATCATTGCCTACACTATGTCACTTGGT<br>GCAGAAAATTCAGTTGCTTACTCTAATAACTCTATTGCCATACC<br>CACAAATTTTACTATTAGTGTTACCACAGAAATTCTACCAGTGT<br>CTATGACCAAGACATCAGTAGATTGTACAATGTACATTTGTGGT<br>GATTCAACTGAATGCAGCAATCTTTTGTTGCAATATGGCAGTTT<br>TTGTACACAATTAAACCGTGCTTTAACTGGAATAGCTGTTGAAC<br>AAGACAAAAACACCCAAGAAGTTTTTGCACAAGTCAAACAAAT<br>TTACAAAACACCACCAATTAAAGATTTTGGTGGTTTTAATTTTT<br>CACAAATATTACCAGATCCATCAAAACCAAGCAAGAGGTCATT<br>TATTGAAGATCTACTTTTCAACAAAGTGACACTTGCAGATGCTG<br>GCTTCATCAAACAATATGGTGATTGCCTTGGTGATATTGCTGCT<br>AGAGACCTCATTTGTGCACAAAAGTTTAACGGCCTTACTGTTTT<br>GCCACCTTTGCTCACAGATGAAATGATTGCTCAATACACTTCTG<br>CACTGTTAGCGGGTACAATCACTTCTGGTTGGACCTTTGGTGCA<br>GGTGCTGCATTACAAATACCATTTGCTATGCAAATGGCTTATAG<br>GTTTAATGGTATTGGAGTTACACAGAATGTTCTCTATGAGAACC<br>AAAAATTGATTGCCAACCAATTTAATAGTGCTATTGGCAAAAT<br>TCAAGACTCACTTTCTTCCACAGCAAGTGCACTTGGAAAACTTC<br>AAGATGTGGTCAACCAAAATGCACAAGCTTTAAACACGCTTGT<br>TAAACAACTTAGCTCCAATTTTGGTGCAATTTCAAGTGTTTTAA<br>ATGATATCCTTTCACGTCTTGACAAAGTTGAGGCTGAAGTGCA<br>AATTGATAGGTTGATCACAGGCAGACTTCAAAGTTTGCAGACA<br>TATGTGACTCAACAATTAATTAGAGCTGCAGAAATCAGAGCTT<br>CTGCTAATCTTGCTGCTACTAAAATGTCAGAGTGTGTACTTGGA<br>CAATCAAAAAGAGTTGATTTTTGTGGAAAGGGCTATCATCTTAT<br>GTCCTTCCCTCAGTCAGCACCTCATGGTGTAGTCTTCTTGCATG<br>TGACTTATGTCCCTGCACAAGAAAAGAACTTCACAACTGCTCCT<br>GCCATTTGTCATGATGGAAAAGCACACTTTCCTCGTGAAGGTGT<br>CTTTGTTTCAAATGGCACACACTGGTTTGTAACACAAAGGAATT<br>TTTATGAACCACAAATCATTACTACAGACAACACATTTGTGTCT<br>GGTAACTGTGATGTTGTAATAGGAATTGTCAACAACACAGTTT<br>ATGATCCTTTGCAACCTGAATTAGACTCATTCAAGGAGGAGTT<br>AGATAAATATTTTAAGAATCATACATCACCAGATGTTGATTTAG<br>GTGACATCTCTGGCATTAATGCTTCAGTTGTAAACATTCAAAAA<br>GAAATTGACCGCCTCAATGAGGTTGCCAAGAATTTAAATGAAT<br>CTCTCATCGATCTCCAAGAACTTGGAAAGTATGAGCAGTATAT<br>AAAA |
| SARS-CoV-2 spike protein S1 subunit amino acid sequence (SEQ ID NO: 6) | QCVNLTTRTQLPPAYTNSFTRGVYYPDKVFRSSVLHSTQDLFLPFF<br>SNVTWFHAIHVSGTNGTKRFDNPVLPFNDGVYFASTEKSNIIRGWI<br>FGTTLDSKTQSLLIVNNATNVVIKVCEFQFCNDPFLGVYYHKNNK<br>SWMESEFRVYSSANNCTFEYVSQPFLMDLEGKQGNFKNLREFVF<br>KNIDGYFKIYSKHTPINLVRDLPQGFSALEPLVDLPIGINITRFQTLL<br>ALHRSYLTPGDSSSGWTAGAAAYYVGYLQPRTFLLKYNENGTITD |

TABLE 1-continued

Exemplary native sequences of SARS-CoV-2 antigens.

| SEQUENCE NAME (SEQ ID NO:) | AMINO ACID OR NUCLEIC ACID SEQUENCE |
|---|---|
| | AVDCALDPLSETKCTLKSFTVEKGIYQTSNFRVQPTESIVRFPNITN<br>LCPFGEVFNATRFASVYAWNRKRISNCVADYSVLYNSASFSTFKC<br>YGVSPTKLNDLCFTNVYADSFVIRGDEVRQIAPGQTGKIADYNYK<br>LPDDFTGCVIAWNSNNLDSKVGGNYNYLYRLFRKSNLKPFERDIS<br>TEIYQAGSTPCNGVEGFNCYFPLQSYGFQPTNGVGYQPYRVVVLS<br>FELLHAPATVCGPKKSTNLVKNKCVNFNFNGLTGTGVLTESNKKF<br>LPFQQFGRDIADTTDAVRDPQTLEILDITPCSFGGVSVITPGTNTSN<br>QVAVLYQDVNCTEVPVAIHADQLTPTWRVYSTGSNVFQTRAGCL<br>IGAEHVNNSYECDIPIGAGICASYQTQTNSPRRAR |
| SARS-CoV-2 spike protein S1 subunit coding sequence (SEQ ID NO: 7) | CAGTGTGTTAATCTTACAACCAGAACTCAATTACCCCCTGCATAC<br>ACTAATTCTTTCACACGTGGTGTTTATTACCCTGACAAAGTTTTC<br>AGATCCTCAGTTTTACATTCAACTCAGGACTTGTTCTTACCTTTC<br>TTTTCCAATGTTACTTGGTTCCATGCTATACATGTCTCTGGGACC<br>AATGGTACTAAGAGGTTTGATAACCCTGTCCTACCATTTAATGAT<br>GGTGTTTATTTTGCTTCCACTGAGAAGTCTAACATAATAAGAGGC<br>TGGATTTTTGGTACTACTTTAGATTCGAAGACCCAGTCCCTACTT<br>ATTGTTAATAACGCTACTAATGTTGTTATTAAAGTCTGTGAATTTC<br>AATTTTGTAATGATCCATTTTTGGGTGTTTATTACCACAAAAACA<br>ACAAAAGTTGGATGGAAAGTGAGTTCAGAGTTTATTCTAGTGCG<br>AATAATTGCACTTTTGAATATGTCTCTCAGCCTTTTCTTATGGACC<br>TTGAAGGAAAACAGGGTAATTTCAAAAATCTTAGGGAATTTGTG<br>TTTAAGAATATTGATGGTTATTTTAAAATATATTCTAAGCACACGC<br>CTATTAATTTAGTGCGTGATCTCCCTCAGGGTTTTTCGGCTTTAG<br>AACCATTGGTAGATTTGCCAATAGGTATTAACATCACTAGGTTTC<br>AAACTTTACTTGCTTTACATAGAAGTTATTTGACTCCTGGTGATT<br>CTTCTTCAGGTTGGACAGCTGGTGCTGCAGCTTATTATGTGGGTT<br>ATCTTCAACCTAGGACTTTTCTATTAAAATATAATGAAAATGGAA<br>CCATTACAGATGCTGTAGACTGTGCACTTGACCCTCTCTCAGAA<br>ACAAAGTGTACGTTGAAATCCTTCACTGTAGAAAAAGGAATCTA<br>TCAAACTTCTAACTTTAGAGTCCAACCAACAGAATCTATTGTTAG<br>ATTTCCTAATATTACAAACTTGTGCCCTTTTGGTGAAGTTTTTAA<br>CGCCACCAGATTTGCATCTGTTTATGCTTGGAACAGGAAGAGAA<br>TCAGCAACTGTGTTGCTGATTATTCTGTCCTATATAATTCCGCATC<br>ATTTTCCACTTTTAAGTGTTATGGAGTGTCTCCTACTAAATTAAAT<br>GATCTCTGCTTTACTAATGTCTATGCAGATTCATTTGTAATTAGAG<br>GTGATGAAGTCAGACAAATCGCTCCAGGGCAAACTGGAAAGAT<br>TGCTGATTATAATTATAAATTACCAGATGATTTTACAGGCTGCGTT<br>ATAGCTTGGAATTCTAACAATCTTGATTCTAAGGTTGGTGGTAAT<br>TATAATTACCTGTATAGATTGTTTAGGAAGTCTAATCTCAAACCTT<br>TTGAGAGAGATATTTCAACTGAAATCTATCAGGCCGGTAGCACA<br>CCTTGTAATGGTGTTGAAGGTTTTAATTGTTACTTTCCTTTACAAT<br>CATATGGTTTCCAACCCACTAATGGTGTTGGTTACCAACCATACA<br>GAGTAGTAGTACTTTCTTTTGAACTTCTACATGCACCAGCAACTG<br>TTTGTGGACCTAAAAAGTCTACTAATTTGGTTAAAAACAAATGT<br>GTCAATTTCAACTTCAATGGTTTAACAGGCACAGGTGTTCTTACT<br>GAGTCTAACAAAAAGTTTCTGCCTTTCCAACAATTTGGCAGAGA<br>CATTGCTGACACTACTGATGCTGTCCGTGATCCACAGACACTTG<br>AGATTCTTGACATTACACCATGTTCTTTTGGTGGTGTCAGTGTTA<br>TAACACCAGGAACAAATACTTCTAACCAGGTTGCTGTTCTTTATC<br>AGGATGTTAACTGCACAGAAGTCCCTGTTGCTATTCATGCAGAT<br>CAACTTACTCCTACTTGGCGTGTTTATTCTACAGGTTCTAATGTTT<br>TTCAAACACGTGCAGGCTGTTTAATAGGGGCTGAACATGTCAAC<br>AACTCATATGAGTGTGACATACCCATTGGTGCAGGTATATGCGCT<br>AGTTATCAGACTCAGACTAATTCTCCTCGGCGGGCACGT |
| SARS-CoV-2 spike protein receptor binding domain (RBD) spanning positions 319-541 (RBD-1) amino acid sequence (SEQ ID NO: 8) | RVQPTESIVRFPNITNLCPFGEVFNATRFASVYAWNRKRISNCVAD<br>YSVLYNSASFSTFKCYGVSPTKLNDLCFTNVYADSFVIRGDEVRQI<br>APGQTGKIADYNYKLPDDFTGCVIAWNSNNLDSKVGGNYNYLYR<br>LFRKSNLKPFERDISTEIYQAGSTPCNGVEGFNCYFPLQSYGFQPT**N**<br>GVGYQPYRVVVLSFELLHAPATVCGPKKSTNLVKNKCVNF |
| SARS-CoV-2 spike protein RBD-1 coding sequence (SEQ ID NO: 9) | AGAGTCCAACCAACAGAATCTATTGTTAGATTTCCTAATATTACA<br>AACTTGTGCCCTTTTGGTGAAGTTTTTAACGCCACCAGATTTGC<br>ATCTGTTTATGCTTGGAACAGGAAGAGAATCAGCAACTGTGTTG<br>CTGATTATTCTGTCCTATATAATTCCGCATCATTTTCCACTTTTAAG<br>TGTTATGGAGTGTCTCCTACTAAATTAAATGATCTCTGCTTTACTA<br>ATGTCTATGCAGATTCATTTGTAATTAGAGGTGATGAAGTCAGAC<br>AAATCGCTCCAGGGCAAACTGGAAAGATTGCTGATTATAATTATA<br>AATTACCAGATGATTTTACAGGCTGCGTTATAGCTTGGAACTCTA<br>ACAATCTTGATTCTAAGGTTGGTGGTAATTATAATTACCTGTATAG |

TABLE 1-continued

Exemplary native sequences of SARS-CoV-2 antigens.

| SEQUENCE NAME (SEQ ID NO:) | AMINO ACID OR NUCLEIC ACID SEQUENCE |
|---|---|
| | ATTGTTTAGGAAGTCTAATCTCAAACCTTTTGAGAGAGATATTTC AACTGAAATCTATCAGGCCGGTAGCACACCTTGTAATGGTGTTG AAGGTTTTAATTGTTACTTTCCTTTACAATCATATGGTTTCCAACC CACTAATGGTGTTGGTTACCAACCATACAGAGTAGTAGTACTTTC TTTTGAACTTCTACATGCACCAGCAACTGTTTGTGGACCTAAAA AGTCTACTAATTTGGTTAAAAACAAATGTGTCAATTTC |
| SARS-CoV-2 spike protein RBD spanning positions 331-529 (RBD-2) amino acid sequence (SEQ ID NO: 10) | NITNLCPFGEVFNATRFASVYAWNRKRISNCVADYSVLYNSASFS TFKCYGVSPTKLNDLCFTNVYADSFVIRGDEVRQIAPGQTGKIAD YNYKLPDDFTGCVIAWNSNNLDSKVGGNYNYLYRLFRKSNLKPF ERDISTEIYQAGSTPCNGVEGFNCYFPLQSYGFQPTNGVGYQPYRV VVLSFELLHAPATVCGPKK |
| SARS-CoV-2 spike protein RBD-2 coding sequence (SEQ ID NO: 11) | AATATTACAAACTTGTGCCCTTTTGGTGAAGTTTTTAACGCCACC AGATTTGCATCTGTTTATGCTTGGAACAGGAAGAGAATCAGCAA CTGTGTTGCTGATTATTCTGTCCTATATAATTCCGCATCATTTTCC ACTTTTAAGTGTTATGGAGTGTCTCCTACTAAATTAAATGATCTC TGCTTTACTAATGTCTATGCAGATTCATTTGTAATTAGAGGTGATG AAGTCAGACAAATCGCTCCAGGGCAAACTGGAAAGATTGCTGA TTATAATTATAAATTACCAGATGATTTTACAGGCTGCGTTATAGCT TGGAACTCTAACAATCTTGATTCTAAGGTTGGTGGTAATTATAAT TACCTGTATAGATTGTTTAGGAAGTCTAATCTCAAACCTTTTGAG AGAGATATTTCAACTGAAATCTATCAGGCCGGTAGCACACCTTG TAATGGTGTTGAAGGTTTTAATTGTTACTTTCCTTTACAATCATAT GGTTTCCAACCCACTAATGGTGTTGGTTACCAACCATACAGAGT AGTAGTACTTTCTTTTGAACTTCTACATGCACCAGCAACTGTTTG TGGACCTAAAAAG |
| SARS-CoV-2 spike protein RBD spanning positions 331-524 (RBD-3) amino acid sequence (SEQ ID NO: 12) | NITNLCPFGEVFNATRFASVYAWNRKRISNCVADYSVLYNSASFS TFKCYGVSPTKLNDLCFTNVYADSFVIRGDEVRQIAPGQTGKIAD YNYKLPDDFTGCVIAWNSNNLDSKVGGNYNYLYRLFRKSNLKPF ERDISTEIYQAGSTPCNGVEGFNCYFPLQSYGFQPTNGVGYQPYRV VVLSFELLHAPATV |
| SARS-CoV-2 spike protein RBD-3 coding sequence (SEQ ID NO: 13) | AATATTACAAACTTGTGCCCTTTTGGTGAAGTTTTTAACGCCAC CAGATTTGCATCTGTTTATGCTTGGAACAGGAAGAGAATCAGC AACTGTGTTGCTGATTATTCTGTCCTATATAATTCCGCATCATTT TCCACTTTTAAGTGTTATGGAGTGTCTCCTACTAAATTAAATGA TCTCTGCTTTACTAATGTCTATGCAGATTCATTTGTAATTAGAG GTGATGAAGTCAGACAAATCGCTCCAGGGCAAACTGGAAAGAT TGCTGATTATAATTATAAATTACCAGATGATTTTACAGGCTGCG TTATAGCTTGGAACTCTAACAATCTTGATTCTAAGGTTGGTGGT AATTATAATTACCTGTATAGATTGTTTAGGAAGTCTAATCTCAA ACCTTTTGAGAGAGATATTTCAACTGAAATCTATCAGGCCGGT AGCACACCTTGTAATGGTGTTGAAGGTTTTAATTGTTACTTTCC TTTACAATCATATGGTTTCCAACCCACTAATGGTGTTGGTTACC AACCATACAGAGTAGTAGTACTTTCTTTTGAACTTCTACATGCA CCAGCAACTGTT |
| SARS-CoV-2 spike protein RBD spanning positions 319-529 (RBD-4) amino acid sequence (SEQ ID NO: 14) | RVQPTESIVRFPNITNLCPFGEVFNATRFASVYAWNRKRISNCVAD YSVLYNSASFSTFKCYGVSPTKLNDLCFTNVYADSFVIRGDEVRQI APGQTGKIADYNYKLPDDFTGCVIAWNSNNLDSKVGGNYNYLYR LFRKSNLKPFERDISTEIYQAGSTPCNGVEGFNCYFPLQSYGFQPTN GVGYQPYRVVVLSFELLHAPATVCGPKK |
| SARS-CoV-2 spike protein RBD-4 coding sequence (SEQ ID NO: 15) | AGAGTCCAACCAACAGAATCTATTGTTAGATTTCCTAATATTACA AACTTGTGCCCTTTTGGTGAAGTTTTTAACGCCACCAGATTTGC ATCTGTTTATGCTTGGAACAGGAAGAGAATCAGCAACTGTGTTG CTGATTATTCTGTCCTATATAATTCCGCATCATTTTCCACTTTTAAG TGTTATGGAGTGTCTCCTACTAAATTAAATGATCTCTGCTTTACTA ATGTCTATGCAGATTCATTTGTAATTAGAGGTGATGAAGTCAGAC AAATCGCTCCAGGGCAAACTGGAAAGATTGCTGATTATAATTATA AATTACCAGATGATTTTACAGGCTGCGTTATAGCTTGGAACTCTA ACAATCTTGATTCTAAGGTTGGTGGTAATTATAATTACCTGTATAG ATTGTTTAGGAAGTCTAATCTCAAACCTTTTGAGAGAGATATTTC AACTGAAATCTATCAGGCCGGTAGCACACCTTGTAATGGTGTTG AAGGTTTTAATTGTTACTTTCCTTTACAATCATATGGTTTCCAACC |

TABLE 1-continued

Exemplary native sequences of SARS-CoV-2 antigens.

| SEQUENCE NAME (SEQ ID NO:) | AMINO ACID OR NUCLEIC ACID SEQUENCE |
|---|---|
| | CACTAATGGTGTTGGTTACCAACCATACAGAGTAGTAGTACTTTC<br>TTTTGAACTTCTACATGCACCAGCAACTGTTTGTGGACCTAAAA<br>AG |
| SARS-CoV-2 spike protein receptor binding motif (RBM) amino acid sequence (SEQ ID NO: 16) | VGGNYNYLYRLFRKSNLKPFERDISTEIYQAGSTPCNGVEGFNCYF<br>PLQSYGFQPT |
| SARS-CoV-2 spike protein RBM coding sequence (SEQ ID NO: 17) | GTTGGTGGTAATTATAATTACCTGTATAGATTGTTTAGGAAGTCTA<br>ATCTCAAACCTTTTGAGAGAGATATTTCAACTGAAATCTATCAGG<br>CCGGTAGCACACCTTGTAATGGTGTTGAAGGTTTTAATTGTTACT<br>TTCCTTTACAATCATATGGTTTCCAACCCACT |
| SARS-CoV-2 nucleocapsid protein amino acid sequence (SEQ ID NO: 18) | MSDNGPQNQRNAPRITFGGPSDSTGSNQNGERSGARSKQRRPQGL<br>PNNTASWFTALTQHGKEDLKFPRGQGVPINTNSSPDDQIGYYRRA<br>TRRIRGGDGKMKDLSPRWYFYYLGTGPEAGLPYGANKDGIIWVA<br>TEGALNTPKDHIGTRNPANNAAIVLQLPQGTTLPKGFYAEGSRGG<br>SQASSRSSSRSRNSSRNSTPGSSRGTSPARMAGNGGDAALALLLLD<br>RLNQLESKMSGKGQQQQGQTVTKKSAAEASKKPRQKRTATKAY<br>NVTQAFGRRGPEQTQGNFGDQELIRQGTDYKHWPQIAQFAPSASA<br>FFGMSRIGMEVTPSGTWLTYTAAIKLDDKDPNFKDQVILLNKHID<br>AYKTFPPTEPKKDKKKKADETQALPQRQKKQQTVTLLPAADLDD<br>FSKQLQQSMSSADSTQA |
| SARS-CoV-2 nucleocapsid protein coding sequence (SEQ ID NO: 19) | ATGTCTGATAATGGACCCCAAAATCAGCGAAATGCACCCCGCA<br>TTACGTTTGGTGGACCCTCAGATTCAACTGGCAGTAACCAGAA<br>TGGAGAACGCAGTGGGGCGCGATCAAAACAACGTCGGCCCCA<br>AGGTTTACCCAATAATACTGCGTCTTGGTTCACCGCTCTCACTC<br>AACATGGCAAGGAAGACCTTAAATTCCCTCGAGGACAAGGCGT<br>TCCAATTAACACCAATAGCAGTCCAGATGACCAAATTGGCTAC<br>TACCGAAGAGCTACCAGACGAATTCGTGGTGGTGACGGTAAAA<br>TGAAAGATCTCAGTCCAAGATGGTATTTCTACTACCTAGGAACT<br>GGGCCAGAAGCTGGACTTCCCTATGGTGCTAACAAAGACGGCA<br>TCATATGGGTTGCAACTGAGGGAGCCTTGAATACACCAAAAGA<br>TCACATTGGCACCCGCAATCCTGCTAACAATGCTGCAATCGTGC<br>TACAACTTCCTCAAGGAACAACATTGCCAAAAGGCTTCTACGC<br>AGAAGGGAGCAGAGGCGGCAGTCAAGCCTCTTCTCGTTCCTCA<br>TCACGTAGTCGCAACAGTTCAAGAAATTCAACTCCAGGCAGCA<br>GTAGGGGAACTTCTCCTGCTAGAATGGCTGGCAATGGCGGTGA<br>TGCTGCTCTTGCTTTGCTGCTGCTTGACAGATTGAACCAGCTTG<br>AGAGCAAAATGTCTGGTAAAGGCCAACAACAACAAGGCCAAA<br>CTGTCACTAAGAAATCTGCTGCTGAGGCTTCTAAGAAGCCTCG<br>GCAAAAACGTACTGCCACTAAAGCATACAATGTAACACAAGCT<br>TTCGGCAGACGTGGTCCAGAACAAACCCAAGGAAATTTTGGGG<br>ACCAGGAACTAATCAGACAAGGAACTGATTACAAACATTGGCC<br>GCAAATTGCACAATTTGCCCCCAGCGCTTCAGCGTTCTTCGGAA<br>TGTCGCGCATTGGCATGGAAGTCACACCTTCGGGAACGTGGTT<br>GACCTACACAGCTGCCATCAAATTGGATGACAAAGATCCAAAT<br>TTCAAAGATCAAGTCATTTTGCTGAATAAGCATATTGACGCATA<br>CAAAACATTCCCACCAACAGAGCCTAAAAAGGACAAAAAGAA<br>GAAGGCTGATGAAACTCAAGCCTTACCGCAGAGACAGAAGAA<br>ACAGCAAACTGTGACTCTTCTTCCTGCTGCAGATTTGGATGATT<br>TCTCCAAACAATTGCAACAATCCATGAGCAGTGCTGACTCAAC<br>TCAGGCC |

In particular embodiments, the therapeutic nucleic acid of the present disclosure encodes the S protein of coronavirus SARS-CoV-2, wherein the S protein has an amino acid sequence of SEQ ID NO:2. In particular embodiments, the therapeutic nucleic acid of the present disclosure encodes the S protein of coronavirus SARS-CoV-2, and wherein the therapeutic nucleic acid comprises a DNA coding sequence of SEQ ID NO:3. In particular embodiments, the therapeutic nucleic acid of the present disclosure encodes the S protein of coronavirus SARS-CoV-2, and wherein the therapeutic nucleic acid comprises a RNA sequence transcribed from the DNA coding sequence of SEQ ID NO:3. In particular embodiments, the nucleic acid molecule is an mRNA molecule.

In particular embodiments, the therapeutic nucleic acid of the present disclosure encodes the ectodomain (ECD) of the S protein of coronavirus SARS-CoV-2, and wherein the ectodomain has an amino acid sequence SEQ ID NO:4. In particular embodiments, the therapeutic nucleic acid of the present disclosure encodes the ECD of the S protein of coronavirus SARS-CoV-2, and wherein the therapeutic nucleic acid comprises a DNA coding sequence of SEQ ID NO:5. In particular embodiments, the therapeutic nucleic acid of the present disclosure encodes the ECD of the S protein of coronavirus SARS-CoV-2, and wherein the therapeutic nucleic acid comprises a RNA sequence transcribed from the DNA coding sequence of SEQ ID NO:5. In some embodiments, the RNA sequence is in vitro transcribed. In particular embodiments, the nucleic acid molecule is an mRNA molecule.

In particular embodiments, the therapeutic nucleic acid of the present disclosure encodes the S1 subunit of the S protein of coronavirus SARS-CoV-2, and wherein the S1 subunit has an amino acid sequence of SEQ ID NO:6. In particular embodiments, the therapeutic nucleic acid of the present disclosure encodes the S1 subunit of the S protein of coronavirus SARS-CoV-2, and wherein the therapeutic nucleic acid comprises a DNA coding sequence SEQ ID NO:7. In particular embodiments, the therapeutic nucleic acid of the present disclosure encodes the S1 subunit of the S protein of coronavirus SARS-CoV-2, and wherein the therapeutic nucleic acid comprises a RNA sequence transcribed from the DNA coding sequence of SEQ ID NO:7. In some embodiments, the RNA sequence is in vitro transcribed. In particular embodiments, the nucleic acid molecule is an mRNA molecule.

In particular embodiments, the therapeutic nucleic acid of the present disclosure encodes an immunogenic fragment of the S protein of coronavirus SARS-CoV-2. In some embodiments, the immunogenic fragment is the receptor binding domain (RBD) of the S protein of coronavirus SARS-CoV-2. In some embodiments, the therapeutic nucleic acid of the present disclosure encodes the RBD sequence locates at residues 319-541 of the S protein, and has an amino acid sequence of SEQ ID NO:8. In particular embodiments, the therapeutic nucleic acid of the present disclosure encodes the RBD sequence of the S protein of coronavirus SARS-CoV-2, and wherein the therapeutic nucleic acid comprises a DNA coding sequence of SEQ ID NO:9. In particular embodiments, the therapeutic nucleic acid of the present disclosure encodes the RBD sequence of the S protein of coronavirus SARS-CoV-2, and wherein the therapeutic nucleic acid comprises a RNA sequence transcribed from the DNA coding sequence of SEQ ID NO:9. In some embodiments, the RNA sequence is in vitro transcribed. In particular embodiments, the nucleic acid molecule is an mRNA molecule.

In particular embodiments, the therapeutic nucleic acid of the present disclosure encodes the RBD sequence located at residues 331-529 of the S protein of coronavirus SARS-CoV-2, and has an amino acid sequence of SEQ ID NO:10. In particular embodiments, the therapeutic nucleic acid of the present disclosure encodes the RBD sequence of the S protein of coronavirus SARS-CoV-2, and wherein the therapeutic nucleic acid comprises a DNA coding sequence of SEQ ID NO:11. In particular embodiments, the therapeutic nucleic acid of the present disclosure encodes the RBD sequence of the S protein of coronavirus SARS-CoV-2, and wherein the therapeutic nucleic acid comprises a RNA sequence transcribed from the DNA coding sequence of SEQ ID NO:11. In some embodiments, the RNA sequence is in vitro transcribed. In particular embodiments, the nucleic acid molecule is an mRNA molecule.

In particular embodiments, the therapeutic nucleic acid of the present disclosure encodes a RBD sequence of the S protein of coronavirus SARS-CoV-2, and wherein the RBD sequence locates at residues 331-524 of the S protein, and has an amino acid sequence of SEQ ID NO:12. In particular embodiments, the therapeutic nucleic acid of the present disclosure encodes a RBD sequence of the S protein of coronavirus SARS-CoV-2, and wherein the therapeutic nucleic acid comprises a DNA coding sequence of SEQ ID NO:13. In particular embodiments, the therapeutic nucleic acid of the present disclosure encodes a RBD sequence of the S protein of coronavirus SARS-CoV-2, and wherein the therapeutic nucleic acid comprises a RNA sequence transcribed from the DNA coding sequence of SEQ ID NO:13. In some embodiments, the RNA sequence is in vitro transcribed. In particular embodiments, the nucleic acid molecule is an mRNA molecule.

In particular embodiments, the therapeutic nucleic acid of the present disclosure encodes a RBD sequence of the S protein of coronavirus SARS-CoV-2, and wherein the RBD domain locates at residues 319-529 of the S protein, and has an amino acid sequence of SEQ ID NO:14. In particular embodiments, the therapeutic nucleic acid of the present disclosure encodes a RBD sequence of the S protein of coronavirus SARS-CoV-2, and wherein the therapeutic nucleic acid comprises a DNA coding sequence of SEQ ID NO:15. In particular embodiments, the therapeutic nucleic acid of the present disclosure encodes a RBD sequence of the S protein of coronavirus SARS-CoV-2, and wherein the therapeutic nucleic acid comprises a RNA sequence transcribed from the DNA coding sequence of SEQ ID NO:15. In some embodiments, the RNA sequence is in vitro transcribed. In particular embodiments, the nucleic acid molecule is an mRNA molecule.

In particular embodiments, the therapeutic nucleic acid of the present disclosure encodes the receptor binding motif (RBM) sequence of the S protein of coronavirus SARS-CoV-2, and wherein the RBM has an amino acid sequence of SEQ ID NO:16. In particular embodiments, the therapeutic nucleic acid of the present disclosure encodes the RBM of the S protein of coronavirus SARS-CoV-2, and wherein the therapeutic nucleic acid comprises a DNA coding sequence of SEQ ID NO:17. In particular embodiments, the therapeutic nucleic acid of the present disclosure encodes the RBM of the S protein of coronavirus SARS-CoV-2, and wherein the therapeutic nucleic acid comprises a RNA sequence transcribed from the DNA coding sequence of SEQ ID NO:17. In some embodiments, the RNA sequence is in vitro transcribed. In particular embodiments, the nucleic acid molecule is an mRNA molecule.

In some embodiments, the therapeutic nucleic acid of the present disclosure encodes a functional derivative of RBD. In particular embodiments, the functional derivative of RBD comprises one or more mutations that increase binding affinity of the RBD to host receptors as compared to RBD without such mutations. In particular embodiments, the coronavirus is SARS-CoV, and wherein the mutation is K479N and/or S487T.

In particular embodiments, the coronavirus is SARS-CoV-2, and wherein the mutation is N501T. Table 2 shows exemplary sequences of S protein of coronavirus SARS-CoV-2 or antigenic fragments thereof having the N501T mutation.

TABLE 2

Exemplary mutated sequences of SARS-CoV-2 antigens.

| SEQUENCE NAME (SEQ ID NO:) | AMINO ACID OR NUCLEIC ACID SEQUENCE |
|---|---|
| SARS-CoV-2 spike protein with native signal peptide and an ***N501T substitution*** amino acid sequence (SEQ ID NO: 20) | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDCALDPLSETKCTLKSFTVEKGIYQTSNFRVQP<br>TESIVRFPNITNLCPFGEVFNATRFASVYAWNRKRISNCVADYSVLY<br>NSASFSTFKCYGVSPTKLNDLCFTNVYADSFVIRGDEVRQIAPGQT<br>GKIADYNYKLPDDFTGCVIAWNSNNLDSKVGGNYNYLYRLFRKSN<br>LKPFERDISTEIYQAGSTPCNGVEGFNCYFPLQSYGFQPT***T***GVGY<br>QPYRVVVLSFELLHAPATVCGPKKSTNLVKNKCVNFNFNGLTGTG<br>VLTESNKKFLPFQQFGRDIADTTDAVRDPQTLEILDITPCSFGGVSVI<br>TPGTNTSNQVAVLYQDVNCTEVPVAIHADQLTPTWRVYSTGSNVF<br>QTRAGCLIGAEHVNNSYECDIPIGAGICASYQTQTNSPRRARSVAS<br>QSIIAYTMSLGAENSVAYSNNSIAIPTNFTISVTlEILPVSMTKTSVD<br>CTMYICGDSTECSNLLLQYGSFCTQLNRALTGIAVEQDKNTQEVFA<br>QVKQIYKTPPIKDFGGFNFSQILPDPSKPSKRSFIEDLLFNKVTLAD<br>AGFIKQYGDCLGDIAARDLICAQKFNGLTVLPPLLTDEMIAQYTSA<br>LLAGTITSGWTFGAGAALQIPFAMQMAYRFNGIGVTQNVLYENQK<br>LIANQFNSAIGKIQDSLSSTASALGKLQDVVNQNAQALNTLVKQLS<br>SNFGAISSVLNDILSRLDKVEAEVQIDRLITGRLQSLQTYVTQQLIR<br>AAEIRASANLAATKMSECVLGQSKRVDFCGKGYHLMSFPQSAPH<br>GVVFLHVTYVPAQEKNFTTAPAICHDGKAHFPREGVFVSNGTHWF<br>VTQRNFYEPQIITTDNTFVSGNCDVVIGIVNNTVYDPLQPELDSFKE<br>ELDKYFKNHTSPDVDLGDISGINASVVNIQKEIDRLNEVAKNLNES<br>LIDLQELGKYEQYIKWPWYIWLGFIAGLIAIVMVTIMLCCMTSCCS<br>CLKGCCSCGSCCKFDEDDSEPVLKGVKLHYT |
| SARS-CoV-2 spike protein ECD with an ***N501T substitution*** amino acid sequence (SEQ ID NO: 21) | QCVNLTTRTQLPPAYTNSFTRGVYYPDKVFRSSVLHSTQDLFLPFF<br>SNVTWFHAIHVSGTNGTKRFDNPVLPFNDGVYFASTEKSNIIRGWI<br>FGTTLDSKTQSLLIVNNATNVVIKVCEFQFCNDPFLGVYYHKNNKS<br>WMESEFRVYSSANNCTFEYVSQPFLMDLEGKQGNFKNLREFVFKNI<br>DGYFKIYSKHTPINLVRDLPQGFSALEPLVDLPIGINITRFQTLLA<br>LHRSYLTPGDSSSGWTAGAAAYYVGYLQPRTFLLKYNENGTITDA<br>VDCALDPLSETKCTLKSFTVEKGIYQTSNFRVQPTESIVRFPNITN<br>LCPFGEVFNATRFASVYAWNRKRISNCVADYSVLYNSASFSTFKC<br>YGVSPTKLNDLCFTNVYADSFVIRGDEVRQIAPGQTGKIADYNYK<br>LPDDFTGCVIAWNSNNLDSKVGGNYNYLYRLFRKSNLKPFERDIS<br>TEIYQAGSTPCNGVEGFNCYFPLQSYGFQPT***T***GVGYQPYRVVVLS<br>FELLHAPATVCGPKKSTNLVKNKCVNFNFNGLTGTGVLTESNKKF<br>LPFQQFGRDIADTTDAVRDPQTLEILDITPCSFGGVSVITPGTNTSN<br>QVAVLYQDVNCTEVPVAIHADQLTPTWRVYSTGSNVFQTRAGCL<br>IGAEHVNNSYECDIPIGAGICASYQTQTNSPRRARSVASQSIIAYTM<br>SLGAENSVAYSNNSIAIPTNFTISVTTEILPVSMTKTSVDCTMYICG<br>DSTECSNLLLQYGSFCTQLNRALTGIAVEQDKNTQEVFAQVKQIY<br>KTPPIKDFGGFNFSQILPDPSKPSKRSFIEDLLFNKVTLADAGFIKQY<br>GDCLGDIAARDLICAQKFNGLTVLPPLLTDEMIAQYTSALLAGTIT<br>SGWTFGAGAALQIPFAMQMAYRFNGIGVTQNVLYENQKLIANQF<br>NSAIGKIQDSLSSTASALGKLQDVVNQNAQALNTLVKQLSSNFGAI<br>SSVLNDILSRLDKVEAEVQIDRLITGRLQSLQTYVTQQLIRAAEIRA<br>SANLAATKMSECVLGQSKRVDFCGKGYHLMSFPQSAPHGVVFLH<br>VTYVPAQEKNFTTAPAICHDGKAHFPREGVFVSNGTHWFVTQRN<br>FYEPQIITTDNTFVSGNCDVVIGIVNNTVYDPLQPELDSFKEELDKY<br>FKNHTSPDVDLGDISGINASVVNIQKEIDRLNEVAKNLNESLIDLQE<br>LGKYEQYIK |
| SARS-CoV-2 spike protein S1 subunit with an ***N501T substitution*** amino acid sequence (SEQ ID NO: 22) | QCVNLTTRTQLPPAYTNSFTRGVYYPDKVFRSSVLHSTQDLFLPFF<br>SNVTWFHAIHVSGTNGTKRFDNPVLPFNDGVYFASTEKSNIIRGWI<br>FGTTLDSKTQSLLIVNNATNWIKVCEFQFCNDPFLGVYYHKNNK<br>SWMESEFRVYSSANNCTFEYVSQPFLMDLEGKQGNFKNLREFVFKN<br>IDGYFKIYSKHTPINLVRDLPQGFSALEPLVDLPIGINITRFQTLL<br>ALHRSYLTPGDSSSGWTAGAAAYYVGYLQPRTFLLKYNENGTITDA<br>VDCALDPLSETKCTLKSFTVEKGIYQTSNFRVQPTESIVRFPNITN<br>LCPFGEVFNATRFASVYAWNRKRISNCVADYSVLYNSASFSTFKC<br>YGVSPTKLNDLCFTNVYADSFVIRGDEVRQIAPGQTGKIADYNYK<br>LPDDFTGCVIAWNSNNLDSKVGGNYNYLYRLFRKSNLKPFERDIS<br>TEIYQAGSTPCNGVEGFNCYFPLQSYGFQPT***T***GVGYQPYRVVVL<br>SFELLHAPATVCGPKKSTNLVKNKCVNFNFNGLTGTGVLTESNKK<br>FLPFQQFGRDIADTTDAVRDPQTLEILDITPCSFGGVSVITPGTN<br>TSNQVAVLYQDVNCTEVPVAIHADQLTPTWRVYSTGSNVFQTRAG<br>CLIGAEHVNNSYECDIPIGAGICASYQTQTNSPRRAR |

TABLE 2-continued

Exemplary mutated sequences of SARS-CoV-2 antigens.

| SEQUENCE NAME (SEQ ID NO:) | AMINO ACID OR NUCLEIC ACID SEQUENCE |
|---|---|
| SARS-CoV-2 spike protein RBD-1 with an ***N501T substitution*** (RBD-5) amino acid sequence (SEQ ID NO: 23) | RVQPTESIVRFPNITNLCPFGEVFNATRFASVYAWNRKRISNCVAD YSVLYNSASFSTFKCYGVSPTKLNDLCFTNVYADSFVIRGDEVRQI APGQTGKIADYNYKLPDDFTGCVIAWNSNNLDSKVGGNYNYLYRLF RKSNLKPFERDISTEIYQAGSTPCNGVEGFNCYFPLQSYGFQPT***T*** GVGYQPYRVVVLSFELLHAPATVCGPKKSTNLVKNKCVNF |
| SARS-CoV-2 spike protein RBD-2 with an ***N501T substitution*** (RBD-6) amino acid sequence (SEQ ID NO: 24) | ITNLCPFGEVFNATRFASVYAWNRKRISNCVADYSVLYNSASFSTF KCYGVSPTKLNDLCFTNVYADSFVIRGDEVRQIAPGQTGKIADYN YKLPDDFTGCVIAWNSNNLDSKVGGNYNYLYRLFRKSNLKPFER DISTEIYQAGSTPCNGVEGFNCYFPLQSYGFQPT***T***GVGYQPYR VVVLSFELLHAPATVCGPKK |
| SARS-CoV-2 spike protein RBD-3 with an ***N501T substitution*** (RBD-7) amino acid sequence (SEQ ID NO: 25) | NITNLCPFGEVFNATRFASVYAWNRKRISNCVADYSVLYNSASFS TFKCYGVSPTKLNDLCFTNVYADSFVIRGDEVRQIAPGQTGKIAD YNYKLPDDFTGCVIAWNSNNLDSKVGGNYNYLYRLFRKSNLKPFE RDISTEIYQAGSTPCNGVEGFNCYFPLQSYGFQPT***T***GVGYQPYR VVVLSFELLHAPATV |
| SARS-CoV-2 spike protein RBD-4 with an (RBD-8) amino acid sequence (SEQ ID NO: 26) | RVQPTESIVRFPNITNLCPFGEVFNATRFASVYAWNRKRISNCVAD YSVLYNSASFSTFKCYGVSPTKLNDLCFTNVYADSFVIRGDEVRQI APGQTGKIADYNYKLPDDFTGCVIAWNSNNLDSKVGGNYNYLYRLF RKSNLKPFERDISTEIYQAGSTPCNGVEGFNCYFPLQSYGFQPT***T*** GVGYQPYRVVVLSFELLHAPATVCGPKK |
| SARS-CoV-2 spike protein RBD-8 coding sequence (SEQ ID NO: 27) | AGAGTCCAACCAACAGAATCTATTGTTAGATTTCCTAATATTACA AACTTGTGCCCTTTTGGTGAAGTTTTTAACGCCACCAGATTTGCA TCTGTTTATGCTTGGAACAGGAAGAGAATCAGCAACTGTGTTGCT GATTATTCTGTCCTATATAATTCCGCATCATTTTCCACTTTTAAG TGTTATGGAGTGTCTCCTACTAAATTAAATGATCTCTGCTTTACT AATGTCTATGCAGATTCATTTGTAATTAGAGGTGATGAAGTCAGA CAAATCGCTCCAGGGCAAACTGGAAAGATTGCTGATTATAATTAT AATTACCAGATGATTTTACAGGCTGCGTTATAGCTTGGAACTCTA AACAATCTTGATTCTAAGGTTGGTGGTAATTATAATTACCTGTAT AGATTGTTTAGGAAGTCTAATCTCAAACCTTTTGAGAGAGATATT TCAACTGAAATCTATCAGGCCGGTAGCACACCTTGTAATGGTGTT GAAGGTTTTAATTGTTACTTTCCTTTACAATCATATGGTTTCCAA CCCACTACTGGTGTTGGTTACCAACCATACAGAGTAGTAGTACTT TCTTTTGAACTTCTACATGCACCAGCAACTGTTTGTGGACCTAAA AAG |

In particular embodiments, the therapeutic nucleic acid encodes a functional derivative of the S protein of coronavirus SARS-CoV-2. In particular embodiments, the encoded functional derivative of the S protein comprises an amino acid substitution N501T. In particular embodiments, the encoded functional derivative of the S protein comprises an amino acid sequence of SEQ ID NO: 20.

In particular embodiments, the therapeutic nucleic acid encodes a functional derivative of the ectodomain of the S protein of coronavirus SARS-CoV-2. In particular embodiments, the encoded functional derivative of the S protein ectodomain comprises an amino acid substitution N501T. In particular embodiments, the encoded functional derivative of the S protein ectodomain comprises an amino acid sequence of SEQ ID NO: 21.

In particular embodiments, the therapeutic nucleic acid encodes a functional derivative of the 51 subunit the S protein of coronavirus SARS-CoV-2. In particular embodiments, the encoded functional derivative of the S protein 51 subunit comprises an amino acid substitution N501T. In particular embodiments, the encoded functional derivative of the S protein 51 subunit comprises an amino acid sequence of SEQ ID NO: 22.

In particular embodiments, the therapeutic nucleic acid encodes a functional derivative of the receptor binding domain (RBD) sequence of the S protein of coronavirus SARS-CoV-2. In particular embodiments, the encoded functional derivative of the S protein RBD sequence comprises an amino acid substitution N501T. In particular embodiments, the encoded functional derivative of the S protein RBD sequence comprises an amino acid sequence of SEQ ID NO: 23, SEQ ID NO: 24, SEQ ID NO: 25, or SEQ ID NO:26. In particular embodiments, the therapeutic nucleic acid encoding a functional derivative of the RBD sequence of the S protein of coronavirus SARS-CoV-2 comprises a DNA coding sequence of SEQ ID NO:27. In particular embodiments, the therapeutic nucleic acid encoding a functional derivative of the RBD sequence of the S protein of coronavirus SARS-CoV-2 comprises a RNA sequence transcribed from the DNA coding sequence of SEQ D NO:27. In particular embodiments, the RNA sequence is in vitro transcribed. In particular embodiments, the therapeutic nucleic acid is an mRNA molecule.

Without being bound by the theory, it is contemplated that in the coronavirus spike structure, three 51 heads sit on top of a trimeric S2 stalk. Between the two major 51 domains, S1-CTD is located at the very top of the spike, whereas S1-NTD directly contacts and structurally constrains S2. Accordingly, in some embodiments, the therapeutic nucleic acid of the present disclosure encodes a functional derivative of the S protein. In some embodiments, the therapeutic nucleic acid encodes a fusion protein comprising an S protein or a fragment thereof fused to a trimmerization peptide, such that the fusion protein is capable of forming a trimeric complex comprising three copies of the S protein or fragment thereof. In some embodiments, the therapeutic nucleic acid encodes a fusion protein comprising an ectodomain of the S protein fused to a trimmerization peptide, wherein the fusion protein is capable of forming a trimeric complex comprising three copies of the ectodomain. In some embodiments, the therapeutic nucleic acid encodes a fusion protein comprising a RBD of the S protein fused to a trimmerization peptide, wherein the fusion protein is capable of forming a trimeric complex comprising three copies of the RBD. In some embodiments, the therapeutic nucleic acid encodes a fusion protein comprising a S1-CTD fused to a trimmerization peptide wherein the fusion protein is capable of forming a trimeric complex comprising three copies of the S1-CTD. In some embodiments, the S protein or fragment thereof is fused to a trimmerization peptide via a peptidic linker. Table 3 shows exemplary trimmerization peptide and linker peptide that can be used in connection with the present disclosure, and sequences of fusion proteins.

TABLE 3

Exemplary sequences of linker peptides, trimmerization peptides, and SARS-CoV-2 antigens.

| SEQUENCE NAME (SEQ ID NO:) | AMINO ACID OR NUCLEIC ACID SEQUENCE |
|---|---|
| (G3S)2 linker peptide amino acid sequence (SEQ ID NO: 28) | GGGSGGGS |
| (G35)2 linker peptide coding sequence (SEQ ID NO: 29) | GGAGGAGGAAGTGGAGGAGGAAGT |
| Trimmerization peptide amino acid sequence (SEQ ID NO: 30) | GYIPEAPRDGQAYVRKDGEWVLLS<br>TFLG |

TABLE 3-continued

Exemplary sequences of linker peptides, trimmerization peptides, and SARS-CoV-2 antigens.

| SEQUENCE NAME (SEQ ID NO:) | AMINO ACID OR NUCLEIC ACID SEQUENCE |
|---|---|
| Trimmerization peptide coding sequence (SEQ ID NO: 31) | GGCTATATTCCGGAAGCGCCGCGC<br>GATGGCCAGGCGTATGTGCGCAAA<br>GATGGCGAATGGGTGCTGCTGAGC<br>ACCTTTCTGGGC |
| SARS-CoV-2 spike protein ECD with C terminal fusion of a (G3S)2 linker and a trimmerization peptide amino acid sequence (SEQ ID NO: 32) | QCVNLTTRTQLPPAYTNSFTRGVY<br>YPDKVFRSSVLHSTQDLFLPFFSN<br>VTWFHAIHVSGTNGTKRFDNPVLP<br>FNDGVYFASTEKSMIRGWIFGTTL<br>DSKTQSLLIVNNATNVVIKVCEFQ<br>FCNDPFLGVYYHKNNKSWMESEFR<br>VYSSANNCTFEYVSQPFLMDLEGK<br>QGNFKNLREFVFKNIDGYFKIYSK<br>HTPINLVRDLPQGFSALEPLVDLP<br>IGINITRFQTLLALHRSYLTPGDS<br>SSGWTAGAAAYYVGYLQPRTFLLK<br>YNENGTITDAVDCALDPLSETKCT<br>LKSFTVEKGIYQTSNFRVQPTESI<br>VRFPNITNLCPFGEVFNATRFASV<br>YAWNRKRISNCVADYSVLYNSASF<br>STFKCYGVSPTKLNDLCFTNVYAD<br>SFVIRGDEVRQIAPGQTGKIADYN<br>YKLPDDFTGCVIAWNSNNLDSKVG<br>GNYNYLYRLFRKSNLKPFERDIST<br>EIYQAGSTPCNGVEGFNCYFPLQS<br>YGFQPTNGVGYQPYRVVVLSFELL<br>HAPATVCGPKKSTNLVKNKCVNFN<br>FNGLTGTGVLTESNKKFLPFQQFG<br>RDIADTTDAVRDPQTLEILDITPC<br>SFGGVSVITPGTNTSNQVAVLYQD<br>VNCTEVPVAIHADQLTPTWRVYST<br>GSNVFQTRAGCLIGAEHVNNSYEC<br>DIPIGAGICASYQTQTNSPRRARS<br>VASQSIIAYTMSLGAENSVAYSNN<br>SIAIPTNFTISVTTEILPVSMTKT<br>SVDCTMYICGDSTECSNLLLQYGS<br>FCTQLNRALTGIAVEQDKNTQEVF<br>AQVKQIYKTPPIKDFGGFNFSQIL<br>PDPSKPSKRSFIEDLLFNKVTLAD<br>AGFIKQYGDCLGDIAARDLICAQK<br>FNGLTVLPPLLTDEMIAQYTSALL<br>AGTITSGWTFGAGAALQIPFAMQM<br>AYRFNGIGVTQNVLYENQKLIANQ<br>FNSAIGKIQDSLSSTASALGKLQD<br>VVNQNAQALNTLVKQLSSNFGAIS<br>SVLNDILSRLDKVEAEVQIDRLIT<br>GRLQSLQTYVTQQLIRAAEIRASA<br>NLAATKMSECVLGQSKRVDFCGKG<br>YHLMSFPQSAPHGVVFLHVTYVP<br>AQEKNFTTAPAICHDGKAHFPREG<br>VFVSNGTHWFVTQRNFYEPQIIT<br>TDNTFVSGNCDVVIGIVNNTVYDP<br>LQPELDSFKEELDKYFKNHTSPDV<br>DLGDISGINASVVNIQKEIDRLNE<br>VAKNLNESLIDLQELGKYEQYIKG<br>GGSGGGSG*YIPEAPRDGQAYVRKD*<br>*GEWVLLSTFLG* |
| SARS-CoV-2 spike protein ECD with C terminal fusion of a (G3S)2 linker and a trimmerization peptide coding sequence (SEQ ID NO: 33) | CAGTGTGTTAATCTTACAACCAGA<br>ACTCAATTACCCCCTGCATACACT<br>AATTCTTTCACACGTGGTGTTTAT<br>TACCCTGACAAAGTTTTCAGATCC<br>TCAGTTTTACATTCAACTCAGGAC<br>TTGTTCTTACCTTTCTTTTCCAAT<br>GTTACTTGGTTCCATGCTATACAT<br>GTCTCTGGGACCAATGGTACTAAG<br>AGGTTTGATAACCCTGTCCTACCA<br>TTTAATGATGGTGTTTATTTTGCT<br>TCCACTGAGAAGTCTAACATAATA<br>AGAGGCTGGATTTTTGGTACTACT |

TABLE 3-continued

Exemplary sequences of linker peptides, trimmerization peptides, and SARS-CoV-2 antigens.

| SEQUENCE NAME (SEQ ID NO:) | AMINO ACID OR NUCLEIC ACID SEQUENCE |
|---|---|
| | TTAGATTCGAAGACCCAGTCCCTA |
| | CTTATTGTTAATAACGCTACTAAT |
| | GTTGTTATTAAAGTCTGTGAATTT |
| | CAATTTTGTAATGATCCATTTTTG |
| | GGTGTTTATTACCACAAAAACAAC |
| | AAAAGTTGGATGGAAAGTGAGTTC |
| | AGAGTTTATTCTAGTGCGAATAAT |
| | TGCACTTTTGAATATGTCTCTCAG |
| | CCTTTTCTTATGGACCTTGAAGGA |
| | AAACAGGGTAATTTCAAAAATCTT |
| | AGGGAATTTGTGTTTAAGAATATT |
| | GATGGTTATTTTAAAATATATTCT |
| | AAGCACACGCCTATTAATTTAGTG |
| | CGTGATCTCCCTCAGGGTTTTTCG |
| | GCTTTAGAACCATTGGTAGATTTG |
| | CCAATAGGTATTAACATCACTAGG |
| | TTTCAAACTTTACTTGCTTTACAT |
| | AGAAGTTATTTGACTCCTGGTGAT |
| | TCTTCTTCAGGTTGGACAGCTGGT |
| | GCTGCAGCTTATTATGTGGGTTAT |
| | CTTCAACCTAGGACTTTTCTATTA |
| | AAATATAATGAAAATGGAACCATT |
| | ACAGATGCTGTAGACTGTGCACTT |
| | GACCCTCTCTCAGAAACAAAGTGT |
| | ACGTTGAAATCCTTCACTGTAGAA |
| | AAAGGAATCTATCAAACTTCTAAC |
| | TTTAGAGTCCAACCAACAGAATCT |
| | ATTGTTAGATTTCCTAATATTACA |
| | AACTTGTGCCCTTTTGGTGAAGTT |
| | TTTAACGCCACCAGATTTGCATCT |
| | GTTTATGCTTGGAACAGGAAGAGA |
| | ATCAGCAACTGTGTTGCTGATTAT |
| | TCTGTCCTATATAATTCCGCATCA |
| | TTTTCCACTTTTAAGTGTTATGGA |
| | GTGTCTCCTACTAAATTAAATGAT |
| | CTCTGCTTTACTAATGTCTATGCA |
| | GATTCATTTGTAATTAGAGGTGAT |
| | GAAGTCAGACAAATCGCTCCAGGG |
| | CAAACTGGAAAGATTGCTGATTAT |
| | AATTATAAATTACCAGATGATTTT |
| | ACAGGCTGCGTTATAGCTTGGAAC |
| | TCTAACAATCTTGATTCTAAGGTT |
| | GGTGGTAATTATAATTACCTGTAT |
| | AGATTGTTTAGGAAGTCTAATCTC |
| | AAACCTTTTGAGAGAGATATTTCA |
| | ACTGAAATCTATCAGGCCGGTAGC |
| | ACACCTTGTAATGGTGTTGAAGGT |
| | TTTAATTGTTACTTTCCTTTACAA |
| | TCATATGGTTTCCAACCCACTAAT |
| | GGTGTTGGTTACCAACCATACAGA |
| | GTAGTAGTACTTTCTTTTGAACTT |
| | CTACATGCACCAGCAACTGTTTGT |
| | GGACCTAAAAAGTCTACTAATTTG |
| | GTTAAAAACAAATGTGTCAATTTC |
| | AACTTCAATGGTTTAACAGGCACA |
| | GGTGTTCTTACTGAGTCTAACAAA |
| | AAGTTTCTGCCTTTCCAACAATTT |
| | GGCAGAGACATTGCTGACACTACT |
| | GATGCTGTCCGTGATCCACAGACA |
| | CTTGAGATTCTTGACATTACACCA |
| | TGTTCTTTTGGTGGTGTCAGTGTT |
| | ATAACACCAGGAACAAATACTTCT |
| | AACCAGGTTGCTGTTCTTTATCAG |
| | GATGTTAACTGCACAGAAGTCCCT |
| | GTTGCTATTCATGCAGATCAACTT |
| | ACTCCTACTTGGCGTGTTTATTCT |
| | ACAGGTTCTAATGTTTTTCAAACA |
| | CGTGCAGGCTGTTTAATAGGGGCT |
| | GAACATGTCAACAACTCATATGAG |
| | TGTGACATACCCATTGGTGCAGGT |
| | ATATGCGCTAGTTATCAGACTCAG |
| | ACTAATTCTCCTCGGCGGGCACGT |

TABLE 3-continued

Exemplary sequences of linker peptides, trimmerization peptides, and SARS-CoV-2 antigens.

| SEQUENCE NAME (SEQ ID NO:) | AMINO ACID OR NUCLEIC ACID SEQUENCE |
|---|---|
| | AGTGTAGCTAGTCAATCCATCATT |
| | GCCTACACTATGTCACTTGGTGCA |
| | GAAAATTCAGTTGCTTACTCTAAT |
| | AACTCTATTGCCATACCCACAAAT |
| | TTTACTATTAGTGTTACCACAGAA |
| | ATTCTACCAGTGTCTATGACCAAG |
| | ACATCAGTAGATTGTACAATGTAC |
| | ATTTGTGGTGATTCAACTGAATGC |
| | AGCAATCTTTTGTTGCAATATGGC |
| | AGTTTTTGTACACAATTAAACCGT |
| | GCTTTAACTGGAATAGCTGTTGAA |
| | CAAGACAAAAACACCCAAGAAGTT |
| | TTTGCACAAGTCAAACAAATTTAC |
| | AAAACACCACCAATTAAAGATTTT |
| | GGTGGTTTTAATTTTTCACAAATA |
| | TTACCAGATCCATCAAAACCAAGC |
| | AAGAGGTCATTTATTGAAGATCTA |
| | CTTTTCAACAAAGTGACACTTGCA |
| | GATGCTGGCTTCATCAAACAATAT |
| | GGTGATTGCCTTGGTGATATTGCT |
| | GCTAGAGACCTCATTTGTGCACAA |
| | AAGTTTAACGGCCTTACTGTTTTG |
| | CCACCTTTGCTCACAGATGAAATG |
| | ATTGCTCAATACACTTCTGCACTG |
| | TTAGCGGGTACAATCACTTCTGGT |
| | TGGACCTTTGGTGCAGGTGCTGCA |
| | TTACAAATACCATTTGCTATGCAA |
| | ATGGCTTATAGGTTTAATGGTATT |
| | GGAGTTACACAGAATGTTCTCTAT |
| | GAGAACCAAAAATTGATTGCCAAC |
| | CAATTTAATAGTGCTATTGGCAAA |
| | ATTCAAGACTCACTTTCTTCCACA |
| | GCAAGTGCACTTGGAAAACTTCAA |
| | GATGTGGTCAACCAAAATGCACAA |
| | GCTTTAAACACGCTTGTTAAACAA |
| | CTTAGCTCCAATTTTGGTGCAATT |
| | TCAAGTGTTTTAAATGATATCCTT |
| | TCACGTCTTGACAAAGTTGAGGCT |
| | GAAGTGCAAATTGATAGGTTGATC |
| | ACAGGCAGACTTCAAAGTTTGCAG |
| | ACATATGTGACTCAACAATTAATT |
| | AGAGCTGCAGAAATCAGAGCTTCT |
| | GCTAATCTTGCTGCTACTAAAATG |
| | TCAGAGTGTGTACTTGGACAATCA |
| | AAAAGAGTTGATTTTTGTGGAAAG |
| | GGCTATCATCTTATGTCCTTCCCT |
| | CAGTCAGCACCTCATGGTGTAGTC |
| | TTCTTGCATGTGACTTATGTCCCT |
| | GCACAAGAAAAGAACTTCACAACT |
| | GCTCCTGCCATTTGTCATGATGGA |
| | AAAGCACACTTTCCTCGTGAAGGT |
| | GTCTTTGTTTCAAATGGCACACAC |
| | TGGTTTGTAACACAAAGGAATTTT |
| | TATGAACCACAAATCATTACTACA |
| | GACAACACATTTGTGTCTGGTAAC |
| | TGTGATGTTGTAATAGGAATTGTC |
| | AACAACACAGTTTATGATCCTTTG |
| | CAACCTGAATTAGACTCATTCAAG |
| | GAGGAGTTAGATAAATATTTTAAG |
| | AATCATACATCACCAGATGTTGAT |
| | TTAGGTGACATCTCTGGCATTAAT |
| | GCTTCAGTTGTAAACATTCAAAAA |
| | GAAATTGACCGCCTCAATGAGGTT |
| | GCCAAGAATTTAAATGAATCTCTC |
| | ATCGATCTCCAAGAACTTGGAAAG |
| | TATGAGCAGTATATAAAAGGAGGA |
| | GGAAGTGGAGGAGGAAGTGGCTAT |
| | ATTCCGGAAGCGCCGCGCGATGGC |
| | CAGGCGTATGTGCGCAAAGATGGC |
| | GAATGGGTGCTGCTGAGCACCTTT |
| | CTGGGC |

TABLE 3-continued

Exemplary sequences of linker peptides, trimmerization peptides, and SARS-CoV-2 antigens.

| SEQUENCE NAME (SEQ ID NO:) | AMINO ACID OR NUCLEIC ACID SEQUENCE |
|---|---|
| SARS-CoV-2 spike protein RBD-2 with C-terminal fusion of a (G3S)2 linker and a trimmerization peptide amino acid sequence (SEQ ID NO: 34) | NITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYNYLYRLFRKSNLKPFERDISYEIYQAGSTPCNGVEGFNCYFPLQSYGFQPTNGVGYQPYRVVVLSFELLHAPATVCGPKKGGGSGGGSG*YIPEAPRDGQAYVRKDGEWVLLSTFLG* |
| SARS-CoV-2 spike protein RBD-2 with C-terminal fusion of a (G3S)2 linker and a trimmerization peptide coding sequence (SEQ ID NO: 35) | AATATTACAAACTTGTGCCCTTTTGGTGAAGTTTTTAACGCCACCAGATTTGCATCTGTTTATGCTTGGAACAGGAAGAGAATCAGCAACTGTGTTGCTGATTATTCTGTCCTATATAATTCCGCATCATTTTCCACTTTTAAGTGTTATGGAGTGTCTCCTACTAAATTAAATGATCTCTGCTTTACTAATGTCTATGCAGATTCATTTGTAATTAGAGGTGATGAAGTCAGACAAATCGCTCCAGGGCAAACTGGAAAGATTGCTGATTATAATTATAAATTACCAGATGATTTTACAGGCTGCGTTATAGCTTGGAACTCTAACAATCTTGATTCTAAGGTTGGTGGTAATTATAATTACCTGTATAGATTGTTTAGGAAGTCTAATCTCAAACCTTTTGAGAGAGATATTTCAACTGAAATCTATCAGGCCGGTAGCACACCTTGTAATGGTGTTGAAGGTTTTAATTGTTACTTTCCTTTACAATCATATGGTTTCCAACCCACTAATGGTGTTGGTTACCAACCATACAGAGTAGTAGTACTTTCTTTTGAACTTCTACATGCACCAGCAACTGTTTGTGGACCTAAAAAGGGAGGAGGAAGTGGAGGAGGAAGTGGCTATATTCCGGAAGCGCCGCGCGATGGCCAGGCGTATGTGCGCAAAGATGGCGAATGGGTGCTGCTGAGCACCTTTCTGGGC |

In some embodiments, the therapeutic nucleic acid encodes a fusion protein comprising the S protein of the coronavirus SARS-CoV-2 or a functional derivative thereof fused to a trimmerization peptide. In some embodiments, the fusion between the S protein and the trimmerization peptide is via a peptide linker. In specific embodiments, the S protein or functional derivative thereof comprises the amino acid sequence of SEQ ID NO:2 or SEQ ID NO:20. In specific embodiments, the peptide linker comprises the amino acid sequence of SEQ ID NO:28. In some embodiments, the trimmerization peptide comprises the amino acid sequence of SEQ ID NO:30.

In some embodiments, the therapeutic nucleic acid encodes a fusion protein comprising the ectodomain (ECD) of S protein of the coronavirus SARS-CoV-2 or a functional derivative thereof fused to a trimmerization peptide. In some embodiments, the fusion between the ectodomain of the S protein and the trimmerization peptide is via a peptide linker. In specific embodiments, the ectodomain of S protein or functional derivative thereof comprises the amino acid sequence of SEQ ID NO:4 or SEQ ID NO:21. In specific embodiments, the peptide linker comprises the amino acid sequence of SEQ ID NO:28. In some embodiments, the trimmerization peptide comprises the amino acid sequence of SEQ ID NO:30.

In some embodiments, the therapeutic nucleic acid encodes a fusion protein comprising an ectodomain of the S protein of the coronavirus SARS-CoV-2 or a functional derivative thereof fused to a trimmerization peptide. In particular embodiments, the fusion protein has an amino acid sequence of SEQ ID NO:32. In particular embodiments, the therapeutic nucleic acid encodes a fusion protein comprising an ectodomain of the S protein of the SARS-CoV-2 fused to a trimmerization peptide, wherein the nucleic acid comprises a DNA coding sequence of SEQ ID NO:33. In particular embodiments, the therapeutic nucleic acid encodes a fusion protein comprising an ectodomain of the S protein of the SARS-CoV-2 fused to a trimmerization peptide, wherein the nucleic acid comprises a RNA sequence transcribed from the DNA coding sequence of SEQ ID NO:33. In some embodiments, the RNA sequence is in vitro transcribed. In particular embodiments, the nucleic acid molecule is an mRNA molecule.

In some embodiments, the therapeutic nucleic acid encodes a fusion protein comprising the S1 subunit of the S protein of the coronavirus SARS-CoV-2 or a functional derivative thereof fused to a trimmerization peptide. In some embodiments, the fusion between the ectodomain of the S protein and the trimmerization peptide is via a peptide linker. In specific embodiments, the S1 subunit of S protein or functional derivative thereof comprises the amino acid sequence of SEQ ID NO:6 or SEQ ID NO:22. In specific embodiments, the peptide linker comprises the amino acid sequence of SEQ ID NO:28. In some embodiments, the trimmerization peptide comprises the amino acid sequence of SEQ ID NO:30.

In some embodiments, the therapeutic nucleic acid encodes a fusion protein comprising a receptor binding domain (RBD) sequence of the S protein of the coronavirus SARS-CoV-2 or a functional derivative thereof fused to a trimmerization peptide. In some embodiments, the fusion between the RBD sequence of the S protein and the trimmerization peptide is via a peptide linker. In specific embodiments, the RBD sequence of S protein or functional derivative thereof comprises the amino acid sequence selected from SEQ ID NOS:8, 10, 12, 14, 23, 24, 25 and 26. In specific embodiments, the peptide linker comprises the amino acid sequence of SEQ ID NO:28. In some embodiments, the trimmerization peptide comprises the amino acid sequence of SEQ ID NO:30.

In particular embodiments, the therapeutic nucleic acid encodes a fusion protein comprising a RBD sequence of the S protein of the SARS-CoV-2 fused to a trimmerization peptide, wherein the fusion protein has an amino acid sequence of SEQ ID NO:34. In particular embodiments, the therapeutic nucleic acid encodes a fusion protein comprising the RBD of the S protein of the SARS-CoV-2 fused to a trimmerization peptide, wherein the nucleic acid comprises a DNA coding sequence of SEQ ID NO:35. In particular embodiments, the therapeutic nucleic acid encodes a fusion protein comprising the RBD of the S protein of the SARS-CoV-2 fused to a trimmerization peptide, wherein the nucleic acid comprises a RNA sequence transcribed from the DNA coding sequence of SEQ ID NO:35. In some embodiments, the RNA sequence is in vitro transcribed. In particular embodiments, the nucleic acid molecule is an mRNA molecule.

In some embodiments, the therapeutic nucleic acid encodes a fusion protein comprising a receptor binding motif (RBM) sequence of the S protein of the coronavirus SARS-CoV-2 or a functional derivative thereof fused to a trimmerization peptide. In some embodiments, the fusion between the RBM sequence of the S protein and the trimmerization peptide is via a peptide linker. In specific embodiments, the RBM sequence of S protein or functional derivative thereof comprises the amino acid sequence of SEQ ID NO:16. In specific embodiments, the peptide linker comprises the amino acid sequence of SEQ ID NO:28. In some embodiments, the trimmerization peptide comprises the amino acid sequence of SEQ ID NO:30.

Without being bound by the theory, it is contemplated that the N protein of coronavirus comprises an N-terminal domain (N-NTD) and a C-terminal domain (N-CTD), which are interspersed by several intrinsically disordered regions (IDRs). For example, SARS-CoV N protein has three IDRs at residues 1-44, 182-247, and 366-422, respectively, and an N-NTD located at residues 45-181, and an N-CTD located at residues 248-365.

Accordingly, in some embodiments, the therapeutic nucleic acid of the present disclosure encodes the coronavirus N protein, or an immunogenic fragment of the N protein, or a functional derivative of the N protein or the immunogenic fragment thereof. In specific embodiments, the therapeutic nucleic acid encodes the full-length N protein. In specific embodiments, the therapeutic nucleic acid encodes one or more immunogenic fragments of the N protein selected from the N-NTD, N-CTD and IDRs.

In particular embodiments, the therapeutic nucleic acid of the present disclosure encodes the nucleocapsid (N) protein of coronavirus SARS-CoV-2, and wherein the N protein has an amino acid sequence of SEQ ID NO:18. In particular embodiments, the therapeutic nucleic acid of the present disclosure encodes the N protein of coronavirus SARS-CoV-2, and wherein the therapeutic nucleic acid comprises a DNA coding sequence of SEQ ID NO:19. In particular embodiments, the therapeutic nucleic acid of the present disclosure encodes the N protein of coronavirus SARS-CoV-2, and wherein the therapeutic nucleic acid comprises a RNA sequence transcribed from the DNA coding sequence of SEQ ID NO:19. In some embodiments, the RNA sequence is in vitro transcribed. In particular embodiments, the nucleic acid molecule is an mRNA molecule.

Without being bound by the theory, it is contemplated that a fusion protein comprising a viral peptide or polypeptide fused to an immunoglobulin Fc region can enhance immunogenicity of the viral peptide or polypeptide. Accordingly, in some embodiments, the therapeutic nucleic acid molecule of the present disclosure encodes a fusion protein comprising a viral peptide or protein derived from a coronavirus fused with an Fc region of an immunoglobulin. In particular embodiments, the viral peptide or protein is one or more selected from (a) the N protein, (b) the M protein, (c) the E protein, (d) the S protein, (e) the HE protein, (f) an immunogenic fragment of any one of (a) to (e), and (g) a functional derivative of any one of (a) to (f). In particular embodiments, the immunoglobulin is human immunoglobulin (Ig). In particular embodiments, the immunoglobulin is human IgG, IgA, IgD, IgE, or IgM. In particular embodiments, the immunoglobulin is human IgG1, IgG2, IgG3 or IgG4. In some embodiments, the immunoglobulin Fc is fused to the N terminus of the viral peptide or polypeptide. In other embodiments, the immunoglobulin Fc is fused to the C terminus of the viral peptide or polypeptide.

Without being bound by theory, it is contemplated that a signal peptide can mediate transportation of a polypeptide fused thereto to particular locations of a cell. Accordingly, in some embodiments, the therapeutic nucleic acid molecule of the present disclosure encodes a fusion protein comprising a viral peptide or protein fused to a signal peptide. In particular embodiments, the viral peptide or protein is one or more selected from (a) the N protein, (b) the M protein, (c) the E protein, (d) the S protein, (e) the HE protein, (f) an immunogenic fragment of any one of (a) to (e), and (g) a functional derivative of any one of (a) to (f). In some embodiments, the signal peptide is fused to the N terminus of the viral peptide or polypeptide. In other embodiments, the signal peptide is fused to the C terminus of the viral peptide or polypeptide. Table 4 shows exemplary sequences for signal peptides that can be use in connection with the present disclosure, and exemplary SARS-CoV-2 antigenic sequences comprising the signal peptides.

TABLE 4

Exemplary sequences of signal peptides and SARS-CoV-2 antigens.

| SEQUENCE NAME (SEQ ID NO:) | AMINO ACID OR NUCLEIC ACID SEQUENCE |
|---|---|
| SARS-CoV-2 spike protein native signal peptide amino acid sequence (SEQ ID NO: 36) | MFVFLVLLPLVSS |
| SARS-CoV-2 spike protein native signal peptide coding sequence (SEQ ID NO: 37) | ATGTTTGTTTTTCTTGTTTTATTG CCATTAGTCTCTAGT |
| Human IgE signal peptide amino acid sequence (SEQ ID NO: 38) | MDWTWILFLVAAATRVHS |
| Human IgE signal peptide coding sequence (SEQ ID NO: 39) | ATGGACTGGACCTGGATTCTCTTC TTGGTGGCAGCAGCCACGCGAGTC CACTCC |
| SARS-CoV-2 spike protein without native signal peptide amino acid sequence (SEQ ID NO: 40) | QCVNLTTRTQLPPAYTNSFTRGVY YPDKVFRSSVLHSTQDLFLPFFSN VTWFHAIHVSGTNGTKRFDNPVLP FNDGVYFASTEKSNIIRGWIFGTT LDSKTQSLLIVNNATNVVIKVCEF QFCNDPFLGVYYHKNNKSWMESE FRVYSSANNCTFEYVSQPFLMDLE GKQGNFKNLREFVFKNIDGYFKIY SKHTPINLVRDLPQGFSALEPLVD LPIGINITRFQTLLALHRSYLTP GDSSSGWTAGAAAYYVGYLQPRTF LLKYNENGTITDAVDCALDPLSET KCTLKSFTVEKGIYQTSNFRVQPT ESIVRFPNITNLCPFGEVFNATRF ASVYAWNRKRISNCVADYSVLYNS ASFSTFKCYGVSPTKLNDLCFTNV YADSFVIRGDEVRQIAPGQTGKIA DYNYKLPDDFTGCVIAWNSNNLDS KVGGNYNYLYRLFRKSNLKPFERD ISTEIYQAGSTPCNGVEGFNCYFP LQSYGFQPTNGVGYQPYRVVVLSF ELLHAPATVCGPKKSTNLVKNKCV NFNFNGLTGTGVLTESNKKFLPFQ QFGRDIADTTDAVRDPQTLEILDI TPCSFGGVSVITPGTNTSNQVAVL |

TABLE 4-continued

Exemplary sequences of signal peptides and SARS-CoV-2 antigens.

| SEQUENCE NAME (SEQ ID NO:) | AMINO ACID OR NUCLEIC ACID SEQUENCE |
|---|---|
| | YQDVNCTEVPVAIHADQLTPTWRV<br>YSTGSNVFQTRAGCLIGAEHVNNS<br>YECDIPIGAGICASYQTQTNSPRR<br>ARSVASQSIIAYTMSLGAENSVAY<br>SNNSIAIPTNFTISVTTEILPVSM<br>TKTSVDCTMYICGDSTECSNLLLQ<br>YGSFCTQLNRALTGIAVEQDKNTQ<br>EVFAQVKQIYKTPPIKDFGGFNFS<br>QILPDPSKPSKRSFIEDLLFNKVT<br>LADAGFIKQYGDCLGDIAARDLIC<br>AQKFNGLTVLPPLLTDEMIAQYTS<br>ALLAGTITSGWTFGAGAALQIPFA<br>MQMAYRFNGIGVTQNVLYENQKLI<br>ANQFNSAIGKIQDSLSSTASALGK<br>LQDVVNQNAQALNTLVKQLSSNFG<br>AISSVLNDILSRLDKVEAEVQIDR<br>LITGRLQSLQTYVTQQLIRAAEIR<br>ASANLAATKMSECVLGQSKRVDFC<br>GKGYHLMSFPQSAPHGVVFLHVT<br>YVPAQEKNFTTAPAICEIDGKAHF<br>PREGVFVSNGTHWFVTQRNFYEP<br>QIITTDNTFVSGNCDVVIGIVNNT<br>VYDPLQPELDSFKEELDKYFKNHT<br>SPDVDLGDISGINASVVNIQKEID<br>RLNEVAKNLNESLIDLQELGKYEQ<br>YIKWPWYIWLGFIAGLIAIVMVTI<br>MLCCMTSCCSCLKGCCSCGSCCKF<br>DEDDSEPVLKGVKLHYT |
| SARS-CoV-2 spike protein without native signal peptide coding sequence (SEQ ID NO: 41) SARS-CoV-2 | ATGTTTGTTTTTCTTGTTTTATTG<br>CCATTAGTCTCTAGTCAGTGTGTT<br>AATCTTACAACCAGAACTCAATTA<br>CCCCCTGCATACACTAATTCTTTC<br>ACACGTGGTGTTTATTACCCTGAC<br>AAAGTTTTCAGATCCTCAGTTTTA<br>CATTCAACTCAGGACTTGTTCTTA<br>CCTTTCTTTTCCAATGTTACTTGG<br>TTCCATGCTATACATGTCTCTGGG<br>ACCAATGGTACTAAGAGGTTTGAT<br>AACCCTGTCCTACCATTTAATGAT<br>GGTGTTTATTTTGCTTCCACTGAG<br>AAGTCTAACATAATAAGAGGCTGG<br>ATTTTTGGTACTACTTTAGATTCG<br>AAGACCCAGTCCCTACTTATTGTT<br>AATAACGCTACTAATGTTGTTATT<br>AAAGTCTGTGAATTTCAATTTTGT<br>AATGATCCATTTTTGGGTGTTTAT<br>TACCACAAAAACAACAAAAGTTGG<br>ATGGAAAGTGAGTTCAGAGTTTAT<br>TCTAGTGCGAATAATTGCACTTTT<br>GAATATGTCTCTCAGCCTTTTCTT<br>ATGGACCTTGAAGGAAAACAGGGT<br>AATTTCAAAAATCTTAGGGAATTT<br>GTGTTTAAGAATATTGATGGTTAT<br>TTTAAAATATATTCTAAGCACACG<br>CCTATTAATTTAGTGCGTGATCTC<br>CCTCAGGGTTTTTCGGCTTTAGAA<br>CCATTGGTAGATTTGCCAATAGGT<br>ATTAACATCACTAGGTTTCAAACT<br>TTACTTGCTTTACATAGAAGTTAT<br>TTGACTCCTGGTGATTCTTCTTCA<br>GGTTGGACAGCTGGTGCTGCAGCT<br>TATTATGTGGGTTATCTTCAACCT<br>AGGACTTTTCTATTAAAATATAAT<br>GAAAATGGAACCATTACAGATGCT<br>GTAGACTGTGCACTTGACCCTCTC<br>TCAGAAACAAAGTGTACGTTGAAA<br>TCCTTCACTGTAGAAAAAGGAATC<br>TATCAAACTTCTAACTTTAGAGTC<br>CAACCAACAGAATCTATTGTTAGA<br>TTTCCTAATATTACAAACTTGTGC<br>CCTTTTGGTGAAGTTTTTAACGCC<br>ACCAGATTTGCATCTGTTTATGCT<br>TGGAACAGGAAGAGAATCAGCAAC<br>TGTGTTGCTGATTATTCTGTCCTA<br>TATAATTCCGCATCATTTTCCACT<br>TTTAAGTGTTATGGAGTGTCTCCT<br>ACTAAATTAAATGATCTCTGCTTT<br>ACTAATGTCTATGCAGATTCATTT<br>GTAATTAGAGGTGATGAAGTCAGA<br>CAAATCGCTCCAGGGCAAACTGGA<br>AAGATTGCTGATTATAATTATAAA<br>TTACCAGATGATTTTACAGGCTGC<br>GTTATAGCTTGGAACTCTAACAAT<br>CTTGATTCTAAGGTTGGTGGTAAT<br>TATAATTACCTGTATAGATTGTTT<br>AGGAAGTCTAATCTCAAACCTTTT<br>GAGAGAGATATTTCAACTGAAATC<br>TATCAGGCCGGTAGCACACCTTGT<br>AATGGTGTTGAAGGTTTTAATTGT<br>TACTTTCCTTTACAATCATATGGT<br>TTCCAACCCACTAATGGTGTTGGT<br>TACCAACCATACAGAGTAGTAGTA<br>CTTTCTTTTGAACTTCTACATGCA<br>CCAGCAACTGTTTGTGGACCTAAA<br>AAGTCTACTAATTTGGTTAAAAAC<br>AAATGTGTCAATTTCAACTTCAAT<br>GGTTTAACAGGCACAGGTGTTCTT<br>ACTGAGTCTAACAAAAAGTTTCTG<br>CCTTTCCAACAATTTGGCAGAGAC<br>ATTGCTGACACTACTGATGCTGTC<br>CGTGATCCACAGACACTTGAGATT<br>CTTGACATTACACCATGTTCTTTT<br>GGTGGTGTCAGTGTTATAACACCA<br>GGAACAAATACTTCTAACCAGGTT<br>GCTGTTCTTTATCAGGATGTTAAC<br>TGCACAGAAGTCCCTGTTGCTATT<br>CATGCAGATCAACTTACTCCTACT<br>TGGCGTGTTTATTCTACAGGTTCT<br>AATGTTTTTCAAACACGTGCAGGC<br>TGTTTAATAGGGGCTGAACATGTC<br>AACAACTCATATGAGTGTGACATA<br>CCCATTGGTGCAGGTATATGCGCT<br>AGTTATCAGACTCAGACTAATTCT<br>CCTCGGCGGGCACGTAGTGTAGCT<br>AGTCAATCCATCATTGCCTACACT<br>ATGTCACTTGGTGCAGAAAATTCA<br>GTTGCTTACTCTAATAACTCTATT<br>GCCATACCCACAAATTTTACTATT<br>AGTGTTACCACAGAAATTCTACCA<br>GTGTCTATGACCAAGACATCAGTA<br>GATTGTACAATGTACATTTGTGGT<br>GATTCAACTGAATGCAGCAATCTT<br>TTGTTGCAATATGGCAGTTTTTGT<br>ACACAATTAAACCGTGCTTTAACT<br>GGAATAGCTGTTGAACAAGACAAA<br>AACACCCAAGAAGTTTTTGCACAA<br>GTCAAACAAATTTACAAAACACCA<br>CCAATTAAAGATTTTGGTGGTTTT<br>AATTTTTCACAAATATTACCAGAT<br>CCATCAAAACCAAGCAAGAGGTCA<br>TTTATTGAAGATCTACTTTTCAAC<br>AAAGTGACACTTGCAGATGCTGGC<br>TTCATCAAACAATATGGTGATTGC<br>CTTGGTGATATTGCTGCTAGAGAC<br>CTCATTTGTGCACAAAAGTTTAAC<br>GGCCTTACTGTTTTGCCACCTTTG<br>CTCACAGATGAAATGATTGCTCAA<br>TACACTTCTGCACTGTTAGCGGGT<br>ACAATCACTTCTGGTTGGACCTTT<br>GGTGCAGGTGCTGCATTACAAATA<br>CCATTTGCTATGCAAATGGCTTAT<br>AGGTTTAATGGTATTGGAGTTACA<br>CAGAATGTTCTCTATGAGAACCAA<br>AAATTGATTGCCAACCAATTTAAT<br>AGTGCTATTGGCAAAATTCAAGAC |

TABLE 4-continued

| Exemplary sequences of signal peptides and SARS-CoV-2 antigens. | |
|---|---|
| SEQUENCE NAME (SEQ ID NO:) | AMINO ACID OR NUCLEIC ACID SEQUENCE |
| | TCACTTTCTTCCACAGCAAGTGCA<br>CTTGGAAAACTTCAAGATGTGGTC<br>AACCAAAATGCACAAGCTTTAAAC<br>ACGCTTGTTAAACAACTTAGCTCC<br>AATTTTGGTGCAATTTCAAGTGTT<br>TTAAATGATATCCTTTCACGTCTT<br>GACAAAGTTGAGGCTGAAGTGCAA<br>ATTGATAGGTTGATCACAGGCAGA<br>CTTCAAAGTTTGCAGACATATGTG<br>ACTCAACAATTAATTAGAGCTGCA<br>GAAATCAGAGCTTCTGCTAATCTT<br>GCTGCTACTAAAATGTCAGAGTGT<br>GTACTTGGACAATCAAAAAGAGTT<br>GATTTTTGTGGAAAGGGCTATCAT<br>CTTATGTCCTTCCCTCAGTCAGCA<br>CCTCATGGTGTAGTCTTCTTGCAT<br>GTGACTTATGTCCCTGCACAAGAA<br>AAGAACTTCACAACTGCTCCTGCC<br>ATTTGTCATGATGGAAAAGCACAC<br>TTTCCTCGTGAAGGTGTCTTTGTT<br>TCAAATGGCACACACTGGTTTGTA<br>ACACAAAGGAATTTTTATGAACCA<br>CAAATCATTACTACAGACAACACA<br>TTTGTGTCTGGTAACTGTGATGTT<br>GTAATAGGAATTGTCAACAACACA<br>GTTTATGATCCTTTGCAACCTGAA<br>TTAGACTCATTCAAGGAGGAGTTA<br>GATAAATATTTTAAGAATCATACA<br>TCACCAGATGTTGATTTAGGTGAC<br>ATCTCTGGCATTAATGCTTCAGTT<br>GTAAACATTCAAAAAGAAATTGAC<br>CGCCTCAATGAGGTTGCCAAGAAT<br>TTAAATGAATCTCTCATCGATCTC<br>CAAGAACTTGGAAAGTATGAGCAG<br>TATATAAAA |
| spike protein ectodomain (ECD) with native signal peptide amino acid sequence (SEQ ID NO: 42) | MFVFLVLLPLVSSQCVNLTTRTQLP<br>PAYTNSFTRGVYYPDKVFRSSVLH<br>STQDLFLPFFSNVTWFHAIHVSGT<br>NGTKRFDNPVLPFNDGVYFASTEK<br>SNIIRGWIFGTTLDSKTQSLLIVN<br>NATNWIKVCEFQFCNDPFLGVYYH<br>KNNKSWMESEFRVYSSANNCTFEY<br>VSQPFLMDLEGKQGNFKNLREFVF<br>KNIDGYFKIYSKHTPINLVRDLPQ<br>GFSALEPLVDLPIGINITRFQTLL<br>ALHRSYLTPGDSSSGWTAGAAAYY<br>VGYLQPRTFLLKYNENGTITDAVD<br>CALDPLSETKCTLKSFTVEKGIYQ<br>TSNFRVQPTESIVRFPNITNLCPF<br>GEVFNATRFASVYAWNRKRISNCV<br>ADYSVLYNSASFSTFKCYGVSPTK<br>LNDLCFTNVYADSFVIRGDEVRQI<br>APGQTGKIADYNYKLPDDFTGCVI<br>AWNSNNLDSKVGGNYNYLYRLFRK<br>SNLKPFERDISTEIYQAGSTPCNG<br>VEGFNCYFPLQSYGFQPTNGVGYQ<br>PYRWVLSFELLHAPATVCGPKKST<br>NLVKNKCVNFNFNGLTGTGVLTES<br>NKKFLPFQQFGRDIADTTDAVRDP<br>QTLEILDITPCSFGGVSVITPGTN<br>TSNQVAVLYQDVNCTEVPVAIHAD<br>QLTPTWRVYSTGSNVFQTRAGCLI<br>GAEHVNNSYECDIPIGAGICASYQ<br>TQTNSPRRARSVASQSIIAYTMSL<br>GAENSVAYSNNSIAIPTNFTISVT<br>TEILPVSMTKTSVDCTMYICGDST<br>ECSNLLLQYGSFCTQLNRALTGIA<br>VEQDKNTQEVFAQVKQIYKTPPIK<br>DFGGFNFSQILPDPSKPSKRSFIE<br>DLLFNKVTLADAGFIKQYGDCLGD<br>IAARDLICAQKFNGLTVLPPLLTD<br>EMIAQYTSALLAGTITSGWTFGAG<br>AALQIPFAMQMAYRFNGIGVTQNV<br>LYENQKLIANQFNSAIGKIQDSLS<br>STASALGKLQDWNQNAQALNTLVK<br>QLSSNFGAISSVLNDILSRLDKVE<br>AEVQIDRLITGRLQSLQTYVTQQL<br>IRAAEIRASANLAATKMSECVLGQ<br>SKRVDFCGKGYHLMSFPQSAPHGW<br>FLHVTYVPAQEKNFTTAPAICHDG<br>KAHFPREGVFVSNGTHWFVTQRNF<br>YEPQIITTDNTFVSGNCDVVIGIV<br>NNTVYDPLQPELDSFKEELDKYFK<br>NHTSPDVDLGDISGINASWNIQKE<br>IDRLNEVAKNLNESLIDLQELGKY<br>EQYIK |
| SARS-CoV-2 spike protein ectodomain (ECD) with native signal peptide coding sequence (SEQ ID NO: 43) | ATGTTTGTTTTTCTTGTTTTATTG<br>CCATTAGTCTCTAGTCAGTGTGTT<br>AATCTTACAACCAGAACTCAATTA<br>CCCCCTGCATACACTAATTCTTTC<br>ACACGTGGTGTTTATTACCCTGAC<br>AAAGTTTTCAGATCCTCAGTTTTA<br>CATTCAACTCAGGACTTGTTCTTA<br>CCTTTCTTTTCCAATGTTACTTGG<br>TTCCATGCTATACATGTCTCTGGG<br>ACCAATGGTACTAAGAGGTTTGAT<br>AACCCTGTCCTACCATTTAATGAT<br>GGTGTTTATTTTGCTTCCACTGAG<br>AAGTCTAACATAATAAGAGGCTGG<br>ATTTTTGGTACTACTTTAGATTCG<br>AAGACCCAGTCCCTACTTATTGTT<br>AATAACGCTACTAATGTTGTTATT<br>AAAGTCTGTGAATTTCAATTTTGT<br>AATGATCCATTTTTGGGTGTTTAT<br>TACCACAAAAACAACAAAAGTTGG<br>ATGGAAAGTGAGTTCAGAGTTTAT<br>TCTAGTGCGAATAATTGCACTTTT<br>GAATATGTCTCTCAGCCTTTTCTT<br>ATGGACCTTGAAGGAAAACAGGGT<br>AATTTCAAAAATCTTAGGGAATTT<br>GTGTTTAAGAATATTGATGGTTAT<br>TTTAAAATATATTCTAAGCACACG<br>CCTATTAATTTAGTGCGTGATCTC<br>CCTCAGGGTTTTTCGGCTTTAGAA<br>CCATTGGTAGATTTGCCAATAGGT<br>ATTAACATCACTAGGTTTCAAACT<br>TTACTTGCTTTACATAGAAGTTAT<br>TTGACTCCTGGTGATTCTTCTTCA<br>GGTTGGACAGCTGGTGCTGCAGCT<br>TATTATGTGGGTTATCTTCAACCT<br>AGGACTTTTCTATTAAAATATAAT<br>GAAAATGGAACCATTACAGATGCT<br>GTAGACTGTGCACTTGACCCTCTC<br>TCAGAAACAAAGTGTACGTTGAAA<br>TCCTTCACTGTAGAAAAAGGAATC<br>TATCAAACTTCTAACTTTAGAGTC<br>CAACCAACAGAATCTATTGTTAGA<br>TTTCCTAATATTACAAACTTGTGC<br>CCTTTTGGTGAAGTTTTTAACGCC<br>ACCAGATTTGCATCTGTTTATGCT<br>TGGAACAGGAAGAGAATCAGCAAC<br>TGTGTTGCTGATTATTCTGTCCTA<br>TATAATTCCGCATCATTTTCCACT<br>TTTAAGTGTTATGGAGTGTCTCCT<br>ACTAAATTAAATGATCTCTGCTTT<br>ACTAATGTCTATGCAGATTCATTT<br>GTAATTAGAGGTGATGAAGTCAGA<br>CAAATCGCTCCAGGGCAAACTGGA<br>AAGATTGCTGATTATAATTATAAA<br>TTACCAGATGATTTTACAGGCTGC<br>GTTATAGCTTGGAACTCTAACAAT<br>CTTGATTCTAAGGTTGGTGGTAAT<br>TATAATTACCTGTATAGATTGTTT<br>AGGAAGTCTAATCTCAAACCTTTT |

TABLE 4-continued

Exemplary sequences of signal peptides and SARS-CoV-2 antigens.

| SEQUENCE NAME (SEQ ID NO:) | AMINO ACID OR NUCLEIC ACID SEQUENCE |
|---|---|
| | GAGAGAGATATTTCAACTGAAATC<br>TATCAGGCCGGTAGCACACCTTGT<br>AATGGTGTTGAAGGTTTTAATTGT<br>TACTTTCCTTTACAATCATATGGT<br>TTCCAACCCACTAATGGTGTTGGT<br>TACCAACCATACAGAGTAGTAGTA<br>CTTTCTTTTGAACTTCTACATGCA<br>CCAGCAACTGTTTGTGGACCTAAA<br>AAGTCTACTAATTTGGTTAAAAAC<br>AAATGTGTCAATTTCAACTTCAAT<br>GGTTTAACAGGCACAGGTGTTCTT<br>ACTGAGTCTAACAAAAAGTTTCTG<br>CCTTTCCAACAATTTGGCAGAGAC<br>ATTGCTGACACTACTGATGCTGTC<br>CGTGATCCACAGACACTTGAGATT<br>CTTGACATTACACCATGTTCTTTT<br>GGTGGTGTCAGTGTTATAACACCA<br>GGAACAAATACTTCTAACCAGGTT<br>GCTGTTCTTTATCAGGATGTTAAC<br>TGCACAGAAGTCCCTGTTGCTATT<br>CATGCAGATCAACTTACTCCTACT<br>TGGCGTGTTTATTCTACAGGTTCT<br>AATGTTTTTCAAACACGTGCAGGC<br>TGTTTAATAGGGGCTGAACATGTC<br>AACAACTCATATGAGTGTGACATA<br>CCCATTGGTGCAGGTATATGCGCT<br>AGTTATCAGACTCAGACTAATTCT<br>CCTCGGCGGGCACGTAGTGTAGCT<br>AGTCAATCCATCATTGCCTACACT<br>ATGTCACTTGGTGCAGAAAATTCA<br>GTTGCTTACTCTAATAACTCTATT<br>GCCATACCCACAAATTTTACTATT<br>AGTGTTACCACAGAAATTCTACCA<br>GTGTCTATGACCAAGACATCAGTA<br>GATTGTACAATGTACATTTGTGGT<br>GATTCAACTGAATGCAGCAATCTT<br>TTGTTGCAATATGGCAGTTTTTGT<br>ACACAATTAAACCGTGCTTTAACT<br>GGAATAGCTGTTGAACAAGACAAA<br>AACACCCAAGAAGTTTTTGCACAA<br>GTCAAACAAATTTACAAAACACCA<br>CCAATTAAAGATTTTGGTGGTTTT<br>AATTTTTCACAAATATTACCAGAT<br>CCATCAAAACCAAGCAAGAGGTCA<br>TTTATTGAAGATCTACTTTTCAAC<br>AAAGTGACACTTGCAGATGCTGGC<br>TTCATCAAACAATATGGTGATTGC<br>CTTGGTGATATTGCTGCTAGAGAC<br>CTCATTTGTGCACAAAAGTTTAAC<br>GGCCTTACTGTTTTGCCACCTTTG<br>CTCACAGATGAAATGATTGCTCAA<br>TACACTTCTGCACTGTTAGCGGGT<br>ACAATCACTTCTGGTTGGACCTTT<br>GGTGCAGGTGCTGCATTACAAATA<br>CCATTTGCTATGCAAATGGCTTAT<br>AGGTTTAATGGTATTGGAGTTACA<br>CAGAATGTTCTCTATGAGAACCAA<br>AAATTGATTGCCAACCAATTTAAT<br>AGTGCTATTGGCAAAATTCAAGAC<br>TCACTTTCTTCCACAGCAAGTGCA<br>CTTGGAAAACTTCAAGATGTGGTC<br>AACCAAAATGCACAAGCTTTAAAC<br>ACGCTTGTTAAACAACTTAGCTCC<br>AATTTTGGTGCAATTTCAAGTGTT<br>TTAAATGATATCCTTTCACGTCTT<br>GACAAAGTTGAGGCTGAAGTGCAA<br>ATTGATAGGTTGATCACAGGCAGA<br>CTTCAAAGTTTGCAGACATATGTG<br>ACTCAACAATTAATTAGAGCTGCA<br>GAAATCAGAGCTTCTGCTAATCTT<br>GCTGCTACTAAAATGTCAGAGTGT<br>GTACTTGGACAATCAAAAAGAGTT<br>GATTTTTGTGGAAAGGGCTATCAT<br>CTTATGTCCTTCCCTCAGTCAGCA<br>CCTCATGGTGTAGTCTTCTTGCAT<br>GTGACTTATGTCCCTGCACAAGAA<br>AAGAACTTCACAACTGCTCCTGCC<br>ATTTGTCATGATGGAAAAGCACAC<br>TTTCCTCGTGAAGGTGTCTTTGTT<br>TCAAATGGCACACACTGGTTTGTA<br>ACACAAAGGAATTTTTATGAACCA<br>CAAATCATTACTACAGACAACACA<br>TTTGTGTCTGGTAACTGTGATGTT<br>GTAATAGGAATTGTCAACAACACA<br>GTTTATGATCCTTTGCAACCTGAA<br>TTAGACTCATTCAAGGAGGAGTTA<br>GATAAATATTTTAAGAATCATACA<br>TCACCAGATGTTGATTTAGGTGAC<br>ATCTCTGGCATTAATGCTTCAGTT<br>GTAAACATTCAAAAAGAAATTGAC<br>CGCCTCAATGAGGTTGCCAAGAAT<br>TTAAATGAATCTCTCATCGATCTC<br>CAAGAACTTGGAAAGTATGAGCAG<br>TATATAAAA |
| SARS-CoV-2 spike protein S1 subunit with native signal peptide amino acid sequence (SEQ ID NO: 44) | MFVFLVLLPLVSSQCVNLTTRTQL<br>PPAYTNSFTRGVYYPDKVFRSSVL<br>HSTQDLFLPFFSNVTWFHAIHVSG<br>TNGTKRFDNPVLPFNDGVYFASIE<br>KSNIIRGWIFGTTLDSKTQSLLIV<br>NNATNVVIKVCEFQFCNDPFLGVY<br>YHKNNKSWMESEFRVYSSANNCTF<br>EYVSQPFLMDLEGKQGNFKNLREF<br>VFKNIDGYFKIYSKHTPINLVRDL<br>PQGFSALEPLVDLPIGINITRFQT<br>LLALHRSYLTPGDSSSGWTAGAAA<br>YYVGYLQPRTFLLKYNENGTITDA<br>VDCALDPLSETKCTLKSFTVEKGI<br>YQTSNFRVQPIESIVRFPNITNLC<br>PFGEVFNATRFASVYAWNRKRISN<br>CVADYSVLYNSASFSTFKCYGVSP<br>TKLNDLCFTNVYADSFVIRGDEVR<br>QIAPGQTGKIADYNYKLPDDFTGC<br>VIAWNSNNLDSKVGGNYNYLYRLF<br>RKSNLKPFERDISTEIYQAGSTPC<br>NGVEGFNCYFPLQSYGFQPTNGVG<br>YQPYRVVVLSFELLHAPATVCGPK<br>KSTNLVKNKCVNFNFNGLTGTGVL<br>TESNKKFLPFQQFGRDIADTTDAV<br>RDPQTLEILDITPCSFGGVSVITP<br>GTNTSNQVAVLYQDVNCTEVPVAI<br>HADQLTPTWRVYSTGSNVFQTRAG<br>CLIGAEHVNNSYECDIPIGAGICA<br>SYQTQTNSPRRAR |
| SARS-CoV-2 spike protein S1 subunit with native signal peptide coding sequence (SEQ ID NO: 45) | ATGTTTGTTTTTCTTGTTTTATTG<br>CCATTAGTCTCTAGTCAGTGTGTT<br>AATCTTACAACCAGAACTCAATTA<br>CCCCCTGCATACACTAATTCTTTC<br>ACACGTGGTGTTTATTACCCTGAC<br>AAAGTTTTCAGATCCTCAGTTTTA<br>CATTCAACTCAGGACTTGTTCTTA<br>CCTTTCTTTTCCAATGTTACTTGG<br>TTCCATGCTATACATGTCTCTGGG<br>ACCAATGGTACTAAGAGGTTTGAT<br>AACCCTGTCCTACCATTTAATGAT<br>GGTGTTTATTTTGCTTCCACTGAG<br>AAGTCTAACATAATAAGAGGCTGG<br>ATTTTTGGTACTACTTTAGATTCG<br>AAGACCCAGTCCCTACTTATTGTT<br>AATAACGCTACTAATGTTGTTATT<br>AAAGTCTGTGAATTTCAATTTTGT<br>AATGATCCATTTTTGGGTGTTTAT<br>TACCACAAAAACAACAAAAGTTGG<br>ATGGAAAGTGAGTTCAGAGTTTAT<br>TCTAGTGCGAATAATTGCACTTTT |

TABLE 4-continued

Exemplary sequences of signal peptides and SARS-CoV-2 antigens.

| SEQUENCE NAME (SEQ ID NO:) | AMINO ACID OR NUCLEIC ACID SEQUENCE |
|---|---|
| | GAATATGTCTCTCAGCCTTTTCTT<br>ATGGACCTTGAAGGAAAACAGGGT<br>AATTTCAAAAATCTTAGGGAATTT<br>GTGTTTAAGAATATTGATGGTTAT<br>TTTAAAATATATTCTAAGCACACG<br>CCTATTAATTTAGTGCGTGATCTC<br>CCTCAGGGTTTTTCGGCTTTAGAA<br>CCATTGGTAGATTTGCCAATAGGT<br>ATTAACATCACTAGGTTTCAAACT<br>TTACTTGCTTTACATAGAAGTTAT<br>TTGACTCCTGGTGATTCTTCTTCA<br>GGTTGGACAGCTGGTGCTGCAGCT<br>TATTATGTGGGTTATCTTCAACCT<br>AGGACTTTTCTATTAAAATATAAT<br>GAAAATGGAACCATTACAGATGCT<br>GTAGACTGTGCACTTGACCCTCTC<br>TCAGAAACAAAGTGTACGTTGAAA<br>TCCTTCACTGTAGAAAAAGGAATC<br>TATCAAACTTCTAACTTTAGAGTC<br>CAACCAACAGAATCTATTGTTAGA<br>TTTCCTAATATTACAAACTTGTGC<br>CCTTTTGGTGAAGTTTTTAACGCC<br>ACCAGATTTGCATCTGTTTATGCT<br>TGGAACAGGAAGAGAATCAGCAAC<br>TGTGTTGCTGATTATTCTGTCCTA<br>TATAATTCCGCATCATTTTCCACT<br>TTTAAGTGTTATGGAGTGTCTCCT<br>ACTAAATTAAATGATCTCTGCTTT<br>ACTAATGTCTATGCAGATTCATTT<br>GTAATTAGAGGTGATGAAGTCAGA<br>CAAATCGCTCCAGGGCAAACTGGA<br>AAGATTGCTGATTATAATTATAAA<br>TTACCAGATGATTTTACAGGCTGC<br>GTTATAGCTTGGAATTCTAACAAT<br>CTTGATTCTAAGGTTGGTGGTAAT<br>TATAATTACCTGTATAGATTGTTT<br>AGGAAGTCTAATCTCAAACCTTTT<br>GAGAGAGATATTTCAACTGAAATC<br>TATCAGGCCGGTAGCACACCTTGT<br>AATGGTGTTGAAGGTTTTAATTGT<br>TACTTTCCTTTACAATCATATGGT<br>TTCCAACCCACTAATGGTGTTGGT<br>TACCAACCATACAGAGTAGTAGTA<br>CTTTCTTTTGAACTTCTACATGCA<br>CCAGCAACTGTTTGTGGACCTAAA<br>AAGTCTACTAATTTGGTTAAAAAC<br>AAATGTGTCAATTTCAACTTCAAT<br>GGTTTAACAGGCACAGGTGTTCTT<br>ACTGAGTCTAACAAAAAGTTTCTG<br>CCTTTCCAACAATTTGGCAGAGAC<br>ATTGCTGACACTACTGATGCTGTC<br>CGTGATCCACAGACACTTGAGATT<br>CTTGACATTACACCATGTTCTTTT<br>GGTGGTGTCAGTGTTATAACACCA<br>GGAACAAATACTTCTAACCAGGTT<br>GCTGTTCTTTATCAGGATGTTAAC<br>TGCACAGAAGTCCCTGTTGCTATT<br>CATGCAGATCAACTTACTCCTACT<br>TGGCGTGTTTATTCTACAGGTTCT<br>AATGTTTTTCAAACACGTGCAGGC<br>TGTTTAATAGGGGCTGAACATGTC<br>AACAACTCATATGAGTGTGACATA<br>CCCATTGGTGCAGGTATATGCGCT<br>AGTTATCAGACTCAGACTAATTCT<br>CCTCGGCGGGCACGT |

In particular embodiments, the signal peptide is encoded by a gene of the coronavirus from which the viral peptide or polypeptide is derived. In particular embodiments, a signal peptide encoded by a gene of the coronavirus is fused to a viral peptide or polypeptide encoded by a different gene of the coronavirus. In other embodiments, a signal peptide encoded by a gene of the coronavirus is fused to a viral peptide or polypeptide encoded by the same gene of the coronavirus. For example, in some embodiments, a signal peptide having amino acid sequence of MFVFLVLLPLVSS (SEQ ID NO:36) is fused to the viral peptide or polypeptide encoded by the nucleic acid molecule of the present disclosure. In various embodiments, the viral peptide or protein is one or more selected from (a) the N protein, (b) the M protein, (c) the E protein, (d) the S protein, (e) the HE protein, (f) an immunogenic fragment of any one of (a) to (e), and (g) a functional derivative of any one of (a) to (f).

In particular embodiments, the therapeutic nucleic acid of the present disclosure encodes the S protein of coronavirus SARS-CoV-2 without the native signal peptide. In particular embodiments, the encoded S protein comprises an amino acid sequence of SEQ ID NO:40. In particular embodiments, the therapeutic nucleic acid of the present disclosure encodes the S protein of coronavirus SARS-CoV-2 having a signal peptide, and wherein the therapeutic nucleic acid comprises a DNA coding sequence of SEQ ID NO:41. In particular embodiments, the therapeutic nucleic acid of the present disclosure encodes the S protein of coronavirus SARS-CoV-2 having a signal peptide, and wherein the therapeutic nucleic acid comprises a RNA sequence transcribed from the DNA coding sequence of SEQ ID NO:41. In some embodiments, the RNA sequence is in vitro transcribed. In particular embodiments, the nucleic acid molecule is an mRNA molecule.

In particular embodiments, the therapeutic nucleic acid of the present disclosure encodes the ectodomain (ECD) of the S protein of coronavirus SARS-CoV-2 having a signal peptide. In particular embodiments, the encoded ectodomain of S protein comprises an amino acid sequence of SEQ ID NO:42. In particular embodiments, the therapeutic nucleic acid of the present disclosure encodes the ectodomain of the S protein of coronavirus SARS-CoV-2 having a signal peptide, and wherein the therapeutic nucleic acid comprises a DNA coding sequence of SEQ ID NO:43. In particular embodiments, the therapeutic nucleic acid of the present disclosure encodes the ectodomain of the S protein of coronavirus SARS-CoV-2 having a signal peptide, and wherein the therapeutic nucleic acid comprises a RNA sequence transcribed from the DNA coding sequence of SEQ ID NO:43. In some embodiments, the RNA sequence is in vitro transcribed. In particular embodiments, the nucleic acid molecule is an mRNA molecule.

In particular embodiments, the therapeutic nucleic acid of the present disclosure encodes the S1 subunit of the S protein of coronavirus SARS-CoV-2 having a signal peptide. In particular embodiments, the encoded S1 subunit of S protein comprises an amino acid sequence of SEQ ID NO:44. In particular embodiments, the therapeutic nucleic acid of the present disclosure encodes the S1 subunit of the S protein of coronavirus SARS-CoV-2 having a signal peptide, and wherein the therapeutic nucleic acid comprises a DNA coding sequence of SEQ ID NO:45. In particular embodiments, the therapeutic nucleic acid of the present disclosure encodes the S1 subunit of the S protein of coronavirus SARS-CoV-2 having a signal peptide, and wherein the therapeutic nucleic acid comprises a RNA sequence transcribed from the DNA coding sequence of SEQ ID NO:45. In some embodiments, the RNA sequence is in vitro transcribed. In particular embodiments, the nucleic acid molecule is an mRNA molecule.

In other embodiments, the signal peptide is encoded by an exogenous gene sequence that does not present in the coronavirus from which the viral peptide or polypeptide is derived. In some embodiments, a heterologous signal peptide replaces a homologous signal peptide in the fusion protein encoded by the nucleic acid molecule of the present disclosure. In specific embodiments, the signal peptide is encoded by a mammalian gene. In specific embodiments, the signal peptide is encoded by human Immunoglobulin gene. In specific embodiments, the signal peptide is encoded by human IgE gene. For example, in some embodiments, a signal peptide having amino acid sequence of MDWTWILFLVAAATRVHS (SEQ ID NO:38) is fused to the viral peptide or polypeptide encoded by the nucleic acid molecule of the present disclosure. In various embodiments, the viral peptide or protein is one or more selected from (a) the N protein, (b) the M protein, (c) the E protein, (d) the S protein, (e) the HE protein, (f) an immunogenic fragment of any one of (a) to (e), and (g) a functional derivative of any one of (a) to (f).

6.3.2 5'-Cap Structure

Without being bound by the theory, it is contemplated that, a 5'-cap structure of a polynucleotide is involved in nuclear export and increasing polynucleotide stability and binds the mRNA Cap Binding Protein (CBP), which is responsible for polynucleotide stability in the cell and translation competency through the association of CBP with poly-A binding protein to form the mature cyclic mRNA species. The 5'-cap structure further assists the removal of 5'-proximal introns removal during mRNA splicing. Accordingly, in some embodiments, the nucleic acid molecules of the present disclosure comprise a 5'-cap structure.

Nucleic acid molecules may be 5'-end capped by the endogenous transcription machinery of a cell to generate a 5'-ppp-5'-triphosphate linkage between a terminal guanosine cap residue and the 5'-terminal transcribed sense nucleotide of the polynucleotide. This 5'-guanylate cap may then be methylated to generate an N7-methyl-guanylate residue. The ribose sugars of the terminal and/or anteterminal transcribed nucleotides of the 5' end of the polynucleotide may optionally also be 2'-O-methylated. 5'-decapping through hydrolysis and cleavage of the guanylate cap structure may target a nucleic acid molecule, such as an mRNA molecule, for degradation.

In some embodiments, the nucleic acid molecules of the present disclosure comprise one or more alterations to the natural 5'-cap structure generated by the endogenous process. Without being bound by the theory, a modification on the 5'-cap may increase the stability of polynucleotide, increase the half-life of the polynucleotide, and could increase the polynucleotide translational efficiency.

Exemplary alterations to the natural 5'-Cap structure include generation of a non-hydrolyzable cap structure preventing decapping and thus increasing polynucleotide half-life. In some embodiments, because cap structure hydrolysis requires cleavage of 5'-ppp-5' phosphorodiester linkages, in some embodiments, modified nucleotides may be used during the capping reaction. For example, in some embodiments, a Vaccinia Capping Enzyme from New England Biolabs (Ipswich, Mass.) may be used with α-thio-guanosine nucleotides according to the manufacturer's instructions to create a phosphorothioate linkage in the 5'-ppp-5' cap. Additional modified guanosine nucleotides may be used, such as α-methyl-phosphonate and seleno-phosphate nucleotides.

Additional exemplary alterations to the natural 5'-Cap structure also include modification at the 2'- and/or 3'-position of a capped guanosine triphosphate (GTP), a replacement of the sugar ring oxygen (that produced the carbocyclic ring) with a methylene moiety (CH2), a modification at the triphosphate bridge moiety of the cap structure, or a modification at the nucleobase (G) moiety.

Additional exemplary alterations to the natural 5'-cap structure include, but are not limited to, 2'-O-methylation of the ribose sugars of 5'-terminal and/or 5'-anteterminal nucleotides of the polynucleotide (as mentioned above) on the 2'-hydroxy group of the sugar. Multiple distinct 5'-cap structures can be used to generate the 5'-cap of a polynucleotide, such as an mRNA molecule. Additional exemplary 5'-Cap structures that can be used in connection with the present disclosure further include those described in International Patent Publication Nos. WO2008127688, WO 2008016473, and WO 2011015347, the entire contents of each of which are incorporated herein by reference.

In various embodiments, 5'-terminal caps can include cap analogs. Cap analogs, which herein are also referred to as synthetic cap analogs, chemical caps, chemical cap analogs, or structural or functional cap analogs, differ from natural (i.e., endogenous, wild-type, or physiological) 5'-caps in their chemical structure, while retaining cap function. Cap analogs may be chemically (i.e., non-enzymatically) or enzymatically synthesized and/linked to a polynucleotide.

For example, the Anti-Reverse Cap Analog (ARCA) cap contains two guanosines linked by a 5'-5'-triphosphate group, wherein one guanosine contains an N7-methyl group as well as a 3'-O-methyl group (i.e., N7,3'-O-dimethyl-guanosine-5'-triphosphate-5'-guanosine, $m^7$G-3'mppp-G, which may equivalently be designated 3' O-Me-m7G(5')ppp (5')G). The 3'-O atom of the other, unaltered, guanosine becomes linked to the 5'-terminal nucleotide of the capped polynucleotide (e.g., an mRNA). The N7- and 3'-O-methlyated guanosine provides the terminal moiety of the capped polynucleotide (e.g., mRNA). Another exemplary cap structure is mCAP, which is similar to ARCA but has a 2'-O-methyl group on guanosine (i.e., N7,2'-O-dimethyl-guanosine-5'-triphosphate-5'-guanosine, $m^7$Gm-ppp-G).

In some embodiments, a cap analog can be a dinucleotide cap analog. As a non-limiting example, the dinucleotide cap analog may be modified at different phosphate positions with a boranophosphate group or a phophoroselenoate group such as the dinucleotide cap analogs described in U.S. Pat. No. 8,519,110, the entire content of which is herein incorporated by reference in its entirety.

In some embodiments, a cap analog can be a N7-(4-chlorophenoxyethyl) substituted dinucleotide cap analog known in the art and/or described herein. Non-limiting examples of N7-(4-chlorophenoxyethyl) substituted dinucleotide cap analogs include a N7-(4-chlorophenoxyethyl)-G(5')ppp(5')G and a N7-(4-chlorophenoxyethyl)-m3'-OG(5')ppp(5')G cap analog (see, e.g., the various cap analogs and the methods of synthesizing cap analogs described in Kore et al. Bioorganic & Medicinal Chemistry 2013 21:4570-4574; the entire content of which is herein incorporated by reference). In other embodiments, a cap analog useful in connection with the nucleic acid molecules of the present disclosure is a 4-chloro/bromophenoxyethyl analog.

In various embodiments, a cap analog can include a guanosine analog. Useful guanosine analogs include but are not limited to, inosine, N1-methyl-guanosine, 2'-fluoro-guanosine, 7-deaza-guanosine, 8-oxo-guanosine, 2-amino-guanosine, LNA-guanosine, and 2-azido-guanosine.

Without being bound by the theory, it is contemplated that while cap analogs allow for the concomitant capping of a polynucleotide in an in vitro transcription reaction, up to 20% of transcripts remain uncapped. This, as well as the structural differences of a cap analog from the natural 5'-cap structures of polynucleotides produced by the endogenous transcription machinery of a cell, may lead to reduced translational competency and reduced cellular stability.

Accordingly, in some embodiments, a nucleic acid molecule of the present disclosure can also be capped post-transcriptionally, using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function, and/or structure as compared to synthetic features or analogs of the prior art, or which outperforms the corresponding endogenous, wild-type, natural, or physiological feature in one or more respects. Non-limiting examples of more authentic 5'-cap structures useful in connection with the nucleic acid molecules of the present disclosure are those which, among other things, have enhanced binding of cap binding proteins, increased half-life, reduced susceptibility to 5'-endonucleases, and/or reduced 5'-decapping, as compared to synthetic 5'-cap structures known in the art (or to a wild-type, natural or physiological 5'-cap structure). For example, in some embodiments, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanosine cap nucleotide wherein the cap guanosine contains an N7-methylation and the 5'-terminal nucleotide of the polynucleotide contains a 2'-O-methyl. Such a structure is termed the Cap1 structure. This cap results in a higher translational-competency, cellular stability, and a reduced activation of cellular pro-inflammatory cytokines, as compared, e.g., to other 5'cap analog structures known in the art. Other exemplary cap structures include 7mG(5')ppp(5')N,pN2p (Cap 0), 7mG(5')ppp(5')NlmpNp (Cap 1), 7mG(5')-ppp(5')NlmpN2mp (Cap 2), and m(7)Gpppm(3)(6,6,2')Apm(2')Apm(2')Cpm(2)(3,2')Up (Cap 4).

Without being bound by the theory, it is contemplated that the nucleic acid molecules of the present disclosure can be capped post-transcriptionally, and because this process is more efficient, nearly 100% of the nucleic acid molecules may be capped.

6.3.3 Untranslated Regions (UTRs)

In some embodiments, the nucleic acid molecules of the present disclosure comprise one or more untranslated regions (UTRs). In some embodiments, an UTR is positioned upstream to a coding region in the nucleic acid molecule, and is termed 5'-UTR. In some embodiments, an UTR is positioned downstream to a coding region in the nucleic acid molecule, and is termed 3'-UTR. The sequence of an UTR can be homologous or heterologous to the sequence of the coding region found in a nucleic acid molecule. Multiple UTRs can be included in a nucleic acid molecule and can be of the same or different sequences, and/or genetic origin. According to the present disclosure, any portion of UTRs in a nucleic acid molecule (including none) can be codon optimized and any may independently contain one or more different structural or chemical modification, before and/or after codon optimization.

In some embodiments, a nucleic acid molecule of the present disclosure (e.g., mRNA) comprises UTRs and coding regions that are homologous with respect to each other. In other embodiments, a nucleic acid molecule of the present disclosure (e.g., mRNA) comprises UTRs and coding regions that are heterologous with respect to each other. In some embodiments, to monitor the activity of a UTR sequence, a nucleic acid molecule comprising the UTR and a coding sequence of a detectable probe can be administered in vitro (e.g., cell or tissue culture) or in vivo (e.g., to a subject), and an effect of the UTR sequence (e.g., modulation on the expression level, cellular localization of the encoded product, or half-life of the encoded product) can be measured using methods known in the art.

In some embodiments, the UTR of a nucleic acid molecule of the present disclosure (e.g., mRNA) comprises at least one translation enhancer element (TEE) that functions to increase the amount of polypeptide or protein produced from the nucleic acid molecule. In some embodiments, the TEE is located in the 5'-UTR of the nucleic acid molecule. In other embodiments, the TEE is located at the 3'-UTR of the nucleic acid molecule. In yet other embodiments, at least two TEE are located at the 5'-UTR and 3'-UTR of the nucleic acid molecule respectively. In some embodiments, a nucleic acid molecule of the present disclosure (e.g., mRNA) can comprise one or more copies of a TEE sequence or comprise more than one different TEE sequences. In some embodiments, different TEE sequences that are present in a nucleic acid molecule of the present disclosure can be homologues or heterologous with respect to one another.

Various TEE sequences that are known in the art and can be used in connection with the present disclosure. For example, in some embodiments, the TEE can be an internal ribosome entry site (IRES), HCV-IRES or an IRES element. Chappell et al. *Proc. Natl. Acad. Sci. USA* 101:9590-9594, 2004; Zhou et al. *Proc. Natl. Acad. Sci.* 102:6273-6278, 2005. Additional internal ribosome entry site (IRES) that can be used in connection with the present disclosure include but are not limited to those described in U.S. Pat. No. 7,468,275, U.S. Patent Publication No. 2007/0048776 and U.S. Patent Publication No. 2011/0124100 and International Patent Publication No. WO2007/025008 and International Patent Publication No. WO2001/055369, the content of each of which is enclosed herein by reference in its entirety. In some embodiments, the TEE can be those described in Supplemental Table 1 and in Supplemental Table 2 of Wellensiek et al Genome-wide profiling of human cap-independent translation-enhancing elements, *Nature Methods,* 2013 August; 10(8): 747-750; the content of which is incorporated by reference in its entirety.

Additional exemplary TEEs that can be used in connection with the present disclosure include but are not limited to the TEE sequences disclosed in U.S. Pat. Nos. 6,310,197, 6,849,405, 7,456,273, 7,183,395, U.S. Patent Publication No. 2009/0226470, U.S. Patent Publication No. 2013/0177581, U.S. Patent Publication No. 2007/0048776, U.S. Patent Publication No. 2011/0124100, U.S. Patent Publication No. 2009/0093049, International Patent Publication No. WO2009/075886, International Patent Publication No. WO2012/009644, and International Patent Publication No. WO1999/024595, International Patent Publication No. WO2007/025008, International Patent Publication No. WO2001/055371, European Patent No. 2610341, European Patent No. 2610340, the content of each of which is enclosed herein by reference in its entirety.

In various embodiments, a nucleic acid molecule of the present disclosure (e.g., mRNA) comprises at least one UTR that comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. In some embodiments, the TEE sequences in the UTR of a nucleic acid molecule are copies of the same TEE sequence. In other embodiments, at least two TEE sequences in the UTR of a nucleic acid molecule are of different TEE sequences. In some embodiments, multiple different TEE sequences are arranged in one or more repeating patterns in the UTR region of a nucleic acid molecule. For illustrating purpose only, a repeating pattern can be, for example, ABABAB, AABBAABBAABB, ABCABCABC, or the like, where in these exemplary patterns, each capitalized letter (A, B, or C) represents a different TEE sequence. In some embodiments, at least two TEE sequences are consecutive with one another (i.e., no spacer sequence in between) in a UTR of a nucleic acid molecule. In other embodiments, at least two TEE sequences are separated by a spacer sequence. In some embodiments, a UTR can comprise a TEE sequence-spacer sequence module that is repeated at least once, at least twice, at least 3 times, at least 4 times, at least 5 times, at least 6 times, at least 7 times, at least 8 times, at least 9 times, or more than 9 times in the UTR. In any of the embodiments described in this paragraph, the UTR can be a 5'-UTR, a 3'-UTR or both 5'-UTR and 3'-UTR of a nucleic acid molecule.

In some embodiments, the UTR of a nucleic acid molecule of the present disclosure (e.g., mRNA) comprises at least one translation suppressing element that functions to decrease the amount of polypeptide or protein produced from the nucleic acid molecule. In some embodiments, the UTR of the nucleic acid molecule comprises one or more miR sequences or fragment thereof (e.g., miR seed sequences) that are recognized by one or more microRNA. In some embodiments, the UTR of the nucleic acid molecule comprises one or more stem-loop structure that downregulates translational activity of the nucleic acid molecule. Other mechanisms for suppressing translational activities associated with a nucleic acid molecules are known in the art. In any of the embodiments described in this paragraph, the UTR can be a 5'-UTR, a 3'-UTR or both 5'-UTR and 3'-UTR of a nucleic acid molecule. Table 5 shows exemplary 5'-UTR and 3'-UTR sequences that can be used in connection with the present disclosure.

TABLE 5

Exemplary Untranslated Region (UTR) Sequences.

| SEQUENCE NAME (SEQ ID NO:) | AMINO ACID OR NUCLEIC ACID SEQUENCE |
|---|---|
| 5'-UTR DNA Sequence (SEQ ID NO: 46) | GAAATAAGAGAGAAAAGAAGAGTAA GAAGAAATATAAGA |
| 5'-UTR RNA Sequence (SEQ ID NO: 47) | GAAAUAAGAGAGAAAAGAAGAGUAA GAAGAAAUAUAAGA |
| 5'-UTR DNA Sequence (SEQ ID NO: 48) | CTTGTTCTTTTTGCAGAAGCTCAGA ATAAACGCTCAACTTTGG |
| 5'-UTR RNA Sequence (SEQ ID NO: 49) | CUUGUUCUUUUUGCAGAAGCUCAGA AUAAACGCUCAACUUUGG |
| 5'-UTR DNA Sequence (SEQ ID NO: 50) | GCAGGAGCCAGGGCTGGGCATAAAA GTCAGGGCAGAGCCATCTATTGCTT ACATTTGCTTCTGACACAACTGTGT TCACTAGCAACCTCAAACAGACACC |

TABLE 5-continued

Exemplary Untranslated Region (UTR) Sequences.

| SEQUENCE NAME (SEQ ID NO:) | AMINO ACID OR NUCLEIC ACID SEQUENCE |
|---|---|
| 5'-UTR RNA Sequence (SEQ ID NO: 51) | GCAGGAGCCAGGGCUGGGCAUAAAA GUCAGGGCAGAGCCAUCUAUUGCUU ACAUUUGCUUCUGACACAACUGUGU UCACUAGCAACCUCAAACAGACACC |
| 3'-UTR DNA Sequence (SEQ ID NO: 52) | TAGGCTGGAGCCTCGGTGGCCATGC TTCTTGCCCCTTGGGCCTCCCCCCA GCCCCTCCTCCCCTTCCTGCACCCG TACCCCCGTGGTCTTTGAATAAAGT CTGAGTGGGCGGC |
| 3'-UTR RNA Sequence (SEQ ID NO: 53) | UAGGCUGGAGCCUCGGUGGCCAUGC UUCUUGCCCCUUGGGCCUCCCCCCA GCCCCUCCUCCCCUUCCUGCACCCG UACCCCCGUGGUCUUUGAAUAAAGU CUGAGUGGGCGGC |
| 3'-UTR DNA Sequence (SEQ ID NO: 54) | GCTCGCTTTCTTGCTGTCCAATTTC TATTAAAGGTTCCTTTGTTCCCTAA GTCCAACTACTAAACTGGGGGATAT TATGAAGGGCCTTGAGCATCTGGAT TCTGCCTAATAAAAAACATTTATTT TCATTGC |
| 3'-UTR RNA Sequence (SEQ ID NO: 55) | GCUCGCUUUCUUGCUGUCCAAUUUC UAUUAAAGGUUCCUUUGUUCCCUAA GUCCAACUACUAAACUGGGGGAUAU UAUGAAGGGCCUUGAGCAUCUGGAU UCUGCCUAAUAAAAAACAUUUAUUU UCAUUGC |
| 3'-UTR DNA Sequence (SEQ ID NO: 56) | CTGGTACTGCATGCACGCAATGCTA GCTGCCCCTTTCCCGTCCTGGGTAC CCCGAGTCTCCCCCGACCTCGGGTC CCAGGTATGCTCCCACCTCCACCTG CCCCACTCACCACCTCTGCTAGTTC CAGACACCTCCCAAGCACGCAGCAA TGCAGCTCAAAACGCTTAGCCTAGC CACACCCCCACGGGAAACAGCAGTG ATTAACCTTTAGCAATAAACGAAAG TTTAACTAAGCTATACTAACCCCAG GGTTGGTCAATTTCGTGCCAGCCAC ACC |
| 3' UTR RNA Sequence (SEQ ID NO: 57) | CUGGUACUGCAUGCACGCAAUGCUA GCUGCCCCUUUCCCGUCCUGGGUAC CCCGAGUCUCCCCCGACCUCGGGUC CCAGGUAUGCUCCCACCUCCACCUG CCCCACUCACCACCUCUGCUAGUUC CAGACACCUCCCAAGCACGCAGCAA UGCAGCUCAAAACGCUUAGCCUAGC CACACCCCCACGGGAAACAGCAGUG AUUAACCUUUAGCAAUAAACGAAAG UUUAACUAAGCUAUACUAACCCCAG GGUUGGUCAAUUUCGUGCCAGCCAC ACC |

In specific embodiments, the nucleic acid molecule of the present disclose comprises a 5'-UTR selected from SEQ ID NOS:46-51. In specific embodiments, the nucleic acid molecule of the present disclose comprises a 3'-UTR selected from SEQ ID NOS:52-57. In specific embodiments, the nucleic acid molecule of the present disclose comprises a 5'-UTR selected from SEQ ID NOS:46-51 and a 3'-UTR selected from SEQ ID NOS:52-57. In any of the embodiments described in this paragraph, the nucleic acid molecule may further comprise a coding region having a sequence as described in Section 6.3.1, such as any of the DNA coding sequences in Tables 1 to 4 or equivalent RNA sequences thereof. In particular embodiments, the nucleic acid molecules described in this paragraph can be RNA molecules in vitro transcribed.

6.3.4 The Polyadenylation (Poly-A) Regions

During natural RNA processing, a long chain of adenosine nucleotides (poly-A region) is normally added to messenger RNA (mRNA) molecules to increase the stability of the molecule. Immediately after transcription, the 3'-end of the transcript is cleaved to free a 3'-hydroxy. Then poly-A polymerase adds a chain of adenosine nucleotides to the RNA. The process, called polyadenylation, adds a poly-A region that is between 100 and 250 residues long. Without being bound by the theory, it is contemplated that a poly-A region can confer various advantages to the nucleic acid molecule of the present disclosure.

Accordingly, in some embodiments, a nucleic acid molecule of the present disclosure (e.g., an mRNA) comprises a polyadenylation signal. In some embodiments, a nucleic acid molecule of the present disclosure (e.g., an mRNA) comprises one or more polyadenylation (poly-A) regions. In some embodiments, a poly-A region is composed entirely of adenine nucleotides or functional analogs thereof. In some embodiments, the nucleic acid molecule comprises at least one poly-A region at its 3'-end. In some embodiments, the nucleic acid molecule comprises at least one poly-A region at its 5'-end. In some embodiments, the nucleic acid molecule comprises at least one poly-A region at its 5'-end and at least one poly-A region at its 3'-end.

According to the present disclosure, the poly-A region can have varied lengths in different embodiments. Particularly, in some embodiments, the poly-A region of a nucleic acid molecule of the present disclosure is at least 30 nucleotides in length. In some embodiments, the poly-A region of a nucleic acid molecule of the present disclosure is at least 35 nucleotides in length. In some embodiments, the poly-A region of a nucleic acid molecule of the present disclosure is at least 40 nucleotides in length. In some embodiments, the poly-A region of a nucleic acid molecule of the present disclosure is at least 45 nucleotides in length. In some embodiments, the poly-A region of a nucleic acid molecule of the present disclosure is at least 50 nucleotides in length. In some embodiments, the poly-A region of a nucleic acid molecule of the present disclosure is at least 55 nucleotides in length. In some embodiments, the poly-A region of a nucleic acid molecule of the present disclosure is at least 60 nucleotides in length. In some embodiments, the poly-A region of a nucleic acid molecule of the present disclosure is at least 65 nucleotides in length. In some embodiments, the poly-A region of a nucleic acid molecule of the present disclosure is at least 70 nucleotides in length. In some embodiments, the poly-A region of a nucleic acid molecule of the present disclosure is at least 75 nucleotides in length. In some embodiments, the poly-A region of a nucleic acid molecule of the present disclosure is at least 80 nucleotides in length. In some embodiments, the poly-A region of a nucleic acid molecule of the present disclosure is at least 85 nucleotides in length. In some embodiments, the poly-A region of a nucleic acid molecule of the present disclosure is at least 90 nucleotides in length. In some embodiments, the poly-A region of a nucleic acid molecule of the present disclosure is at least 95 nucleotides in length. In some embodiments, the poly-A region of a nucleic acid molecule of the present disclosure is at least 100 nucleotides in length. In some embodiments, the poly-A region of a nucleic acid molecule of the present disclosure is at least 110 nucleotides in length. In some embodiments, the poly-A region of a nucleic acid molecule of the present disclosure is at least 120 nucleotides in length. In some embodiments, the poly-A region of a nucleic acid molecule of the present disclosure is at least 130 nucleotides in length. In some embodiments, the poly-A region of a nucleic acid molecule of the present disclosure is at least 140 nucleotides in length. In some embodiments, the poly-A region of a nucleic acid molecule of the present disclosure is at least 150 nucleotides in length. In some embodiments, the poly-A region of a nucleic acid molecule of the present disclosure is at least 160 nucleotides in length. In some embodiments, the poly-A region of a nucleic acid molecule of the present disclosure is at least 170 nucleotides in length. In some embodiments, the poly-A region of a nucleic acid molecule of the present disclosure is at least 180 nucleotides in length. In some embodiments, the poly-A region of a nucleic acid molecule of the present disclosure is at least 190 nucleotides in length. In some embodiments, the poly-A region of a nucleic acid molecule of the present disclosure is at least 200 nucleotides in length. In some embodiments, the poly-A region of a nucleic acid molecule of the present disclosure is at least 225 nucleotides in length. In some embodiments, the poly-A region of a nucleic acid molecule of the present disclosure is at least 250 nucleotides in length. In some embodiments, the poly-A region of a nucleic acid molecule of the present disclosure is at least 275 nucleotides in length. In some embodiments, the poly-A region of a nucleic acid molecule of the present disclosure is at least 300 nucleotides in length. In some embodiments, the poly-A region of a nucleic acid molecule of the present disclosure is at least 350 nucleotides in length. In some embodiments, the poly-A region of a nucleic acid molecule of the present disclosure is at least 400 nucleotides in length. In some embodiments, the poly-A region of a nucleic acid molecule of the present disclosure is at least 450 nucleotides in length. In some embodiments, the poly-A region of a nucleic acid molecule of the present disclosure is at least 500 nucleotides in length. In some embodiments, the poly-A region of a nucleic acid molecule of the present disclosure is at least 600 nucleotides in length. In some embodiments, the poly-A region of a nucleic acid molecule of the present disclosure is at least 700 nucleotides in length. In some embodiments, the poly-A region of a nucleic acid molecule of the present disclosure is at least 800 nucleotides in length. In some embodiments, the poly-A region of a nucleic acid molecule of the present disclosure is at least 900 nucleotides in length. In some embodiments, the poly-A region of a nucleic acid molecule of the present disclosure is at least 1000 nucleotides in length. In some embodiments, the poly-A region of a nucleic acid molecule of the present disclosure is at least 1100 nucleotides in length. In some embodiments, the poly-A region of a nucleic acid molecule of the present disclosure is at least 1200 nucleotides in length. In some embodiments, the poly-A region of a nucleic acid molecule of the present disclosure is at least 1300 nucleotides in length. In some embodiments, the poly-A region of a nucleic acid molecule of the present disclosure is at least 1400 nucleotides in length. In some embodiments, the poly-A region of a nucleic acid molecule of the present disclosure is at least 1500 nucleotides in length. In some embodiments, the poly-A region of a nucleic acid molecule of the present disclosure is at least 1600 nucleotides in length. In some embodiments, the poly-A region of a nucleic acid molecule of the present disclosure is at least 1700 nucleotides in length. In some embodiments, the poly-A region of a nucleic acid molecule of the present disclosure is at least 1800 nucleotides in length. In some embodiments, the poly-A region of a nucleic acid molecule of the present disclosure is at least 1900 nucleotides in length. In some embodiments, the poly-A region of a nucleic acid molecule of the present disclosure is at least 2000 nucleotides in length. In some embodiments, the poly-A region of a nucleic acid molecule of the present disclosure is at least 2250 nucleotides in length. In some embodiments, the poly-A region of a nucleic acid molecule of the present disclosure is at least 2500 nucleotides in length. In some embodiments, the poly-A region of a nucleic acid molecule of the present disclosure is at least 2750 nucleotides in length. In some embodiments, the poly-A region of a nucleic acid molecule of the present disclosure is at least 3000 nucleotides in length.

In some embodiments, length of a poly-A region in a nucleic acid molecule can be selected based on the overall length of the nucleic acid molecule, or a portion thereof (such as the length of the coding region or the length of an open reading frame of the nucleic acid molecule, etc.). For example, in some embodiments, the poly-A region accounts for about 5%, 10%, 15%, 20%, 25%, 30%, 35%, 40%, 45%, 50%, 55%, 60%, 65%, 70%, 75%, 80%, 85%, 90%, 95% or more of the total length of nucleic acid molecule containing the poly-A region.

Without being bound by the theory, it is contemplated that certain RNA-binding proteins can bind to the poly-A region located at the 3'-end of an mRNA molecule. These poly-A binding proteins (PABP) can modulate mRNA expression, such as interacting with translation initiation machinery in a cell and/or protecting the 3'-poly-A tails from degradation. Accordingly, in some embodiments, in some embodiments, the nucleic acid molecule of the present disclosure (e.g., mRNA) comprises at least one binding site for poly-A binding protein (PABP). In other embodiments, the nucleic acid molecule is conjugated or complex with a PABP before loaded into a delivery vehicle (e.g., lipid nanoparticles).

In some embodiments, the nucleic acid molecule of the present disclosure (e.g., mRNA) comprises a poly-A-G Quartet. The G-quartet is a cyclic hydrogen bonded array of four guanosine nucleotides that can be formed by G-rich sequences in both DNA and RNA. In this embodiment, the G-quartet is incorporated at the end of the poly-A region. The resultant polynucleotides (e.g., mRNA) may be assayed for stability, protein production and other parameters including half-life at various time points. It has been discovered that the polyA-G quartet structure results in protein production equivalent to at least 75% of that seen using a poly-A region of 120 nucleotides alone.

In some embodiments, the nucleic acid molecule of the present disclosure (e.g., mRNA) may include a poly-A region and may be stabilized by the addition of a 3'-stabilizing region. In some embodiments, the 3'-stabilizing region which may be used to stabilize a nucleic acid molecule (e.g., mRNA) including the poly-A or poly-A-G Quartet structures as described in International Patent Publication No. WO2013/103659, the content of which is incorporated herein by reference in its entirety.

In other embodiments, the 3'-stabilizing region which may be used in connection with the nucleic acid molecules of the present disclosure include a chain termination nucleoside such as but is not limited to 3'-deoxyadenosine (cordycepin), 3'-deoxyuridine, 3'-deoxycytosine, 3'-deoxyguanosine, 3'-deoxythymine, 2',3'-dideoxynucleosides, such as 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, or an O-methylnucleoside, 3'-deoxynucleoside, 2',3'-dideoxynucleoside 3'-O-methylnucleosides, 3'-O-ethylnucleosides, 3'-arabinosides, and other alternative nucleosides known in the art and/or described herein.

6.3.5 Secondary Structure

Without being bound by the theory, it is contemplated that a stem-loop structure can direct RNA folding, protect structural stability of a nucleic acid molecule (e.g., mRNA), provide recognition sites for RNA binding proteins, and serve as a substrate for enzymatic reactions. For example, the incorporation of a miR sequence and/or a TEE sequence changes the shape of the stem loop region which may increase and/or decrease translation (Kedde et al. A Pumilio-induced RNA structure switch in p27-3'UTR controls miR-221 and miR-222 accessibility. Nat Cell Biol., 2010 October; 12(10):1014-20, the content of which is herein incorporated by reference in its entirety).

Accordingly, in some embodiments, the nucleic acid molecules as described herein (e.g., mRNA) or a portion thereof may assume a stem-loop structure, such as but is not limited to a histone stem loop. In some embodiments, the stem-loop structure is formed from a stem-loop sequence that is about 25 or about 26 nucleotides in length such as, but not limited to, those as described in International Patent Publication No. WO2013/103659, the content of which is incorporated herein by reference in its entirety. Additional examples of stem-loop sequences include those described in International Patent Publication No. WO2012/019780 and International Patent Publication No. WO201502667, the contents of which are incorporated herein by reference. In some embodiments, the step-loop sequence comprises a TEE as described herein. In some embodiments, the step-loop sequence comprises a miR sequence as described herein. In specific embodiments, the stem loop sequence may include a miR-122 seed sequence. In specific embodiments, the nucleic acid molecule comprises the stem-loop sequence CAAAGGCTCTTTTCAGAGCCACCA (SEQ ID NO:58). In other embodiments, the nucleic acid molecule comprises the stem-loop sequence CAAAGGCUC-UUUUCAGAGCCACCA (SEQ ID NO:59).

In some embodiments, the nucleic acid molecule of the present disclosure (e.g., mRNA) comprises a stem-loop sequence located upstream (to the 5'-end) of the coding region in a nucleic acid molecule. In some embodiments, the stem-loop sequence is located within the 5'-UTR of the nucleic acid molecule. In some embodiments, the nucleic acid molecule of the present disclosure (e.g., mRNA) comprises a stem-loop sequence located downstream (to the 3'-end) of the coding region in a nucleic acid molecule. In some embodiments, the stem-loop sequence is located within the 3'-UTR of the nucleic acid molecule. In some cases, a nucleic acid molecule can contain more than one stem-loop sequences. In some embodiment, the nucleic acid molecule comprises at least one stem-loop sequence in the 5'-UTR, and at least one stem-loop sequence in the 3'-UTR.

In some embodiments, a nucleic acid molecule comprising a stem-loop structure further comprises a stabilization region. In some embodiment, the stabilization region comprises at least one chain terminating nucleoside that functions to slow down degradation and thus increases the half-life of the nucleic acid molecule. Exemplary chain terminating nucleoside that can be used in connection with the present disclosure include but are not limited to 3'-deoxyadenosine (cordycepin), 3'-deoxyuridine, 3'-deoxycytosine, 3'-deoxyguanosine, 3'-deoxythymine, 2',3'-dideoxynucleosides, such as 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, or an O-methylnucleoside, 3'-deoxynucleoside, 2',3'-dideoxynucleoside 3'-O-methylnucleosides, 3'-O-ethylnucleosides, 3'-arabinosides, and other alternative nucleosides known in the art and/or described herein. In other embodiments, a stem-loop structure may be stabilized by an alteration to the 3'-region of the polynucleotide that can prevent and/or inhibit the addition of oligio(U) (International Patent Publication No. WO2013/103659, incorporated herein by reference in its entirety).

In some embodiments, a nucleic acid molecule of the present disclosure comprises at least one stem-loop sequence and a poly-A region or polyadenylation signal. Non-limiting examples of polynucleotide sequences comprising at least one stem-loop sequence and a poly-A region or a polyadenylation signal include those described in International Patent Publication No. WO2013/120497, International Patent Publication No. WO2013/120629, International Patent Publication No. WO2013/120500, International Patent Publication No. WO2013/120627, International Patent Publication No. WO2013/120498, International Patent Publication No. WO2013/120626, International Patent Publication No. WO2013/120499 and International Patent Publication No. WO2013/120628, the content of each of which is incorporated herein by reference in its entirety.

In some embodiments, the nucleic acid molecule comprising a stem-loop sequence and a poly-A region or a polyadenylation signal can encode for a pathogen antigen or fragment thereof such as the polynucleotide sequences described in International Patent Publication No. WO2013/120499 and International Patent Publication No. WO2013/120628, the content of each of which is incorporated herein by reference in its entirety.

In some embodiments, the nucleic acid molecule comprising a stem-loop sequence and a poly-A region or a polyadenylation signal can encode for a therapeutic protein such as the polynucleotide sequences described in International Patent Publication No. WO2013/120497 and International Patent Publication No. WO2013/120629, the content of each of which is incorporated herein by reference in its entirety.

In some embodiments, the nucleic acid molecule comprising a stem-loop sequence and a poly-A region or a polyadenylation signal can encode for a tumor antigen or fragment thereof such as the polynucleotide sequences described in International Patent Publication No. WO2013/120500 and International Patent Publication No. WO2013/120627, the content of each of which is incorporated herein by reference in its entirety.

In some embodiments, the nucleic acid molecule comprising a stem-loop sequence and a poly-A region or a polyadenylation signal can code for an allergenic antigen or an autoimmune self-antigen such as the polynucleotide sequences described in International Patent Publication No. WO2013/120498 and International Patent Publication No. WO2013/120626, the content of each of which is incorporated herein by reference in its entirety.

6.3.6 Functional Nucleotide Analogs

In some embodiments, a payload nucleic acid molecule described herein contains only canonical nucleotides selected from A (adenosine), G (guanosine), C (cytosine), U (uridine), and T (thymidine). Without being bound by the theory, it is contemplated that certain functional nucleotide analogs can confer useful properties to a nucleic acid molecule. Examples of such as useful properties in the context of the present disclosure include but are not limited to increased stability of the nucleic acid molecule, reduced immunogenicity of the nucleic acid molecule in inducing innate immune responses, enhanced production of protein encoded by the nucleic acid molecule, increased intracellular delivery and/or retention of the nucleic acid molecule, and/or reduced cellular toxicity of the nucleic acid molecule, etc.

Accordingly, in some embodiments, a payload nucleic acid molecule comprises at least one functional nucleotide analog as described herein. In some embodiments, the functional nucleotide analog contains at least one chemical modification to the nucleobase, the sugar group and/or the phosphate group. Accordingly, a payload nucleic acid molecule comprising at least one functional nucleotide analog contains at least one chemical modification to the nucleobases, the sugar groups, and/or the internucleoside linkage. Exemplary chemical modifications to the nucleobases, sugar groups, or internucleoside linkages of a nucleic acid molecule are provided herein.

As described herein, ranging from 0% to 100% of all nucleotides in a payload nucleic acid molecule can be functional nucleotide analogs as described herein. For example, in various embodiments, from about 1% to about 20%, from about 1% to about 25%, from about 1% to about 50%, from about 1% to about 60%, from about 1% to about 70%, from about 1% to about 80%, from about 1% to about 90%, from about 1% to about 95%, from about 10% to about 20%, from about 10% to about 25%, from about 10% to about 50%, from about 10% to about 60%, from about 10% to about 70%, from about 10% to about 80%, from about 10% to about 90%, from about 10% to about 95%, from about 10% to about 100%, from about 20% to about 25%, from about 20% to about 50%, from about 20% to about 60%, from about 20% to about 70%, from about 20% to about 80%, from about 20% to about 90%, from about 20% to about 95%, from about 20% to about 100%, from about 50% to about 60%, from about 50% to about 70%, from about 50% to about 80%, from about 50% to about 90%, from about 50% to about 95%, from about 50% to about 100%, from about 70% to about 80%, from about 70% to about 90%, from about 70% to about 95%, from about 70% to about 100%, from about 80% to about 90%, from about 80% to about 95%, from about 80% to about 100%, from about 90% to about 95%, from about 90% to about 100%, or from about 95% to about 100% of all nucleotides in a nucleic acid molecule are functional nucleotide analogs described herein. In any of these embodiments, a functional nucleotide analog can be present at any position(s) of a nucleic acid molecule, including the 5'-terminus, 3'-terminus, and/or one or more internal positions. In some embodiments, a single nucleic acid molecule can contain different sugar modifications, different nucleobase modifications, and/or different types internucleoside linkages (e.g., backbone structures).

As described herein, ranging from 0% to 100% of all nucleotides of a kind (e.g., all purine-containing nucleotides as a kind, or all pyrimidine-containing nucleotides as a kind, or all A, G, C, T or U as a kind) in a payload nucleic acid molecule can be functional nucleotide analogs as described herein. For example, in various embodiments, from about 1% to about 20%, from about 1% to about 25%, from about 1% to about 50%, from about 1% to about 60%, from about 1% to about 70%, from about 1% to about 80%, from about 1% to about 90%, from about 1% to about 95%, from about 10% to about 20%, from about 10% to about 25%, from about 10% to about 50%, from about 10% to about 60%, from about 10% to about 70%, from about 10% to about 80%, from about 10% to about 90%, from about 10% to about 95%, from about 10% to about 100%, from about 20% to about 25%, from about 20% to about 50%, from about 20% to about 60%, from about 20% to about 70%, from about 20% to about 80%, from about 20% to about 90%, from about 20% to about 95%, from about 20% to about 100%, from about 50% to about 60%, from about 50% to about 70%, from about 50% to about 80%, from about 50% to about 90%, from about 50% to about 95%, from about 50% to about 100%, from about 70% to about 80%, from about 70% to about 90%, from about 70% to about 95%, from about 70% to about 100%, from about 80% to about 90%, from about 80% to about 95%, from about 80% to about 100%, from about 90% to about 95%, from about 90% to about 100%, or from about 95% to about 100% of a kind of nucleotides in a nucleic acid molecule are functional nucleotide analogs described herein. In any of these embodiments, a functional nucleotide analog can be present at any position(s) of a nucleic acid molecule, including the 5'-terminus, 3'-terminus, and/or one or more internal positions. In some embodiments, a single nucleic acid molecule can contain different sugar modifications, different nucleobase modifications, and/or different types internucleoside linkages (e.g., backbone structures).

6.3.7 Modification to Nucleobases

In some embodiments, a functional nucleotide analog contains a non-canonical nucleobase. In some embodiments, canonical nucleobases (e.g., adenine, guanine, uracil, thymine, and cytosine) in a nucleotide can be modified or replaced to provide one or more functional analogs of the nucleotide. Exemplary modification to nucleobases include but are not limited to one or more substitutions or modifications including but not limited to alkyl, aryl, halo, oxo, hydroxyl, alkyloxy, and/or thio substitutions; one or more fused or open rings, oxidation, and/or reduction.

In some embodiments, the non-canonical nucleobase is a modified uracil. Exemplary nucleobases and nucleosides having an modified uracil include pseudouridine (ψ), pyridin-4-one ribonucleoside, 5-aza-uracil, 6-aza-uracil, 2-thio-5-aza-uracil, 2-thio-uracil ($s^2U$), 4-thio-uracil ($s^4U$), 4-thio-pseudouridine, 2-thio-pseudouridine, 5-hydroxy-uracil ($ho^5U$), 5-aminoallyl-uracil, 5-halo-uracil (e.g., 5-iodo-uracil or 5-bromo-uracil), 3-methyl-uracil ($m^3U$), 5-methoxy-uracil ($mo^5U$), uracil 5-oxyacetic acid ($cmo^5U$), uracil 5-oxyacetic acid methyl ester ($mcmo^5U$), 5-carboxymethyl-uracil ($cm^5U$), 1-carboxymethyl-pseudouridine, 5-carboxyhydroxymethyl-uracil ($chm^5U$), 5-carboxyhydroxymethyl-uracil methyl ester ($mchm^5U$), 5-methoxycarbonylmethyl-uracil ($mcm^5U$), 5-methoxycarbonylmethyl-2-thio-uracil ($mcm^5s^2U$), 5-aminomethyl-2-thio-uracil ($nm^5s^2U$), 5-methylaminomethyl-uracil ($mnm^5U$), 5-methylaminomethyl-2-thio-uracil ($mnm^5s^2U$), 5-methylaminomethyl-2-seleno-uracil ($mnm^5se^2U$), 5-carbamoylmethyl-uracil ($ncm^5U$), 5-carboxymethylaminomethyl-uracil ($cmnm^5U$), 5-carboxymethylaminomethyl-2-thio-uracil ($cmnm^5s^2U$), 5-propynyl-uracil, 1-propynyl-pseudouracil, 5-taurinomethyl-uracil ($Tm^5U$), 1-taurinomethyl-pseudouridine, 5-taurinomethyl-2-thio-uracil ($\tau m^5 5s^2U$), 1-taurinomethyl-4-thio-pseudouridine, 5-methyl-uracil ($m^5U$, i.e., having the nucleobase deoxythymine), 1-methyl-pseudouridine 1-ethyl-pseudouridine ($Et^1\psi$), 5-methyl-2-thio-uracil ($m^5s^2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouracil (D), dihydropseudouridine, 5,6-dihydrouracil, 5-methyl-dihydrouracil ($m^5D$), 2-thio-dihydrouracil, 2-thio-dihydropseudouridine, 2-methoxy-uracil, 2-methoxy-4-thio-uracil, 4-methoxy-pseudouridine, 4-methoxy-2-thio-pseudouridine, N1-methyl-pseudouridine, 3-(3-amino-3-carboxypropyl)uracil($acp^3U$), 1-methyl-3-(3-amino-3-carboxypropyl)pseudouridine ($acp^3\psi$), 5-(isopentenylaminomethyl)uracil ($m^5U$), 5-(isopentenylaminomethyl)-2-thio-uracil ($m^5s^2U$), 5,2'-O-dimethyl-uridine ($m^5Um$), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uracil, deoxythymidine, 5-(2-carbomethoxyvinyl)-uracil, 5-(carbamoylhydroxymethyl)-uracil, 5-carbamoylmethyl-2-thio-uracil, 5-carboxymethyl-2-thio-uracil, 5-cyanomethyl-uracil, 5-methoxy-2-thio-uracil, and 5-[3-(1-E-propenylamino)] uracil.

In some embodiments, the non-canonical nucleobase is a modified cytosine. Exemplary nucleobases and nucleosides having a modified cytosine include 5-aza-cytosine, 6-aza-cytosine, pseudoisocytidine, 3-methyl-cytosine (m3C), N4-acetyl-cytosine (ac4C), 5-formyl-cytosine (f5C), N4-methyl-cytosine (m4C), 5-methyl-cytosine (m5C), 5-halo-cytosine (e.g., 5-iodo-cytosine), 5-hydroxymethyl-cytosine (hm5C), 1-methyl-pseudoisocytidine, pyrrolo-cytosine, pyrrolo-pseudoisocytidine, 2-thio-cytosine (s2C), 2-thio-5-methyl-cytosine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytosine, 2-methoxy-5-methyl-cytosine, 4-methoxy-pseudoisocytidine, 4-methoxy-1-methyl-pseudoisocytidine, lysidine (k2C), 5,2'-O-dimethyl-cytidine (m5Cm), N4-acetyl-2'-O-methyl-cytidine (ac4Cm), N4,2'-O-dimethyl-cytidine (m4Cm), 5-formyl-2'-O-methyl-cytidine (fSCm), N4,N4,2'-O-trimethyl-cytidine (m42Cm), 1-thio-cytosine, 5-hydroxy-cytosine, 5-(3-azidopropyl)-cytosine, and 5-(2-azidoethyl)-cytosine.

In some embodiments, the non-canonical nucleobase is a modified adenine. Exemplary nucleobases and nucleosides having an alternative adenine include 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenine (m1 A), 2-methyl-adenine (m2A), N6-methyl-adenine (m6A), 2-methylthio-N6-methyl-adenine (ms2m6A), N6-isopentenyl-adenine (i6A), 2-methylthio-N6-isopentenyl-adenine (ms2i6A), N6-(cis-hydroxyisopentenyl)adenine (io6A), 2-methylthio-N6-(cis-hydroxyisopentenyl)adenine (ms2io6A), N6-glycinylcarbamoyl-adenine (g6A), N6-threonylcarbamoyl-adenine (t6A), N6-methyl-N6-threonylcarbamoyl-adenine (m6t6A), 2-methylthio-N6-threonylcarbamoyl-adenine (ms2g6A), N6,N6-dimethyl-adenine (m62A), N6-hydroxynorvalylcarbamoyl-adenine (hn6A), 2-methylthio-N6-hydroxynorvalylcarbamoyl-adenine (ms2hn6A), N6-acetyl-adenine (ac6A), 7-methyl-adenine, 2-methylthio-adenine, 2-methoxy-adenine, N6,2'-O-dimethyl-adenosine (m6Am), N6,N6,2'-O-trimethyl-adenosine (m62Am), 1,2'-O-dimethyl-adenosine (m1Am), 2-amino-N6-methyl-purine, 1-thio-adenine, 8-azido-adenine, N6-(19-amino-pentaoxanonadecyl)-adenine, 2,8-dimethyl-adenine, N6-formyl-adenine, and N6-hydroxymethyl-adenine.

In some embodiments, the non-canonical nucleobase is a modified guanine. Exemplary nucleobases and nucleosides having a modified guanine include inosine (I), 1-methyl-inosine (m1I), wyosine (imG), methylwyosine (mimG), 4-demethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanine, queuosine (Q), epoxyqueuosine (oQ), galactosyl-queuosine (galQ), mannosyl-queuosine (manQ), 7-cyano-7-deaza-guanine (preQO), 7-aminomethyl-7-deaza-guanine (preQ1), archaeosine (G+), 7-deaza-8-aza-guanine, 6-thio-guanine, 6-thio-7-deaza-guanine, 6-thio-7-deaza-8-aza-guanine, 7-methyl-guanine (m7G), 6-thio-7-methyl-guanine, 7-methyl-inosine, 6-methoxy-guanine, 1-methyl-guanine (m1 G), N2-methyl-guanine (m2G), N2,N2-dimethyl-guanine (m22G), N2,7-dimethyl-guanine (m2,7G), N2, N2,7-dimethyl-guanine (m2,2,7G), 8-oxo-guanine, 7-methyl-8-oxo-guanine, 1-methyl-6-thio-guanine, N2-methyl-6-thio-guanine, N2,N2-dimethyl-6-thio-guanine, N2-methyl-2'-O-methyl-guanosine (m2Gm), N2,N2-dimethyl-2'-O-methyl-guanosine (m22Gm), 1-methyl-2'-O-methyl-guanosine (m1Gm), N2,7-dimethyl-2'-O-methyl-guanosine (m2,7Gm), 2'-O-methyl-inosine (Im), 1,2'-O-dimethyl-inosine (m1Im), 1-thio-guanine, and O-6-methyl-guanine.

In some embodiments, the non-canonical nucleobase of a functional nucleotide analog can be independently a purine, a pyrimidine, a purine or pyrimidine analog. For example, in some embodiments, the non-canonical nucleobase can be modified adenine, cytosine, guanine, uracil, or hypoxanthine. In other embodiments, the non-canonical nucleobase can also include, for example, naturally-occurring and synthetic derivatives of a base, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxy and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d] pyrimidines, pyrazin-2-ones, 1,2,4-triazine, pyridazine; or 1,3,5 triazine.

6.3.8 Modification to the Sugar

In some embodiments, a functional nucleotide analog contains a non-canonical sugar group. In various embodiments, the non-canonical sugar group can be a 5-carbon or 6-carbon sugar (such as pentose, ribose, arabinose, xylose, glucose, galactose, or a deoxy derivative thereof) with one or more substitutions, such as a halo group, a hydroxy group, a thiol group, an alkyl group, an alkoxy group, an alkenyloxy group, an alkynyloxy group, an cycloalkyl group, an aminoalkoxy group, an alkoxyalkoxy group, an hydroxyalkoxy group, an amino group, an azido group, an aryl group, an aminoalkyl group, an aminoalkenyl group, an aminoalkynyl group, etc.

Generally, RNA molecules contains the ribose sugar group, which is a 5-membered ring having an oxygen. Exemplary, non-limiting alternative nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino (that also has a phosphoramidate backbone)); multicyclic forms (e.g., tricyclo and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone).

In some embodiments, the sugar group contains one or more carbons that possess the opposite stereochemical configuration of the corresponding carbon in ribose. Thus, a nucleic acid molecule can include nucleotides containing, e.g., arabinose or L-ribose, as the sugar. In some embodiments, the nucleic acid molecule includes at least one nucleoside wherein the sugar is L-ribose, 2'-O-methyl-ribose, 2'-fluoro-ribose, arabinose, hexitol, an LNA, or a PNA.

6.3.9 Modifications to the Internucleoside Linkage

In some embodiments, the payload nucleic acid molecule of the present disclosure can contain one or more modified internucleoside linkage (e.g., phosphate backbone). Backbone phosphate groups can be altered by replacing one or more of the oxygen atoms with a different substituent.

In some embodiments, the functional nucleotide analogs can include the replacement of an unaltered phosphate moiety with another internucleoside linkage as described herein. Examples of alternative phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be altered by the replacement of a linking oxygen with nitrogen (bridged phosphoramidates), sulfur (bridged phosphorothioates), and carbon (bridged methylene-phosphonates).

The alternative nucleosides and nucleotides can include the replacement of one or more of the non-bridging oxygens with a borane moiety ($BH_3$), sulfur (thio), methyl, ethyl, and/or methoxy. As a non-limiting example, two non-bridging oxygens at the same position (e.g., the alpha (α), beta (β) or gamma (γ) position) can be replaced with a sulfur (thio) and a methoxy. The replacement of one or more of the oxygen atoms at the position of the phosphate moiety (e.g., α-thio phosphate) is provided to confer stability (such as against exonucleases and endonucleases) to RNA and DNA through the unnatural phosphorothioate backbone linkages. Phosphorothioate DNA and RNA have increased nuclease resistance and subsequently a longer half-life in a cellular environment.

Other internucleoside linkages that may be employed according to the present disclosure, including internucleoside linkages which do not contain a phosphorous atom, are described herein.

Additional examples of nucleic acid molecules (e.g., mRNA), compositions, formulations and/or methods associated therewith that can be used in connection with the present disclosure further include those described in WO2002/098443, WO2003/051401, WO2008/052770, WO2009127230, WO2006122828, WO2008/083949, WO2010088927, WO2010/037539, WO2004/004743, WO2005/016376, WO2006/024518, WO2007/095976, WO2008/014979, WO2008/077592, WO2009/030481, WO2009/095226, WO2011069586, WO2011026641, WO2011/144358, WO2012019780, WO2012013326, WO2012089338, WO2012113513, WO2012116811, WO2012116810, WO2013113502, WO2013113501, WO2013113736, WO2013143698, WO2013143699, WO2013143700, WO2013/120626, WO2013120627, WO2013120628, WO2013120629, WO2013174409, WO2014127917, WO2015/024669, WO2015/024668, WO2015/024667, WO2015/024665, WO2015/024666, WO2015/024664, WO2015101415, WO2015101414, WO2015024667, WO2015062738, WO2015101416, the content of each of which is incorporated herein in its entirety.

Therapeutic nucleic acid molecules as described herein can by isolated or synthesized using methods known in the art. In some embodiments, DNA or RNA molecules to be used in connection with the present disclosure are chemically synthesized. In other embodiments, DNA or RNA molecules to be used in connection with the present disclosure are isolated from a natural source.

In some embodiments, mRNA molecules to be used in connection with the present disclosure are biosynthesized using a host cell. In particular embodiments, an mRNA is produced by transcribing a corresponding DNA sequencing using a host cell. In some embodiments, a DNA sequence encoding an mRNA sequence is incorporated into an expression vector, which vector is then introduced into a host cell (e.g., *E. coli*) using methods known in the art. The host cell is then cultured under a suitable condition to produce mRNA transcripts. Other methods for producing an mRNA molecule from an encoding DNA are known in the art. For example, in some embodiments, a cell-free (in vitro) transcription system comprising enzymes of the transcription machinery of a host cell can be used to produce mRNA transcripts. An exemplary cell-free transcription reaction system is described in Example 1 of the present disclosure.

6.4 Nanoparticle Compositions

In one aspect, nucleic acid molecules described herein are formulated for in vitro and in vivo delivery. Particularly, in some embodiments the nucleic acid molecule is formulated into a lipid-containing composition. In some embodiments, the lipid-containing composition forms lipid nanoparticles enclosing the nucleic acid molecule within a lipid shell. In some embodiments, the lipid shells protects the nucleic acid molecules from degradation. In some embodiments, the lipid nanoparticles also facilitate transportation of the enclosed nucleic acid molecules into intracellular compartments and/or machinery to exert an intended therapeutic of prophylactic function. In certain embodiments, nucleic acids, when present in the lipid nanoparticles, are resistant in aqueous solution to degradation with a nuclease. Lipid nanoparticles comprising nucleic acids and their method of preparation are known in the art, such as those disclosed in, e.g., U.S. Patent Publication No. 2004/0142025, U.S. Patent Publication No. 2007/0042031, PCT Publication No. WO 2017/004143, PCT Publication No. WO 2015/199952, PCT Publication No. WO 2013/016058, and PCT Publication No. WO 2013/086373, the full disclosures of each of which are herein incorporated by reference in their entirety for all purposes.

In some embodiments, the largest dimension of a nanoparticle composition provided herein is 1 μm or shorter (e.g., ≤1 μm, ≤900 nm, ≤800 nm, ≤700 nm, ≤600 nm, ≤500 nm, ≤400 nm, ≤300 nm, ≤200 nm, ≤175 nm, ≤150 nm, ≤125 nm, ≤100 nm, ≤75 nm, ≤50 nm, or shorter), such as when measured by dynamic light scattering (DLS), transmission electron microscopy, scanning electron microscopy, or another method. In one embodiment, the lipid nanoparticle provided herein has at least one dimension that is in the range of from about 40 to about 200 nm. In one embodiment, the at least one dimension is in the range of from about 40 to about 100 nm.

Nanoparticle compositions that can be used in connection with the present disclosure include, for example, lipid nanoparticles (LNPs), nano liproprotein particles, liposomes, lipid vesicles, and lipoplexes. In some embodiments, nanoparticle compositions are vesicles including one or more lipid bilayers. In some embodiments, a nanoparticle composition includes two or more concentric bilayers separated by aqueous compartments. Lipid bilayers may be functionalized and/or crosslinked to one another. Lipid bilayers may include one or more ligands, proteins, or channels.

In some embodiments, nanoparticle compositions as described comprise a lipid component including at least one lipid, such as a compound according to one of Formulae (I) to (IV) (and sub-formulas thereof) as described herein. For example, in some embodiments, a nanoparticle composition may include a lipid component including one of compounds provided herein. Nanoparticle compositions may also include one or more other lipid or non-lipid components as described below.

6.4.1 Cationic Lipids

In some embodiments, the lipid-containing composition comprises at least one lipid compound according to Formula (I):

(I)

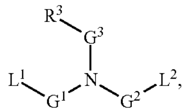

or a pharmaceutically acceptable salt, prodrug or stereoisomer thereof, wherein:

$G^1$ and $G^2$ are each independently a bond, $C_2$-$C_{12}$ alkylene, or $C_2$-$C_{12}$ alkenylene, wherein one or more —$CH_2$— in the alkylene or alkenylene is optionally replaced by —O—;

$L^1$ is —OC(═O)$R^1$, —C(═O)O$R^1$, —OC(═O)O$R^1$, —C(═O)$R^1$, —O$R^1$, —S(O)$_x$$R^1$, —C(═O)S$R^1$, —SC(═O)$R^1$, —N$R^a$c(═O)$R^1$, —C(═O)N$R^b$$R^c$, —N$R^a$C(═O)N$R^b$$R^c$, ≤OC(═O)N$R^b$$R^c$, —N$R^a$C(═O)O$R^1$, —SC(═S)$R^1$, —C(═S)S$R^1$, —C(═S)$R^1$, —CH(OH)$R^1$, —P(═O)(O$R^b$)(O$R^c$), —($C_6$-$C_{10}$ arylene)-$R^1$, -(6- to 10-membered heteroarylene)-$R^1$, or $R^1$;

$L^2$ is —OC(═O)$R^2$, —C(═O)O$R^2$, —OC(═O)O$R^2$, —C(═O)$R^2$, —O$R^2$, —S(O)$_x$$R^2$, —S—S$R^2$, —C(═O)S$R^2$, —SC(═O)$R^2$, —N$R^d$C(═O)$R^2$, —C(═O)N$R^e$$R^f$, —N$R^d$C(═O)N$R^e$$R^f$, —OC(═O)N$R^e$$R^f$, —N$R^d$C(═O)O$R^2$, —SC(═S)$R^2$, —C(═S)S$R^2$, —C(═S)$R^2$, —CH(OH)$R^2$, —P(═O)(O$R^e$)(O$R^f$), —($C_6$-$C_{10}$ arylene)-$R^2$, -(6- to 10-membered heteroarylene)-$R^2$, or $R^2$;

$R^1$ and $R^2$ are each independently $C_6$-$C_{32}$ alkyl or $C_6$-$C_{32}$ alkenyl;

$R^a$, $R^b$, $R^d$, and $R^c$ are each independently H, $C_1$-$C_{24}$ alkyl, or $C_2$-$C_{24}$ alkenyl;

$R^c$ and $R^f$ are each independently $C_1$-$C_{32}$ alkyl or $C_2$-$C_{32}$ alkenyl;

$G^3$ is $C_2$-$C_{24}$ alkylene, $C_2$-$C_{24}$ alkenylene, $C_3$-$C_8$ cycloalkylene, or $C_3$-$C_8$ cycloalkenylene;

$R^3$ is —N($R^4$)$R^5$;

$R^4$ is $C_3$-$C_8$ cycloalkyl, $C_3$-$C_8$ cycloalkenyl, 4- to 8-membered heterocyclyl, or $C_6$-$C_{10}$ aryl; or $R^4$, $G^3$ or part of $G^3$, together with the nitrogen to which they are attached form a cyclic moiety;

$R^5$ is $C_1$-$C_{12}$ alkyl or $C_3$-$C_8$ cycloalkyl; or $R^4$, $R^5$, together with the nitrogen to which they are attached form a cyclic moiety;

x is 0, 1 or 2; and wherein each alkyl, alkenyl, cycloalkyl, cycloalkenyl, heterocyclyl, aryl, alkylene, alkenylene, cycloalkylene, cycloalkenylene, arylene, heteroarylene, and cyclic moiety is independently optionally substituted.

In one embodiment, provided herein is a compound of Formula (I):

(I)

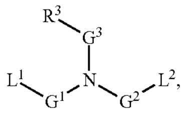

or a pharmaceutically acceptable salt, prodrug or stereoisomer thereof, wherein:

$G^1$ and $G^2$ are each independently a bond, $C_2$-$C_{12}$ alkylene, or $C_2$-$C_{12}$ alkenylene;

$L^1$ is —OC(=O)$R^1$, —C(=O)O$R^1$, —OC(=O)O$R^1$, —C(=O)$R^1$, —S(O)$_x$$R^1$, —C(=O)S$R^1$, —SC(=O)$R^1$, —N$R^a$C(=O)$R^1$, —C(=O)N$R^b$$R^c$, —N$R^a$C(=O)N$R^b$$R^c$, —OC(=O)N$R^b$$R^c$, —N$R^a$C(=O)O$R^1$, —SC(=S)$R^1$, —C(=S)S$R^1$, —C(=S)$R^1$, —CH(OH)$R^1$, —P(=O)(O$R^b$)(O$R^c$), —($C_6$-$C_{10}$ arylene)-$R^1$, -(6- to 10-membered heteroarylene)-$R^1$, or $R^1$;

$L^2$ is —OC(=O)$R^2$, —C(=O)O$R^2$, —OC(=O)O$R^2$, —C(=O)$R^2$, —O$R^2$, —S(O)$_x$$R^2$, —S—S$R^2$, —C(=O)S$R^2$, —SC(=O)$R^2$, —N$R^d$C(=O)$R^2$, —C(=O)N$R^e$$R^f$, —N$R^d$C(=O)N$R^e$$R^f$, —OC(=O)N$R^e$$R^f$, —N$R^d$C(=O)O$R^2$, —SC(=S)$R^2$, —C(=S)S$R^2$, —C(=S)$R^2$, —CH(OH)$R^2$, —P(=O)(P$R^e$)(O$R^f$), —($C_6$-$C_{10}$ arylene)-$R^2$, -(6- to 10-membered heteroarylene)-$R^2$, or $R^2$;

$R^1$ and $R^2$ are each independently $C_6$-$C_{24}$ alkyl or $C_6$-$C_{24}$ alkenyl;

$R^a$, $R^b$, $R^d$, and W are each independently H, $C_1$-$C_{12}$ alkyl, or $C_2$-$C_{12}$ alkenyl;

$R^c$ and $R^f$ are each independently $C_1$-$C_{12}$ alkyl or $C_2$-$C_{12}$ alkenyl;

$G^3$ is $C_2$-$C_{24}$ alkylene, $C_2$-$C_{24}$ alkenylene, $C_3$-$C_8$ cycloalkylene, or $C_3$-$C_8$ cycloalkenylene;

$R^3$ is —N($R^4$)$R^5$;

$R^4$ is $C_3$-$C_8$ cycloalkyl, $C_3$-$C_8$ cycloalkenyl, or $C_6$-$C_{10}$ aryl;

$R^5$ is $C_1$-$C_{12}$ alkyl;

x is 0, 1 or 2; and wherein each alkyl, alkenyl, cycloalkyl, cycloalkenyl, aryl, alkylene, alkenylene, cycloalkylene, cycloalkenylene, arylene, and heteroarylene is independently optionally substituted.

In one embodiment, provided herein is a compound of Formula (II):

(II)

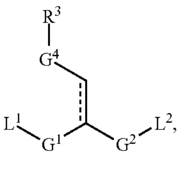

or a pharmaceutically acceptable salt, prodrug or stereoisomer thereof, wherein:

------ is a single bond or a double bond;

$G^1$ and $G^2$ are each independently a bond, $C_2$-$C_{12}$ alkylene, or $C_2$-$C_{12}$ alkenylene, wherein one or more —$CH_2$— in the alkylene or alkenylene is optionally replaced by —O—;

$L^1$ is —OC(=O)$R^1$, —C(=O)O$R^1$, —OC(=O)O$R^1$, —C(=O)$R^1$, —O$R^1$, —S(O)$_x$$R^1$, —S—S$R^1$, —C(=O)S$R^1$, —SC(=O)$R^1$, —N$R^a$C(=O)$R^1$, —C(=O)N$R^b$$R^c$, —N$R^a$C(=O)N$R^b$$R^c$, —OC(=O)N$R^b$$R^c$, —N$R^a$C(=O)O$R^1$, —SC(=S)$R^1$, —C(=S)S$R^1$, —C(=S)$R^1$, —CH(OH)$R^1$, —P(=O)(O$R^b$)(O$R^c$), —($C_6$-$C_{10}$ arylene)-$R^1$, -(6- to 10-membered heteroarylene)-$R^1$, or $R^1$;

$L^2$ is —OC(=O)$R^2$, —C(=O)O$R^2$, —OC(=O)O$R^2$, —C(=O)$R^2$, —O$R^2$, —S(O)$_x$$R^2$, —S—S$R^2$, —C(=O)S$R^2$, —SC(=O)$R^2$, —N$R^d$C(=O)$R^2$, —C(=O)N$R^e$$R^f$, —N$R^d$C(=O)N$R^e$$R^f$, —OC(=O)N$R^e$$R^f$, —N$R^d$C(=O)O$R^2$, —SC(=S)$R^2$, —C(=S)S$R^2$, —C(=S)$R^2$, —CH(OH)$R^2$, —P(=O)(O$R^e$)(O$R^f$), —($C_6$-$C_{10}$ arylene)-$R^2$, -(6- to 10-membered heteroarylene)-$R^2$, or $R^2$;

$R^1$ and $R^2$ are each independently $C_6$-$C_{32}$ alkyl or $C_6$-$C_{32}$ alkenyl;

$R^a$, $R^b$, $R^d$, and $R^e$ are each independently H, $C_1$-$C_{24}$ alkyl, or $C_2$-$C_{24}$ alkenyl;

$R^c$ and $R^f$ are each independently $C_1$-$C_{32}$ alkyl or $C_2$-$C_{32}$ alkenyl;

$G^4$ is a bond, $C_1$-$C_{23}$ alkylene, $C_2$-$C_{23}$ alkenylene, $C_3$-$C_8$ cycloalkylene, or $C_3$-$C_8$ cycloalkenylene;

$R^3$ is —N($R^4$)$R^5$;

$R^4$ is $C_1$-$C_{12}$ alkyl, $C_3$-$C_8$ cycloalkyl, $C_3$-$C_8$ cycloalkenyl, 4- to 8-membered heterocyclyl, or $C_6$-$C_{10}$ aryl; or $R^4$, $G^3$ or part of $G^3$, together with the nitrogen to which they are attached form a cyclic moiety;

$R^5$ is $C_1$-$C_{12}$ alkyl or $C_3$-$C_8$ cycloalkyl; or $R^4$, $R^5$, together with the nitrogen to which they are attached form a cyclic moiety;

x is 0, 1 or 2; and wherein each alkyl, alkenyl, cycloalkyl, cycloalkenyl, heterocyclyl, aryl, alkylene, alkenylene, cycloalkylene, cycloalkenylene, arylene, heteroarylene, and cyclic moiety is independently optionally substituted.

In one embodiment, provided herein is a compound of Formula (II):

(II)

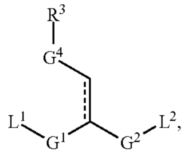

or a pharmaceutically acceptable salt, prodrug or stereoisomer thereof, wherein:

------ is a single bond or a double bond;

$G^1$ and $G^2$ are each independently a bond, $C_2$-$C_{12}$ alkylene, or $C_2$-$C_{12}$ alkenylene;

$L^1$ is —OC(=O)$R^1$, —C(=O)O$R^1$, —OC(=O)O$R^1$, —C(=O)$R^1$, —S(O)$_x$$R^1$, —S—S$R^1$, —C(=O)S$R^1$, —SC(=O)$R^1$, —N$R^a$C(=O)$R^1$, —C(=O)N$R^b$$R^c$, —N$R^a$C(=O)N$R^b$$R^c$, —OC(=O)N$R^b$$R^c$, —N$R^a$C(=O)O$R^1$, —SC(=S)$R^1$, —C(=S)S$R^1$, —C(=S)$R^1$, —CH(OH)$R^1$, —P(=O)(O$R^b$)(O$R^c$), —($C_6$-$C_{10}$ arylene)-$R^1$, -(6- to 10-membered heteroarylene)-$R^1$, or $R^1$;

$L^2$ is —OC(═O)$R^2$, —C(═O)O$R^2$, —OC(═O)O$R^2$, —C(═O)$R^2$, —O$R^2$, —S(O)$_x$$R^2$, —S—S$R^2$, —C(═O)S$R^2$, —SC(═O)$R^2$, —N$R^d$C(═O)$R^2$, —C(═O)N$R^eR^f$, —N$R^d$C(═O)N$R^eR^f$, —OC(═O)N$R^eR^f$, —N$R^d$C(═O)O$R^2$, —SC(═S)$R^2$, —C(═S)S$R^2$, —C(═S)$R^2$, —CH(OH)$R^2$, —P(═O)(O$R^e$)(O$R^f$), —($C_6$-$C_{10}$ arylene)-$R^2$, -(6- to 10-membered heteroarylene)-$R^2$, or $R^2$;

$R^1$ and $R^2$ are each independently $C_6$-$C_{24}$ alkyl or $C_6$-$C_{24}$ alkenyl;

$R^a$, $R^b$, $R^d$, and $R^e$ are each independently H, $C_1$-$C_{12}$ alkyl, or $C_2$-$C_{12}$ alkenyl;

$R^c$ and $R^f$ are each independently $C_1$-$C_{12}$ alkyl or $C_2$-$C_{12}$ alkenyl;

$G^4$ is a bond, $C_1$-$C_{23}$ alkylene, $C_2$-$C_{23}$ alkenylene, $C_3$-$C_8$ cycloalkylene, or $C_3$-$C_8$ cycloalkenylene;

$R^3$ is —N($R^4$)$R^5$;

$R^4$ is $C_1$-$C_{12}$ alkyl, $C_3$-$C_8$ cycloalkyl, $C_3$-$C_8$ cycloalkenyl, or $C_6$-$C_{10}$ aryl;

$R^5$ is $C_1$-$C_{12}$ alkyl;

x is 0, 1 or 2; and wherein each alkyl, alkenyl, cycloalkyl, cycloalkenyl, aryl, alkylene, alkenylene, cycloalkylene, cycloalkenylene, arylene, and heteroarylene is independently optionally substituted.

In one embodiment, ------ is a single bond. In one embodiment, ------ is a double bond. In one embodiment, ------ is a double bond, and the compound has a (Z)-configuration. In one embodiment, ------ is a double bond, and the compound has a (E)-configuration.

In one embodiment, provided herein is a compound of Formula (III):

(III)

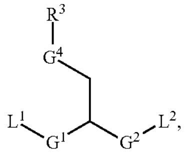

or a pharmaceutically acceptable salt, prodrug or stereoisomer thereof.

In one embodiment, provided herein is a compound of Formula (IV):

(IV)

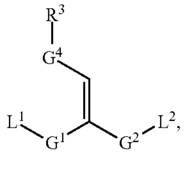

or a pharmaceutically acceptable salt, prodrug or stereoisomer thereof.

In one embodiment, $G^1$ is a bond. In one embodiment, $G^2$ is a bond. In one embodiment, $G^1$ and $G^2$ are both a bond.

In one embodiment, $G^1$ and $G^2$ are each independently $C_2$-$C_{12}$ alkylene or $C_2$-$C_{12}$ alkenylene. In one embodiment, $G^1$ and $G^2$ are each independently $C_2$-$C_{12}$ alkylene. In one embodiment, $G^1$ and $G^2$ are each independently $C_2$-$C_{12}$ alkenylene. In one embodiment, $G^1$ and $G^2$ are each independently $C_3$-$C_7$ alkylene. In one embodiment, $G^1$ and $G^2$ are each independently $C_5$ alkylene.

In one embodiment, $G^1$ is unsubstituted. In one embodiment, $G^1$ is substituted. In one embodiment, $G^1$ is substituted with —OH. In one embodiment, $G^1$ is substituted with (a second) $L^1$ (i.e., $G^1$ is connected to two $L^1$). In one embodiment, $G^1$ is substituted with —O—($C_6$-$C_{24}$ alkyl). In one embodiment, $G^1$ is substituted with —O—($C_6$-$C_{24}$ alkenyl). In one embodiment, $G^1$ is substituted with —C(═O)—($C_6$-$C_{24}$ alkyl). In one embodiment, $G^1$ is substituted with —C(═O)—($C_6$-$C_{24}$ alkenyl).

In one embodiment, $G^2$ is unsubstituted. In one embodiment, $G^2$ is substituted. In one embodiment, $G^2$ is substituted with —OH. In one embodiment, $G^2$ is substituted with (a second) $L^2$ (i.e., $G^2$ is connected to two $L^2$). In one embodiment, $G^2$ is substituted with —O—($C_6$-$C_{24}$ alkyl). In one embodiment, $G^2$ is substituted with —O—($C_6$-$C_{24}$ alkenyl). In one embodiment, $G^2$ is substituted with —C(═O)—($C_6$-$C_{24}$ alkyl). In one embodiment, $G^2$ is substituted with —C(═O)—($C_6$-$C_{24}$ alkenyl).

In one embodiment, one or more —$CH_2$— in the alkylene or alkenylene in $G^1$ and/or $G^2$ is optionally replaced by —O—. In one embodiment, $G^1$ and $G^2$ are each independently $C_5$-$C_9$ alkylene, wherein one or more —$CH_2$— in the alkylene is optionally replaced by —O—. In one embodiment, $G^1$ and $G^2$ are each independently $C_5$-$C_7$ alkylene, wherein one or more —$CH_2$— in the alkylene is optionally replaced by —O—. In one embodiment, $G^1$ and $G^2$ are both —$CH_2$—$CH_2$—O—$CH_2$—$CH_2$—. In one embodiment, $G^1$ and $G^2$ are both —$CH_2$—$CH_2$—O—$CH_2$—$CH_2$—O—$CH_2$—.

In one embodiment, the compound is a compound of Formula (I-A):

(I-A)

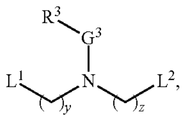

wherein y and z are each independently an integer from 2 to 12, or a pharmaceutically acceptable salt, prodrug or stereoisomer thereof.

In one embodiment, the compound is a compound of Formula (II-A):

(II-A)

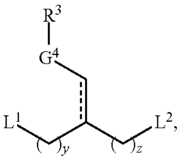

wherein y and z are each independently an integer from 2 to 12, or a pharmaceutically acceptable salt, prodrug or stereoisomer thereof.

In one embodiment, the compound is a compound of Formula (III-A):

(III-A)

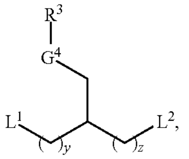

wherein y and z are each independently an integer from 2 to 12, or a pharmaceutically acceptable salt, prodrug or stereoisomer thereof.

In one embodiment, the compound is a compound of Formula (IV-A):

(IV-A)

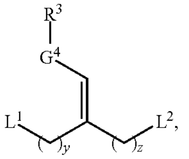

wherein y and z are each independently an integer from 2 to 12, or a pharmaceutically acceptable salt, prodrug or stereoisomer thereof.

In one embodiment, y and z are each independently an integer from 2 to 10. In one embodiment, y and z are each independently an integer from 2 to 6. In one embodiment, y and z are each independently an integer from 4 to 10.

In one embodiment, y and z are different. In one embodiment, y and z are the same. In one embodiment, y and z are the same and are selected from 4, 5, 6, 7, 8, and 9. In one embodiment, y is 5 and z is 5.

In one embodiment, $L^1$ is —OC(═O)$R^1$, —C(═O)O$R^1$, —OC(═O)O$R^1$, —C(═O)$R^1$, —O$R^1$, —S(O)$_x$$R^1$, —S—S$R^1$, —C(═O)S$R^1$, —SC(═O)$R^1$, —N$R^a$C(═O)$R^1$, —C(═O)N$R^b$$R^c$, —N$R^a$C(═O)N$R^b$$R^c$, —OC(═O)N$R^b$$R^c$, —N$R^a$C(═O)O$R^1$, —SC(═S)$R^1$, —C(═S)S$R^1$, —C(═S)$R^1$, —CH(OH)$R^1$, or —P(═O)(O$R^b$)(O$R^c$). In one embodiment, $L^1$ is —($C_6$-$C_{10}$ arylene)-$R^1$. In one embodiment, $L^1$ is -(6- to 10-membered heteroarylene)-$R^1$. In one embodiment, $L^1$ is $R^1$.

In one embodiment, $L^1$ is —OC(═O)$R^1$, —C(═O)O$R^1$, —C(═O)S$R^1$, —SC(═O)$R^1$, —N$R^a$C(═O)$R^1$, or —C(═O)N$R^b$$R^c$. In one embodiment, $L^1$ is —OC(═O)$R^1$, —C(═O)O$R^1$, —N$R^a$C(═O)$R^1$, or —C(═O)N$R^b$$R^c$. In one embodiment, $L^1$ is —OC(═O)$R^1$. In one embodiment, $L^1$ is —C(═O)O$R^1$. In one embodiment, $L^1$ is —N$R^a$C(═O)$R^1$. In one embodiment, $L^1$ is —C(═O)N$R^b$$R^c$. In one embodiment, $L^1$ is —N$R^a$C(═O)N$R^b$$R^c$. In one embodiment, $L^1$ is —OC(═O)N$R^b$$R^c$. In one embodiment, $L^1$ is —N$R^a$C(═O)O$R^1$, In one embodiment, $L^2$ is —OC(═O)$R^2$, —C(═O)O$R^2$, —OC(═O)O$R^2$, —C(═O)$R^2$, —O$R^2$, —S(O)$_x$$R^2$, —S—S$R^2$, —C(═O)S$R^2$, —SC(═O)$R^2$, —N$R^d$C(═O)$R^2$, —C(═O)N$R^e$$R^f$, —N$R^d$C(═O)N$R^e$$R^f$, —OC(═O)N$R^e$$R^f$, —N$R^d$C(═O)O$R^2$, —SC(═S)$R^2$, —C(═S)S$R^2$, —C(═S)$R^2$, —CH(OH)$R^2$, or —P(═O)(O$R^e$)(O$R^f$). In one embodiment, $L^2$ is —($C_6$-$C_{10}$ arylene)-$R^2$. In one embodiment, $L^2$ is -(6- to 10-membered heteroarylene)-$R^2$. In one embodiment, $L^2$ is $R^2$.

In one embodiment, $L^2$ is —OC(═O)$R^2$, —C(═O)O$R^2$, —C(═O)S$R^2$, —SC(═O)$R^2$, —N$R^d$C(═O)$R^2$, or —C(═O)N$R^e$$R^f$. In one embodiment, $L^2$ is —OC(═O)$R^2$, —C(═O)O$R^2$, —N$R^d$C(═O)$R^2$, or —C(═O)N$R^e$$R^f$. In one embodiment, $L^2$ is —OC(═O)$R^2$. In one embodiment, $L^2$ is —C(═O)O$R^2$. In one embodiment, $L^2$ is —N$R^d$C(═O)$R^2$. In one embodiment, $L^2$ is —C(═O)N$R^e$$R^f$. In one embodiment, $L^2$ is —N$R^d$C(═O)N$R^e$$R^f$. In one embodiment, $L^2$ is —OC(═O)N$R^e$$R^f$. In one embodiment, $L^2$ is —N$R^d$C(═O)O$R^2$.

In one embodiment, $L^1$ is —OC(═O)$R^1$, —N$R^a$C(═O)$R^1$, —C(═O)O$R^1$, or —C(═O)N$R^b$$R^c$ and $L^2$ is —OC(═O)$R^2$, —N$R^d$C(═O)$R^2$, —C(═O)O$R^2$, or —C(═O)N$R^e$$R^f$. In one embodiment, $L^1$ is —OC(═O)$R^1$, —C(═O)O$R^1$, or —C(═O)N$R^b$$R^c$ and $L^2$ is —OC(═O)$R^2$, —C(═O)O$R^2$, or —C(═O)N$R^e$$R^f$. In one embodiment, $L^1$ is —OC(═O)$R^1$ and $L^2$ is —OC(═O)$R^2$. In one embodiment, $L^1$ is —OC(═O)$R^1$ and $L^2$ is —N$R^d$C(═O)$R^2$. In one embodiment, $L^1$ is —N$R^a$C(═O)$R^1$ and $L^2$ is —N$R^d$C(═O)$R^2$. In one embodiment, $L^1$ is —C(═O)O$R^1$ and $L^2$ is —C(═O)O$R^2$. In one embodiment, $L^1$ is —C(═O)O$R^1$ and $L^2$ is —C(═O)N$R^e$$R^f$. In one embodiment, $L^1$ is —C(═O)N$R^b$$R^c$ and $L^2$ is —C(═O)N$R^e$$R^f$.

In one embodiment, $L^1$ is —N$R^a$C(═O)N$R^b$$R^c$ and $L^2$ is —N$R^d$C(═O)N$R^e$$R^f$. In one embodiment, $L^1$ is —OC(═O)N$R^b$$R^c$ and $L^2$ is —OC(═O)N$R^e$$R^f$. In one embodiment, $L^1$ is —N$R^a$C(═O)O$R^1$ and $L^2$ is —N$R^d$C(═O)O$R^2$.

In one embodiment, the compound is a compound of Formula (I-B), (I-B'), (I-B"), (I-C), (I-D), or (I-E):

(I-B)

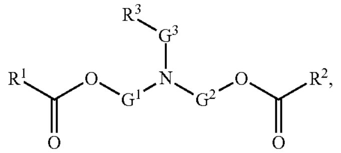

(I-B')

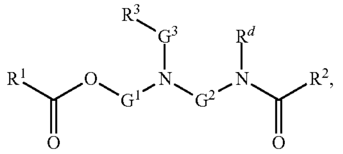

(I-B")

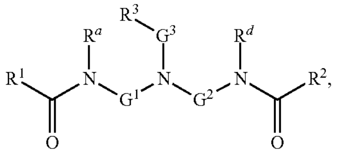

(I-C)

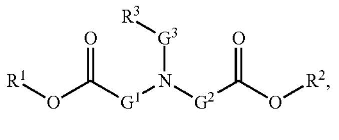

(I-D)

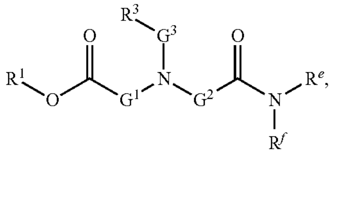

or

-continued (I-E)

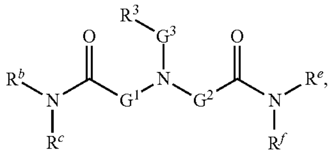

or a pharmaceutically acceptable salt, prodrug or stereoisomer thereof.

In one embodiment, the compound is a compound of Formula (II-B), (II-B'), (II-B"), (II-C), (II-D), or (II-E):

(II-B)

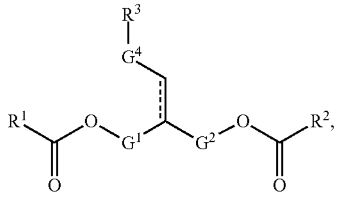

(II-B')

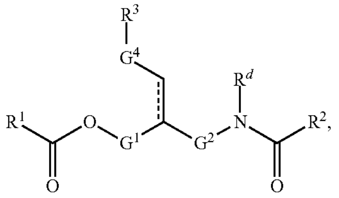

(II-B")

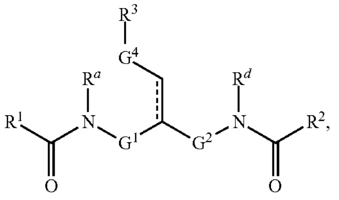

(II-C)

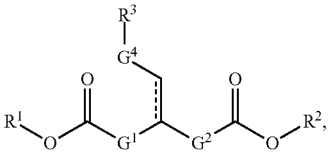

(II-D)

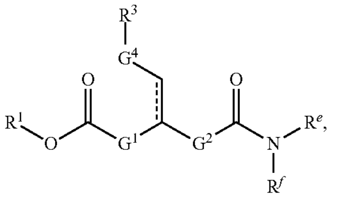

or (II-E)

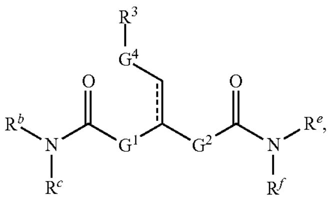

or a pharmaceutically acceptable salt, prodrug or stereoisomer thereof.

In one embodiment, the compound is a compound of Formula (III-B), (III-B'), (III-B"), (III-C), (III-D), or (III-E):

(III-B)

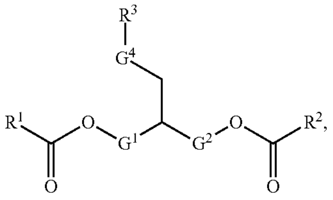

(III-B')

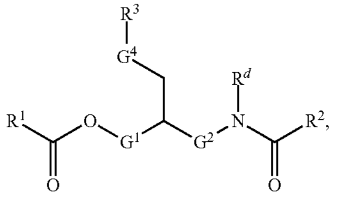

(III-B")

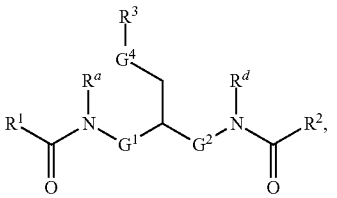

(III-C)

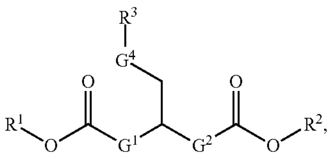

(III-D)

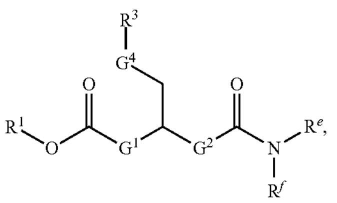

or (III-E)

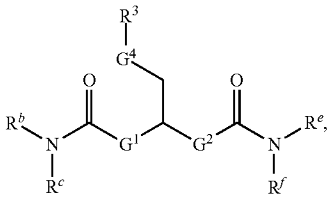

or a pharmaceutically acceptable salt, prodrug or stereoisomer thereof.

In one embodiment, the compound is a compound of Formula (IV-B), (IV-B'), (IV-B"), (IV-C), (IV-D), or (IV-E):

(IV-B)

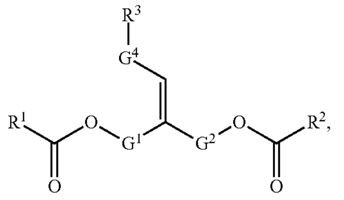

(IV-B')

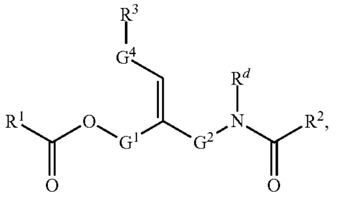

(IV-B")

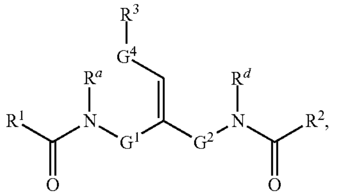

(IV-C)

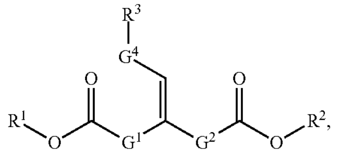

(IV-D)

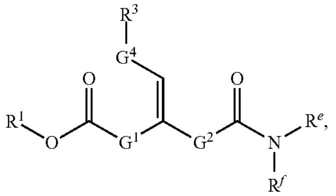

or (IV-E)

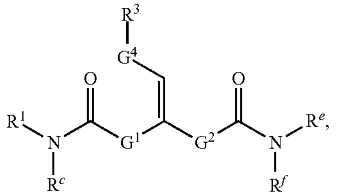

or a pharmaceutically acceptable salt, prodrug or stereoisomer thereof.

In one embodiment, the compound is a compound of Formula (I-F), (I-F'), (I-F"), (I-G), (I-H), or (I-I):

(I-F)

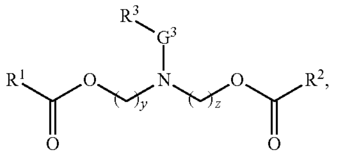

-continued (I-F')

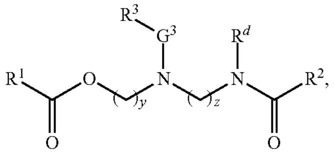

(I-F")

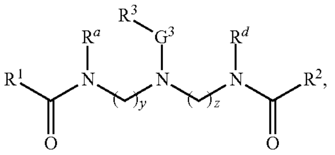

(I-G)

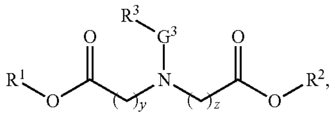

(I-H)

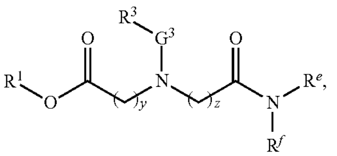

or (I-I)

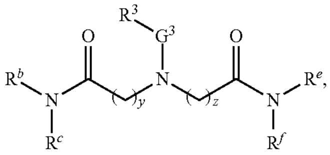

wherein y and z are each independently an integer from 2 to 12, or a pharmaceutically acceptable salt, prodrug or stereoisomer thereof.

In one embodiment, the compound is a compound of Formula (II-F), (II-F'), (II-F"), (II-G), (II-H), or (II-I):

(II-F)

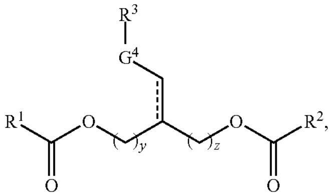

(II-F')

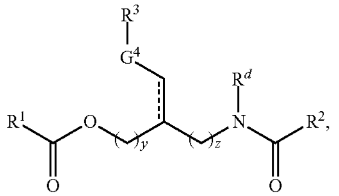

-continued (II-F″)

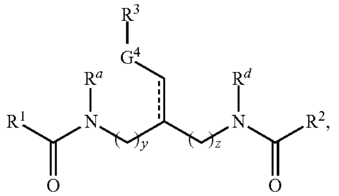

(II-G)

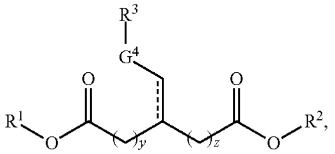

(II-H)

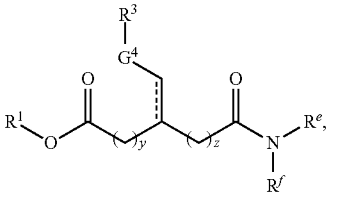

or (II-I)

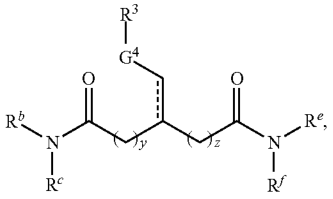

wherein y and z are each independently an integer from 2 to 12, or a pharmaceutically acceptable salt, prodrug or stereoisomer thereof.

In one embodiment, the compound is a compound of Formula (III-F), (III-F'), (III-F''), (III-G), (III-H), or (III-I):

(III-F)

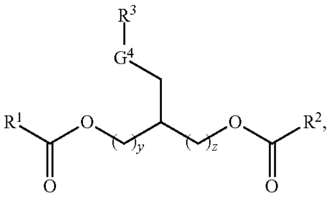

(III-F′)

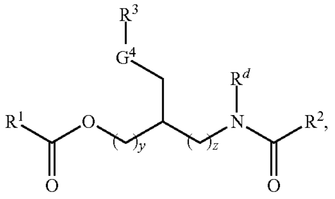

(III-F″)

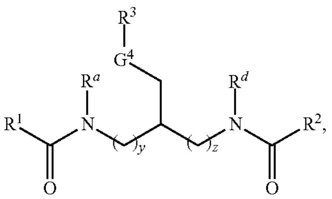

-continued (III-G)

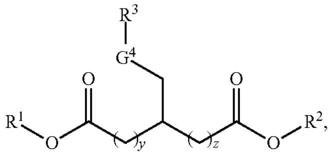

(III-H)

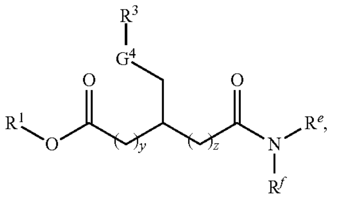

or (III-I)

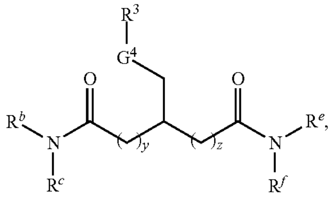

wherein y and z are each independently an integer from 2 to 12, or a pharmaceutically acceptable salt, prodrug or stereoisomer thereof.

In one embodiment, the compound is a compound of Formula (IV-F), (IV-F'), (IV-F''), (IV-G), (IV-H), or (IV-I):

(IV-F)

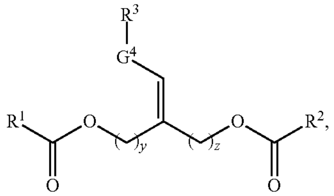

(IV-F′)

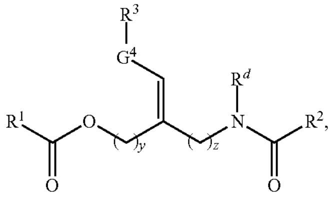

(IV-F″)

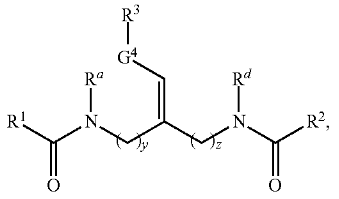

(IV-G)

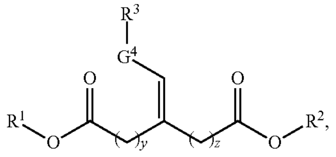

-continued (IV-H)

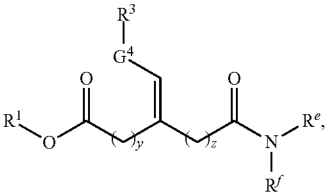

or (IV-I)

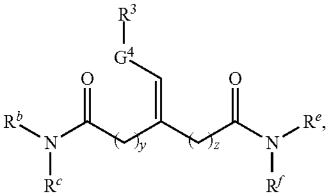

wherein y and z are each independently an integer from 2 to 12, or a pharmaceutically acceptable salt, prodrug or stereoisomer thereof.

In one embodiment, y and z are each independently an integer from 2 to 10. In one embodiment, y and z are each independently an integer from 2 to 6. In one embodiment, y and z are each independently an integer from 4 to 10.

In one embodiment, y and z are different. In one embodiment, y and z are the same. In one embodiment, y and z are the same and are selected from 4, 5, 6, 7, 8, and 9. In one embodiment, y is 5 and z is 5.

In one embodiment, $G^3$ is $C_2$-$C_{24}$ alkylene. In one embodiment, $G^3$ is $C_2$-$C_{12}$ alkylene. In one embodiment, $G^3$ is $C_2$-$C_8$ alkylene. In one embodiment, $G^3$ is $C_2$-$C_6$ alkylene. In one embodiment, $G^3$ is $C_2$-$C_4$ alkylene. In one embodiment, $G^3$ is $C_2$ alkylene. In one embodiment, $G^3$ is $C_4$ alkylene.

In one embodiment, $G^3$ is substituted with one or more oxo. In one embodiment, $G^3$ is —($C_1$-$C_{23}$ alkylene)-C(═O)—. In one embodiment, $G^3$ is —($C_1$-$C_{11}$ alkylene)-C(═O)—. In one embodiment, $G^3$ is —($C_1$-$C_7$ alkylene)-C(═O)—. In one embodiment, $G^3$ is —($C_1$-$C_5$ alkylene)-C(═O)—. In one embodiment, $G^3$ is —($C_1$-$C_3$ alkylene)-C(═O)—. In one embodiment, $G^3$ is —$CH_2$—C(═O)—. In one embodiment, $G^3$ is —$CH_2$—$CH_2$—$CH_2$—C(═O)—. In one embodiment, the —C(═O)— is connected to the nitrogen atom, and the alkylene is connected to $R^3$.

In one embodiment, the compound is a compound of Formula (I-J), (I-J'), (I-J"), (I-K), (I-L), or (I-M):

(I-J)

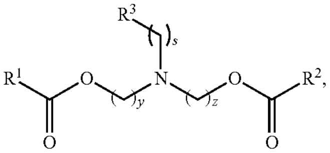

(I-J')

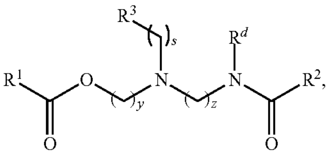

-continued (I-J")

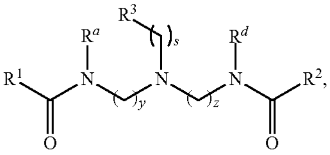

(I-K)

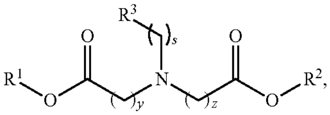

(I-L)

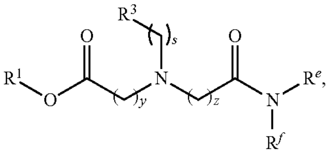

or (I-M)

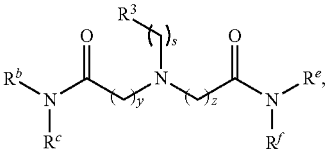

wherein y and z are each independently an integer from 2 to 12, and s is an integer from 2 to 24, or a pharmaceutically acceptable salt, prodrug or stereoisomer thereof.

In one embodiment, y and z are each independently an integer from 2 to 10. In one embodiment, y and z are each independently an integer from 2 to 6. In one embodiment, y and z are each independently an integer from 4 to 10.

In one embodiment, y and z are different. In one embodiment, y and z are the same. In one embodiment, y and z are the same and are selected from 4, 5, 6, 7, 8, and 9. In one embodiment, y is 5 and z is 5.

In one embodiment, s is an integer from 2 to 12. In one embodiment, s is an integer from 2 to 8. In one embodiment, s is an integer from 2 to 6. In one embodiment, s is an integer from 2 to 4. In one embodiment, s is 2. In one embodiment, s is 4.

In one embodiment, y is 5, z is 5, and s is 2.

In one embodiment, y is 5, z is 5, and s is 4.

In one embodiment, $G^3$ is $C_2$-$C_{24}$ alkenylene. In one embodiment, $G^3$ is $C_2$-$C_{12}$ alkenylene. In one embodiment, $G^3$ is $C_2$-$C_8$ alkenylene. In one embodiment, $G^3$ is $C_2$-$C_6$ alkenylene. In one embodiment, $G^3$ is $C_2$-$C_4$ alkenylene.

In one embodiment, $G^3$ is $C_3$-$C_8$ cycloalkylene. In one embodiment, $G^3$ is $C_5$-$C_6$ cycloalkylene.

In one embodiment, $G^3$ is $C_3$-$C_8$ cycloalkenylene. In one embodiment, $G^3$ is $C_5$-$C_6$ cycloalkenylene.

In one embodiment, $G^4$ is a bond.

In one embodiment, $G^4$ is $C_1$-$C_{23}$ alkylene. In one embodiment, $G^4$ is $C_1$-$C_{11}$ alkylene. In one embodiment, $G^4$ is $C_1$-$C_7$ alkylene. In one embodiment, $G^4$ is $C_1$-$C_5$ alkylene. In one embodiment, $G^4$ is $C_1$-$C_3$ alkylene. In one embodiment, $G^4$ is $C_1$ alkylene. In one embodiment, $G^4$ is $C_2$ alkylene. In one embodiment, $G^4$ is $C_3$ alkylene. In one embodiment, $G^4$ is $C_4$ alkylene.

In one embodiment, the compound is a compound of Formula (II-J), (II-J'), (II-J"), (II-K), (II-L), or (II-M):

(II-J)

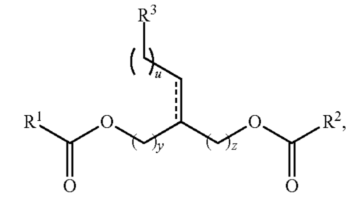

(II-J')

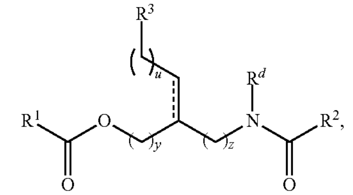

(II-J")

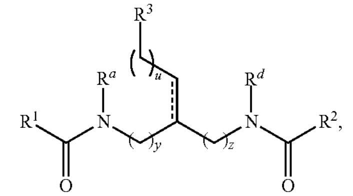

(II-K)

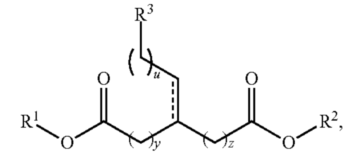

(II-L)

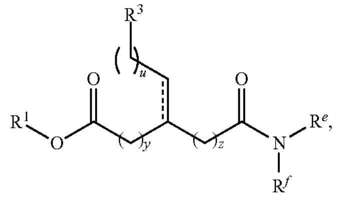

or (II-M)

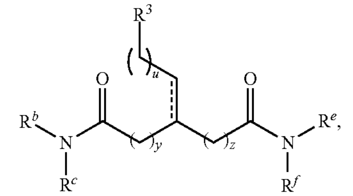

wherein y and z are each independently an integer from 2 to 12, and u is an integer from 0 to 23, or a pharmaceutically acceptable salt, prodrug or stereoisomer thereof.

In one embodiment, the compound is a compound of Formula (III-J), (III-J'), (III-J"), (III-K), (III-L), or (III-M):

(III-J)

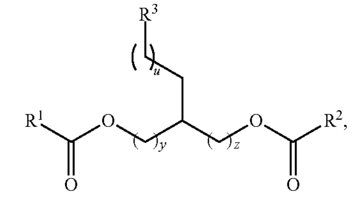

(III-J')

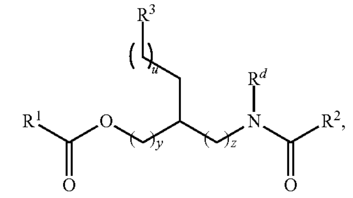

(III-J")

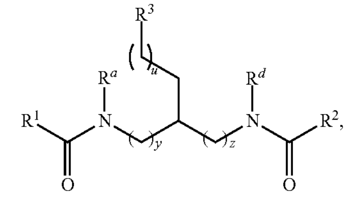

(III-K)

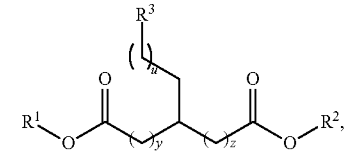

(III-L)

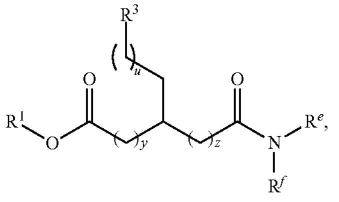

or (III-M)

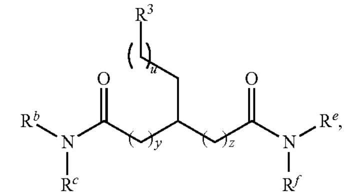

wherein y and z are each independently an integer from 2 to 12, and u is an integer from 0 to 23, or a pharmaceutically acceptable salt, prodrug or stereoisomer thereof.

In one embodiment, the compound is a compound of Formula (IV-J), (IV-J'), (IV-J"), (IV-K), (IV-L), or (IV-M):

(IV-J)

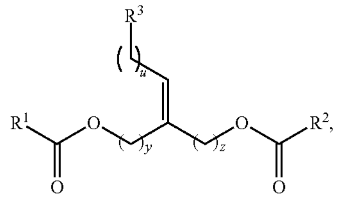

(IV-J')

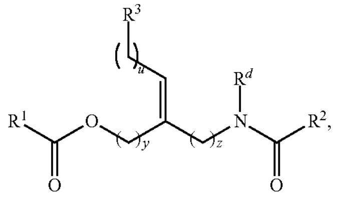

(IV-J")

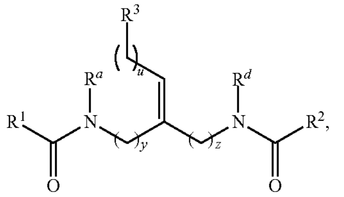

(IV-K)

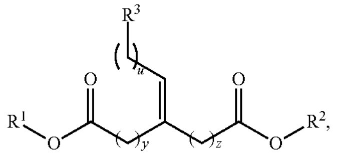

(IV-L)

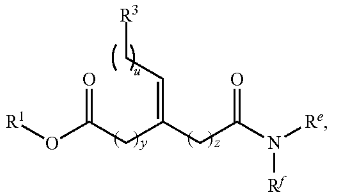

or (IV-M)

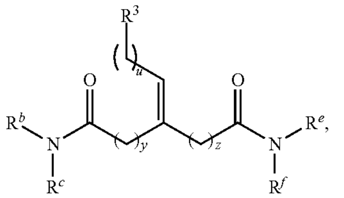

wherein y and z are each independently an integer from 2 to 12, and u is an integer from 0 to 23, or a pharmaceutically acceptable salt, prodrug or stereoisomer thereof.

In one embodiment, y and z are each independently an integer from 2 to 10. In one embodiment, y and z are each independently an integer from 2 to 6. In one embodiment, y and z are each independently an integer from 4 to 10.

In one embodiment, y and z are different. In one embodiment, y and z are the same. In one embodiment, y and z are the same and are selected from 4, 5, 6, 7, 8, and 9. In one embodiment, y is 5 and z is 5.

In one embodiment, u is an integer from 0 to 12. In one embodiment, u is an integer from 0 to 8. In one embodiment, u is an integer from 0 to 6. In one embodiment, u is an integer from 0 to 4. In one embodiment, u is 0. In one embodiment, u is 1. In one embodiment, u is 2. In one embodiment, u is 3. In one embodiment, u is 4.

In one embodiment, y is 5, z is 5, and u is 0.

In one embodiment, y is 5, z is 5, and u is 2.

In one embodiment, $G^4$ is $C_2$-$C_{23}$ alkenylene. In one embodiment, $G^4$ is $C_2$-$C_{12}$ alkenylene. In one embodiment, $G^4$ is $C_2$-$C_8$ alkenylene. In one embodiment, $G^4$ is $C_2$-$C_6$ alkenylene. In one embodiment, $G^4$ is $C_2$-$C_4$ alkenylene.

In one embodiment, $G^4$ is $C_3$-$C_8$ cycloalkylene. In one embodiment, $G^4$ is $C_5$-$C_6$ cycloalkylene.

In one embodiment, $G^4$ is $C_3$-$C_8$ cycloalkenylene. In one embodiment, $G^4$ is $C_5$-$C_6$ cycloalkenylene.

In one embodiment, $R^5$ is $C_1$-$C_{12}$ alkyl. In one embodiment, $R^5$ is $C_1$-$C_{10}$ alkyl. In one embodiment, $R^5$ is $C_1$-$C_8$ alkyl. In one embodiment, $R^5$ is $C_1$-$C_6$ alkyl. In one embodiment, $R^5$ is $C_1$-$C_4$ alkyl. In one embodiment, $R^5$ is $C_1$-$C_2$ alkyl. In one embodiment, $R^5$ is methyl. In one embodiment, $R^5$ is ethyl. In one embodiment, $R^5$ is propyl. In one embodiment, $R^5$ is n-butyl. In one embodiment, $R^5$ is n-hexyl. In one embodiment, $R^5$ is n-octyl. In one embodiment, $R^5$ is n-nonyl.

In one embodiment, $R^5$ is $C_3$-$C_8$ cycloalkyl. In one embodiment, $R^5$ is cyclopropyl. In one embodiment, $R^5$ is cyclobutyl. In one embodiment, $R^5$ is cyclopentyl. In one embodiment, $R^5$ is cyclohexyl. In one embodiment, $R^5$ is cycloheptyl. In one embodiment, $R^5$ is cyclooctyl.

In one embodiment, $R^4$, $R^5$, together with the nitrogen to which they are attached form a cyclic moiety.

In one embodiment, the cyclic moiety (formed by $R^4$ and $R^5$ together with the nitrogen to which they are attached) is heterocyclyl. In one embodiment, the cyclic moiety is heterocycloalkyl. In one embodiment, the cyclic moiety is 4- to 8-membered heterocycloalkyl. In one embodiment, the cyclic moiety is 4-membered heterocycloalkyl. In one embodiment, the cyclic moiety is 5-membered heterocycloalkyl. In one embodiment, the cyclic moiety is 6-membered heterocycloalkyl. In one embodiment, the cyclic moiety is 7-membered heterocycloalkyl. In one embodiment, the cyclic moiety is 8-membered heterocycloalkyl.

In one embodiment, the cyclic moiety (formed by $R^4$ and $R^5$ together with the nitrogen to which they are attached) is azetidin-1-yl. In one embodiment, the cyclic moiety is pyrrolidin-1-yl. In one embodiment, the cyclic moiety is piperidin-1-yl. In one embodiment, the cyclic moiety is azepan-1-yl. In one embodiment, the cyclic moiety is azocan-1-yl. In one embodiment, the cyclic moiety is morpholinyl. In one embodiment, the cyclic moiety is piperazin-1-yl. The point of attachment in these groups is to $G^3$.

As described herein and unless otherwise specified, the substitution patterns for $R^5$ also applies to the cyclic moiety formed by $R^4$ and $R^5$ together with the nitrogen to which they are attached.

In one embodiment, $R^5$ is unsubstituted.

In one embodiment, $R^5$ is substituted with one or more substituents selected from the group consisting of oxo, —$OR^g$, —$NR^gC({=}O)R^h$, —$C({=}O)NR^gR^h$, —$C({=}O)R^h$, —$OC({=}O)R^h$, —$C({=}O)OR^h$ and —O—$R^i$—OH, wherein:

$R^g$ is at each occurrence independently H or $C_1$-$C_6$ alkyl;

$R^h$ is at each occurrence independently $C_1$-$C_6$ alkyl; and $R^i$ is at each occurrence independently $C_1$-$C_6$ alkylene.

In one embodiment, $R^5$ is substituted with one or more hydroxyl. In one embodiment, $R^5$ is substituted with one hydroxyl.

In one embodiment, $R^5$ is substituted with one or more hydroxyl and one or more oxo. In one embodiment, $R^5$ is substituted with one hydroxyl and one oxo. In one embodiment, $R^5$ is $—CH_2CH_2OH$.

In one embodiment, $R^5$ is $—(CH_2)_pQ$, $—(CH_2)_pCHQR$, —CHQR, or $—CQ(R)_2$, wherein Q is $C_3$-$C_8$ cycloalkyl, $C_3$-$C_8$ cycloalkenyl, $C_3$-$C_8$ cycloalkynyl, 4- to 8-membered heterocyclyl, $C_6$-$C_{10}$ aryl, 5- to 10-membered heteroaryl, —OR, $—O(CH_2)_pN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, $—N(R)R^{22}$, $—O(CH_2)_pOR$, $—N(R)C(=NR^{23})N(R)_2$, $—N(R)C(=CHR^{23})N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR^{23})N(R)_2$, $—N(OR)C(=CHR^{23})N(R)_2$, $—C(=NR^{23})N(R)_2$, $—C(=NR^{23})R$, —C(O)N(R)OR, or $—C(R)N(R)_2C(O)OR$, and each p is independently 1, 2, 3, 4, or 5;

$R^{22}$ is $C_3$-$C_8$ cycloalkyl, $C_3$-$C_8$ cycloalkenyl, $C_3$-$C_8$ cycloalkynyl, 4- to 8-membered heterocyclyl, $C_6$-$C_{10}$ aryl, or 5- to 10-membered heteroaryl;

$R^{23}$ is H, —CN, $—NO_2$, $C_1$-$C_6$ alkyl, —OR, $—S(O)_2R$, $—S(O)_2N(R)_2$, $C_2$-$C_6$ alkenyl, $C_3$-$C_8$ cycloalkyl, $C_3$-$C_8$ cycloalkenyl, $C_3$-$C_8$ cycloalkynyl, 4- to 8-membered heterocyclyl, $C_6$-$C_{10}$ aryl, or 5- to 10-membered heteroaryl;

each R is independently H, $C_1$-$C_3$ alkyl, or $C_2$-$C_3$ alkenyl; or two R in a $N(R)_2$ moiety together with the nitrogen to which they are attached form a cyclic moiety; and each X is independently F, CI, Br, or I.

In one embodiment, the compound is a compound of Formula (I-N), (I-N'), (I-N"), (I-O), (I-P), or (I-Q):

(I-N)

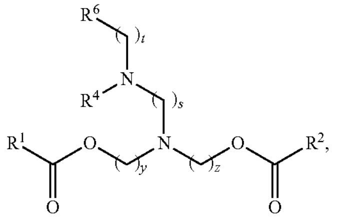

(I-N')

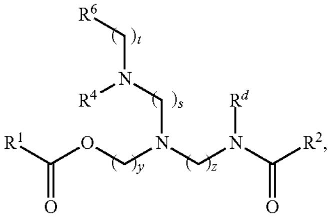

(I-N")

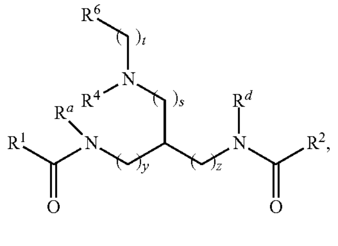

-continued (I-O)

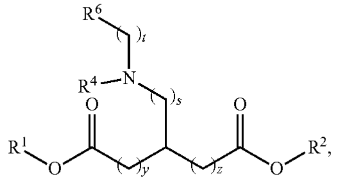

(I-P)

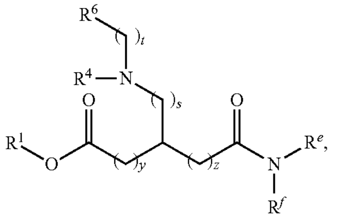

or (I-Q)

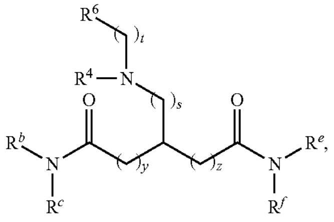

wherein y and z are each independently an integer from 2 to 12, s is an integer from 2 to 24, t is an integer from 1 to 12, and $R^6$ is hydrogen or hydroxyl, or a pharmaceutically acceptable salt, prodrug or stereoisomer thereof.

In one embodiment, the compound is a compound of Formula (II-N), (II-N'), (II-N"), (II-O), (II-P), or (II-Q):

(II-N)

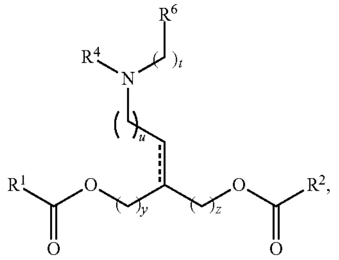

(II-N')

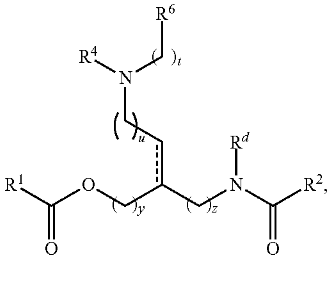

-continued (II-N'')

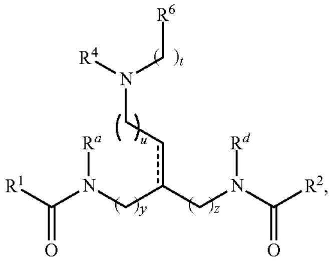

(II-O)

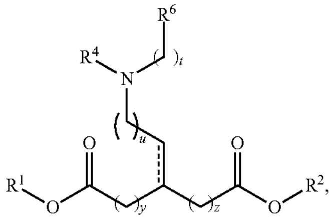

(II-P)

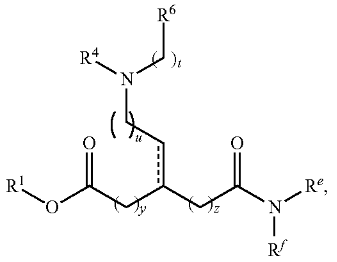

or (II-Q)

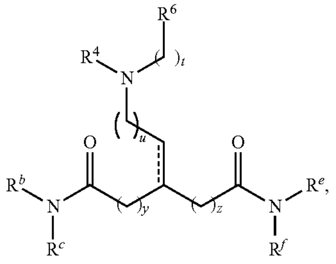

wherein y and z are each independently an integer from 2 to 12, u is an integer from 0 to 23, t is an integer from 1 to 12, and $R^6$ is hydrogen or hydroxyl, or a pharmaceutically acceptable salt, prodrug or stereoisomer thereof.

In one embodiment, the compound is a compound of Formula (III-N), (III-N'), (III-N''), (III-O), (III-P), or (III-Q):

(III-N)

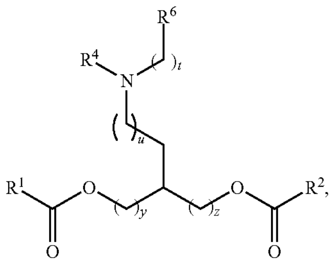

-continued (III-N')

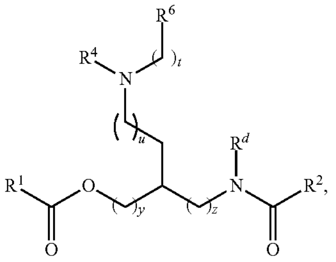

(III-N'')

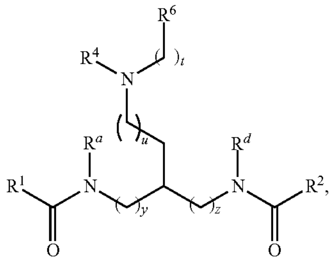

(III-O)

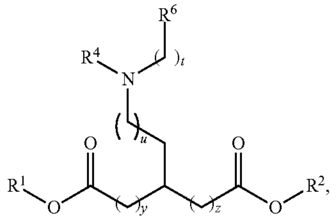

(III-P)

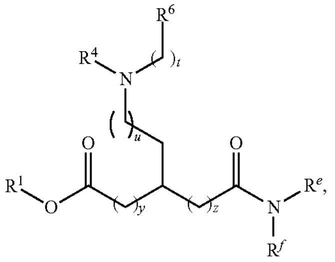

or (III-Q)

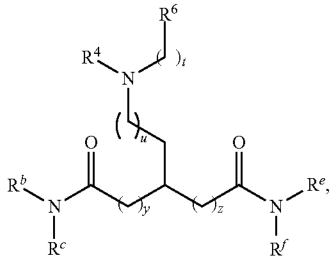

wherein y and z are each independently an integer from 2 to 12, u is an integer from 0 to 23, t is an integer from 1 to 12, and $R^6$ is hydrogen or hydroxyl, or a pharmaceutically acceptable salt, prodrug or stereoisomer thereof.

In one embodiment, the compound is a compound of Formula (IV-N), (IV-N'), (IV-N''), (IV-O), (IV-P), or (IV-Q):

(IV-N)
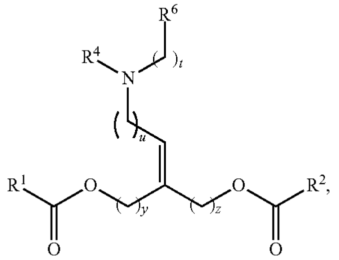
(IV-N')
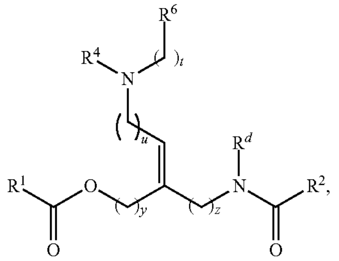
(IV-N")
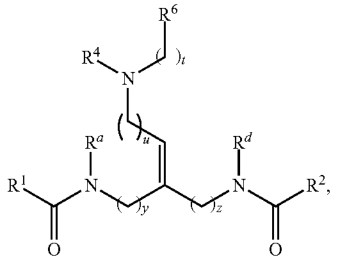
(IV-O)
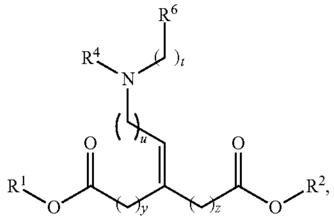
(IV-P)
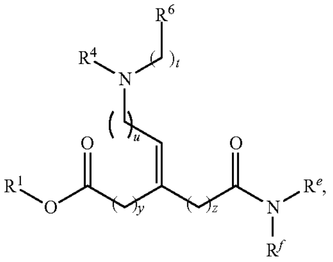
or
(IV-Q)
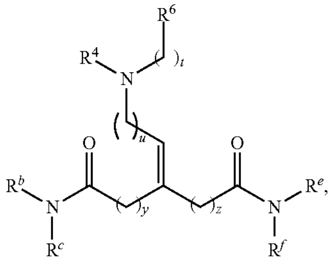
wherein y and z are each independently an integer from 2 to 12,
u is an integer from 0 to 23,
t is an integer from 1 to 12, and
$R^6$ is hydrogen or hydroxyl,
or a pharmaceutically acceptable salt, prodrug or stereoisomer thereof.
In one embodiment, the compound is a compound of Formula (I-R), (I-R"), (I-S), (I-T), or (I-U):
(I-R)
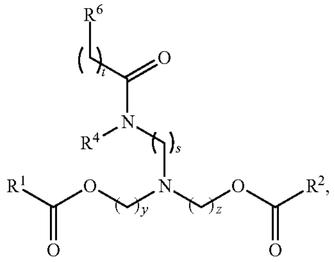
(I-R')
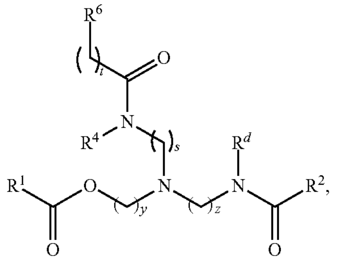
(I-R")
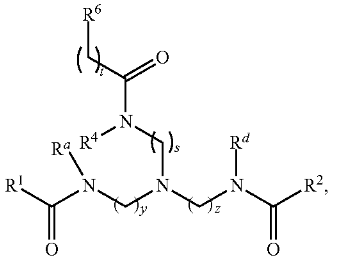
(I-S)
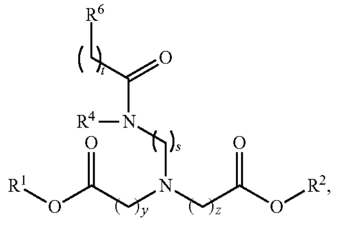
(I-T)
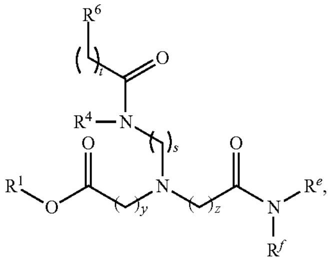
or -continued (I-U)

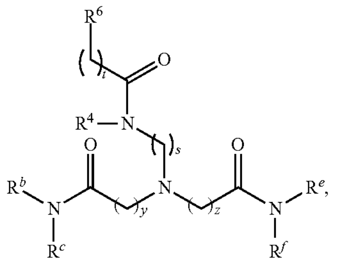

wherein y and z are each independently an integer from 2 to 12, s is an integer from 2 to 24, t is an integer from 1 to 12, and $R^6$ is hydrogen or hydroxyl, or a pharmaceutically acceptable salt, prodrug or stereoisomer thereof.

In one embodiment, the compound is a compound of Formula (II-R), (II-R'), (II-R"), (II-S), (II-T), or (II-U):

(II-R)

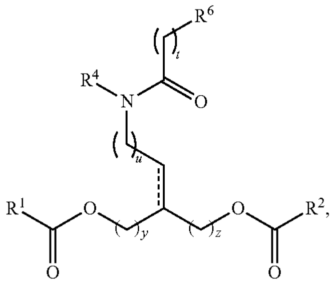

(II-R')

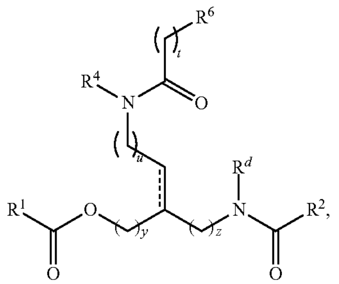

(II-R")

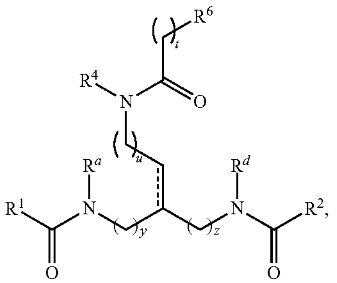

-continued (II-S)

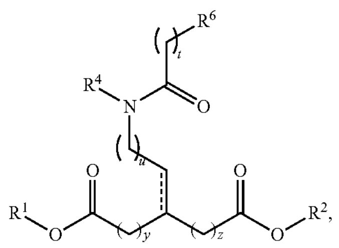

(II-T)

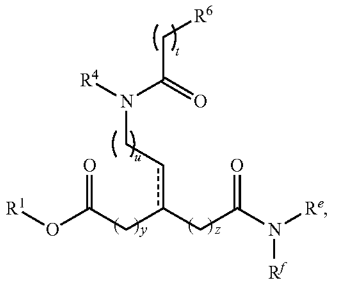

or (II-U)

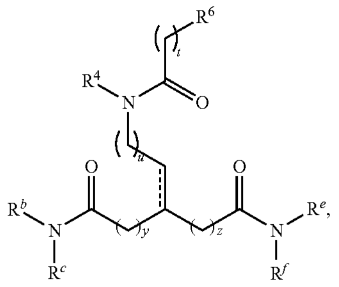

wherein y and z are each independently an integer from 2 to 12, u is an integer from 0 to 23, t is an integer from 1 to 12, and $R^6$ is hydrogen or hydroxyl, or a pharmaceutically acceptable salt, prodrug or stereoisomer thereof.

In one embodiment, the compound is a compound of Formula (III-R), (III-R'), (III-R"), (III-S), (III-T), or (III-U):

(III-R)

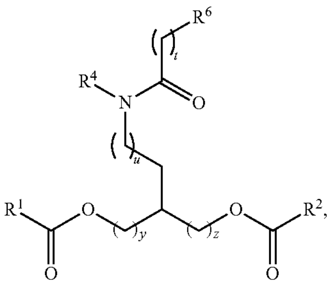

-continued
(III-R')
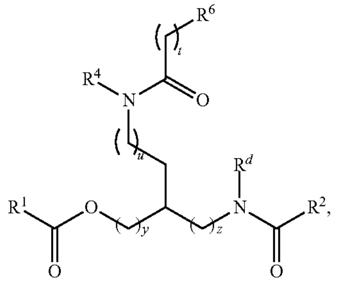
(III-R'')
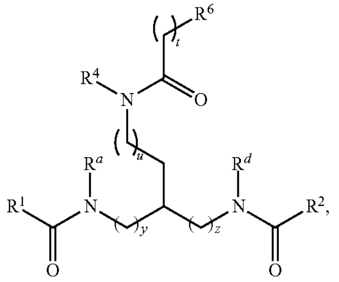
(III-S)
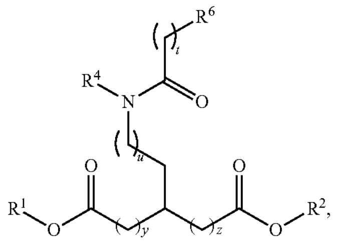
(III-T)
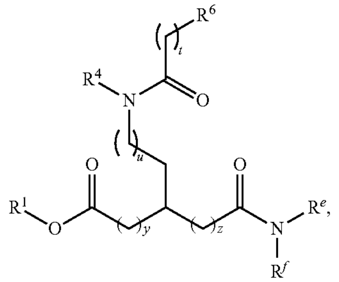
or
(III-U)
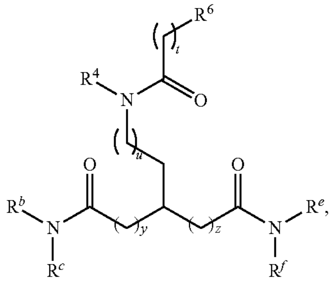
wherein y and z are each independently an integer from 2 to 12,
u is an integer from 0 to 23,
t is an integer from 1 to 12, and
$R^6$ is hydrogen or hydroxyl,
or a pharmaceutically acceptable salt, prodrug or stereoisomer thereof.
In one embodiment, the compound is a compound of Formula (IV-R), (IV-R'), (IV-R''), (IV-S), (IV-T), or (IV-U):
(IV-R)
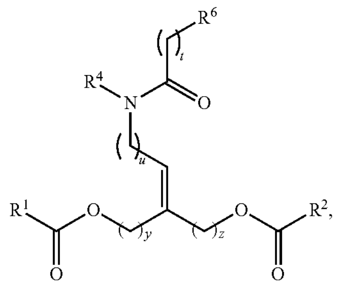
(IV-R')
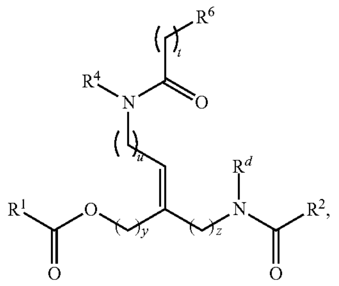
(IV-R'')
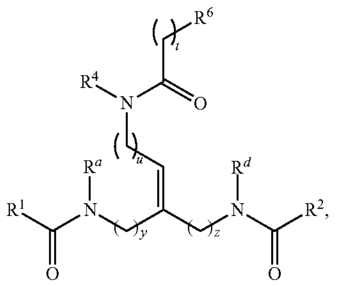
(IV-S)
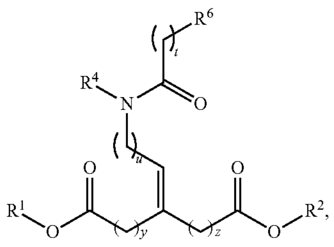
(IV-T)
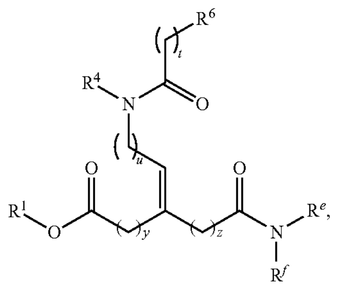
or -continued (IV-U)

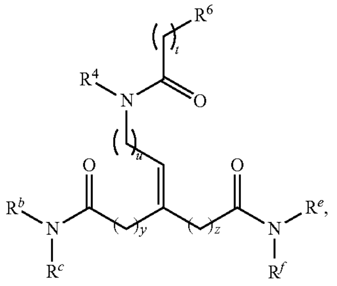

wherein y and z are each independently an integer from 2 to 12, u is an integer from 0 to 23, t is an integer from 1 to 12, and $R^6$ is hydrogen or hydroxyl, or a pharmaceutically acceptable salt, prodrug or stereoisomer thereof.

In one embodiment, y and z are each independently an integer from 2 to 10. In one embodiment, y and z are each independently an integer from 2 to 6. In one embodiment, y and z are each independently an integer from 4 to 10.

In one embodiment, y and z are different. In one embodiment, y and z are the same. In one embodiment, y and z are the same and are selected from 4, 5, 6, 7, 8, and 9. In one embodiment, y is 5 and z is 5.

In one embodiment, s is an integer from 2 to 12. In one embodiment, s is an integer from 2 to 8. In one embodiment, s is an integer from 2 to 6. In one embodiment, s is an integer from 2 to 4. In one embodiment, s is 2. In one embodiment, s is 4.

In one embodiment, y is 5, z is 5, and s is 2.

In one embodiment, y is 5, z is 5, and s is 4.

In one embodiment, u is an integer from 0 to 12. In one embodiment, u is an integer from 0 to 8. In one embodiment, u is an integer from 0 to 6. In one embodiment, u is an integer from 0 to 4. In one embodiment, u is 0. In one embodiment, u is 1. In one embodiment, u is 2. In one embodiment, u is 3. In one embodiment, u is 4.

In one embodiment, y is 5, z is 5, and u is 0.

In one embodiment, y is 5, z is 5, and u is 2.

In one embodiment, t is an integer from 1 to 10. In one embodiment, t is an integer from 1 to 8. In one embodiment, t is an integer from 1 to 6. In one embodiment, t is an integer from 1 to 4. In one embodiment, t is an integer from 1 to 3. In one embodiment, t is an integer from 1 to 2. In one embodiment, t is 1. In one embodiment, t is 2. In one embodiment, t is 3. In one embodiment, t is 4. In one embodiment, t is 5. In one embodiment, t is 6. In one embodiment, t is 7.

In one embodiment, $R^4$ is $C_1$-$C_{12}$ alkyl. In one embodiment, $R^4$ is $C_1$-$C_8$ alkyl. In one embodiment, $R^4$ is $C_1$-$C_6$ alkyl. In one embodiment, $R^4$ is $C_1$-$C_4$ alkyl. In one embodiment, $R^4$ is methyl. In one embodiment, $R^4$ is ethyl. In one embodiment, $R^4$ is n-propyl. In one embodiment, $R^4$ is n-butyl. In one embodiment, $R^4$ is n-pentyl. In one embodiment, $R^4$ is n-hexyl. In one embodiment, $R^4$ is n-octyl. In one embodiment, $R^4$ is n-nonyl.

In one embodiment, $R^4$ is $C_3$-$C_8$ cycloalkyl. In one embodiment, $R^4$ is cyclopropyl. In one embodiment, $R^4$ is cyclobutyl. In one embodiment, $R^4$ is cyclopentyl. In one embodiment, $R^4$ is cyclohexyl. In one embodiment, $R^4$ is cycloheptyl. In one embodiment, $R^4$ is cyclooctyl.

In one embodiment, $R^4$ is $C_3$-$C_8$ cycloalkenyl. In one embodiment, $R^4$ is cyclopropenyl. In one embodiment, $R^4$ is cyclobutenyl. In one embodiment, $R^4$ is cyclopentenyl. In one embodiment, $R^4$ is cyclohexenyl. In one embodiment, $R^4$ is cycloheptenyl. In one embodiment, $R^4$ is cyclooctenyl.

In one embodiment, $R^4$ is $C_6$-$C_{10}$ aryl. In one embodiment, $R^4$ is phenyl.

In one embodiment, $R^4$ is 4- to 8-membered heterocyclyl. In one embodiment, $R^4$ is 4- to 8-membered heterocycloalkyl. In one embodiment, $R^4$ is oxetanyl. In one embodiment, $R^4$ is tetrahydrofuranyl. In one embodiment, $R^4$ is tetrahydropyranyl. In one embodiment, $R^4$ is tetrahydrothiopyranyl. In one embodiment, $R^4$ is N-methylpiperidinyl.

In one embodiment, $R^4$, $G^3$ or part of $G^3$, together with the nitrogen to which they are attached form a cyclic moiety.

In one embodiment, the cyclic moiety (formed by $R^4$, $G^3$ or part of $G^3$, together with the nitrogen to which they are attached) is heterocyclyl. In one embodiment, the cyclic moiety is heterocycloalkyl. In one embodiment, the cyclic moiety is 4- to 8-membered heterocycloalkyl. In one embodiment, the cyclic moiety is 4-membered heterocycloalkyl. In one embodiment, the cyclic moiety is 5-membered heterocycloalkyl. In one embodiment, the cyclic moiety is 6-membered heterocycloalkyl. In one embodiment, the cyclic moiety is 7-membered heterocycloalkyl. In one embodiment, the cyclic moiety is 8-membered heterocycloalkyl.

In one embodiment, the cyclic moiety (formed by $R^4$, $G^3$ or part of $G^3$, together with the nitrogen to which they are attached) is azetidin-3-yl. In one embodiment, the cyclic moiety is pyrrolidin-3-yl. In one embodiment, the cyclic moiety is piperidin-4-yl. In one embodiment, the cyclic moiety is azepan-4-yl. In one embodiment, the cyclic moiety is azocan-5-yl. The point of attachment for these groups is to the direction of the nitrogen that is connected to $G^1$ and $G^2$.

As described herein and unless otherwise specified, the substitution patterns for $R^4$ also applies to the cyclic moiety formed by $R^4$, $G^3$ or part of $G^3$, together with the nitrogen to which they are attached.

In one embodiment, $R^4$ is unsubstituted.

In one embodiment, $R^4$ is substituted with one or more substituents selected from the group consisting of oxo, $-OR^g$, $-NR^gC(=O)R^h$, $-C(=O)NR^gR^h$, $-C(=O)R^h$, $-OC(=O)R^h$, $-C(=O)OR^h$ and $-O-R^i-OH$, wherein:

$R^g$ is at each occurrence independently H or $C_1$-$C_6$ alkyl;

$R^h$ is at each occurrence independently $C_1$-$C_6$ alkyl; and $R^i$ is at each occurrence independently $C_1$-$C_6$ alkylene.

In one embodiment, $R^4$ is substituted with one or more hydroxyl. In one embodiment, $R^4$ is substituted with one hydroxyl.

In one embodiment, $R^4$ is substituted with one or more hydroxyl and one or more oxo. In one embodiment, $R^4$ is substituted with one hydroxyl and one oxo.

In one embodiment, $R^3$ has one of the following structures:

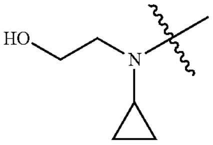

,

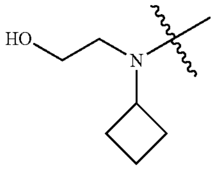

,

-continued

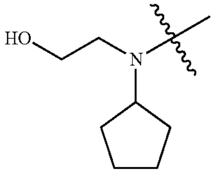, 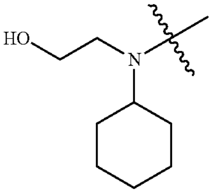,

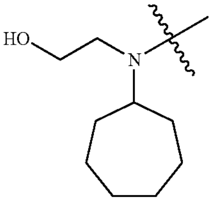, 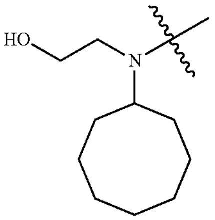,

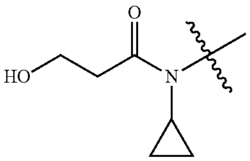, 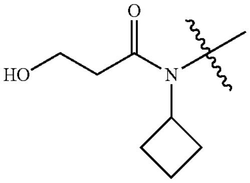,

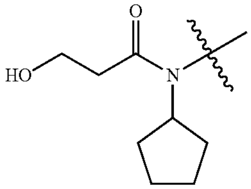, 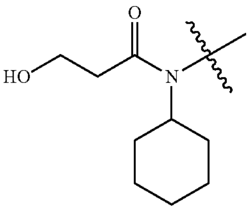,

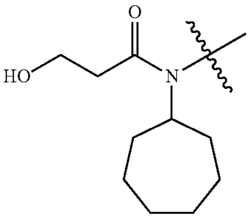, or

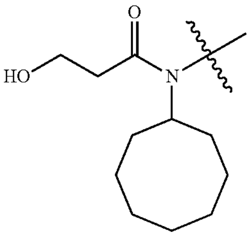.

In one embodiment, $R^3$ has the structure of

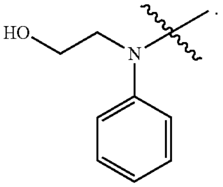 [SMILES: *N(CCO)c1ccccc1].

In one embodiment, $R^3$ has the structure of

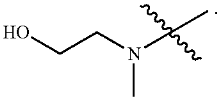 [SMILES: *N(C)CCO].

In one embodiment, $R^1$ and $R^2$ are each independently branched $C_6$-$C_{32}$ alkyl or branched $C_6$-$C_{32}$ alkenyl. In one embodiment, $R^1$ and $R^2$ are each independently branched $C_6$-$C_{24}$ alkyl or branched $C_6$-$C_{24}$ alkenyl.

In one embodiment, $R^1$ and $R^2$ are each independently —$R^7$—$CH(R^8)(R^9)$, wherein $R^7$ is $C_1$-$C_5$ alkylene, and $R^8$ and $R^9$ are independently $C_2$-$C_{10}$ alkyl or $C_2$-$C_{10}$ alkenyl.

In one embodiment, $R^1$ is straight $C_6$-$C_{32}$ alkyl. In one embodiment, $R^1$ is straight $C_6$-$C_{24}$ alkyl. In one embodiment, $R^1$ is straight $C_7$-$C_{15}$ alkyl. In one embodiment, $R^1$ is straight $C_7$ alkyl. In one embodiment, $R^1$ is straight $C_8$ alkyl. In one embodiment, $R^1$ is straight $C_9$ alkyl. In one embodiment, $R^1$ is straight $C_{10}$ alkyl. In one embodiment, $R^1$ is straight $C_{11}$ alkyl. In one embodiment, $R^1$ is straight $C_{12}$ alkyl. In one embodiment, $R^1$ is straight $C_{13}$ alkyl. In one embodiment, $R^1$ is straight $C_{14}$ alkyl. In one embodiment, $R^1$ is straight $C_{15}$ alkyl.

In one embodiment, $R^1$ is straight $C_6$-$C_{32}$ alkenyl. In one embodiment, $R^1$ is straight $C_6$-$C_{24}$ alkenyl. In one embodiment, $R^1$ is straight $C_7$-$C_{17}$ alkenyl. In one embodiment, $R^1$ is straight $C_7$ alkenyl. In one embodiment, $R^1$ is straight $C_8$ alkenyl. In one embodiment, $R^1$ is straight $C_9$ alkenyl. In one embodiment, $R^1$ is straight $C_{10}$ alkenyl. In one embodiment, $R^1$ is straight $C_{11}$ alkenyl. In one embodiment, $R^1$ is straight $C_{12}$ alkenyl. In one embodiment, $R^1$ is straight $C_{13}$ alkenyl. In one embodiment, $R^1$ is straight $C_{14}$ alkenyl. In one embodiment, $R^1$ is straight $C_{15}$ alkenyl. In one embodiment, $R^1$ is straight $C_{16}$ alkenyl. In one embodiment, $R^1$ is straight $C_{17}$ alkenyl.

In one embodiment, $R^1$ is branched $C_6$-$C_{32}$ alkyl. In one embodiment, $R^1$ is branched $C_6$-$C_{24}$ alkyl. In one embodiment, $R^1$ is —$R^7$—$CH(R^8)(R^9)$, wherein $R^7$ is $C_0$-$C_5$ alkylene, and $R^8$ and $R^9$ are independently $C_2$-$C_{10}$ alkyl. In one embodiment, $R^1$ is —$R^7$—$CH(R^8)(R^9)$, wherein $R^7$ is $C_0$-$C_1$ alkylene, and $R^8$ and $R^9$ are independently $C_4$-$C_8$ alkyl.

In one embodiment, $R^1$ is branched $C_6$-$C_{32}$ alkenyl. In one embodiment, $R^1$ is branched $C_6$-$C_{24}$ alkenyl. In one embodiment, $R^1$ is —$R^7$—$CH(R^8)(R^9)$, wherein $R^7$ is $C_0$-$C_5$ alkylene, and $R^8$ and $R^9$ are independently $C_2$-$C_{10}$ alkenyl. In one embodiment, $R^1$ is —$R^7$—$CH(R^8)(R^9)$, wherein $R^7$ is $C_0$-$C_1$ alkylene, and $R^8$ and $R^9$ are independently $C_6$-$C_{10}$ alkenyl.

In one embodiment, $R^2$ is straight $C_6$-$C_{32}$ alkyl. In one embodiment, $R^2$ is straight $C_6$-$C_{24}$ alkyl. In one embodiment, $R^2$ is straight $C_7$-$C_{15}$ alkyl. In one embodiment, $R^2$ is straight $C_7$ alkyl. In one embodiment, $R^2$ is straight $C_8$ alkyl. In one embodiment, $R^2$ is straight $C_9$ alkyl. In one embodiment, $R^2$ is straight $C_{10}$ alkyl. In one embodiment, $R^2$ is straight $C_{11}$ alkyl. In one embodiment, $R^2$ is straight $C_{12}$ alkyl. In one embodiment, $R^2$ is straight $C_{13}$ alkyl. In one embodiment, $R^2$ is straight $C_{14}$ alkyl. In one embodiment, $R^2$ is straight $C_{15}$ alkyl.

In one embodiment, $R^2$ is straight $C_6$-$C_{32}$ alkenyl. In one embodiment, $R^2$ is straight $C_6$-$C_{24}$ alkenyl. In one embodiment, $R^2$ is straight $C_7$-$C_{17}$ alkenyl. In one embodiment, $R^2$ is straight $C_7$ alkenyl. In one embodiment, $R^2$ is straight $C_8$ alkenyl. In one embodiment, $R^2$ is straight $C_9$ alkenyl. In one embodiment, $R^2$ is straight $C_{10}$ alkenyl. In one embodiment, $R^2$ is straight $C_{11}$ alkenyl. In one embodiment, $R^2$ is straight $C_{12}$ alkenyl. In one embodiment, $R^2$ is straight $C_{13}$ alkenyl. In one embodiment, $R^2$ is straight $C_{14}$ alkenyl. In one embodiment, $R^2$ is straight $C_{15}$ alkenyl. In one embodiment, $R^2$ is straight $C_{16}$ alkenyl. In one embodiment, $R^2$ is straight $C_{17}$ alkenyl.

In one embodiment, $R^2$ is branched $C_6$-$C_{32}$ alkyl. In one embodiment, $R^2$ is branched $C_6$-$C_{24}$ alkyl. In one embodiment, $R^2$ is —$R^7$—$CH(R^8)(R^9)$, wherein $R^7$ is $C_0$-$C_5$ alkylene, and $R^8$ and $R^9$ are independently $C_2$-$C_{10}$ alkyl. In one embodiment, $R^2$ is —$R^7$—$CH(R^8)(R^9)$, wherein $R^7$ is $C_0$-$C_1$ alkylene, and $R^8$ and $R^9$ are independently $C_4$-$C_8$ alkyl.

In one embodiment, $R^2$ is branched $C_6$-$C_{32}$ alkenyl. In one embodiment, $R^2$ is branched $C_6$-$C_{24}$ alkenyl. In one embodiment, $R^2$ is —$R^7$—$CH(R^8)(R^9)$, wherein $R^7$ is $C_0$-$C_5$ alkylene, and $R^8$ and $R^9$ are independently $C_2$-$C_{10}$ alkenyl. In one embodiment, $R^2$ is —$R^7$—$CH(R^8)(R^9)$, wherein $R^7$ is $C_0$-$C_1$ alkylene, and $R^8$ and $R^9$ are independently $C_6$-$C_{10}$ alkenyl.

In one embodiment, $R^c$ is straight $C_6$-$C_{32}$ alkyl. In one embodiment, $R^c$ is straight $C_6$-$C_{24}$ alkyl. In one embodiment, $R^c$ is straight $C_7$-$C_{15}$ alkyl. In one embodiment, $R^c$ is straight $C_7$ alkyl. In one embodiment, $R^c$ is straight $C_8$ alkyl. In one embodiment, $R^c$ is straight $C_9$ alkyl. In one embodiment, $R^c$ is straight $C_{10}$ alkyl. In one embodiment, $R^c$ is straight $C_{11}$ alkyl. In one embodiment, $R^c$ is straight $C_{12}$ alkyl. In one embodiment, $R^c$ is straight C13 alkyl. In one embodiment, $R^c$ is straight $C_{14}$ alkyl. In one embodiment, $R^c$ is straight $C_{15}$ alkyl.

In one embodiment, $R^c$ is straight $C_6$-$C_{32}$ alkenyl. In one embodiment, $R^c$ is straight $C_6$-$C_{24}$ alkenyl. In one embodiment, $R^c$ is straight $C_7$-$C_{17}$ alkenyl. In one embodiment, $R^c$ is straight $C_7$ alkenyl. In one embodiment, $R^c$ is straight $C_8$ alkenyl. In one embodiment, $R^c$ is straight $C_9$ alkenyl. In one embodiment, $R^c$ is straight $C_{10}$ alkenyl. In one embodiment, $R^c$ is straight $C_{11}$ alkenyl. In one embodiment, $R^c$ is straight $C_{12}$ alkenyl. In one embodiment, $R^c$ is straight $C_{13}$ alkenyl. In one embodiment, $R^c$ is straight $C_{14}$ alkenyl. In one embodiment, $R^c$ is straight $C_{15}$ alkenyl. In one embodiment, $R^c$ is straight $C_{16}$ alkenyl. In one embodiment, $R^c$ is straight $C_{17}$ alkenyl.

In one embodiment, $R^c$ is branched $C_6$-$C_{32}$ alkyl. In one embodiment, $R^c$ is branched $C_6$-$C_{24}$ alkyl. In one embodiment, $R^c$ is —$R^7$—$CH(R^8)(R^9)$, wherein $R^7$ is $C_0$-$C_5$ alkylene, and $R^8$ and $R^9$ are independently $C_2$-$C_{10}$ alkyl. In one embodiment, $R^c$ is —$R^7$—$CH(R^8)(R^9)$, wherein $R^7$ is $C_0$-$C_1$ alkylene, and $R^8$ and $R^9$ are independently $C_4$-$C_8$ alkyl.

In one embodiment, $R^c$ is branched $C_6$-$C_{32}$ alkenyl. In one embodiment, $R^c$ is branched $C_6$-$C_{24}$ alkenyl. In one embodiment, $R^c$ is —$R^7$—$CH(R^8)(R^9)$, wherein $R^7$ is $C_0$-$C_5$ alkylene, and $R^8$ and $R^9$ are independently $C_2$-$C_{10}$ alkenyl. In one embodiment, $R^c$ is —$R^7$—$CH(R^8)(R^9)$, wherein $R^7$ is $C_0$-$C_1$ alkylene, and $R^8$ and $R^9$ are independently $C_6$-$C_{10}$ alkenyl.

In one embodiment, $R^f$ is straight $C_6$-$C_{32}$ alkyl. In one embodiment, $R^f$ is straight $C_6$-$C_{24}$ alkyl. In one embodiment, $R^f$ is straight $C_7$-$C_{15}$ alkyl. In one embodiment, $R^f$ is straight $C_7$ alkyl. In one embodiment, $R^f$ is straight $C_8$ alkyl. In one embodiment, $R^f$ is straight $C_9$ alkyl. In one embodiment, $R^f$ is straight $C_{10}$ alkyl. In one embodiment, $R^f$ is straight $C_{11}$ alkyl. In one embodiment, $R^f$ is straight $C_{12}$ alkyl. In one embodiment, $R^f$ is straight $C_{13}$ alkyl. In one embodiment, $R^f$ is straight $C_{14}$ alkyl. In one embodiment, $R^f$ is straight $C_{15}$ alkyl.

In one embodiment, $R^f$ is straight $C_6$-$C_{32}$ alkenyl. In one embodiment, $R^f$ is straight $C_6$-$C_{24}$ alkenyl. In one embodiment, $R^f$ is straight $C_7$-$C_{17}$ alkenyl. In one embodiment, $R^f$ is straight $C_7$ alkenyl. In one embodiment, $R^f$ is straight $C_8$ alkenyl. In one embodiment, $R^f$ is straight $C_9$ alkenyl. In one embodiment, $R^f$ is straight $C_{10}$ alkenyl. In one embodiment, $R^f$ is straight $C_{11}$ alkenyl. In one embodiment, $R^f$ is straight $C_{12}$ alkenyl. In one embodiment, $R^f$ is straight $C_{13}$ alkenyl. In one embodiment, $R^f$ is straight $C_{14}$ alkenyl. In one embodiment, $R^f$ is straight $C_{15}$ alkenyl. In one embodiment, $R^f$ is straight $C_{16}$ alkenyl. In one embodiment, $R^f$ is straight $C_{17}$ alkenyl.

In one embodiment, $R^f$ is branched $C_6$-$C_{32}$ alkyl. In one embodiment, $R^f$ is branched $C_6$-$C_{24}$ alkyl. In one embodiment, $R^f$ is —$R^7$—$CH(R^8)(R^9)$, wherein $R^7$ is $C_0$-$C_5$ alkylene, and $R^8$ and $R^9$ are independently $C_2$-$C_{10}$ alkyl. In one embodiment, $R^f$ is —$R^7$—$CH(R^8)(R^9)$, wherein $R^7$ is $C_0$-$C_1$ alkylene, and $R^8$ and $R^9$ are independently $C_4$-$C_8$ alkyl.

In one embodiment, $R^f$ is branched $C_6$-$C_{32}$ alkenyl. In one embodiment, $R^f$ is branched $C_6$-$C_{24}$ alkenyl. In one embodiment, $R^f$ is —$R^7$—$CH(R^8)(R^9)$, wherein $R^7$ is $C_0$-$C_5$ alkylene, and $R^8$ and $R^9$ are independently $C_2$-$C_{10}$ alkenyl. In one embodiment, $R^f$ is —$R^7$—$CH(R^8)(R^9)$, wherein $R^7$ is $C_0$-$C_1$ alkylene, and $R^8$ and $R^9$ are independently $C_6$-$C_{10}$ alkenyl.

In one embodiment, $R^1$, $R^2$, $R^c$, and $R^f$ are each independently straight $C_6$-$C_{18}$ alkyl, straight $C_6$-$C_{18}$ alkenyl, or —$R^7$—$CH(R^8)(R^9)$, wherein $R^7$ is $C_0$-$C_5$ alkylene, and $R^8$ and $R^9$ are independently $C_2$-$C_{10}$ alkyl or $C_2$-$C_{10}$ alkenyl.

In one embodiment, $R^1$, $R^2$, $R^c$, and $R^f$ are each independently straight $C_7$-$C_{15}$ alkyl, straight $C_7$-$C_{15}$ alkenyl, or —$R^7$—$CH(R^8)(R^9)$, wherein $R^7$ is $C_0$-$C_1$ alkylene, and $R^8$ and $R^9$ are independently $C_4$-$C_8$ alkyl or $C_0$-$C_{10}$ alkenyl.

In one embodiment, $R^1$, $R^2$, $R^c$, and $R^f$ are each independently one of the following structures:

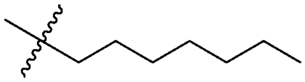
,
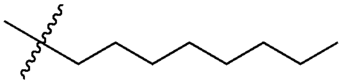
,
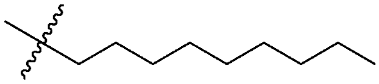
,
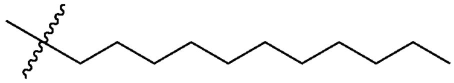
,
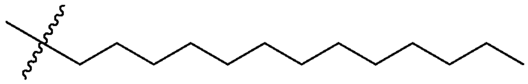
,
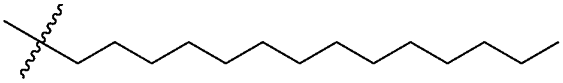
,
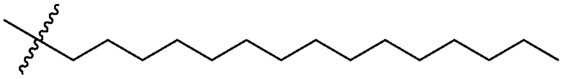
,
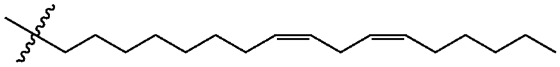
,
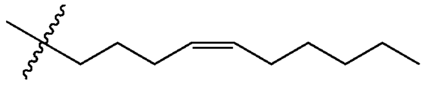
, -continued

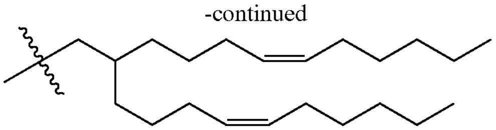

,

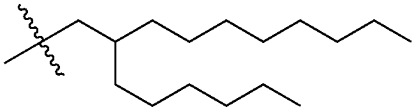

,

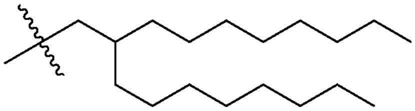

,

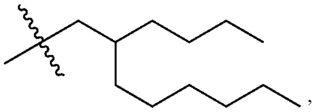

,

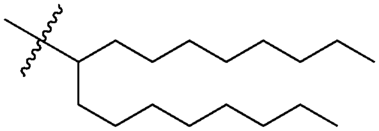

,

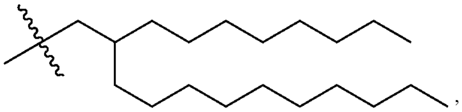

,

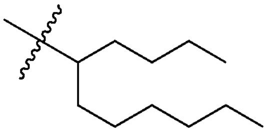

,

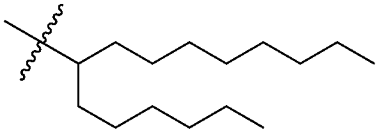

,

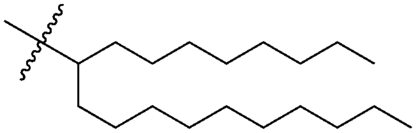

,

-continued

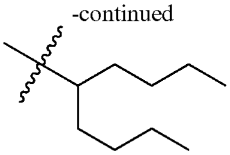

,

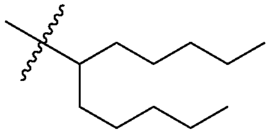

, or

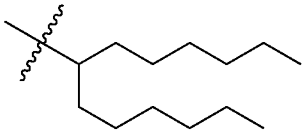

.

In one embodiment, $R^1$, $R^2$, $R^c$, and $R^f$ are each independently optionally substituted. In one embodiment, the optional substituent is —O—($C_6$-$C_{24}$ alkyl). In one embodiment, the optional substituent is —O—($C_6$-$C_{24}$ alkenyl). In one embodiment, the optional substituent is —C(═O)—($C_6$-$C_{24}$ alkyl). In one embodiment, the optional substituent is —C(═O)—($C_6$-$C_{24}$ alkenyl).

In one embodiment, $R^a$ and $R^d$ are each independently H. In one embodiment, $R^a$, $R^b$, $R^d$, and $R^e$ are each independently H. In one embodiment, $R^a$ and $R^d$ are each independently $C_1$-$C_{24}$ alkyl. In one embodiment, $R^a$ and $R^d$ are each independently $C_1$-$C_{18}$ alkyl. In one embodiment, $R^a$ and $R^d$ are each independently $C_1$-$C_{12}$ alkyl. In one embodiment, $R^a$ and $R^d$ are each independently $C_1$-$C_6$ alkyl.

In one embodiment, $R^b$, $R^c$, $R^e$, and $R^f$ are each independently n-hexyl or n-octyl.

In one embodiment, $R^c$ and $R^f$ are each independently branched $C_6$-$C_{24}$ alkyl or branched $C_6$-$C_{24}$ alkenyl. In one embodiment, $R^c$ and $R^f$ are each independently —$R^7$—CH($R^8$)($R^9$), wherein $R^7$ is $C_1$-$C_5$ alkylene, and $R^8$ and $R^9$ are independently $C_2$-$C_{10}$ alkyl or $C_2$-$C_{10}$ alkenyl.

In one embodiment, the compound is a compound in Table 1, or a pharmaceutically acceptable salt, prodrug or stereoisomer thereof.

TABLE 1

Compound 1

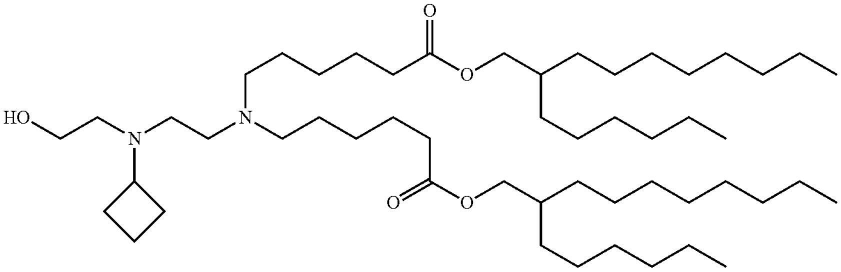 [SMILES: CCCCCCCCC(CCCCCC)COC(=O)CCCCCN(CCCCCC(=O)OCC(CCCCCC)CCCCCCCC)CCN(CCO)C1CCC1]

Compound 2

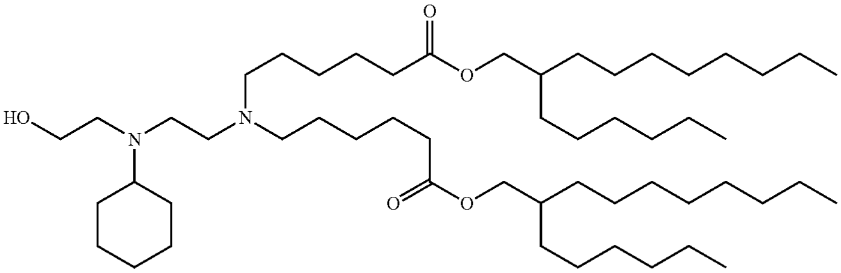 [SMILES: CCCCCCCCC(CCCCCC)COC(=O)CCCCCN(CCCCCC(=O)OCC(CCCCCC)CCCCCCCC)CCN(CCO)C1CCCCC1]

TABLE 1-continued
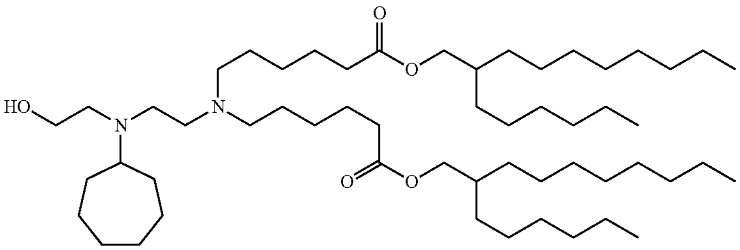 [SMILES: CCCCCCCCC(CCCCCC)COC(=O)CCCCCN(CCCCCC(=O)OCC(CCCCCC)CCCCCCCC)CCN(CCO)C1CCCCCC1]
Compound 3
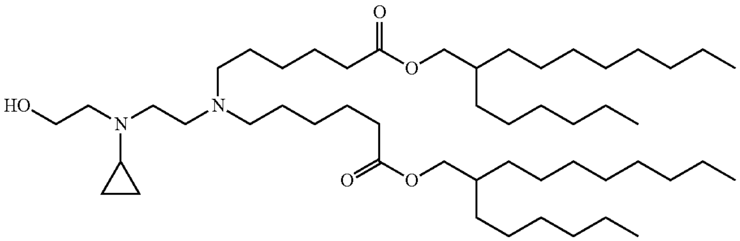 [SMILES: CCCCCCCCC(CCCCCC)COC(=O)CCCCCN(CCCCCC(=O)OCC(CCCCCC)CCCCCCCC)CCN(CCO)C1CC1]
Compound 4
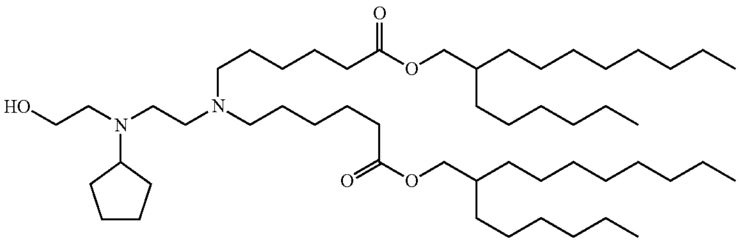 [SMILES: CCCCCCCCC(CCCCCC)COC(=O)CCCCCN(CCCCCC(=O)OCC(CCCCCC)CCCCCCCC)CCN(CCO)C1CCCC1]
Compound 5
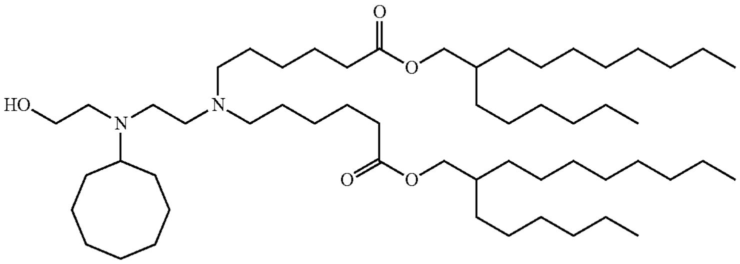 [SMILES: CCCCCCCCC(CCCCCC)COC(=O)CCCCCN(CCCCCC(=O)OCC(CCCCCC)CCCCCCCC)CCN(CCO)C1CCCCCCC1]
Compound 6
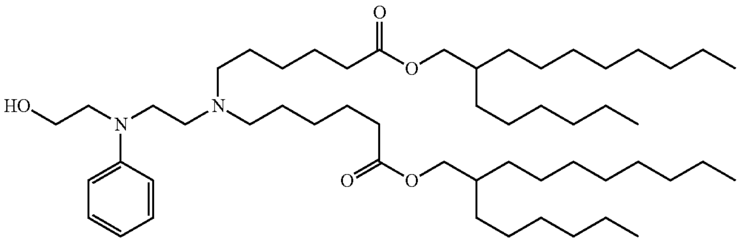 [SMILES: CCCCCCCCC(CCCCCC)COC(=O)CCCCCN(CCCCCC(=O)OCC(CCCCCC)CCCCCCCC)CCN(CCO)c1ccccc1]
Compound 7
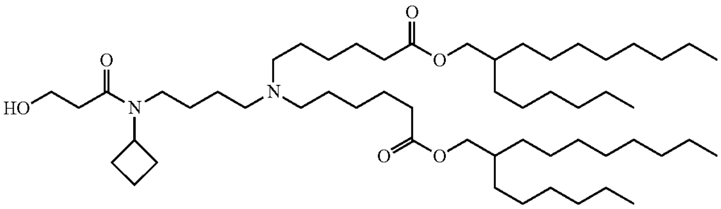 [SMILES: CCCCCCCCC(CCCCCC)COC(=O)CCCCCN(CCCCCC(=O)OCC(CCCCCC)CCCCCCCC)CCCCN(C(=O)CCO)C1CCC1]
Compound 8

TABLE 1-continued
Compound 9
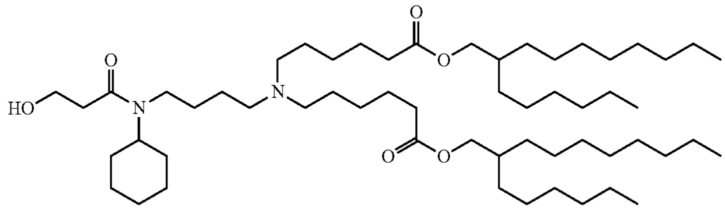 [SMILES: CCCCCCCCC(CCCCCC)COC(=O)CCCCCN(CCCCCC(=O)OCC(CCCCCC)CCCCCCCC)CCCCN(C(=O)CCO)C1CCCCC1]
Compound 10
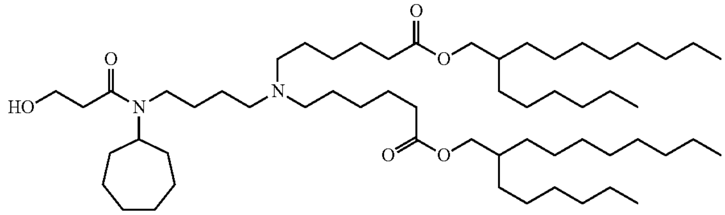 [SMILES: CCCCCCCCC(CCCCCC)COC(=O)CCCCCN(CCCCCC(=O)OCC(CCCCCC)CCCCCCCC)CCCCN(C(=O)CCO)C1CCCCCC1]
Compound 11
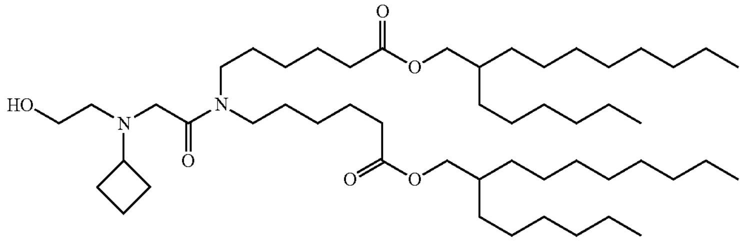 [SMILES: CCCCCCCCC(CCCCCC)COC(=O)CCCCCN(CCCCCC(=O)OCC(CCCCCC)CCCCCCCC)C(=O)CN(CCO)C1CCC1]
Compound 12
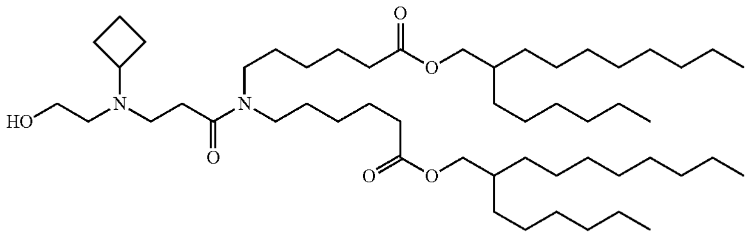 [SMILES: CCCCCCCCC(CCCCCC)COC(=O)CCCCCN(CCCCCC(=O)OCC(CCCCCC)CCCCCCCC)C(=O)CCN(CCO)C1CCC1]
Compound 13
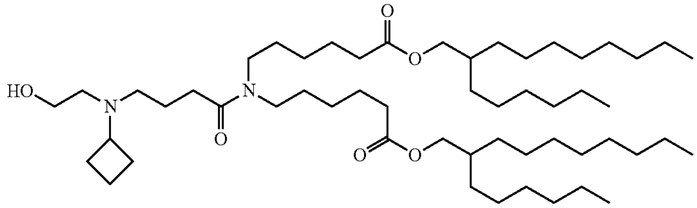 [SMILES: CCCCCCCCC(CCCCCC)COC(=O)CCCCCN(CCCCCC(=O)OCC(CCCCCC)CCCCCCCC)C(=O)CCCN(CCO)C1CCC1]
Compound 14
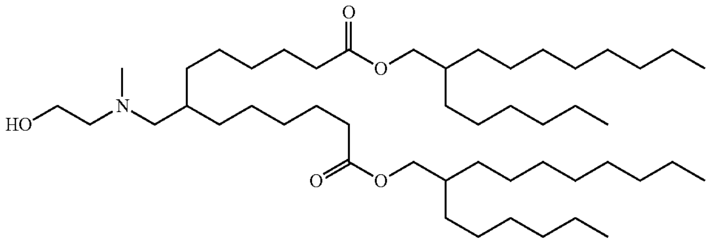 [SMILES: CCCCCCCCC(CCCCCC)COC(=O)CCCCCC(CCCCCC(=O)OCC(CCCCCC)CCCCCCCC)CN(C)CCO]
Compound 15
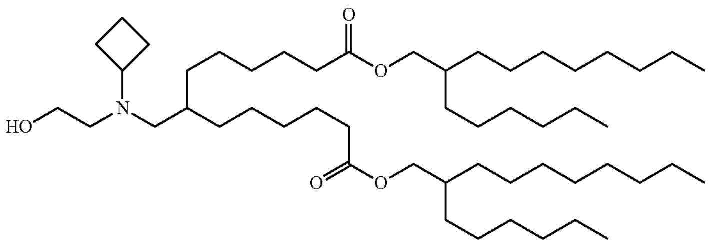 [SMILES: CCCCCCCCC(CCCCCC)COC(=O)CCCCCC(CCCCCC(=O)OCC(CCCCCC)CCCCCCCC)CN(CCO)C1CCC1]

TABLE 1-continued
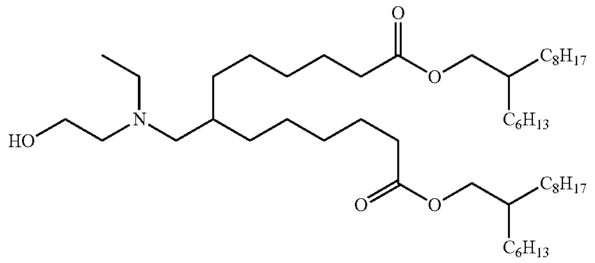
Compound 16
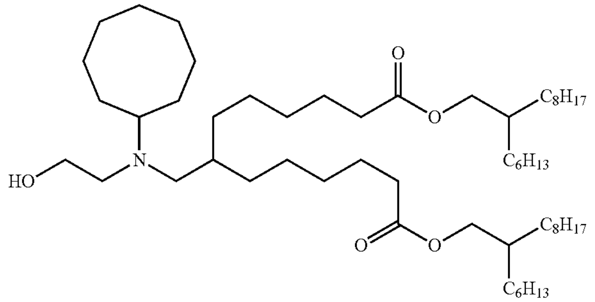
Compound 17
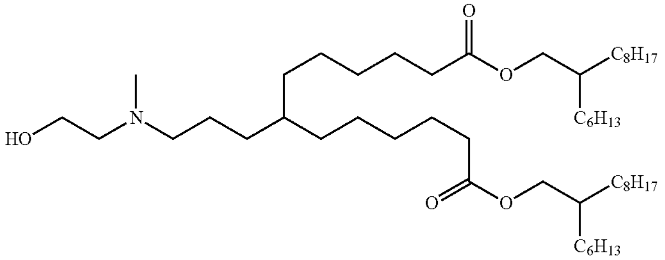
Compound 18
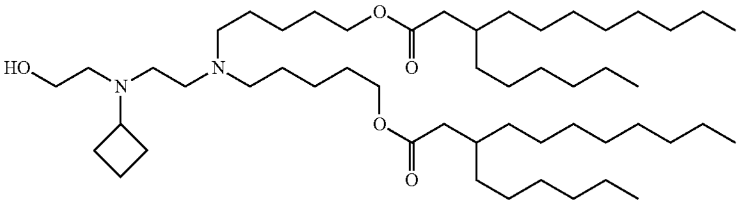 [SMILES: CCCCCCCCC(CCCCCC)CC(=O)OCCCCCN(CCCCCOC(=O)CC(CCCCCC)CCCCCCCC)CCN(CCO)C1CCC1]
Compound 20
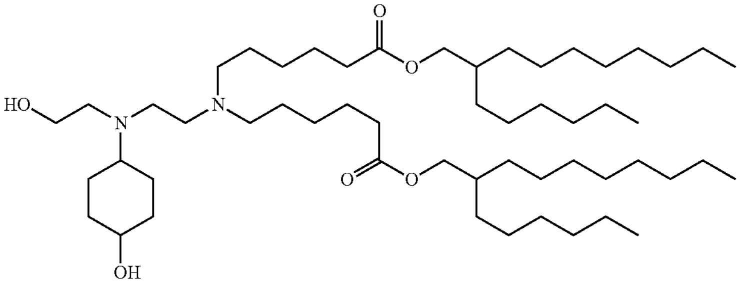 [SMILES: CCCCCCCCC(CCCCCC)COC(=O)CCCCCN(CCCCCC(=O)OCC(CCCCCC)CCCCCCCC)CCN(CCO)C1CCC(O)CC1]
Compound 21
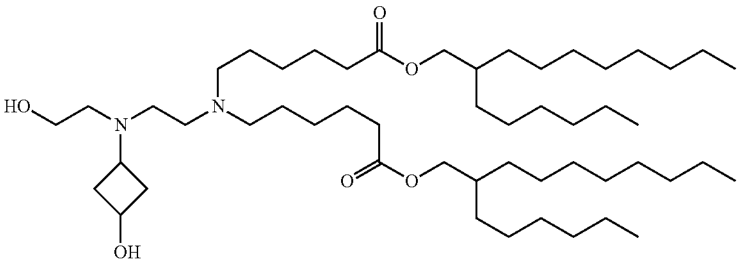 [SMILES: CCCCCCCCC(CCCCCC)COC(=O)CCCCCN(CCCCCC(=O)OCC(CCCCCC)CCCCCCCC)CCN(CCO)C1CC(O)C1]
Compound 22

TABLE 1-continued
Compound 23
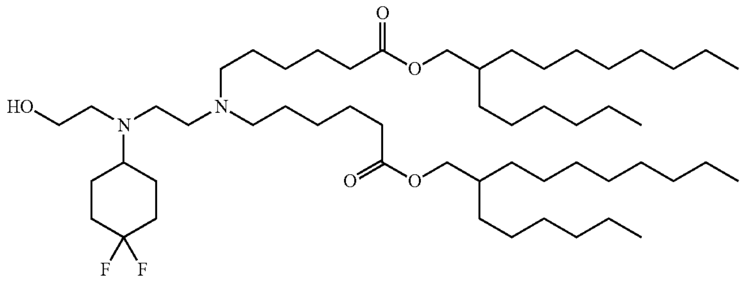 [SMILES: CCCCCCCCC(CCCCCC)COC(=O)CCCCCN(CCCCCC(=O)OCC(CCCCCC)CCCCCCCC)CCN(CCO)C1CCC(F)(F)CC1]
Compound 24
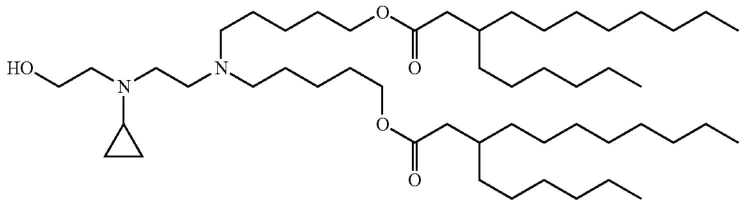 [SMILES: CCCCCCCCC(CCCCCC)CC(=O)OCCCCCN(CCCCCOC(=O)CC(CCCCCC)CCCCCCCC)CCN(CCO)C1CC1]
Compound 25
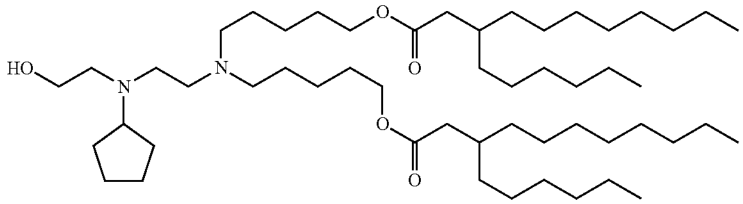 [SMILES: CCCCCCCCC(CCCCCC)CC(=O)OCCCCCN(CCCCCOC(=O)CC(CCCCCC)CCCCCCCC)CCN(CCO)C1CCCC1]
Compound 26
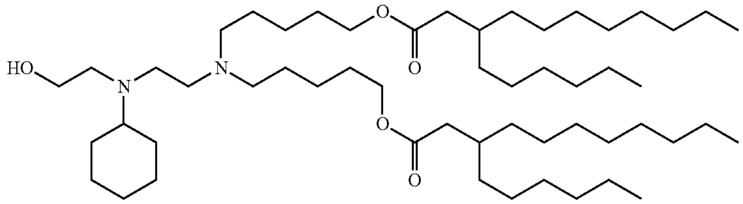 [SMILES: CCCCCCCCC(CCCCCC)CC(=O)OCCCCCN(CCCCCOC(=O)CC(CCCCCC)CCCCCCCC)CCN(CCO)C1CCCCC1]
Compound 27
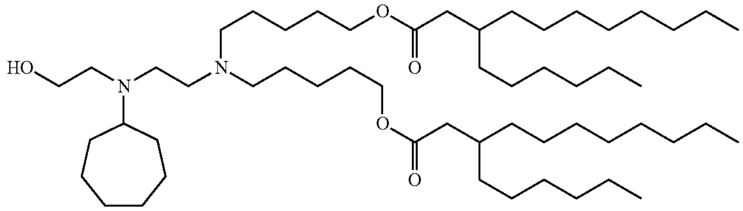 [SMILES: CCCCCCCCC(CCCCCC)CC(=O)OCCCCCN(CCCCCOC(=O)CC(CCCCCC)CCCCCCCC)CCN(CCO)C1CCCCCC1]
Compound 28
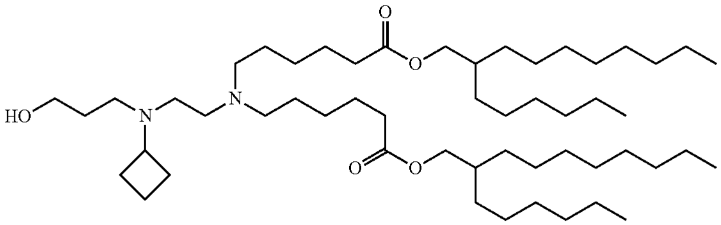 [SMILES: CCCCCCCCC(CCCCCC)COC(=O)CCCCCN(CCCCCC(=O)OCC(CCCCCC)CCCCCCCC)CCN(CCCO)C1CCC1]
Compound 29
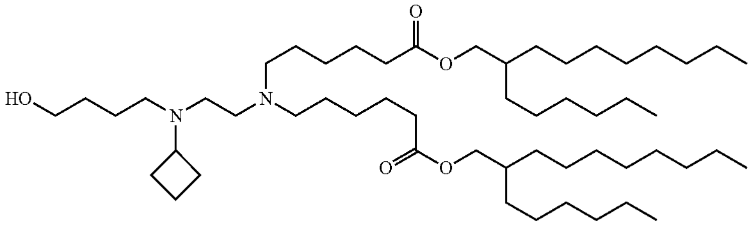 [SMILES: CCCCCCCCC(CCCCCC)COC(=O)CCCCCN(CCCCCC(=O)OCC(CCCCCC)CCCCCCCC)CCN(CCCCO)C1CCC1]

TABLE 1-continued
Compound 30
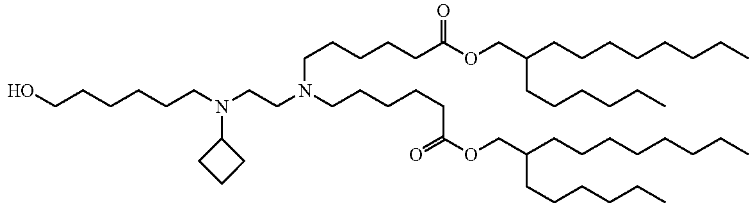 [SMILES: CCCCCCCCC(CCCCCC)COC(=O)CCCCCN(CCCCCC(=O)OCC(CCCCCC)CCCCCCCC)CCN(CCCCCCO)C1CCC1]
Compound 31
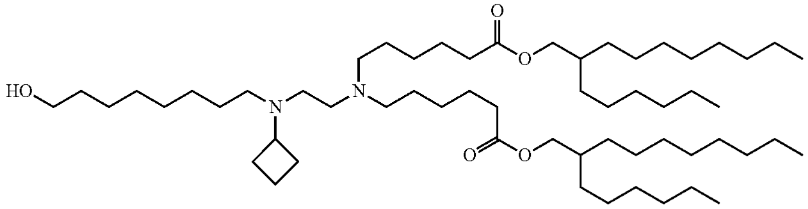 [SMILES: CCCCCCCCC(CCCCCC)COC(=O)CCCCCN(CCCCCC(=O)OCC(CCCCCC)CCCCCCCC)CCN(CCCCCCCCO)C1CCC1]
Compound 32
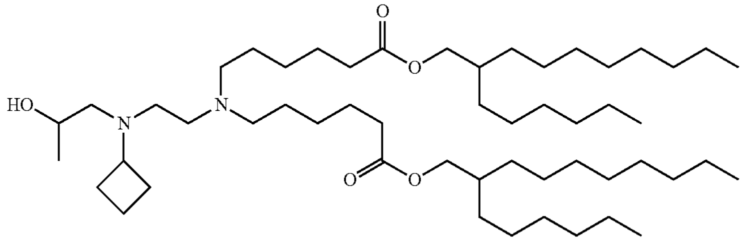 [SMILES: CCCCCCCCC(CCCCCC)COC(=O)CCCCCN(CCCCCC(=O)OCC(CCCCCC)CCCCCCCC)CCN(CC(C)O)C1CCC1]
Compound 33
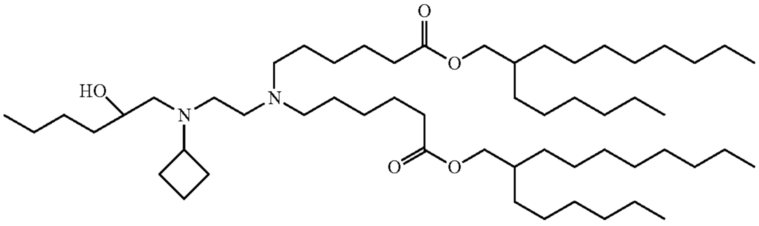 [SMILES: CCCCCCCCC(CCCCCC)COC(=O)CCCCCN(CCCCCC(=O)OCC(CCCCCC)CCCCCCCC)CCN(CC(O)CCCC)C1CCC1]
Compound 34
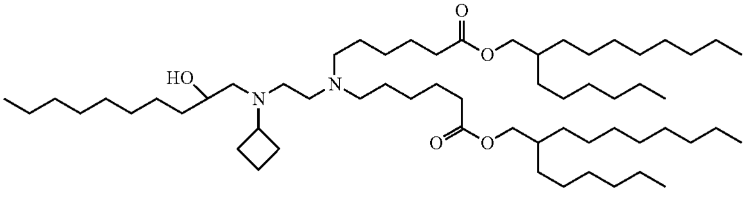 [SMILES: CCCCCCCCC(O)CN(CCN(CCCCCC(=O)OCC(CCCCCC)CCCCCCCC)CCCCCC(=O)OCC(CCCCCC)CCCCCCCC)C1CCC1]
Compound 35
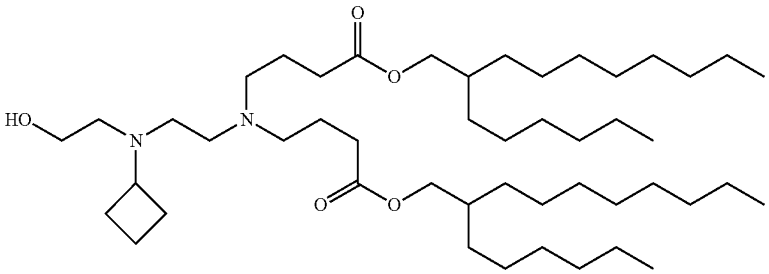 [SMILES: CCCCCCCCC(CCCCCC)COC(=O)CCCN(CCCC(=O)OCC(CCCCCC)CCCCCCCC)CCN(CCO)C1CCC1]

TABLE 1-continued
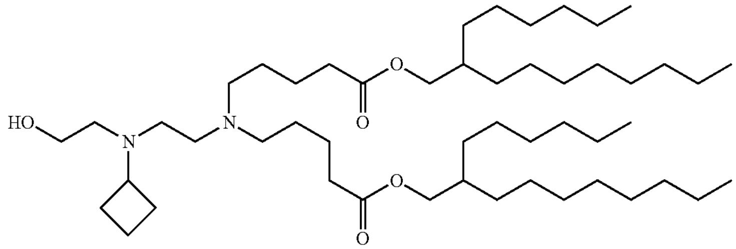 [SMILES: CCCCCCCCC(CCCCCC)COC(=O)CCCCN(CCCCC(=O)OCC(CCCCCC)CCCCCCCC)CCN(CCO)C1CCC1]
Compound 36
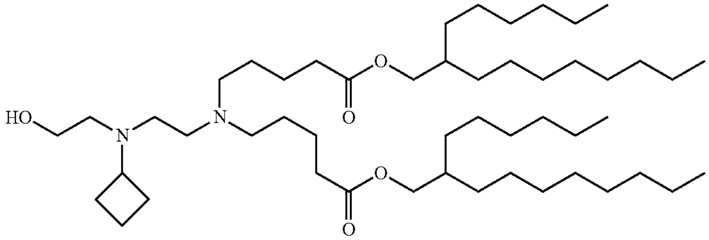 [SMILES: CCCCCCCCC(CCCCCC)COC(=O)CCCCN(CCCCC(=O)OCC(CCCCCC)CCCCCCCC)CCN(CCO)C1CCC1]
Compound 37
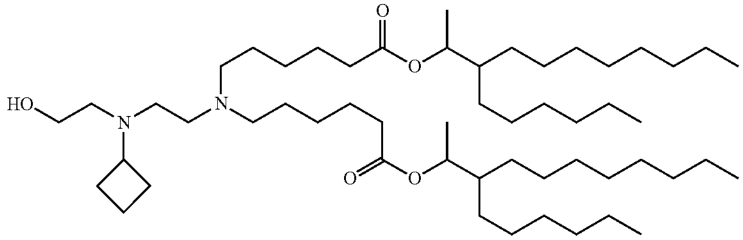 [SMILES: CCCCCCCCC(CCCCCC)C(C)OC(=O)CCCCCN(CCCCCC(=O)OC(C)C(CCCCCC)CCCCCCCC)CCN(CCO)C1CCC1]
Compound 38
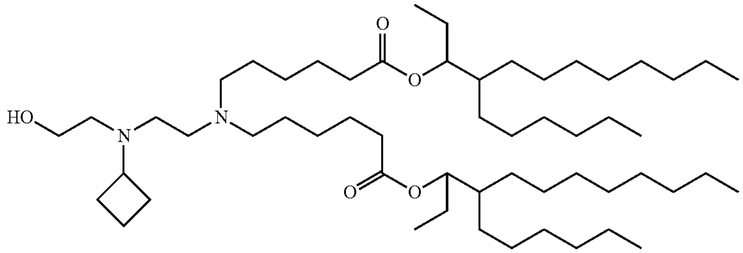 [SMILES: CCCCCCCCC(CCCCCC)C(CC)OC(=O)CCCCCN(CCCCCC(=O)OC(CC)C(CCCCCC)CCCCCCCC)CCN(CCO)C1CCC1]
Compound 39
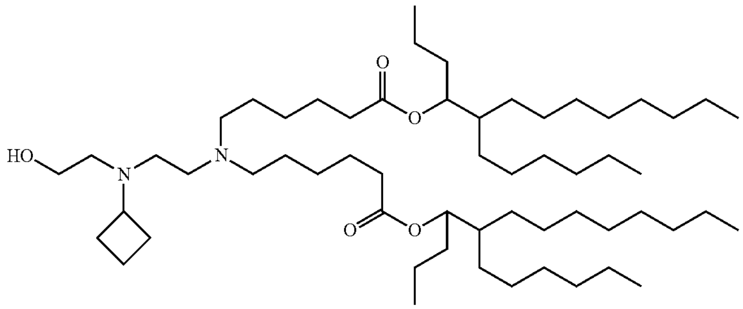 [SMILES: CCCCCCCCC(CCCCCC)C(CCC)OC(=O)CCCCCN(CCCCCC(=O)OC(CCC)C(CCCCCC)CCCCCCCC)CCN(CCO)C1CCC1]
Compound 40
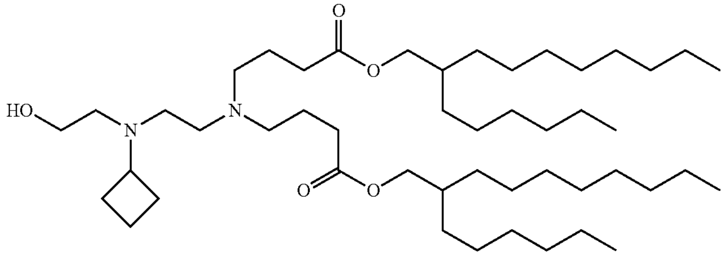 [SMILES: CCCCCCCCC(CCCCCC)COC(=O)CCCN(CCCC(=O)OCC(CCCCCC)CCCCCCCC)CCN(CCO)C1CCC1]
Compound 41

TABLE 1-continued
Compound 42
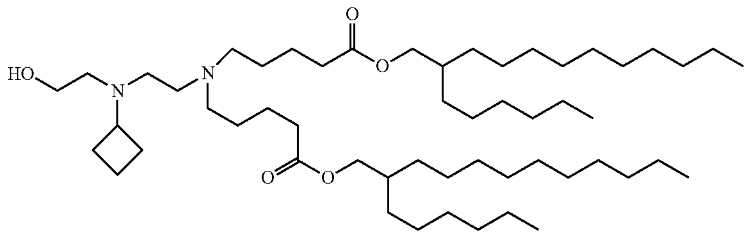 [SMILES: CCCCCCCCCCC(CCCCCC)COC(=O)CCCCN(CCCCC(=O)OCC(CCCCCC)CCCCCCCCCC)CCN(CCO)C1CCC1]
Compound 43
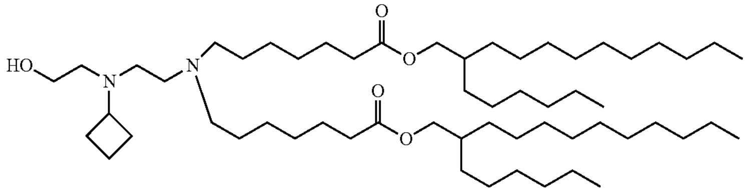 [SMILES: CCCCCCCCCCC(CCCCCC)COC(=O)CCCCCCN(CCCCCCC(=O)OCC(CCCCCC)CCCCCCCCCC)CCN(CCO)C1CCC1]
Compound 44
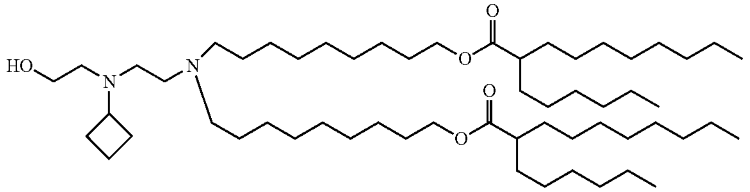 [SMILES: CCCCCCCCC(CCCCCC)C(=O)OCCCCCCCCCN(CCCCCCCCCOC(=O)C(CCCCCC)CCCCCCCC)CCN(CCO)C1CCC1]
Compound 45
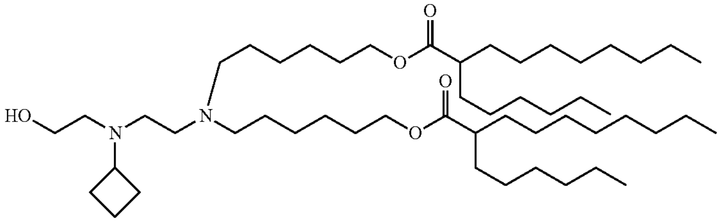 [SMILES: CCCCCCCCC(CCCCCC)C(=O)OCCCCCCN(CCCCCCOC(=O)C(CCCCCC)CCCCCCCC)CCN(CCO)C1CCC1]
Compound 46
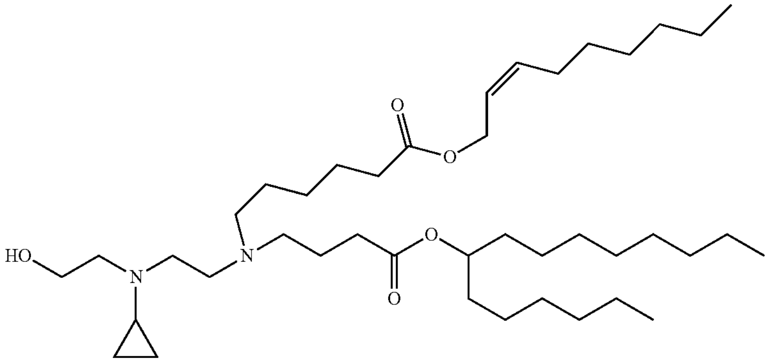 [SMILES: CCCCCC/C=C\COC(=O)CCCCCN(CCCC(=O)OC(CCCCCC)CCCCCCCC)CCN(CCO)C1CC1]
Compound 47
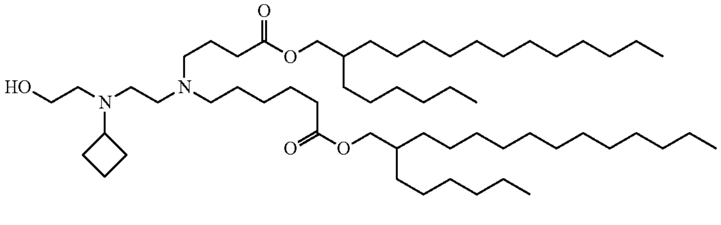 [SMILES: CCCCCCCCCCCCC(CCCCCC)COC(=O)CCCCCN(CCCC(=O)OCC(CCCCCC)CCCCCCCCCCCC)CCN(CCO)C1CCC1]

TABLE 1-continued
Compound 48
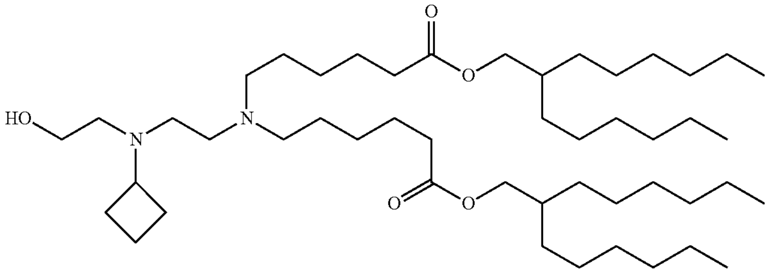 [SMILES: CCCCCCC(CCCCCC)COC(=O)CCCCCN(CCCCCC(=O)OCC(CCCCCC)CCCCCC)CCN(CCO)C1CCC1]
Compound 49
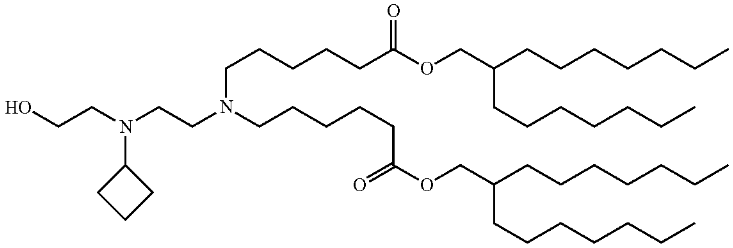 [SMILES: CCCCCCCC(CCCCCCC)COC(=O)CCCCCN(CCCCCC(=O)OCC(CCCCCCC)CCCCCCC)CCN(CCO)C1CCC1]
Compound 50
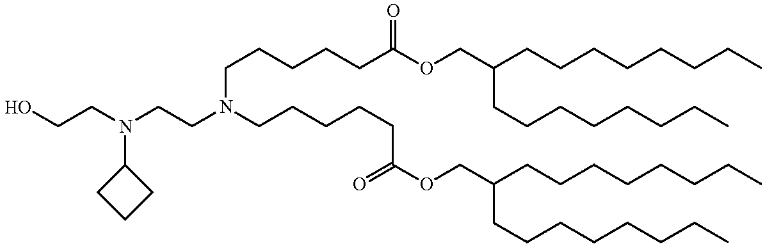 [SMILES: CCCCCCCCC(CCCCCCCC)COC(=O)CCCCCN(CCCCCC(=O)OCC(CCCCCCCC)CCCCCCCC)CCN(CCO)C1CCC1]
Compound 51
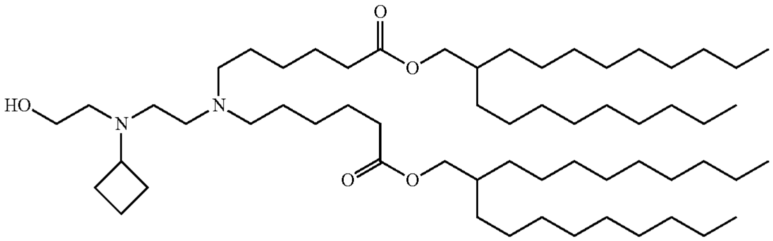 [SMILES: CCCCCCCCCC(CCCCCCCCC)COC(=O)CCCCCN(CCCCCC(=O)OCC(CCCCCCCCC)CCCCCCCCC)CCN(CCO)C1CCC1]
Compound 52
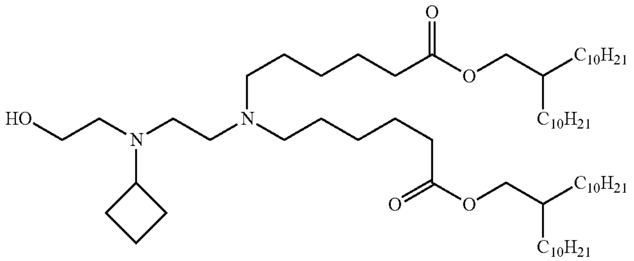
Compound 54
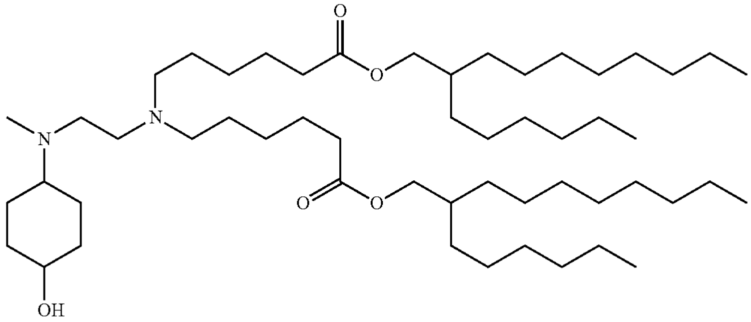 [SMILES: CCCCCCCCC(CCCCCC)COC(=O)CCCCCN(CCCCCC(=O)OCC(CCCCCC)CCCCCCCC)CCN(C)C1CCC(O)CC1]

TABLE 1-continued
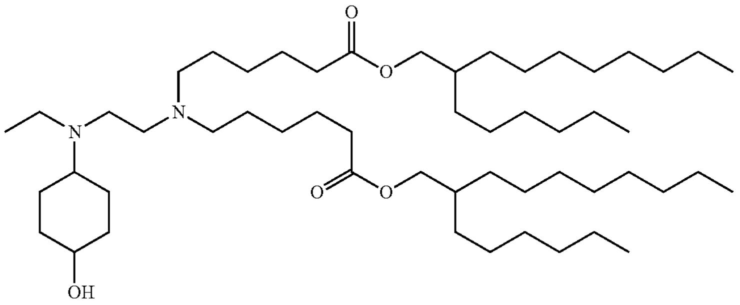 [SMILES: CCCCCCCCC(CCCCCC)COC(=O)CCCCCN(CCCCCC(=O)OCC(CCCCCC)CCCCCCCC)CCN(CC)C1CCC(O)CC1]
Compound 55
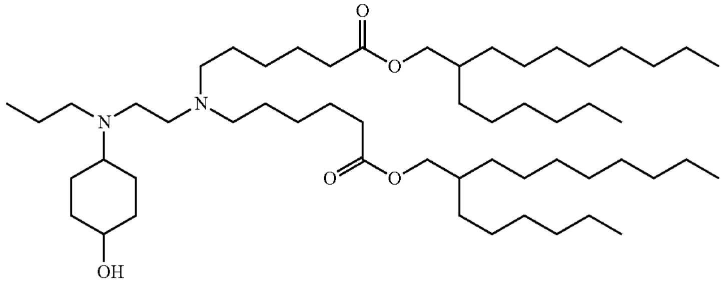 [SMILES: CCCCCCCCC(CCCCCC)COC(=O)CCCCCN(CCCCCC(=O)OCC(CCCCCC)CCCCCCCC)CCN(CCC)C1CCC(O)CC1]
Compound 56
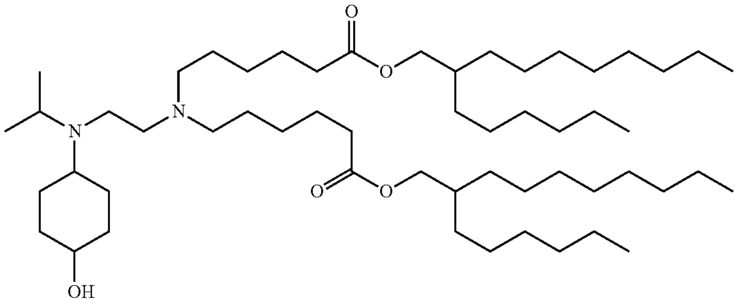 [SMILES: CCCCCCCCC(CCCCCC)COC(=O)CCCCCN(CCCCCC(=O)OCC(CCCCCC)CCCCCCCC)CCN(C(C)C)C1CCC(O)CC1]
Compound 57
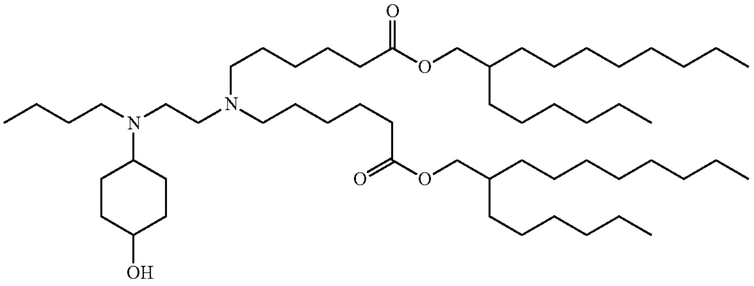 [SMILES: CCCCCCCCC(CCCCCC)COC(=O)CCCCCN(CCCCCC(=O)OCC(CCCCCC)CCCCCCCC)CCN(CCCC)C1CCC(O)CC1]
Compound 58
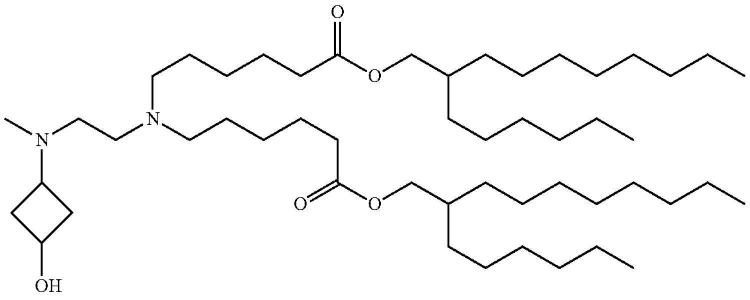 [SMILES: CCCCCCCCC(CCCCCC)COC(=O)CCCCCN(CCCCCC(=O)OCC(CCCCCC)CCCCCCCC)CCN(C)C1CC(O)C1]
Compound 59

TABLE 1-continued
Compound 60
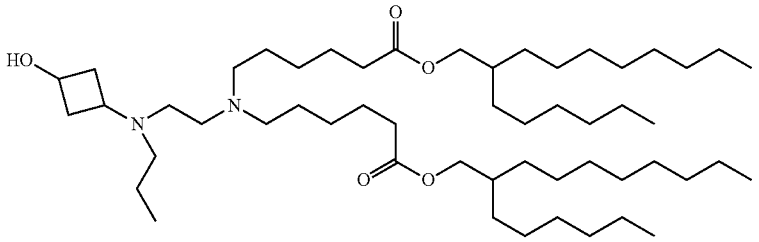 [SMILES: CCCCCCCCC(CCCCCC)COC(=O)CCCCCN(CCCCCC(=O)OCC(CCCCCC)CCCCCCCC)CCN(CCC)C1CC(O)C1]
Compound 61
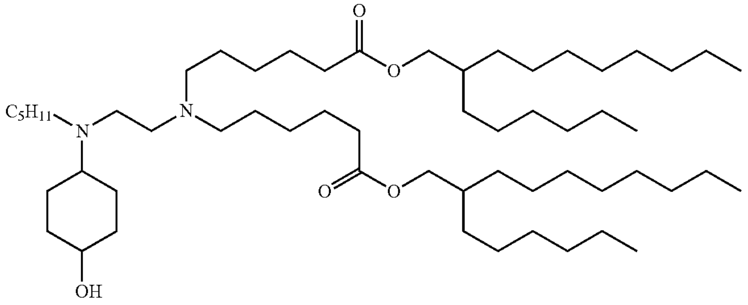
Compound 62
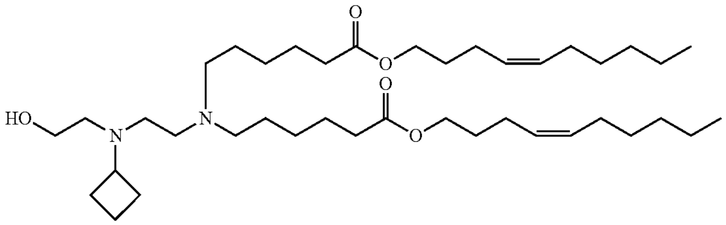 [SMILES: CCCCC/C=C\CCCOC(=O)CCCCCN(CCCCCC(=O)OCCC/C=C\CCCCC)CCN(CCO)C1CCC1]
Compound 63
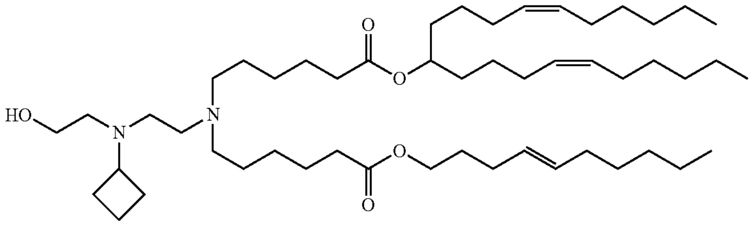 [SMILES: CCCCC/C=C\CCCC(CCC/C=C\CCCCC)OC(=O)CCCCCN(CCCCCC(=O)OCCC/C=C/CCCCC)CCN(CCO)C1CCC1]
Compound 64
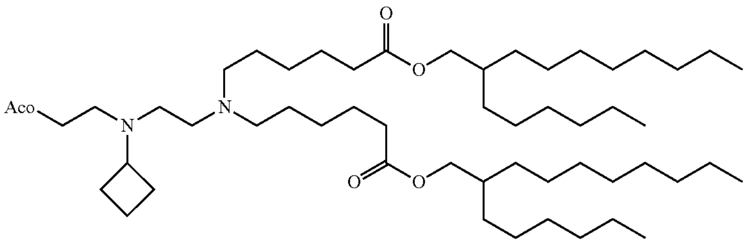
Compound 65
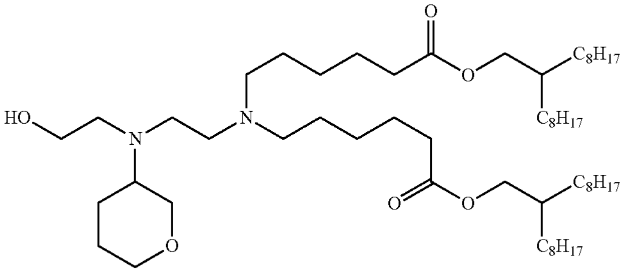

TABLE 1-continued
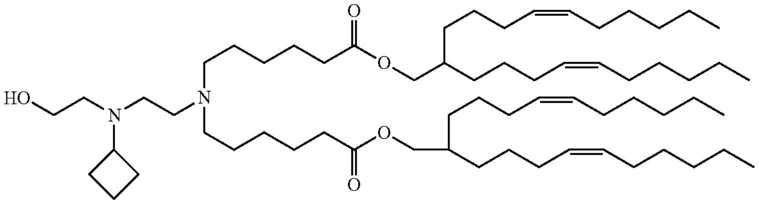 [SMILES: CCCCC/C=C\CCCC(CCC/C=C\CCCCC)COC(=O)CCCCCN(CCCCCC(=O)OCC(CCC/C=C\CCCCC)CCC/C=C\CCCCC)CCN(CCO)C1CCC1]
Compound 66
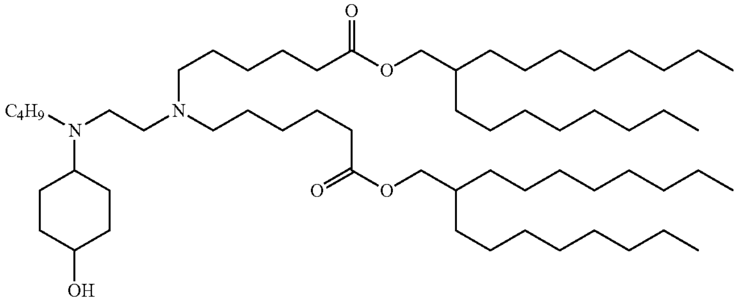
Compound 67
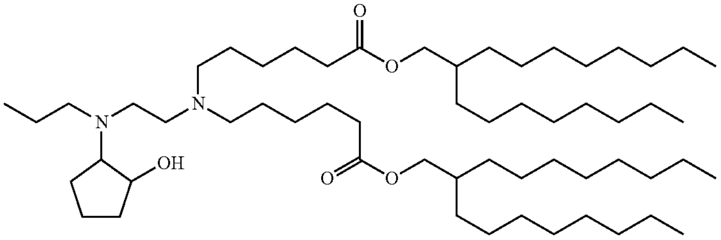 [SMILES: CCCCCCCCC(CCCCCCCC)COC(=O)CCCCCN(CCCCCC(=O)OCC(CCCCCCCC)CCCCCCCC)CCN(CCC)C1CCCC1O]
Compound 68
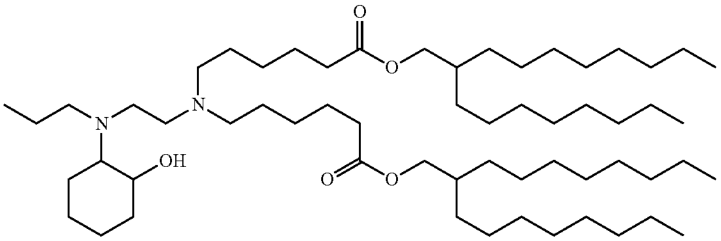 [SMILES: CCCCCCCCC(CCCCCCCC)COC(=O)CCCCCN(CCCCCC(=O)OCC(CCCCCCCC)CCCCCCCC)CCN(CCC)C1CCCCC1O]
Compound 69
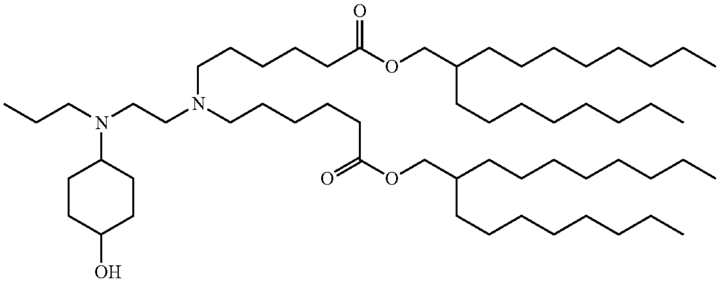 [SMILES: CCCCCCCCC(CCCCCCCC)COC(=O)CCCCCN(CCCCCC(=O)OCC(CCCCCCCC)CCCCCCCC)CCN(CCC)C1CCC(O)CC1]
Compound 70
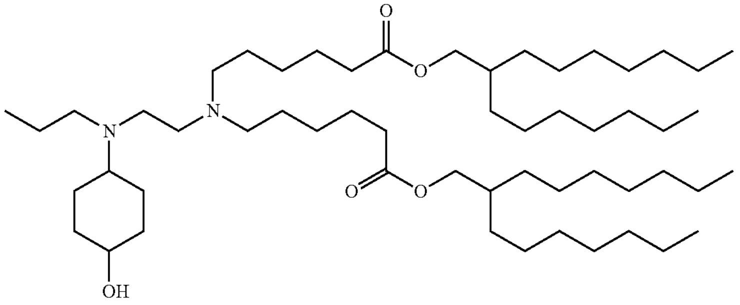 [SMILES: CCCCCCCC(CCCCCCC)COC(=O)CCCCCN(CCCCCC(=O)OCC(CCCCCCC)CCCCCCC)CCN(CCC)C1CCC(O)CC1]
Compound 71

TABLE 1-continued
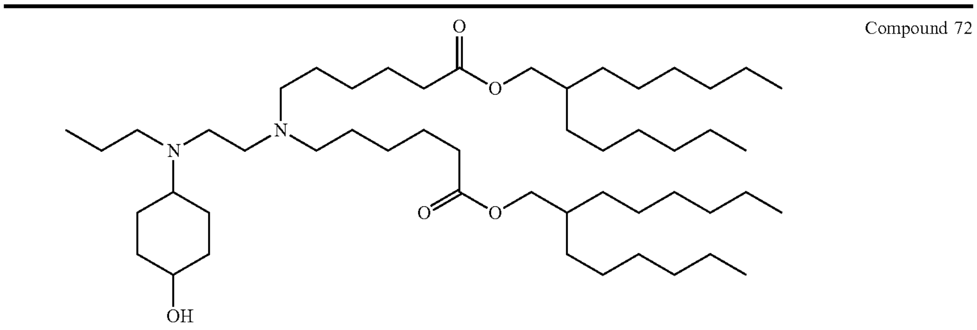
Compound 72
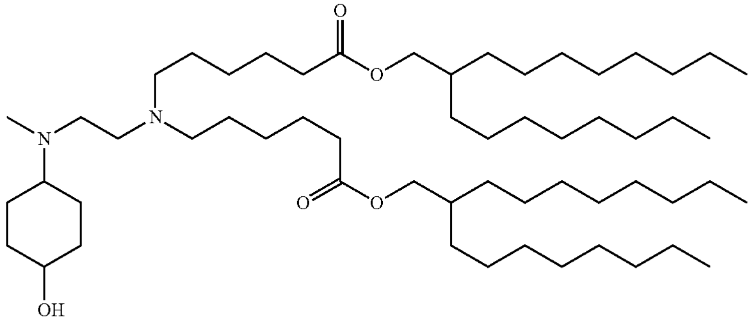 [SMILES: CCCCCCCCC(CCCCCCCC)COC(=O)CCCCCN(CCCCCC(=O)OCC(CCCCCCCC)CCCCCCCC)CCN(C)C1CCC(O)CC1]
Compound 73
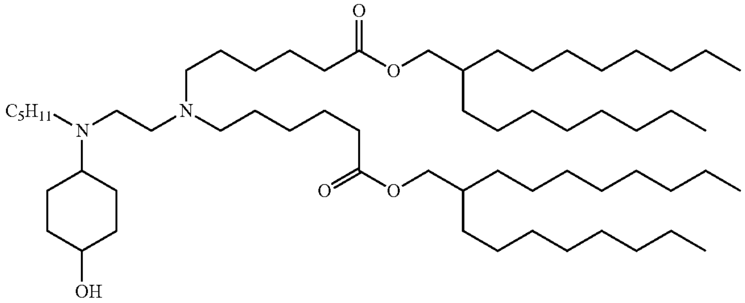
Compound 74
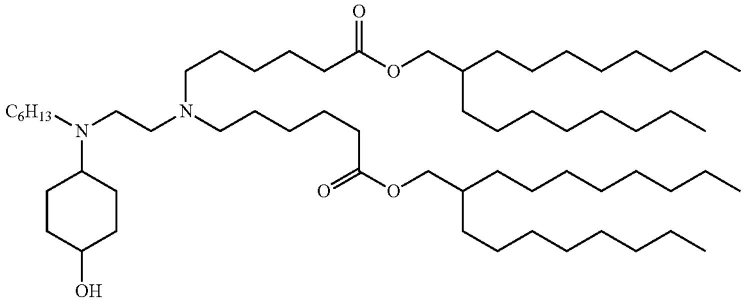
Compound 75
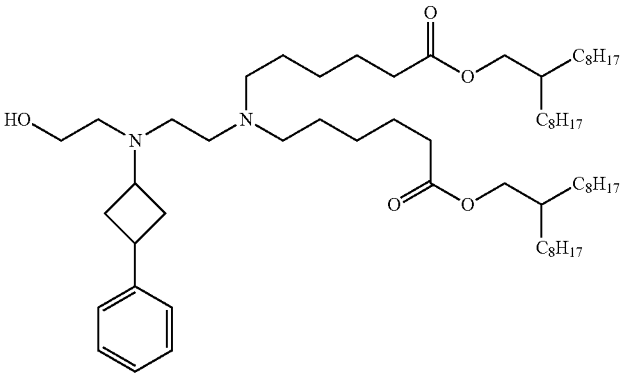
Compound 76

TABLE 1-continued
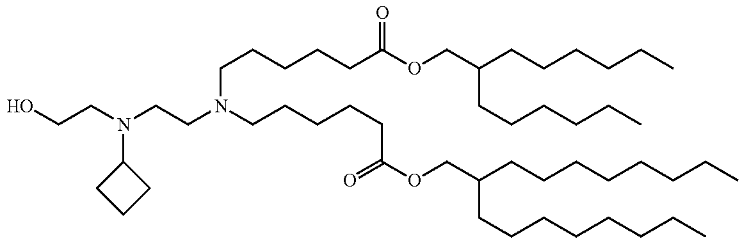 [SMILES: CCCCCCCCC(CCCCCCCC)COC(=O)CCCCCN(CCCCCC(=O)OCC(CCCCCC)CCCCCC)CCN(CCO)C1CCC1]
Compound 77
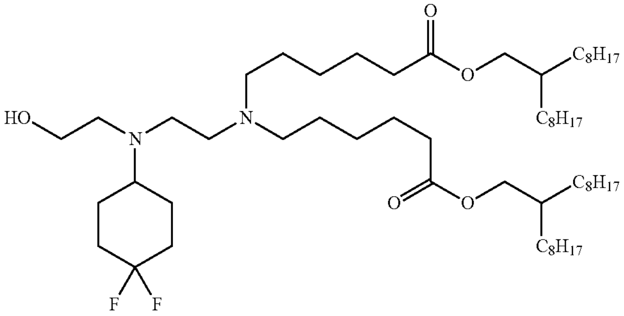
Compound 78
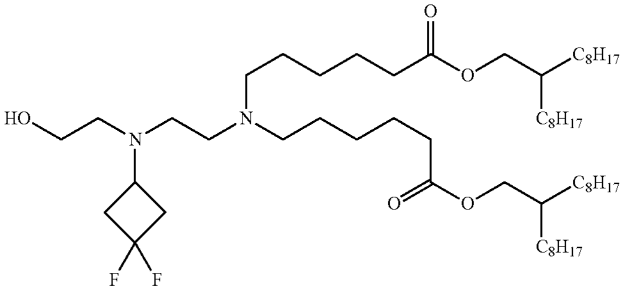
Compound 79
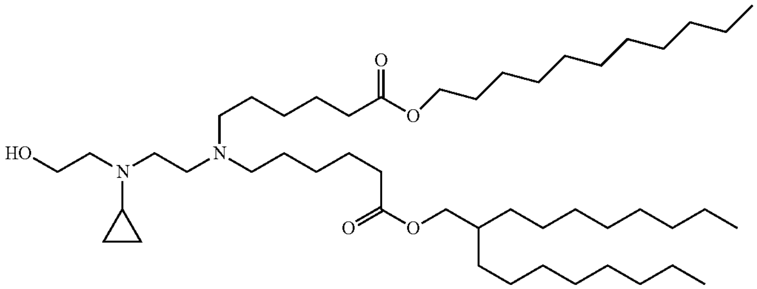 [SMILES: CCCCCCCCCCCOC(=O)CCCCCN(CCCCCC(=O)OCC(CCCCCCCC)CCCCCCCC)CCN(CCO)C1CC1]
Compound 80
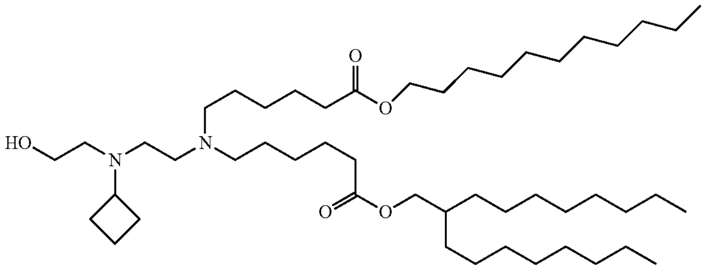 [SMILES: CCCCCCCCCCCOC(=O)CCCCCN(CCCCCC(=O)OCC(CCCCCCCC)CCCCCCCC)CCN(CCO)C1CCC1]
Compound 81

TABLE 1-continued
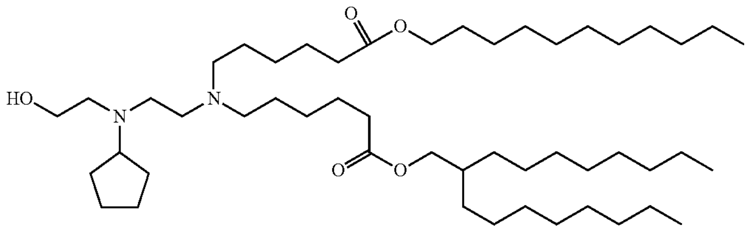 [SMILES: CCCCCCCCCCCOC(=O)CCCCCN(CCCCCC(=O)OCC(CCCCCCCC)CCCCCCCC)CCN(CCO)C1CCCC1]
Compound 82
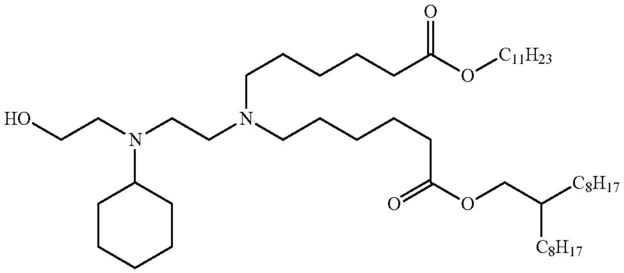
Compound 83
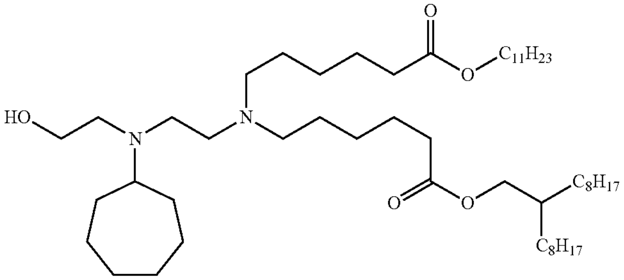
Compound 84
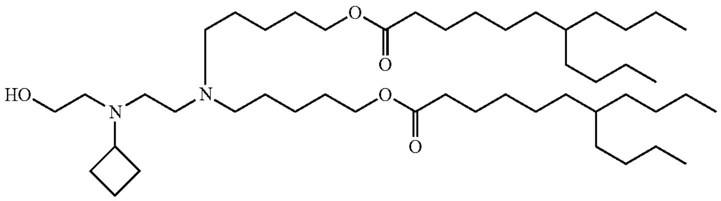 [SMILES: CCCCC(CCCC)CCCCCC(=O)OCCCCCN(CCCCCOC(=O)CCCCCC(CCCC)CCCC)CCN(CCO)C1CCC1]
Compound 85
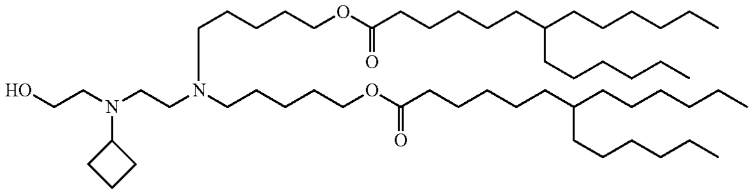 [SMILES: CCCCCCC(CCCCCC)CCCCCC(=O)OCCCCCN(CCCCCOC(=O)CCCCCC(CCCCCC)CCCCCC)CCN(CCO)C1CCC1]
Compound 86
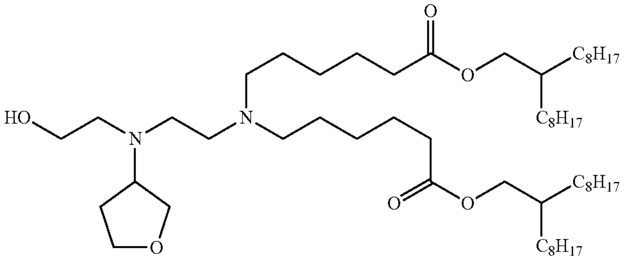
Compound 87

TABLE 1-continued
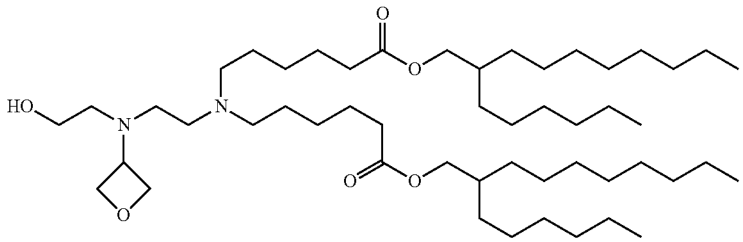 [SMILES: CCCCCCCCC(CCCCCC)COC(=O)CCCCCN(CCCCCC(=O)OCC(CCCCCC)CCCCCCCC)CCN(CCO)C1COC1]
Compound 88
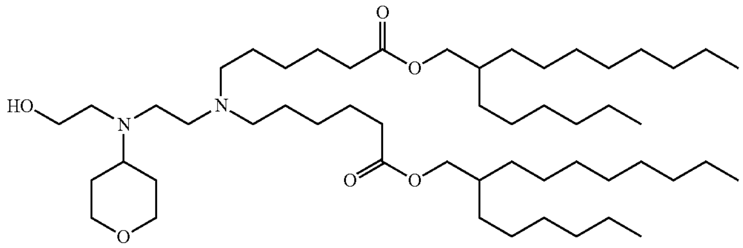 [SMILES: CCCCCCCCC(CCCCCC)COC(=O)CCCCCN(CCCCCC(=O)OCC(CCCCCC)CCCCCCCC)CCN(CCO)C1CCOCC1]
Compound 89
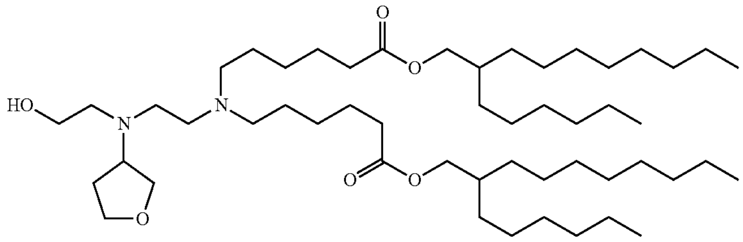 [SMILES: CCCCCCCCC(CCCCCC)COC(=O)CCCCCN(CCCCCC(=O)OCC(CCCCCC)CCCCCCCC)CCN(CCO)C1CCOC1]
Compound 90
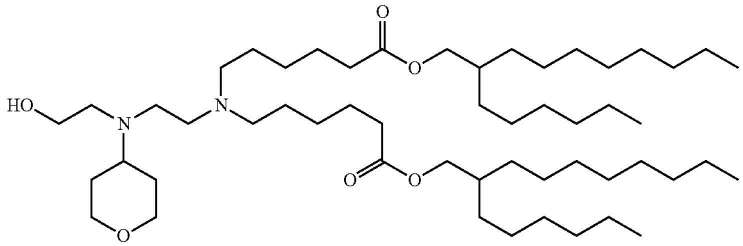 [SMILES: CCCCCCCCC(CCCCCC)COC(=O)CCCCCN(CCCCCC(=O)OCC(CCCCCC)CCCCCCCC)CCN(CCO)C1CCOCC1]
Compound 91
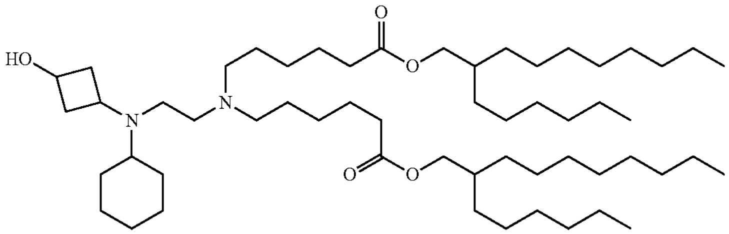 [SMILES: CCCCCCCCC(CCCCCC)COC(=O)CCCCCN(CCCCCC(=O)OCC(CCCCCC)CCCCCCCC)CCN(C1CCCCC1)C1CC(O)C1]
Compound 92
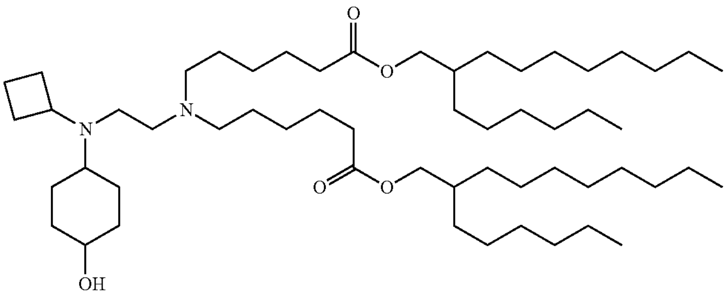 [SMILES: CCCCCCCCC(CCCCCC)COC(=O)CCCCCN(CCCCCC(=O)OCC(CCCCCC)CCCCCCCC)CCN(C1CCC1)C1CCC(O)CC1]
Compound 93

TABLE 1-continued
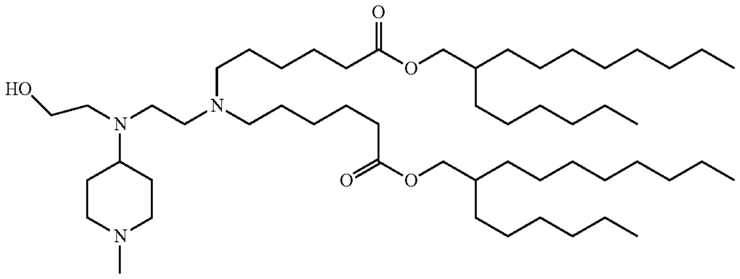 [SMILES: CCCCCCCCC(CCCCCC)COC(=O)CCCCCN(CCCCCC(=O)OCC(CCCCCC)CCCCCCCC)CCN(CCO)C1CCN(C)CC1]
Compound 94
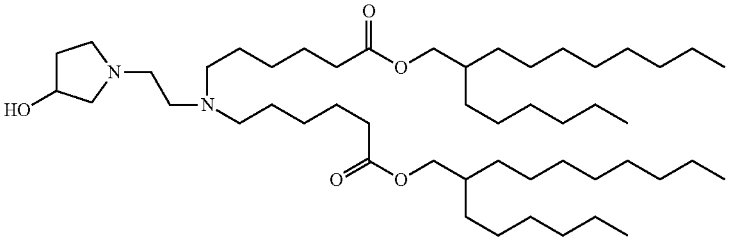 [SMILES: CCCCCCCCC(CCCCCC)COC(=O)CCCCCN(CCCCCC(=O)OCC(CCCCCC)CCCCCCCC)CCN1CCC(O)C1]
Compound 95
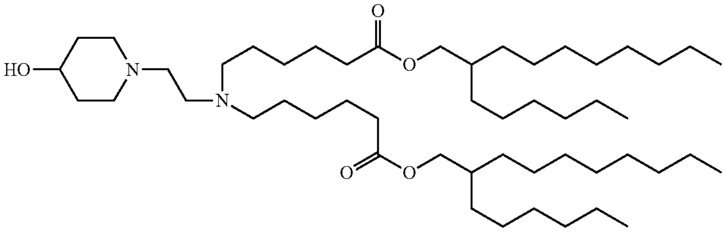 [SMILES: CCCCCCCCC(CCCCCC)COC(=O)CCCCCN(CCCCCC(=O)OCC(CCCCCC)CCCCCCCC)CCN1CCC(O)CC1]
Compound 96
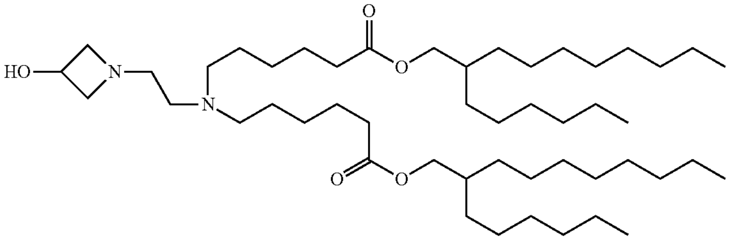 [SMILES: CCCCCCCCC(CCCCCC)COC(=O)CCCCCN(CCCCCC(=O)OCC(CCCCCC)CCCCCCCC)CCN1CC(O)C1]
Compound 97
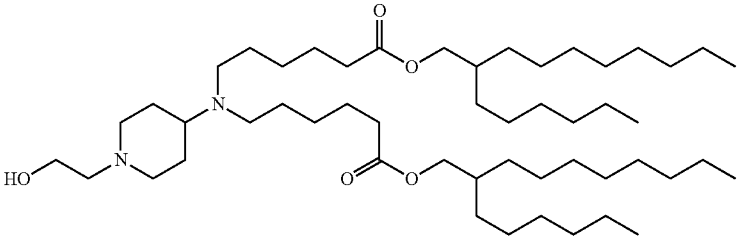 [SMILES: CCCCCCCCC(CCCCCC)COC(=O)CCCCCN(CCCCCC(=O)OCC(CCCCCC)CCCCCCCC)C1CCN(CCO)CC1]
Compound 98
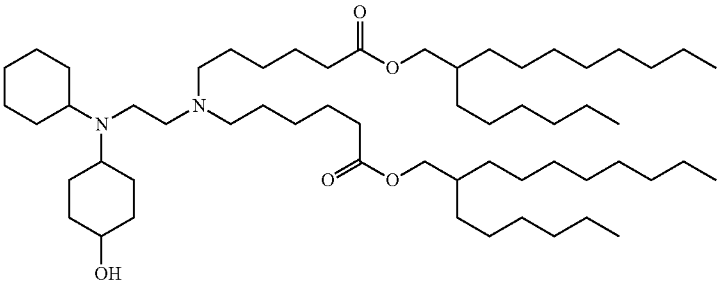 [SMILES: CCCCCCCCC(CCCCCC)COC(=O)CCCCCN(CCCCCC(=O)OCC(CCCCCC)CCCCCCCC)CCN(C1CCCCC1)C1CCC(O)CC1]
Compound 99

TABLE 1-continued
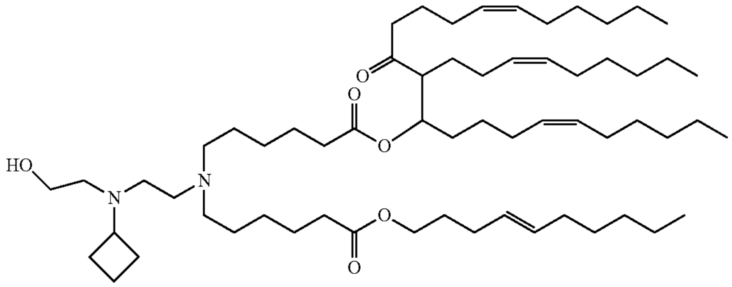 [SMILES: CCCCC/C=C\CCCC(=O)C(CC/C=C\CCCCC)C(CCC/C=C\CCCCC)OC(=O)CCCCCN(CCCCCC(=O)OCCC/C=C/CCCCC)CCN(CCO)C1CCC1]
Compound 101
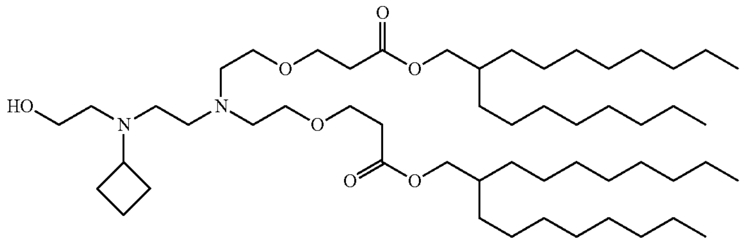 [SMILES: CCCCCCCCC(CCCCCCCC)COC(=O)CCOCCN(CCOCCC(=O)OCC(CCCCCCCC)CCCCCCCC)CCN(CCO)C1CCC1]
Compound 102
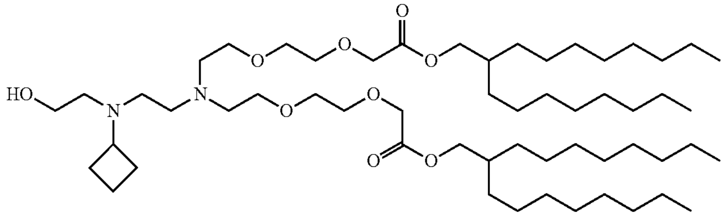 [SMILES: CCCCCCCCC(CCCCCCCC)COC(=O)COCCOCCN(CCOCCOCC(=O)OCC(CCCCCCCC)CCCCCCCC)CCN(CCO)C1CCC1]
Compound 103
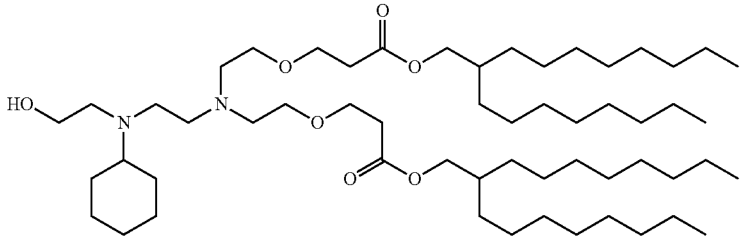 [SMILES: CCCCCCCCC(CCCCCCCC)COC(=O)CCOCCN(CCOCCC(=O)OCC(CCCCCCCC)CCCCCCCC)CCN(CCO)C1CCCCC1]
Compound 104
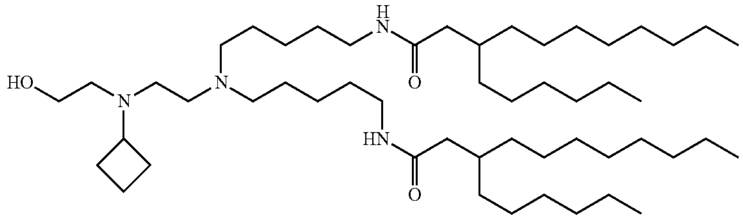 [SMILES: CCCCCCCCC(CCCCCC)CC(=O)NCCCCCN(CCCCCNC(=O)CC(CCCCCC)CCCCCCCC)CCN(CCO)C1CCC1]
Compound 105
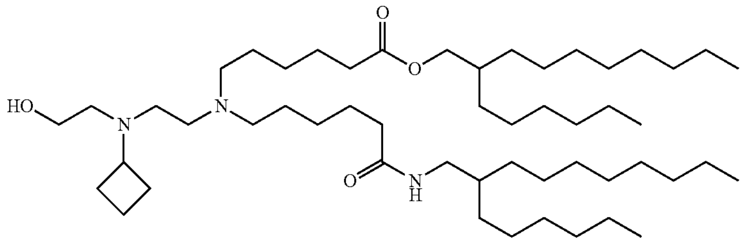 [SMILES: CCCCCCCCC(CCCCCC)CNC(=O)CCCCCN(CCCCCC(=O)OCC(CCCCCC)CCCCCCCC)CCN(CCO)C1CCC1]
Compound 106

TABLE 1-continued
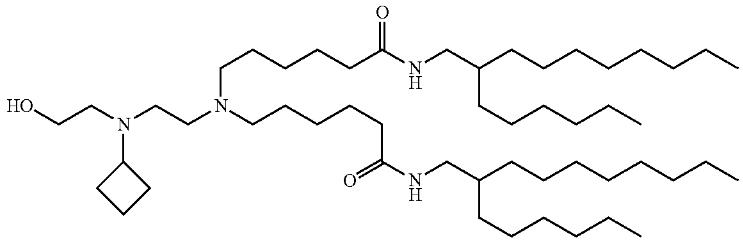 [SMILES: CCCCCCCCC(CCCCCC)CNC(=O)CCCCCN(CCCCCC(=O)NCC(CCCCCC)CCCCCCCC)CCN(CCO)C1CCC1]
Compound 107
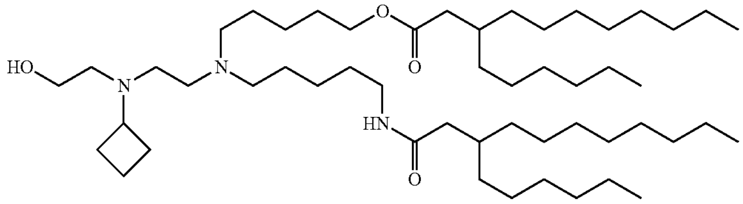 [SMILES: CCCCCCCCC(CCCCCC)CC(=O)NCCCCCN(CCCCCOC(=O)CC(CCCCCC)CCCCCCCC)CCN(CCO)C1CCC1]
Compound 108
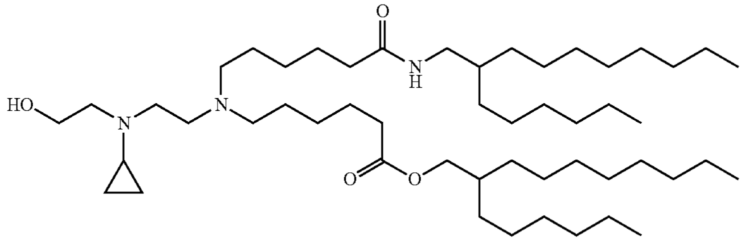
Compound 109
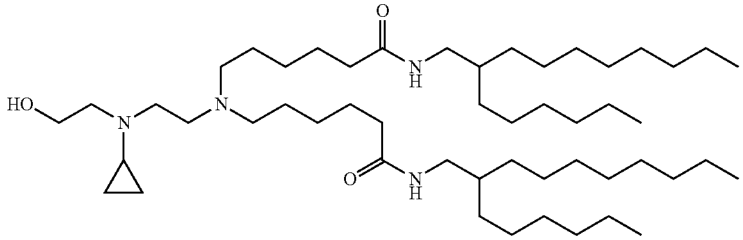 [SMILES: CCCCCCCCC(CCCCCC)CNC(=O)CCCCCN(CCCCCC(=O)NCC(CCCCCC)CCCCCCCC)CCN(CCO)C1CC1]
Compound 110
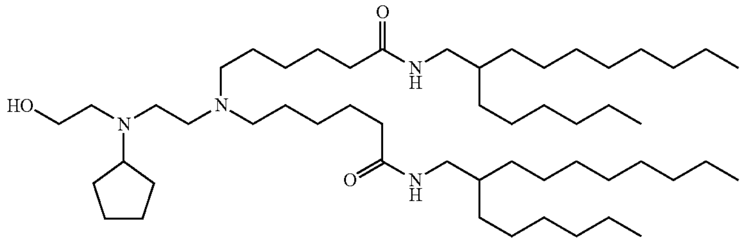 [SMILES: CCCCCCCCC(CCCCCC)CNC(=O)CCCCCN(CCCCCC(=O)NCC(CCCCCC)CCCCCCCC)CCN(CCO)C1CCCC1]
Compound 111
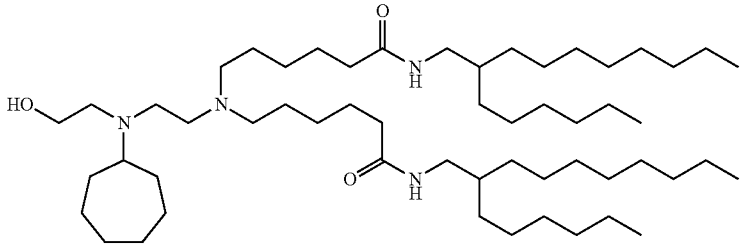 [SMILES: CCCCCCCCC(CCCCCC)CNC(=O)CCCCCN(CCCCCC(=O)NCC(CCCCCC)CCCCCCCC)CCN(CCO)C1CCCCCC1]
Compound 112

TABLE 1-continued
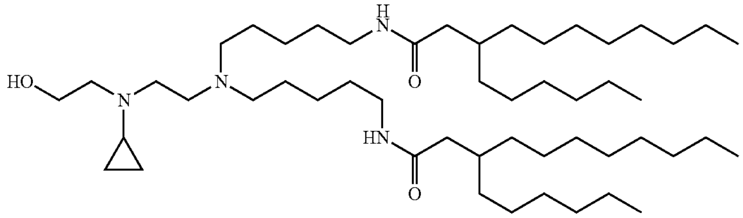 [SMILES: CCCCCCCCC(CCCCCC)CC(=O)NCCCCCN(CCCCCNC(=O)CC(CCCCCC)CCCCCCCC)CCN(CCO)C1CC1]
Compound 113
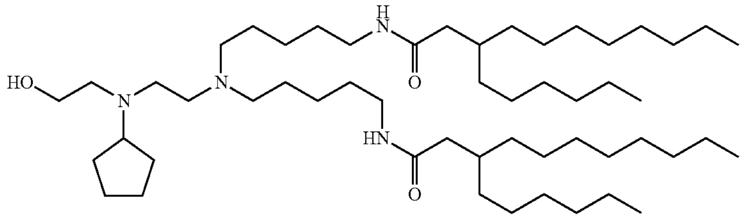 [SMILES: CCCCCCCCC(CCCCCC)CC(=O)NCCCCCN(CCCCCNC(=O)CC(CCCCCC)CCCCCCCC)CCN(CCO)C1CCCC1]
Compound 114
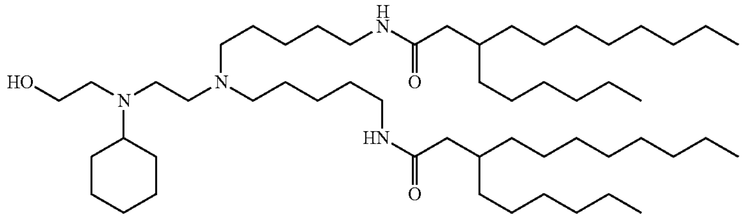 [SMILES: CCCCCCCCC(CCCCCC)CC(=O)NCCCCCN(CCCCCNC(=O)CC(CCCCCC)CCCCCCCC)CCN(CCO)C1CCCCC1]
Compound 115
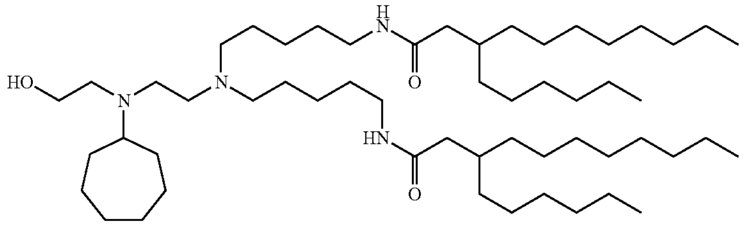
Compound 116
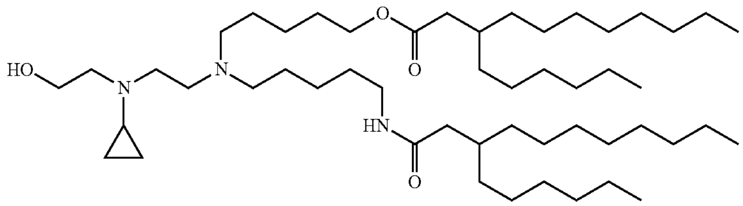 [SMILES: CCCCCCCCC(CCCCCC)CC(=O)NCCCCCN(CCCCCOC(=O)CC(CCCCCC)CCCCCCCC)CCN(CCO)C1CC1]
Compound 117
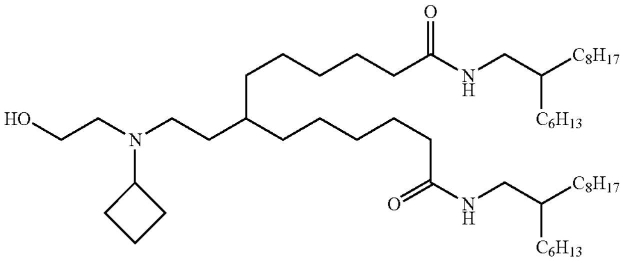
Compound 118

TABLE 1-continued
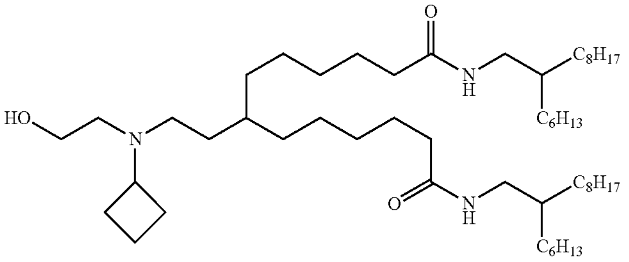
Compound 119
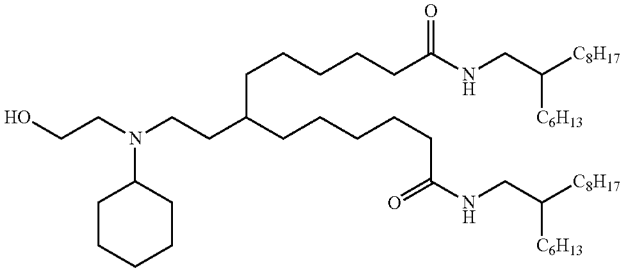
Compound 120
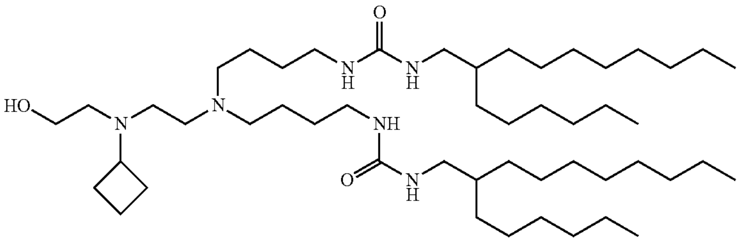 [SMILES: CCCCCCCCC(CCCCCC)CNC(=O)NCCCCN(CCCCNC(=O)NCC(CCCCCC)CCCCCCCC)CCN(CCO)C1CCC1]
Compound 121
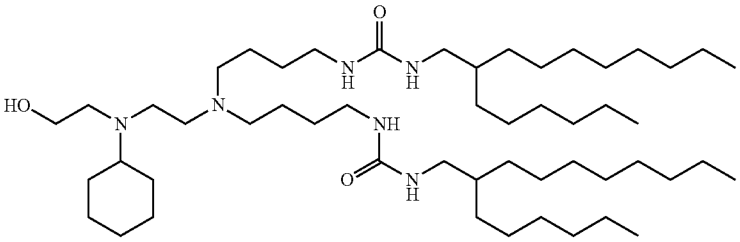 [SMILES: CCCCCCCCC(CCCCCC)CNC(=O)NCCCCN(CCCCNC(=O)NCC(CCCCCC)CCCCCCCC)CCN(CCO)C1CCCCC1]
Compound 122
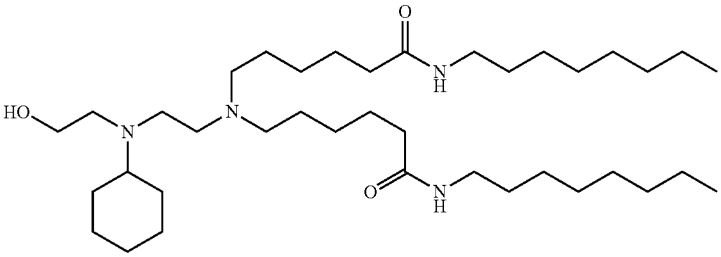 [SMILES: CCCCCCCCNC(=O)CCCCCN(CCCCCC(=O)NCCCCCCCC)CCN(CCO)C1CCCCC1]
Compound 123
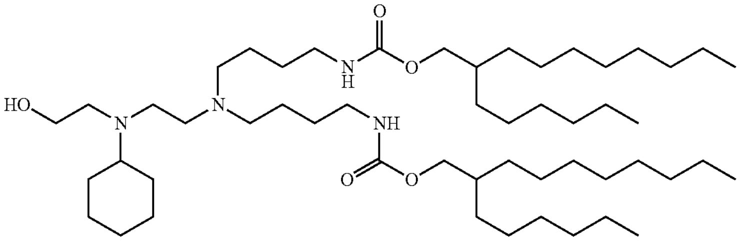 [SMILES: CCCCCCCCC(CCCCCC)COC(=O)NCCCCN(CCCCNC(=O)OCC(CCCCCC)CCCCCCCC)CCN(CCO)C1CCCCC1]
Compound 124

TABLE 1-continued
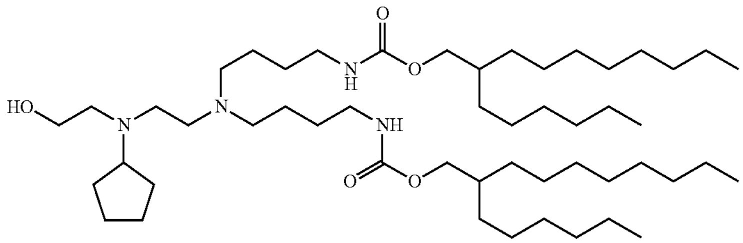 [SMILES: CCCCCCCCC(CCCCCC)COC(=O)NCCCCN(CCCCNC(=O)OCC(CCCCCC)CCCCCCCC)CCN(CCO)C1CCCC1]
Compound 125
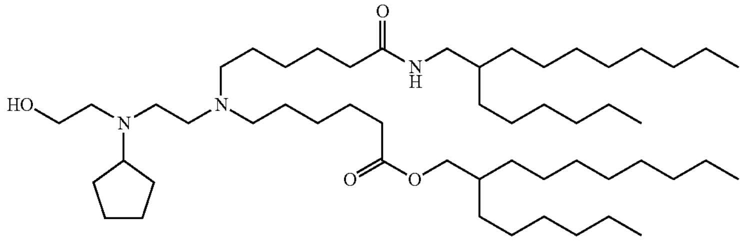 [SMILES: CCCCCCCCC(CCCCCC)CNC(=O)CCCCCN(CCCCCC(=O)OCC(CCCCCC)CCCCCCCC)CCN(CCO)C1CCCC1]
Compound 126
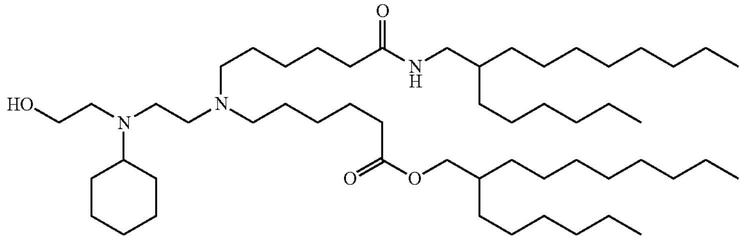 [SMILES: CCCCCCCCC(CCCCCC)CNC(=O)CCCCCN(CCCCCC(=O)OCC(CCCCCC)CCCCCCCC)CCN(CCO)C1CCCCC1]
Compound 127
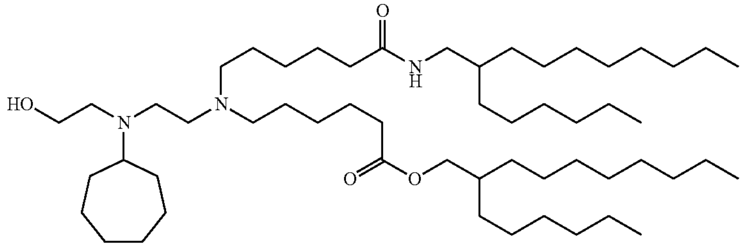 [SMILES: CCCCCCCCC(CCCCCC)CNC(=O)CCCCCN(CCCCCC(=O)OCC(CCCCCC)CCCCCCCC)CCN(CCO)C1CCCCCC1]
Compound 128
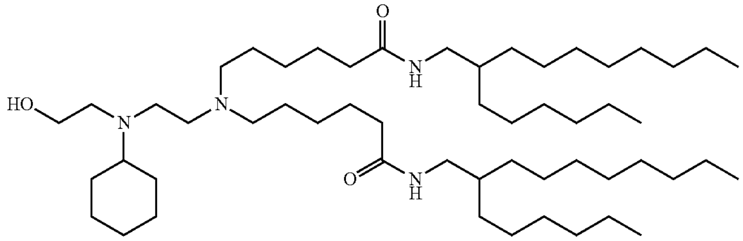 [SMILES: CCCCCCCCC(CCCCCC)CNC(=O)CCCCCN(CCCCCC(=O)NCC(CCCCCC)CCCCCCCC)CCN(CCO)C1CCCCC1]
Compound 129
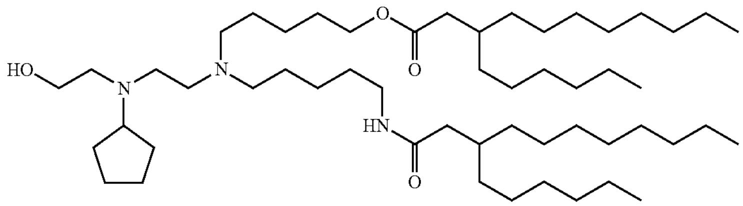 [SMILES: CCCCCCCCC(CCCCCC)CC(=O)NCCCCCN(CCCCCOC(=O)CC(CCCCCC)CCCCCCCC)CCN(CCO)C1CCCC1]
Compound 130

TABLE 1-continued
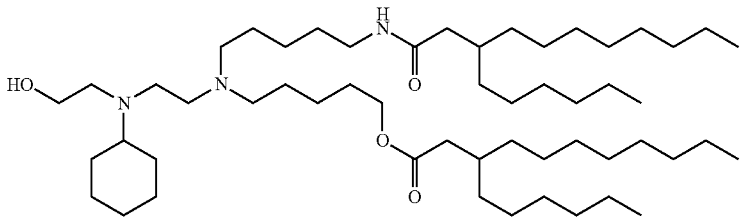 [SMILES: CCCCCCCCC(CCCCCC)CC(=O)NCCCCCN(CCCCCOC(=O)CC(CCCCCC)CCCCCCCC)CCN(CCO)C1CCCCC1]
Compound 131
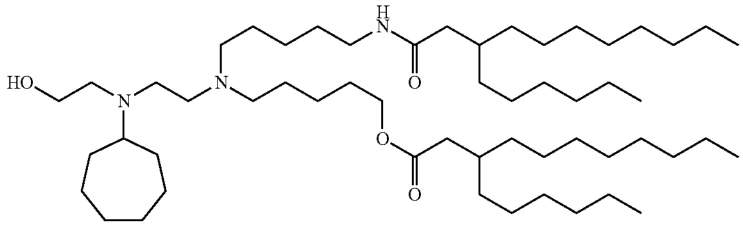 [SMILES: CCCCCCCCC(CCCCCC)CC(=O)NCCCCCN(CCCCCOC(=O)CC(CCCCCC)CCCCCCCC)CCN(CCO)C1CCCCCC1]
Compound 132
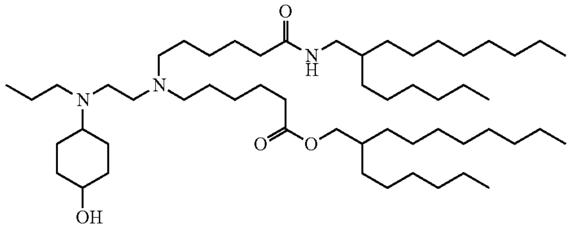 [SMILES: CCCCCCCCC(CCCCCC)CNC(=O)CCCCCN(CCCCCC(=O)OCC(CCCCCC)CCCCCCCC)CCN(CCC)C1CCC(O)CC1]
Compound 133
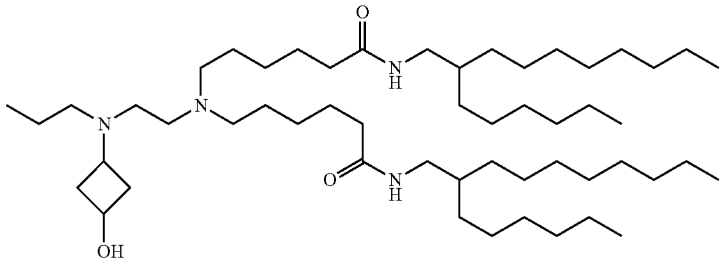 [SMILES: CCCCCCCCC(CCCCCC)CNC(=O)CCCCCN(CCCCCC(=O)NCC(CCCCCC)CCCCCCCC)CCN(CCC)C1CC(O)C1]
Compound 134
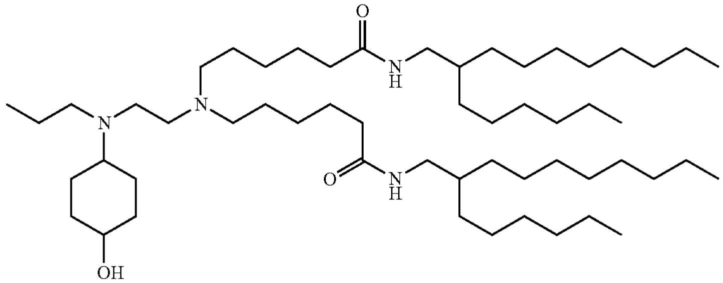 [SMILES: CCCCCCCCC(CCCCCC)CNC(=O)CCCCCN(CCCCCC(=O)NCC(CCCCCC)CCCCCCCC)CCN(CCC)C1CCC(O)CC1]
Compound 135
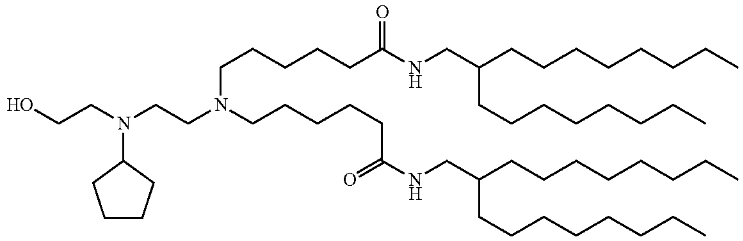 [SMILES: CCCCCCCCC(CCCCCCCC)CNC(=O)CCCCCN(CCCCCC(=O)NCC(CCCCCCCC)CCCCCCCC)CCN(CCO)C1CCCC1]
Compound 136

TABLE 1-continued
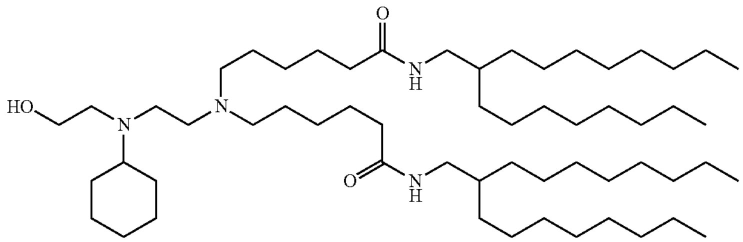 [SMILES: CCCCCCCCC(CCCCCCCC)CNC(=O)CCCCCN(CCCCCC(=O)NCC(CCCCCCCC)CCCCCCCC)CCN(CCO)C1CCCCC1]
Compound 137
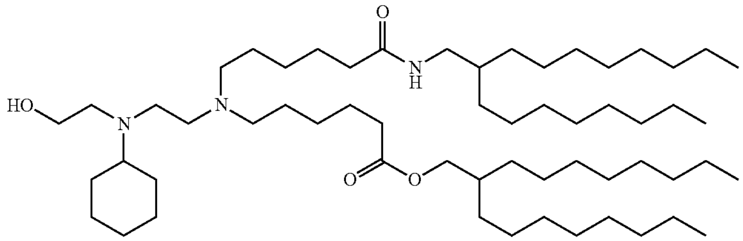 [SMILES: CCCCCCCCC(CCCCCCCC)CNC(=O)CCCCCN(CCCCCC(=O)OCC(CCCCCCCC)CCCCCCCC)CCN(CCO)C1CCCCC1]
Compound 138
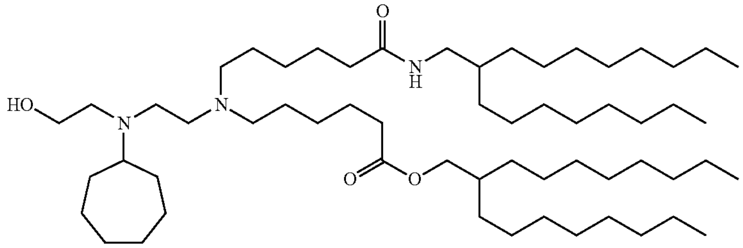 [SMILES: CCCCCCCCC(CCCCCCCC)CNC(=O)CCCCCN(CCCCCC(=O)OCC(CCCCCCCC)CCCCCCCC)CCN(CCO)C1CCCCCC1]
Compound 139
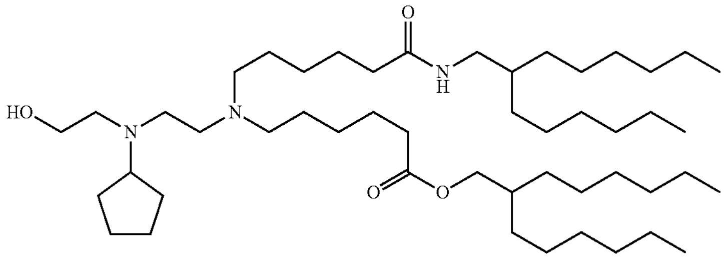 [SMILES: CCCCCCC(CCCCCC)CNC(=O)CCCCCN(CCCCCC(=O)OCC(CCCCCC)CCCCCC)CCN(CCO)C1CCCC1]
Compound 140
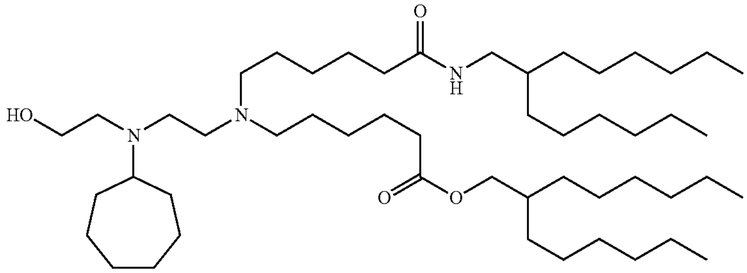 [SMILES: CCCCCCC(CCCCCC)CNC(=O)CCCCCN(CCCCCC(=O)OCC(CCCCCC)CCCCCC)CCN(CCO)C1CCCCCC1]
Compound 141
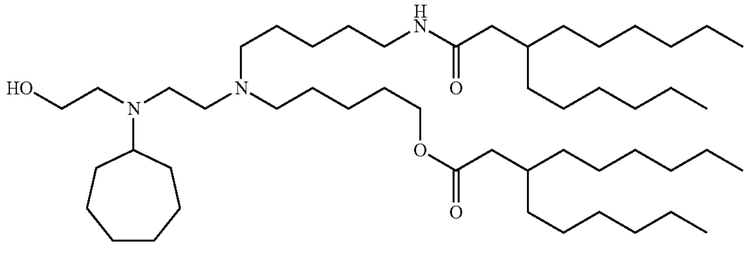 [SMILES: CCCCCCC(CCCCCC)CC(=O)NCCCCCN(CCCCCOC(=O)CC(CCCCCC)CCCCCC)CCN(CCO)C1CCCCCC1]
Compound 142

TABLE 1-continued
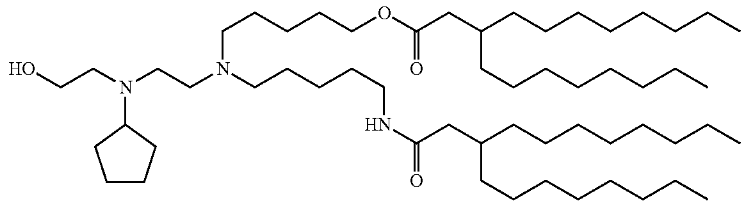 [SMILES: CCCCCCCCC(CCCCCCCC)CC(=O)NCCCCCN(CCCCCOC(=O)CC(CCCCCCCC)CCCCCCCC)CCN(CCO)C1CCCC1]
Compound 143
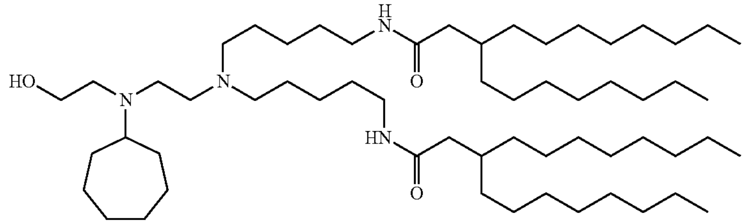 [SMILES: CCCCCCCCC(CCCCCCCC)CC(=O)NCCCCCN(CCCCCNC(=O)CC(CCCCCCCC)CCCCCCCC)CCN(CCO)C1CCCCCC1]
Compound 144
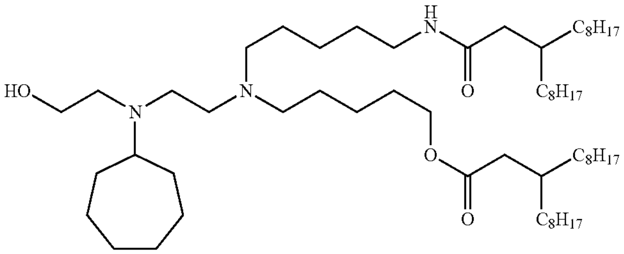
Compound 145
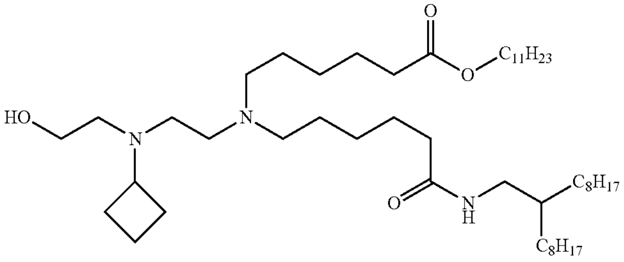
Compound 146
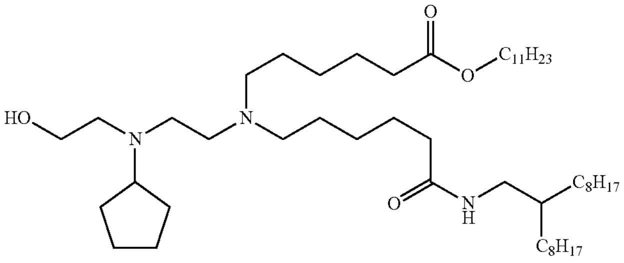
Compound 147
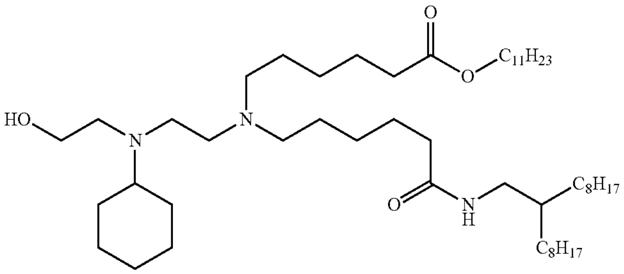
Compound 148

TABLE 1-continued
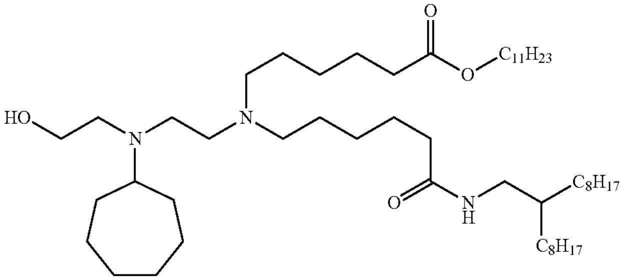
Compound 149
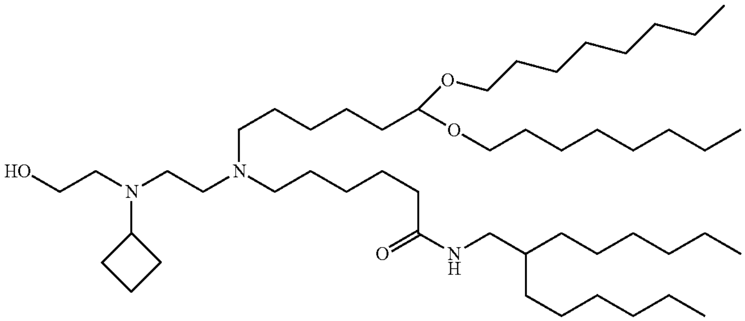 [SMILES: CCCCCCCCOC(CCCCCN(CCCCCC(=O)NCC(CCCCCC)CCCCCC)CCN(CCO)C1CCC1)OCCCCCCCC]
Compound 150
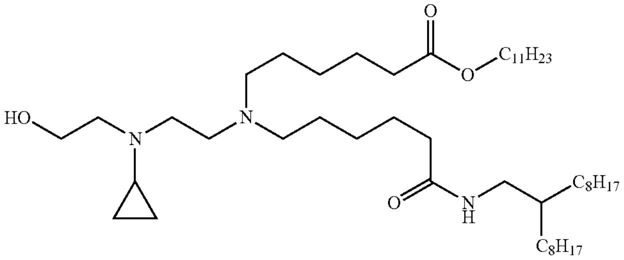
Compound 151
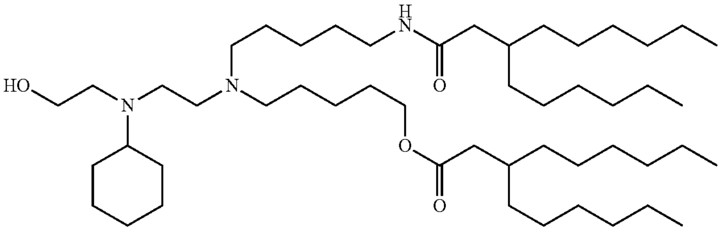 [SMILES: CCCCCCC(CCCCCC)CC(=O)NCCCCCN(CCCCCOC(=O)CC(CCCCCC)CCCCCC)CCN(CCO)C1CCCCC1]
Compound 152
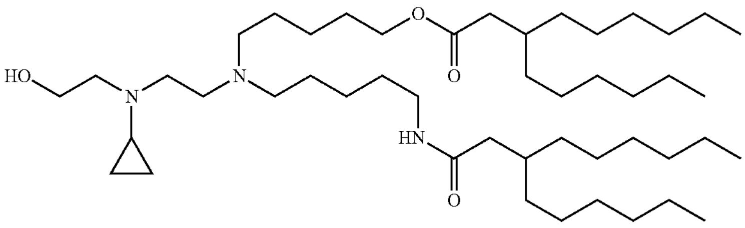 [SMILES: CCCCCCC(CCCCCC)CC(=O)NCCCCCN(CCCCCOC(=O)CC(CCCCCC)CCCCCC)CCN(CCO)C1CC1]
Compound 153
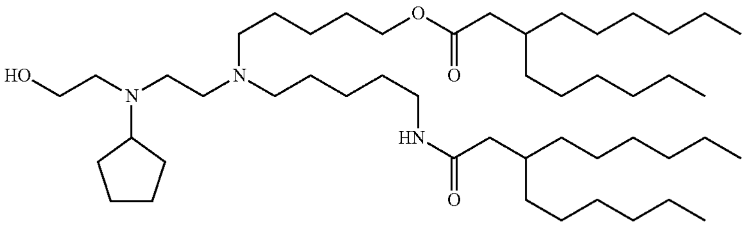 [SMILES: CCCCCCC(CCCCCC)CC(=O)NCCCCCN(CCCCCOC(=O)CC(CCCCCC)CCCCCC)CCN(CCO)C1CCCC1]
Compound 154

TABLE 1-continued

Compound 155

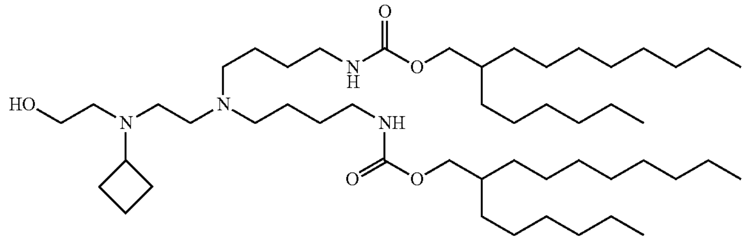 [SMILES: CCCCCCCCC(CCCCCC)COC(=O)NCCCCN(CCCCNC(=O)OCC(CCCCCC)CCCCCCCC)CCN(CCO)C1CCC1]

It is understood that any embodiment of the compounds provided herein, as set forth above, and any specific substituent and/or variable in the compound provided herein, as set forth above, may be independently combined with other embodiments and/or substituents and/or variables of the compounds to form embodiments not specifically set forth above. In addition, in the event that a list of substituents and/or variables is listed for any particular group or variable, it is understood that each individual substituent and/or variable may be deleted from the particular embodiment and/or claim and that the remaining list of substituents and/or variables will be considered to be within the scope of embodiments provided herein.

It is understood that in the present description, combinations of substituents and/or variables of the depicted formulae are permissible only if such contributions result in stable compounds.

6.4.2 Other Ionizable Lipids

As described herein, in some embodiments, a nanoparticle composition provided herein comprises one or more charged or ionizable lipids in addition to a lipid according Formulae (I) to (IV) (and sub-formulas thereof). Without being bound by the theory, it is contemplated that certain charged or zwitterionic lipid components of a nanoparticle composition resembles the lipid component in the cell membrane, thereby can improve cellular uptake of the nanoparticle. Exemplary charged or ionizable lipids that can form part of the present nanoparticle composition include but are not limited to 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLinDMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3 [(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)- -octadeca-9,12-dien-1-yloxy]propan-1-amine (Octyl-CLinDMA (2R)), (2S)-2-({8-[(3β)-cholest-5-en-3-yloxy]octyl}oxy)-N,N-dimethyl-3-[(9Z-,12Z)-octadeca-9,12-dien-1-yloxy]propan-1-amine (Octyl-CLinDMA (2S)), (12Z,15Z)—N,N-dimethyl-2-nonylhenicosa-12,15-den-1-amine, N,N-dimethyl-1-{(1S,2R)-2-octylcyclopropyl}heptadecan-8-amine. Additional exemplary charged or ionizable lipids that can form part of the present nanoparticle composition include the lipids (e.g., lipid 5) described in Sabnis et al. "A Novel Amino Lipid Series for mRNA Delivery: Improved Endosomal Escape and Sustained Pharmacology and Safety in Non-human Primates", Molecular Therapy Vol. 26 No 6, 2018, the entirety of which is incorporated herein by reference.

In some embodiments, suitable cationic lipids include N-[1-(2,3-dioleyloxy)propyl]-N,N,N-trimethylammonium chloride (DOTMA); N-[1-(2,3-dioleoyloxy)propyl]-N,N,N-trimethylammonium chloride (DOTAP); 1,2-dioleoyl-sn-glycero-3-ethylphosphocholine (DOEPC); 1,2-dilauroyl-sn-glycero-3-ethylphosphocholine (DLEPC); 1,2-dimyristoyl-sn-glycero-3-ethylphosphocholine (DMEPC); 1,2-dimyristoleoyl-sn-glycero-3-ethylphosphocholine (14:1); N1-[2-((1S)-1-[(3-aminopropyl)amino]-4-[di(3-amino-propyl)amino]butylcarboxamido)ethyl]-3,4-di[oleyloxy]-benzamide (MVL5); dioctadecylamido-glycylspermine (DOGS); 3b-[N—(N',N'-dimethylaminoethyl)carbamoyl]cholesterol (DC-Chol); dioctadecyldimethylammonium bromide (DDAB); SAINT-2, N-methyl-4-(dioleyl)methylpyridinium; 1,2-dimyristyloxypropyl-3-dimethylhydroxyethylammonium bromide (DMRIE); 1,2-dioleoyl-3-dimethyl-hydroxyethyl ammonium bromide (DORIE); 1,2-dioleoyloxypropyl-3-dimethylhydroxyethyl ammonium chloride (DORI); di-alkylated amino acid ($DILA^2$) (e.g., C18:1-norArg-C16); dioleyldimethylammonium chloride (DODAC); 1-palmitoyl-2-oleoyl-sn-glycero-3-ethylphosphocholine (POEPC); 1,2-dimyristoleoyl-sn-glycero-3-ethylphosphocholine (MOEPC); (R)-5-(dimethylamino)pentane-1,2-diyl dioleate hydrochloride (DODAPen-Cl); (R)-5-guanidinopentane-1,2-diyl dioleate hydrochloride (DOPen-G); and (R)—N,N,N-trimethyl-4,5-bis(oleoyloxy)pentan-1-aminium chloride (DOTAPen). Also suitable are cationic lipids with headgroups that are charged at physiological pH, such as primary amines (e.g., DODAG N',N'-dioctadecyl-N-4,8-diaza-10-aminodecanoylglycine amide) and guanidinium head groups (e.g., bis-guanidinium-spermidine-cholesterol (BGSC), bis-guanidiniumtren-cholesterol (BGTC), PONA, and (R)-5-guanidinopentane-1,2-diyl dioleate hydrochloride (DOPen-G)). Yet another suitable cationic lipid is (R)-5-(dimethylamino)pentane-1,2-diyl dioleate hydrochloride (DODAPen-Cl). In certain embodiments, the cationic lipid is a particular enantiomer or the racemic form, and includes the various salt forms of a cationic lipid as above (e.g., chloride or sulfate). For example, in some embodiments, the cationic lipid is N-[1-(2,3-dioleoyloxy)propyl]-N,N,N-trimethylammonium chloride (DOTAP-Cl) or N-[1-(2,3-dioleoyloxy)propyl]-N,N,N-trimethylammonium sulfate (DOTAP-Sulfate). In some embodiments, the cationic lipid is an ionizable cationic lipid such as, e.g., dioctadecyldimethylammonium bromide (DDAB); 1,2-dilinoleyloxy-3-dimethylaminopropane (DLinDMA); 2,2-dilinoleyl-4-(2dimethylaminoethyl)-[1,3]-dioxolane (DLin-KC2-DMA); heptatriaconta-6,9,28,31-tetraen-19-yl 4-(dimethylamino)butanoate (DLin-MC3-DMA); 1,2-dioleoyloxy-3-dimethylaminopropane (DODAP); 1,2-dioleyloxy-3-dimethylaminopropane (DODMA); and morpholinocholesterol (Mo-CHOL). In certain embodiments, a lipid nanoparticle includes a combination or two or more cationic lipids (e.g., two or more cationic lipids as above).

Additionally, in some embodiments, the charged or ionizable lipid that can form part of the present nanoparticle composition is a lipid including a cyclic amine group. Additional cationic lipids that are suitable for the formulations and methods disclosed herein include those described in WO2015199952, WO2016176330, and WO2015011633, the entire contents of each of which are hereby incorporated by reference in their entireties. Additionally, in some embodiments, the charged or ionizable lipid that can form part of the present nanoparticle composition is a lipid including a cyclic amine group. Additional cationic lipids that are suitable for the formulations and methods disclosed herein include those described in WO2015199952, WO2016176330, and WO2015011633, the entire contents of each of which are hereby incorporated by reference in their entireties.

6.4.3 Polymer Conjugated Lipids

In some embodiments, the lipid component of a nanoparticle composition can include one or more polymer conjugated lipids, such as PEGylated lipids (PEG lipids). Without being bound by the theory, it is contemplated that a polymer conjugated lipid component in a nanoparticle composition can improve of colloidal stability and/or reduce protein absorption of the nanoparticles. Exemplary cationic lipids that can be used in connection with the present disclosure include but are not limited to PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, PEG-DSPE, Ceramide-PEG2000, or Chol-PEG2000.

In one embodiment, the polymer conjugated lipid is a pegylated lipid. For example, some embodiments include a pegylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-O-(2',3'-di(tetradecanoyloxy)propyl-1-O-(ω-methoxy(polyethoxy)ethyl)butanedioate (PEG-S-DMG), a pegylated ceramide (PEG-cer), or a PEG dialkoxypropylcarbamate such as ω-methoxy(polyethoxy)ethyl-N-(2,3-di(tetradecanoxy)propyl)carbamate or 2,3-di(tetradecanoxy)propyl-N-(ω-methoxy(polyethoxy)ethyl)carbamate.

In one embodiment, the polymer conjugated lipid is present in a concentration ranging from 1.0 to 2.5 molar percent. In one embodiment, the polymer conjugated lipid is present in a concentration of about 1.7 molar percent. In one embodiment, the polymer conjugated lipid is present in a concentration of about 1.5 molar percent.

In one embodiment, the molar ratio of cationic lipid to the polymer conjugated lipid ranges from about 35:1 to about 25:1. In one embodiment, the molar ratio of cationic lipid to polymer conjugated lipid ranges from about 100:1 to about 20:1.

In one embodiment, the molar ratio of cationic lipid to the polymer conjugated lipid ranges from about 35:1 to about 25:1. In one embodiment, the molar ratio of cationic lipid to polymer conjugated lipid ranges from about 100:1 to about 20:1.

In one embodiment, the pegylated lipid has the following Formula:

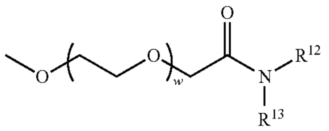

or a pharmaceutically acceptable salt, tautomer or stereoisomer thereof, wherein:

$R^{12}$ and $R^{13}$ are each independently a straight or branched, saturated or unsaturated alkyl chain containing from 10 to 30 carbon atoms, wherein the alkyl chain is optionally interrupted by one or more ester bonds; and w has a mean value ranging from 30 to 60.

In one embodiment, $R^{12}$ and $R^{13}$ are each independently straight, saturated alkyl chains containing from 12 to 16 carbon atoms. In other embodiments, the average w ranges from 42 to 55, for example, the average w is 42, 43, 44, 45, 46, 47, 48, 49, 50, 51, 52, 53, 54 or 55. In some specific embodiments, the average w is about 49.

In one embodiment, the pegylated lipid has the following Formula:

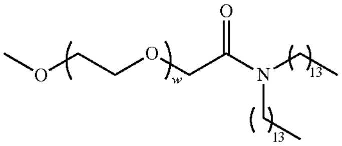

wherein the average w is about 49.

6.4.4 Structural Lipids

In some embodiments, the lipid component of a nanoparticle composition can include one or more structural lipids. Without being bound by the theory, it is contemplated that structural lipids can stabilize the amphiphilic structure of a nanoparticle, such as but not limited to the lipid bilayer structure of a nanoparticle. Exemplary structural lipids that can be used in connection with the present disclosure include but are not limited to cholesterol, fecosterol, sitosterol, ergosterol, campesterol, stigmasterol, brassicasterol, tomatidine, tomatine, ursolic acid, alpha-tocopherol, and mixtures thereof. In certain embodiments, the structural lipid is cholesterol. In some embodiments, the structural lipid includes cholesterol and a corticosteroid (such as prednisolone, dexamethasone, prednisone, and hydrocortisone), or a combination thereof.

In one embodiment, the lipid nanoparticles provided herein comprise a steroid or steroid analogue. In one embodiment, the steroid or steroid analogue is cholesterol. In one embodiment, the steroid is present in a concentration ranging from 39 to 49 molar percent, 40 to 46 molar percent, from 40 to 44 molar percent, from 40 to 42 molar percent, from 42 to 44 molar percent, or from 44 to 46 molar percent. In one embodiment, the steroid is present in a concentration of 40, 41, 42, 43, 44, 45, or 46 molar percent.

In one embodiment, the molar ratio of cationic lipid to the steroid ranges from 1.0:0.9 to 1.0:1.2, or from 1.0:1.0 to 1.0:1.2. In one embodiment, the molar ratio of cationic lipid to cholesterol ranges from about 5:1 to 1:1. In one embodiment, the steroid is present in a concentration ranging from 32 to 40 mol percent of the steroid.

In one embodiment, the molar ratio of cationic lipid to the steroid ranges from 1.0:0.9 to 1.0:1.2, or from 1.0:1.0 to 1.0:1.2. In one embodiment, the molar ratio of cationic lipid to cholesterol ranges from about 5:1 to 1:1. In one embodiment, the steroid is present in a concentration ranging from 32 to 40 mol percent of the steroid.

6.4.5 Phospholipids

In some embodiments, the lipid component of a nanoparticle composition can include one or more phospholipids, such as one or more (poly)unsaturated lipids. Without being bound by the theory, it is contemplated that phospholipids may assemble into one or more lipid bilayers structures. Exemplary phospholipids that can form part of the present nanoparticle composition include but are not limited to 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. In certain embodiments, a nanoparticle composition includes DSPC. In certain embodiments, a nanoparticle composition includes DOPE. In some embodiments, a nanoparticle composition includes both DSPC and DOPE.

Additional exemplary neutral lipids include, for example, dipalmitoylphosphatidylglycerol (DPPG), palmitoyloleoyl-phosphatidylethanolamine (POPE) and dioleoyl-phosphatidylethanolamine 4-(N-maleimidomethyl)-cyclohexane-1carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoylphosphatidyethanol amine (SOPE), and 1,2-dielaidoyl-sn-glycero-3-phophoethanolamine (transDOPE). In one embodiment, the neutral lipid is 1,2-distearoyl-sn-glycero-3phosphocholine (DSPC). In one embodiment, the neutral lipid is selected from DSPC, DPPC, DMPC, DOPC, POPC, DOPE and SM.

In one embodiment, the neutral lipid is phosphatidylcholine (PC), phosphatidylethanolamine (PE) phosphatidylserine (PS), phosphatidic acid (PA), or phosphatidylglycerol (PG).

Additionally phospholipids that can form part of the present nanoparticle composition also include those described in WO2017/112865, the entire content of which is hereby incorporated by reference in its entirety.

6.4.6 Formulation

According to the present disclosure, nanoparticle compositions described herein can include at least one lipid component and one or more additional components, such as a therapeutic and/or prophylactic agent (e.g., the therapeutic nucleic acid described herein). A nanoparticle composition may be designed for one or more specific applications or targets. The elements of a nanoparticle composition may be selected based on a particular application or target, and/or based on the efficacy, toxicity, expense, ease of use, availability, or other feature of one or more elements. Similarly, the particular formulation of a nanoparticle composition may be selected for a particular application or target according to, for example, the efficacy and toxicity of particular combinations of elements.

The lipid component of a nanoparticle composition may include, for example, a lipid according to one of formulae (I) to (IV) (and sub-formulas thereof) described herein, a phospholipid (such as an unsaturated lipid, e.g., DOPE or DSPC), a PEG lipid, and a structural lipid. The elements of the lipid component may be provided in specific fractions.

In one embodiment, provided herein is a nanoparticle compositions comprising a cationic or ionizable lipid compound provided herein, a therapeutic agent, and one or more excipients. In one embodiment, cationic or ionizable lipid compound comprises a compound according to one of Formulae (I) to (IV) (and sub-formulas thereof) as described herein, and optionally one or more additional ionizable lipid compounds. In one embodiment, the one or more excipients are selected from neutral lipids, steroids, and polymer conjugated lipids. In one embodiment, the therapeutic agent is encapsulated within or associated with the lipid nanoparticle.

In one embodiment, provided herein is a nanoparticle composition (lipid nanoparticle) comprising:

i) between 40 and 50 mol percent of a cationic lipid;
ii) a neutral lipid;
iii) a steroid;
iv) a polymer conjugated lipid; and
v) a therapeutic agent.

As used herein, "mol percent" refers to a component's molar percentage relative to total mols of all lipid components in the LNP (i.e., total mols of cationic lipid(s), the neutral lipid, the steroid and the polymer conjugated lipid).

In one embodiment, the lipid nanoparticle comprises from 41 to 49 mol percent, from 41 to 48 mol percent, from 42 to 48 mol percent, from 43 to 48 mol percent, from 44 to 48 mol percent, from 45 to 48 mol percent, from 46 to 48 mol percent, or from 47.2 to 47.8 mol percent of the cationic lipid. In one embodiment, the lipid nanoparticle comprises about 47.0, 47.1, 47.2, 47.3, 47.4, 47.5, 47.6, 47.7, 47.8, 47.9 or 48.0 mol percent of the cationic lipid.

In one embodiment, the neutral lipid is present in a concentration ranging from 5 to 15 mol percent, 7 to 13 mol percent, or 9 to 11 mol percent. In one embodiment, the neutral lipid is present in a concentration of about 9.5, 10 or 10.5 mol percent. In one embodiment, the molar ratio of the cationic lipid to the neutral lipid ranges from about 4.1:1.0 to about 4.9:1.0, from about 4.5:1.0 to about 4.8:1.0, or from about 4.7:1.0 to 4.8:1.0.

In one embodiment, the steroid is present in a concentration ranging from 39 to 49 molar percent, 40 to 46 molar percent, from 40 to 44 molar percent, from 40 to 42 molar percent, from 42 to 44 molar percent, or from 44 to 46 molar percent. In one embodiment, the steroid is present in a concentration of 40, 41, 42, 43, 44, 45, or 46 molar percent. In one embodiment, the molar ratio of cationic lipid to the steroid ranges from 1.0:0.9 to 1.0:1.2, or from 1.0:1.0 to 1.0:1.2. In one embodiment, the steroid is cholesterol.

In one embodiment, the therapeutic agent to lipid ratio in the LNP (i.e., N/P, were N represents the moles of cationic lipid and P represents the moles of phosphate present as part of the nucleic acid backbone) range from 2:1 to 30:1, for example 3:1 to 22:1. In one embodiment, N/P ranges from 6:1 to 20:1 or 2:1 to 12:1. Exemplary N/P ranges include about 3:1. About 6:1, about 12:1 and about 22:1.

In one embodiment, provided herein is a lipid nanoparticle comprising:

i) a cationic lipid having an effective pKa greater than 6.0;

ii) from 5 to 15 mol percent of a neutral lipid;

iii) from 1 to 15 mol percent of an anionic lipid;

iv) from 30 to 45 mol percent of a steroid;

v) a polymer conjugated lipid; and vi) a therapeutic agent, or a pharmaceutically acceptable salt or prodrug thereof, wherein the mol percent is determined based on total mol of lipid present in the lipid nanoparticle.

In one embodiment, the cationic lipid can be any of a number of lipid species which carry a net positive charge at a selected pH, such as physiological pH. Exemplary cationic lipids are described herein below. In one embodiment, the cationic lipid has a pKa greater than 6.25. In one embodiment, the cationic lipid has a pKa greater than 6.5. In one embodiment, the cationic lipid has a pKa greater than 6.1, greater than 6.2, greater than 6.3, greater than 6.35, greater than 6.4, greater than 6.45, greater than 6.55, greater than 6.6, greater than 6.65, or greater than 6.7.

In one embodiment, the lipid nanoparticle comprises from 40 to 45 mol percent of the cationic lipid. In one embodiment, the lipid nanoparticle comprises from 45 to 50 mole percent of the cationic lipid.

In one embodiment, the molar ratio of the cationic lipid to the neutral lipid ranges from about 2:1 to about 8:1. In one embodiment, the lipid nanoparticle comprises from 5 to 10 mol percent of the neutral lipid.

Exemplary anionic lipids include, but are not limited to, phosphatidylglycerol, dioleoylphosphatidylglycerol (DOPG), dipalmitoylphosphatidylglycerol (DPPG) or 1,2-distearoyl-sn-glycero-3-phospho-(1'-rac-glycerol) (DSPG).

In one embodiment, the lipid nanoparticle comprises from 1 to 10 mole percent of the anionic lipid. In one embodiment, the lipid nanoparticle comprises from 1 to 5 mole percent of the anionic lipid. In one embodiment, the lipid nanoparticle comprises from 1 to 9 mole percent, from 1 to 8 mole percent, from 1 to 7 mole percent, or from 1 to 6 mole percent of the anionic lipid. In one embodiment, the mol ratio of anionic lipid to neutral lipid ranges from 1:1 to 1:10.

In one embodiment, the steroid cholesterol. In one embodiment, the molar ratio of the cationic lipid to cholesterol ranges from about 5:1 to 1:1. In one embodiment, the lipid nanoparticle comprises from 32 to 40 mol percent of the steroid.

In one embodiment, the sum of the mol percent of neutral lipid and mol percent of anionic lipid ranges from 5 to 15 mol percent. In one embodiment, wherein the sum of the mol percent of neutral lipid and mol percent of anionic lipid ranges from 7 to 12 mol percent.

In one embodiment, the mol ratio of anionic lipid to neutral lipid ranges from 1:1 to 1:10. In one embodiment, the sum of the mol percent of neutral lipid and mol percent steroid ranges from 35 to 45 mol percent.

In one embodiment, the lipid nanoparticle comprises:

i) from 45 to 55 mol percent of the cationic lipid;

ii) from 5 to 10 mol percent of the neutral lipid;

iii) from 1 to 5 mol percent of the anionic lipid; and iv) from 32 to 40 mol percent of the steroid.

In one embodiment, the lipid nanoparticle comprises from 1.0 to 2.5 mol percent of the conjugated lipid. In one embodiment, the polymer conjugated lipid is present in a concentration of about 1.5 mol percent.

In one embodiment, the neutral lipid is present in a concentration ranging from 5 to 15 mol percent, 7 to 13 mol percent, or 9 to 11 mol percent. In one embodiment, the neutral lipid is present in a concentration of about 9.5, 10 or 10.5 mol percent. In one embodiment, the molar ratio of the cationic lipid to the neutral lipid ranges from about 4.1:1.0 to about 4.9:1.0, from about 4.5:1.0 to about 4.8:1.0, or from about 4.7:1.0 to 4.8:1.0.

In one embodiment, the steroid is cholesterol. In some embodiments, the steroid is present in a concentration ranging from 39 to 49 molar percent, 40 to 46 molar percent, from 40 to 44 molar percent, from 40 to 42 molar percent, from 42 to 44 molar percent, or from 44 to 46 molar percent. In one embodiment, the steroid is present in a concentration of 40, 41, 42, 43, 44, 45, or 46 molar percent. In certain embodiments, the molar ratio of cationic lipid to the steroid ranges from 1.0:0.9 to 1.0:1.2, or from 1.0:1.0 to 1.0:1.2.

In one embodiment, the molar ratio of cationic lipid to steroid ranges from 5:1 to 1:1.

In one embodiment, the lipid nanoparticle comprises from 1.0 to 2.5 mol percent of the conjugated lipid. In one embodiment, the polymer conjugated lipid is present in a concentration of about 1.5 mol percent.

In one embodiment, the molar ratio of cationic lipid to polymer conjugated lipid ranges from about 100:1 to about 20:1. In one embodiment, the molar ratio of cationic lipid to the polymer conjugated lipid ranges from about 35:1 to about 25:1.

In one embodiment, the molar ratio of cationic lipid to polymer conjugated lipid ranges from about 100:1 to about 20:1. In one embodiment, the molar ratio of cationic lipid to the polymer conjugated lipid ranges from about 35:1 to about 25:1.

In one embodiment, the lipid nanoparticle has a mean diameter ranging from 50 nm to 100 nm, or from 60 nm to 85 nm.

In one embodiment, the composition comprises a cationic lipid provided herein, DSPC, cholesterol, and PEG-lipid, and mRNA. In one embodiment, the a cationic lipid provided herein, DSPC, cholesterol, and PEG-lipid are at a molar ratio of about 50:10:38.5:1.5.

Nanoparticle compositions can be designed for one or more specific applications or targets. For example, a nanoparticle composition can be designed to deliver a therapeutic and/or prophylactic agent such as an RNA to a particular cell, tissue, organ, or system or group thereof in a mammal's body. Physiochemical properties of nanoparticle compositions can be altered in order to increase selectivity for particular bodily targets. For instance, particle sizes can be adjusted based on the fenestration sizes of different organs. The therapeutic and/or prophylactic agent included in a nanoparticle composition can also be selected based on the desired delivery target or targets. For example, a therapeutic and/or prophylactic agent can be selected for a particular indication, condition, disease, or disorder and/or for delivery to a particular cell, tissue, organ, or system or group thereof (e.g., localized or specific delivery). In certain embodiments, a nanoparticle composition can include an mRNA encoding a polypeptide of interest capable of being translated within a cell to produce the polypeptide of interest. Such a composition can be designed to be specifically delivered to a particular organ. In certain embodiments, a composition can be designed to be specifically delivered to a mammalian liver.

The amount of a therapeutic and/or prophylactic agent in a nanoparticle composition can depend on the size, composition, desired target and/or application, or other properties of the nanoparticle composition as well as on the properties of the therapeutic and/or prophylactic agent. For example, the amount of an RNA useful in a nanoparticle composition can depend on the size, sequence, and other characteristics of the RNA. The relative amounts of a therapeutic and/or prophylactic agent and other elements (e.g., lipids) in a nanoparticle composition can also vary. In some embodiments, the wt/wt ratio of the lipid component to a therapeutic and/or prophylactic agent in a nanoparticle composition can be from about 5:1 to about 60:1, such as about 5:1, 6:1, 7:1, 8:1, 9:1, 10:1, 11:1, 12:1, 13:1, 14:1, 15:1, 16:1, 17:1, 18:1, 19:1, 20:1, 22:1, 25:1, 30:1, 35:1, 40:1, 45:1, 50:1, and 60:1. For example, the wt/wt ratio of the lipid component to a therapeutic and/or prophylactic agent can be from about 10:1 to about 40:1. In certain embodiments, the wt/wt ratio is about 20:1. The amount of a therapeutic and/or prophylactic agent in a nanoparticle composition can, for example, be measured using absorption spectroscopy (e.g., ultraviolet-visible spectroscopy).

In some embodiments, a nanoparticle composition includes one or more RNAs, and the one or more RNAs, lipids, and amounts thereof can be selected to provide a specific N:P ratio. The N:P ratio of the composition refers to the molar ratio of nitrogen atoms in one or more lipids to the number of phosphate groups in an RNA. In some embodiments, a lower N:P ratio is selected. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1. For example, the N:P ratio may be about 5.0:1, about 5.5:1, about 5.67:1, about 6.0:1, about 6.5:1, or about 7.0:1. For example, the N:P ratio may be about 5.67:1.

The physical properties of a nanoparticle composition can depend on the components thereof. For example, a nanoparticle composition including cholesterol as a structural lipid can have different characteristics compared to a nanoparticle composition that includes a different structural lipid. Similarly, the characteristics of a nanoparticle composition can depend on the absolute or relative amounts of its components. For instance, a nanoparticle composition including a higher molar fraction of a phospholipid may have different characteristics than a nanoparticle composition including a lower molar fraction of a phospholipid. Characteristics may also vary depending on the method and conditions of preparation of the nanoparticle composition.

Nanoparticle compositions may be characterized by a variety of methods. For example, microscopy (e.g., transmission electron microscopy or scanning electron microscopy) may be used to examine the morphology and size distribution of a nanoparticle composition. Dynamic light scattering or potentiometry (e.g., potentiometric titrations) may be used to measure zeta potentials. Dynamic light scattering may also be utilized to determine particle sizes. Instruments such as the Zetasizer Nano ZS (Malvem Instruments Ltd, Malvem, Worcestershire, UK) may also be used to measure multiple characteristics of a nanoparticle composition, such as particle size, polydispersity index, and zeta potential.

In various embodiments, the mean size of a nanoparticle composition can be between 10s of nm and 100s of nm. For example, the mean size can be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the mean size of a nanoparticle composition can be from about 50 nm to about 100 nm, from about 50 nm to about 90 nm, from about 50 nm to about 80 nm, from about 50 nm to about 70 nm, from about 50 nm to about 60 nm, from about 60 nm to about 100 nm, from about 60 nm to about 90 nm, from about 60 nm to about 80 nm, from about 60 nm to about 70 nm, from about 70 nm to about 100 nm, from about 70 nm to about 90 nm, from about 70 nm to about 80 nm, from about 80 nm to about 100 nm, from about 80 nm to about 90 nm, or from about 90 nm to about 100 nm. In certain embodiments, the mean size of a nanoparticle composition can be from about 70 nm to about 100 nm. In some embodiments, the mean size can be about 80 nm. In other embodiments, the mean size can be about 100 nm.

A nanoparticle composition can be relatively homogenous. A polydispersity index can be used to indicate the homogeneity of a nanoparticle composition, e.g., the particle size distribution of the nanoparticle compositions. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition can be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

The efficiency of encapsulation of a therapeutic and/or prophylactic agent describes the amount of therapeutic and/or prophylactic agent that is encapsulated or otherwise associated with a nanoparticle composition after preparation, relative to the initial amount provided. The encapsulation efficiency is desirably high (e.g., close to 100%). The encapsulation efficiency can be measured, for example, by comparing the amount of therapeutic and/or prophylactic agent in a solution containing the nanoparticle composition before and after breaking up the nanoparticle composition with one or more organic solvents or detergents. Fluorescence can be used to measure the amount of free therapeutic and/or prophylactic agent (e.g., RNA) in a solution. For the nanoparticle compositions described herein, the encapsulation efficiency of a therapeutic and/or prophylactic agent can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

A nanoparticle composition can optionally comprise one or more coatings. For example, a nanoparticle composition can be formulated in a capsule, film, or tablet having a coating. A capsule, film, or tablet including a composition described herein can have any useful size, tensile strength, hardness, or density.

6.4.7 Pharmaceutical Compositions

According to the present disclosure, nanoparticle compositions can be formulated in whole or in part as pharmaceutical compositions. Pharmaceutical compositions can include one or more nanoparticle compositions. For example, a pharmaceutical composition can include one or more nanoparticle compositions including one or more different therapeutic and/or prophylactic agents. Pharmaceutical compositions can further include one or more pharmaceutically acceptable excipients or accessory ingredients such as those described herein. General guidelines for the formulation and manufacture of pharmaceutical compositions and agents are available, for example, in Remington's The Science and Practice of Pharmacy, 21$^{st}$ Edition, A. R. Gennaro; Lippincott, Williams & Wilkins, Baltimore, Md., 2006. Conventional excipients and accessory ingredients can be used in any pharmaceutical composition, except insofar as any conventional excipient or accessory ingredient can be incompatible with one or more components of a nanoparticle composition. An excipient or accessory ingredient can be incompatible with a component of a nanoparticle composition if its combination with the component can result in any undesirable biological effect or otherwise deleterious effect.

In some embodiments, one or more excipients or accessory ingredients can make up greater than 50% of the total mass or volume of a pharmaceutical composition including a nanoparticle composition. For example, the one or more excipients or accessory ingredients can make up 50%, 60%, 70%, 80%, 90%, or more of a pharmaceutical convention. In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Relative amounts of the one or more nanoparticle compositions, the one or more pharmaceutically acceptable excipients, and/or any additional ingredients in a pharmaceutical composition in accordance with the present disclosure will vary, depending upon the identity, size, and/or condition of the subject treated and further depending upon the route by which the composition is to be administered. By way of example, a pharmaceutical composition can comprise between 0.1% and 100% (wt/wt) of one or more nanoparticle compositions.

In certain embodiments, the nanoparticle compositions and/or pharmaceutical compositions of the disclosure are refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition comprising a compound of any of Formulae (I) to (IV) (and sub-formulas thereof) is a solution that is refrigerated for storage and/or shipment at, for example, about −20° C., −30° C., −40° C., −50° C., −60° C., −70° C., or −80° C. In certain embodiments, the disclosure also relates to a method of increasing stability of the nanoparticle compositions and/or pharmaceutical compositions comprising a compound of any of Formulae (I) to (IV) (and sub-formulas thereof) by storing the nanoparticle compositions and/or pharmaceutical compositions at a temperature of 4° C. or lower, such as a temperature between about −150° C. and about 0° C. or between about −80° C. and about −20° C., e.g., about −5° C., −10° C., −15° C., −20° C., −25° C., −30° C., −40° C., −50° C., −60° C., −70° C., −80° C., −90° C., −130° C. or −150° C.). For example, the nanoparticle compositions and/or pharmaceutical compositions disclosed herein are stable for about at least 1 week, at least 2 weeks, at least 3 weeks, at least 4 weeks, at least 5 weeks, at least 6 weeks, at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months, e.g., at a temperature of 4° C. or lower (e.g., between about 4° C. and −20° C.). In one embodiment, the formulation is stabilized for at least 4 weeks at about 4° C. In certain embodiments, the pharmaceutical composition of the disclosure comprises a nanoparticle composition disclosed herein and a pharmaceutically acceptable carrier selected from one or more of Tris, an acetate (e.g., sodium acetate), an citrate (e.g., sodium citrate), saline, PBS, and sucrose. In certain embodiments, the pharmaceutical composition of the disclosure has a pH value between about 7 and 8 (e.g., 6.8, 6.9, 7.0, 7.1, 7.2, 7.3, 7.4, 7.5, 7.6, 7.7, 7.8, 7.9 or 8.0, or between 7.5 and 8 or between 7 and 7.8). For example, a pharmaceutical composition of the disclosure comprises a nanoparticle composition disclosed herein, Tris, saline and sucrose, and has a pH of about 7.5-8, which is suitable for storage and/or shipment at, for example, about −20° C. For example, a pharmaceutical composition of the disclosure comprises a nanoparticle composition disclosed herein and PBS and has a pH of about 7-7.8, suitable for storage and/or shipment at, for example, about 4° C. or lower. "Stability," "stabilized," and "stable" in the context of the present disclosure refers to the resistance of nanoparticle compositions and/or pharmaceutical compositions disclosed herein to chemical or physical changes (e.g., degradation, particle size change, aggregation, change in encapsulation, etc.) under given manufacturing, preparation, transportation, storage and/or in-use conditions, e.g., when stress is applied such as shear force, freeze/thaw stress, etc.

Nanoparticle compositions and/or pharmaceutical compositions including one or more nanoparticle compositions can be administered to any patient or subject, including those patients or subjects that can benefit from a therapeutic effect provided by the delivery of a therapeutic and/or prophylactic agent to one or more particular cells, tissues, organs, or systems or groups thereof, such as the renal system. Although the descriptions provided herein of nanoparticle compositions and pharmaceutical compositions including nanoparticle compositions are principally directed to compositions which are suitable for administration to humans, it will be understood by the skilled artisan that such compositions are generally suitable for administration to any other mammal. Modification of compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the compositions is contemplated include, but are not limited to, humans, other primates, and other mammals, including commercially relevant mammals such as cattle, pigs, hoses, sheep, cats, dogs, mice, and/or rats.

A pharmaceutical composition including one or more nanoparticle compositions can be prepared by any method known or hereafter developed in the art of pharmacology. In general, such preparatory methods include bringing the active ingredient into association with an excipient and/or one or more other accessory ingredients, and then, if desirable or necessary, dividing, shaping, and/or packaging the product into a desired single- or multi-dose unit.

A pharmaceutical composition in accordance with the present disclosure can be prepared, packaged, and/or sold in bulk, as a single unit dose, and/or as a plurality of single unit doses. As used herein, a "unit dose" is discrete amount of the pharmaceutical composition comprising a predetermined amount of the active ingredient (e.g., nanoparticle composition). The amount of the active ingredient is generally equal to the dosage of the active ingredient which would be administered to a subject and/or a convenient fraction of such a dosage such as, for example, one-half or one-third of such a dosage.

Pharmaceutical compositions can be prepared in a variety of forms suitable for a variety of routes and methods of administration. For example, pharmaceutical compositions can be prepared in liquid dosage forms (e.g., emulsions, microemulsions, nanoemulsions, solutions, suspensions, syrups, and elixirs), injectable forms, solid dosage forms (e.g., capsules, tablets, pills, powders, and granules), dosage forms for topical and/or transdermal administration (e.g., ointments, pastes, creams, lotions, gels, powders, solutions, sprays, inhalants, and patches), suspensions, powders, and other forms.

Liquid dosage forms for oral and parenteral administration include, but are not limited to, pharmaceutically acceptable emulsions, microemulsions, nanoemulsions, solutions, suspensions, syrups, and/or elixirs. In addition to active ingredients, liquid dosage forms can comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include additional therapeutic and/or prophylactic agents, additional agents such as wetting agents, emulsifying and suspending agents, sweetening, flavoring, and/or perfuming agents. In certain embodiments for parenteral administration, compositions are mixed with solubilizing agents such as Cremophor™, alcohols, oils, modified oils, glycols, polysorbates, cyclodextrins, polymers, and/or combinations thereof.

Injectable preparations, for example, sterile injectable aqueous or oleaginous suspensions can be formulated according to the known art using suitable dispersing agents, wetting agents, and/or suspending agents. Sterile injectable preparations can be sterile injectable solutions, suspensions, and/or emulsions in nontoxic parenterally acceptable diluents and/or solvents, for example, as a solution in 1,3-butanediol. Among the acceptable vehicles and solvents that can be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

The disclosure features methods of delivering a therapeutic and/or prophylactic agent to a mammalian cell or organ, producing a polypeptide of interest in a mammalian cell, and treating a disease or disorder in a mammal in need thereof comprising administering to a mammal and/or contacting a mammalian cell with a nanoparticle composition including a therapeutic and/or prophylactic agent.

6.5 Methods

In one aspect, provided herein are also methods for managing, preventing and treating an infectious disease caused by coronavirus infection in a subject. In some embodiments, the infectious disease being managed, prevented or treated with the methods described herein is caused by infection of a coronavirus selected from SARS-CoV-2, severe acute respiratory syndrome coronavirus (SARS-CoV), Middle East respiratory syndrome coronavirus (MERS-CoV), human coronavirus NL63 (HCoV-NL63), human coronavirus OC43, the porcine epidemic diarrhea coronavirus (PEDV), porcine transmissible gastroenteritis coronavirus (TGEV), porcine respiratory coronavirus (PRCV), bat coronavirus HKU4, mouse hepatitis coronavirus (MHV), bovine coronavirus (BCoV), avian infectious bronchitis coronavirus (IBV), porcine deltacoronavirus (PdCV).

In specific embodiments, the infectious disease being managed, prevented or treated with the methods described herein is caused by coronavirus infection of the respiratory system, the nervous system, the immune system, the digestion system and/or a major organ of the subject (e.g., a human or non-human mammal). In specific embodiments, the infectious disease being managed, prevented or treated with the methods described herein is respiratory tract infection, lung infection, renal infection, liver infection, enteric infection, neurologic infections, respiratory syndrome, bronchitis, pneumonia, gastroenteritis, encephalomyelitis, encephalitis, sarcoidosis, diarrhea, hepatitis, or demyelinating disease. In specific embodiments, the infectious disease is respiratory tract infection, lung infection, pneumonia or respiratory syndrome caused by infection by the SARS-CoV-2.

In some embodiments, the present method for managing, preventing and treating an infectious disease caused by coronavirus infection in a subject comprises administering to the subject a therapeutic effective amount of a therapeutic nucleic acid as described herein. In specific embodiments, the therapeutic nucleic acid is an mRNA molecule as described herein.

In some embodiments, the present method for managing, preventing and treating an infectious disease caused by coronavirus infection in a subject comprises administering to the subject a therapeutic effective amount of a therapeutic composition comprising a therapeutic nucleic acid as described herein. In specific embodiments, the therapeutic nucleic acid is an mRNA molecule as described herein.

In some embodiments, the present method for managing, preventing and treating an infectious disease caused by coronavirus infection in a subject comprises administering to the subject a therapeutic effective amount of a vaccine composition comprising a therapeutic nucleic acid as described herein. In specific embodiments, the therapeutic nucleic acid is an mRNA molecule as described herein.

In some embodiments, the present method for managing, preventing and treating an infectious disease caused by coronavirus infection in a subject comprises administering to the subject a therapeutic effective amount of a lipid-containing composition comprising a therapeutic nucleic acid as described herein. In specific embodiments, the therapeutic nucleic acid is an mRNA molecule as described herein.

In some embodiments, the present method for managing, preventing and treating an infectious disease caused by coronavirus infection in a subject comprises administering to the subject a therapeutic effective amount of a lipid-containing composition comprising a therapeutic nucleic acid as described herein, wherein the lipid-containing composition is formulated as a lipid nanoparticle encapsulating the therapeutic nucleic acid in a lipid shell. In specific embodiments, the therapeutic nucleic acid is an mRNA molecule as described herein. In specific embodiments, the cells in the subject effectively intake the lipid-containing composition (e.g., lipid nanoparticles) described herein upon administration. In specific embodiments, lipid-containing composition (e.g., lipid nanoparticles) described herein are endocytosed by cells of the subject.

In some embodiments, upon administration to a subject in need thereof of the therapeutic nucleic acid as described herein, a vaccine composition comprising the therapeutic nucleic acids described herein, a lipid-containing composition (e.g., lipid nanoparticles) comprising the therapeutic nucleic acids described herein, the cells in the subject uptake and express the administered therapeutic nucleic acids to produce a peptide or polypeptide encoded by the nucleic acid. In some embodiments, the encoded peptide or polypeptide is derived from the coronavirus causing the infectious disease being managed, prevented, or treated by the method.

6.5.1 Immune Responses

In some embodiments, upon administration to a subject in need thereof of the therapeutic nucleic acid as described herein, a vaccine composition comprising the therapeutic nucleic acids described herein, a lipid-containing composition (e.g., lipid nanoparticles) comprising the therapeutic nucleic acids described herein, one or more immune responses against the coronavirus is elicited in the subject. In some embodiments, the elicited immune response comprises one or more adaptive immune responses against the coronavirus. In some embodiments, the elicited immune response comprises one or more innate immune responses against the coronavirus. The one or more immune responses can be in the form of, e.g., an antibody response (humoral response) or a cellular immune response, e.g., cytokine secretion (e.g., interferon-gamma), helper activity or cellular cytotoxicity. In some embodiments, expression of an activation marker on immune cells, expression of a co-stimulatory receptor on immune cells, expression of a ligand for a co-stimulatory receptor, cytokine secretion, infiltration of immune cells (e.g., T-lymphocytes, B lymphocytes and/or NK cells) to a infected cell, production of antibody specifically recognizing one or more viral proteins (e.g., the viral peptide or protein encoded by the therapeutic nucleic acid), effector function, T cell activation, T cell differentiation, T cell proliferation, B cell differentiation, B cell proliferation, and/or NK cell proliferation is induced, activated and/or enhanced. In some embodiments, activation and proliferation of myeloid-derived suppressor cell (MDSC) and Treg cells are inhibited.

In some embodiments, upon administration to a subject in need thereof of the therapeutic nucleic acid as described herein, a vaccine composition comprising the therapeutic nucleic acids described herein, a lipid-containing composition (e.g., lipid nanoparticles) comprising the therapeutic nucleic acids described herein, one or more neutralizing antibody against the coronavirus or cells infected by the coronavirus is produced in the subject.

In specific embodiments, the neutralizing antibody specifically binds to one or more epitopes of the S protein of the coronavirus and inhibits or reduces one or more S protein function or activity. In specific embodiments, binding of the S protein to its cellular receptor is reduced or inhibited. In specific embodiments, binding of the coronavirus S protein to angiotensin-converting enzyme 2 (ACE2), aminopeptidase N (APN), dipeptidyl peptidase 4 (DPP4), carcinoembryonic antigen-related cell adhesion molecule 1 (CEACAM1) and/or sugar on the host cell surface is reduced or inhibited. In specific embodiments, attachment of the coronavirus with host cells in the subject is reduced or inhibited. In specific embodiments, host cell membrane fusion induced by the coronavirus is reduced or inhibited. In specific embodiments, infection (e.g., entry) of host cells in the subject by the coronavirus is reduced or inhibited. In some embodiments, the neutralizing antibody reduces the S protein function or activity by 10%, 20%, 30%, 40%, 50%, 60%, 70%, 80%, 90%, 95% or 100%.

In another embodiments, the neutralizing antibody against the coronavirus or cells infected by the coronavirus is produced in the subject. In specific embodiments, the neutralizing antibody specifically binds to one or more epitopes of the N protein of the coronavirus, and inhibits or reduces one or more N protein function or activity. In specific embodiments, binding of the coronavirus N protein to reproduced viral genomic sequences is reduced or inhibited. In specific embodiments, packaging of reproduced viral genomic sequence into a functional viral capsid is reduced or inhibited. In specific embodiments, reproduction of viable progenies of the coronavirus is reduced or inhibited. In some embodiments, the neutralizing antibody reduces the S protein function or activity by 10%, 20%, 30%, 40%, 50%, 60%, 70%, 80%, 90%, 95% or 100%.

In specific embodiments, the neutralizing antibody binds to one or more viral proteins present on a viral particle or the surface of infected cells, and mark the viral particles or infected cells for destruction by the subject's immune system. In some embodiments, endocytosis of viral particles by white blood cells (e.g., macrophage) is induced or enhanced. In some embodiments, antibody-dependent cell-mediated cytotoxicity (ADCC) against infected cells in the subject is induced or enhanced. In some embodiments, antibody-dependent cellular phagocytosis (ADCP) against infected cells in the subject is induced or enhanced. In some embodiments, complement dependent cytotoxicity (CDC) against infected cells in the subject is induced or enhanced.

6.5.2 Combination Therapy

In some embodiments, the composition of the present disclosure can further comprise one or more additional therapeutic agents. In some embodiments, the additional therapeutic agent is an adjuvant capable of bolstering immunogenicity of the composition (e.g., a genetic vaccine). In some embodiments, the additional therapeutic agent is an immune modulator that enhances immune responses in a subject. In some embodiments, the adjuvant and the therapeutic nucleic acid in the composition can have a synergistic action in eliciting an immune response in a subject.

In some embodiments, the additional therapeutic agent and the therapeutic nucleic acid of the present disclosure can be co-formulated in one composition. For example, the additional therapeutic agent can be formulated as part of the composition comprising the therapeutic nucleic acid of the present disclosure. Alternatively, in some embodiments, the additional therapeutic agent and therapeutic nucleic acid of the present disclosure can be formulated as separate compositions or dose units for co-administration either sequentially or simultaneously to a subject.

In particular embodiments, the therapeutic nucleic acid of the present disclosure is formulated as part of a lipid-containing composition as described in Section 6.4, and the additional therapeutic agent is formulated as a separate composition. In particular embodiments, the therapeutic nucleic acid of the present disclosure is formulated as part of a lipid-containing composition as described in Section 6.4, wherein the additional therapeutic agent is also formulated as part of the lipid-containing composition.

In particular embodiments, the therapeutic nucleic acid of the present disclosure is formulated so that the therapeutic nucleic acid is encapsulated in a lipid shell of a lipid nanoparticle as described in Section 6.4, and the additional therapeutic agent is formulated as a separate composition. In particular embodiments, the therapeutic nucleic acid of the present disclosure is formulated so that the therapeutic nucleic acid is encapsulated in a lipid shell of a lipid nanoparticle as described in Section 6.4, wherein the lipid nanoparticles also enclose the additional therapeutic agent molecule or a nucleic acid encoding the additional therapeutic agent molecule. In particular embodiments, the therapeutic nucleic acid of the present disclosure is formulated so that the therapeutic nucleic acid is encapsulated in a lipid shell of a lipid nanoparticle as described in Section 6.4, wherein the lipid nanoparticles and the additional therapeutic agent are formulated into a single composition.

In specific embodiments, the additional therapeutic agent is an adjuvant. In some embodiments, the adjuvant comprises an agent that promotes maturation of dendritic cells (DCs) in a vaccinated subject, such as but not limited to lipopolysaccharides, TNF-alpha or CD40 ligand. In some embodiments, the adjuvant is an agent that recognized by the immune system of the vaccinated subject as a "danger signal," such as LPS, GP96, etc.

In some embodiments, the adjuvant comprises an immunostimulating cytokine such as but not limited to IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, INF-alpha, IFN-beta, INF-gamma, GM-CSF, G-CSF, M-CSF, LT-beta or TNF-alpha, growth factors, such as hGH.

In some embodiments, the adjuvant comprises a compound known as capable of eliciting an innate immune response. One exemplary class of such compound are Toll-like receptor ligands, such as ligands of human Toll-like receptors TLR1, TLR2, TLR3, TLR4, TLR5, TLR6, TLR7, TLR8, TLR9, TLR10, and ligands of murine Toll-like receptors TLR1, TLR2, TLR3, TLR4, TLR5, TLR6, TLR7, TLR8, TLR9, TLR10, TLR11, TLR12 or TLR13. Another exemplar class of such compounds are immuno-stimulating nucleic acids, such as oligonucleotides containing the CpG motif. CpG containing nucleic acids can be DNA (CpG-DNA) or RNA (CpG-RNA) molecules. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). In some embodiments, the CpG nucleic acid is in the form of CpG-RNA. In particular embodiments, the CpG nucleic acid is in the form of single-stranded CpG-RNA (ss CpG-RNA). In some embodiments, the CpG nucleic acid contains at least one or more (mitogenic) cytosine/guanine dinucleotide sequence(s) (CpG motif(s)). In some embodiments, at least one CpG motif contained in these sequences (i.e., the C (cytosine) and/or the G (guanine) forming the CpG motif) is unmethylated.

In some embodiments, the additional therapeutic agent is an immune modulator that activate, boost or restore normal immune functions. In specific embodiments, the immune modulator is an agonist of a co-stimulatory signal of an immune cell, such as a T-lymphocyte, NK cell or antigen-presenting cell (e.g., a dendritic cell or macrophage). In specific embodiments, the immune modulator is an antagonist of an inhibitory signal of an immune cell, such as a T-lymphocyte, NK cell or antigen-presenting cell (e.g., a dendritic cell or macrophage).

Various immune cell stimulatory agents are known to one of skill in the art and can be used in connection with the present disclosure. In certain embodiments, the agonist of a co-stimulatory signal is an agonist of a co-stimulatory molecule (e.g., co-stimulatory receptor) found on immune cells, such as, T-lymphocytes (e.g., CD4+ or CD8+ T-lymphocytes), NK cells and/or antigen-presenting cells (e.g., dendritic cells or macrophages). Specific examples of co-stimulatory molecules include glucocorticoid-induced tumor necrosis factor receptor (GITR), Inducible T-cell costimulator (ICOS or CD278), OX40 (CD134), CD27, CD28, 4-IBB (CD137), CD40, lymphotoxin alpha (LT alpha), LIGHT (lymphotoxin-like, exhibits inducible expression, and competes with herpes simplex virus glycoprotein D for HVEM, a receptor expressed by T lymphocytes), CD226, cytotoxic and regulatory T cell molecule (CRT AM), death receptor 3 (DR3), lymphotoxin-beta receptor (LTBR), transmembrane activator and CAML interactor (TACI), B cell-activating factor receptor (BAFFR), and B cell maturation protein (BCMA).

In specific embodiments, the agonist of a co-stimulatory receptor is an antibody or antigen-binding fragment thereof that specifically binds to the co-stimulatory receptor. Specific examples of co-stimulatory receptors include GITR, ICOS, OX40, CD27, CD28, 4-1BB, CD40, LT alpha, LIGHT, CD226, CRT AM, DR3, LTBR, TACI, BAFFR, and BCMA. In certain specific embodiments, the antibody is a monoclonal antibody. In other specific embodiments, the antibody is an sc-Fv. In a specific embodiment, the antibody is a bispecific antibody that binds to two receptors on an immune cell. In other embodiments, the bispecific antibody binds to a receptor on an immune cell and to another receptor on a virus infected diseased cell. In specific embodiments, the antibody is a human or humanized antibody.

In another embodiment, the agonist of a co-stimulatory receptor is a ligand of the co-stimulatory receptor or a functional derivative thereof. In certain embodiments, the ligand is fragment of a native ligand. Specific examples of native ligands include ICOSL, B7RP1, CD137L, OX40L, CD70, herpes virus entry mediator (HVEM), CD80, and CD86. The nucleotide sequences encoding native ligands as well as the amino acid sequences of native ligands are known in the art.

In specific embodiments, the antagonist is an antagonist of an inhibitory molecule (e.g., inhibitory receptor) found on immune cells, such as, e.g., T-lymphocytes (e.g., CD4+ or CD8+ T-lymphocytes), NK cells and/or antigen-presenting cells (e.g., dendritic cells or macrophages). Specific examples of inhibitory molecules include cytotoxic T-lymphocyte-associated antigen 4 (CTLA-4 or CD52), programmed cell death protein 1 (PD1 or CD279), B and T-lymphocyte attenuator (BTLA), killer cell immunoglobulin-like receptor (KIR), lymphocyte activation gene 3 (LAG3), T-cell membrane protein 3 (TIM3), CD 160, adenosine A2a receptor (A2aR), T cell immunoreceptor with immunoglobulin and ITIM domains (TIGIT), leukocyte-associated immunoglobulin-like receptor 1 (LAIR1), and CD 160.

In another embodiment, the antagonist of an inhibitory receptor is an antibody (or an antigen-binding fragment) that specifically binds to the native ligand for the inhibitory receptor and blocks the native ligand from binding to the inhibitory receptor and transducing an inhibitory signal(s). In certain specific embodiments, the antibody is a monoclonal antibody. In other specific embodiments, the antibody is an sc-Fv. In a specific embodiment, the antibody is a bispecific antibody that binds to two receptors on an immune cell. In other embodiments, the bispecific antibody binds to a receptor on an immune cell and to another receptor on a virus infected diseased cell. In specific embodiments, the antibody is a human or humanized antibody.

In another embodiments, the antagonist of an inhibitory receptor is a soluble receptor or a functional derivative thereof that specifically binds to the native ligand for the inhibitory receptor and blocks the native ligand from binding to the inhibitory receptor and transducing an inhibitory signal(s). Specific examples of native ligands for inhibitory receptors include PDL-1, PDL-2, B7-H3, B7-H4, HVEM, Gal9 and adenosine. Specific examples of inhibitory receptors that bind to a native ligand include CTLA-4, PD-1, BTLA, KIR, LAG3, TIM3, and A2aR.

In another embodiment, the antagonist of an inhibitory receptor is an antibody (or an antigen-binding fragment) or ligand that binds to the inhibitory receptor, but does not transduce an inhibitory signal(s). Specific examples of inhibitory receptors include CTLA-4, PD1, BTLA, KIR, LAG3, TIM3, and A2aR. In certain specific embodiments, the antibody is a monoclonal antibody. In other specific embodiments, the antibody is an scFv. In particular embodiments, the antibody is a human or humanized antibody. A specific example of an antibody to inhibitory receptor is anti-CTLA-4 antibody (Leach D R, et al. Science 1996; 271: 1734-1736). Another example of an antibody to inhibitory receptor is anti-PD-1 antibody (Topalian SL, NEJM 2012; 28:3167-75).

6.5.3 Patient Population

In some embodiments, a therapeutic nucleic acid described herein, a vaccine composition comprising the therapeutic nucleic acids described herein, a lipid-containing composition (e.g., lipid nanoparticles) comprising the therapeutic nucleic acids described herein, or a combination therapy described herein is administered to a subject in need thereof.

In some embodiments, a therapeutic nucleic acid described herein, a vaccine composition comprising the therapeutic nucleic acids described herein, a lipid-containing composition (e.g., lipid nanoparticles) comprising the therapeutic nucleic acids described herein, or a combination therapy described herein is administered to a human subject. In some embodiments, a subject administered with a therapeutic nucleic acid described herein, a vaccine composition comprising the therapeutic nucleic acids described herein, a lipid-containing composition (e.g., lipid nanoparticles) comprising a therapeutic nucleic acids described herein or a combination therapy described herein is an elderly human. In some embodiments, a subject administered with a therapeutic nucleic acid described herein, a vaccine composition comprising the therapeutic nucleic acids described herein, a lipid-containing composition (e.g., lipid nanoparticles) comprising the therapeutic nucleic acids described herein or a combination therapy described herein is a human adult. In some embodiments, a subject administered with a therapeutic nucleic acid described herein, a vaccine composition comprising the therapeutic nucleic acids described herein, a lipid-containing composition (e.g., lipid nanoparticles) comprising the therapeutic nucleic acids described herein or a combination therapy described herein is human child. In some embodiments, a subject administered with a therapeutic nucleic acid described herein, a vaccine composition comprising the therapeutic nucleic acids described herein, a lipid-containing composition (e.g., lipid nanoparticles) comprising the therapeutic nucleic acids described herein or a combination therapy described herein is human toddler. In some embodiments, a subject administered with a therapeutic nucleic acid described herein, a vaccine composition comprising the therapeutic nucleic acids described herein, a lipid-containing composition (e.g., lipid nanoparticles) comprising the therapeutic nucleic acids described herein or a combination therapy described herein is human infant.

In some embodiments, a subject administered with a therapeutic nucleic acid described herein, a vaccine composition comprising the therapeutic nucleic acids described herein, a lipid-containing composition (e.g., lipid nanoparticles) comprising the therapeutic nucleic acids described herein or a combination therapy described herein is administered to a non-human mammal.

In some embodiments, a subject administered with a therapeutic nucleic acid described herein, a vaccine composition comprising the therapeutic nucleic acids described herein, a lipid-containing composition (e.g., lipid nanoparticles) comprising the therapeutic nucleic acids described herein, or the combination therapy described herein is administered to a subject exhibiting at least one symptom associated with coronavirus infection. In some embodiments, the subject receiving administration of a therapeutic nucleic acid described herein, a vaccine composition comprising the therapeutic nucleic acids described herein, a lipid-containing composition (e.g., lipid nanoparticles) comprising the therapeutic nucleic acids described herein, or a combination therapy described herein exhibits one or more symptoms of upper respiratory tract infection, lower respiratory tract infection, lung infection, renal infection, liver infection, enteric infection, hepatic infection, neurologic infections, respiratory syndrome, pneumonia, gastroenteritis, encephalomyelitis, encephalitis, sarcoidosis, diarrhea, hepatitis, and demyelinating disease.

In some embodiments, a therapeutic nucleic acid described herein, a vaccine composition comprising the therapeutic nucleic acids described herein, a lipid-containing composition (e.g., lipid nanoparticles) comprising the therapeutic nucleic acids described herein, or a combination therapy as described herein is administered to a subject that is asymptomatic for coronavirus infection.

In some embodiments, a therapeutic nucleic acid described herein, a vaccine composition comprising the therapeutic nucleic acids described herein, a lipid-containing composition (e.g., lipid nanoparticles) comprising the therapeutic nucleic acids described herein, or a combination therapy described herein is administered to a subject who is at risk of, or susceptible to, coronavirus infection. In some embodiments, a subject at risk of, or susceptible to, coronavirus infection is an elderly human. In some embodiments, a subject at risk of, or susceptible to, coronavirus infection is a human adult. In some embodiments, a subject at risk of, or susceptible to, coronavirus infection is a human child. In some embodiments, a subject at risk of, or susceptible to, coronavirus infection is a human adult toddler. In some embodiments, a subject at risk of, or susceptible to, coronavirus infection is a human adult infant. In some embodiments, a subject at risk of, or susceptible to, coronavirus infection is a human subject having existing health condition that affects the subject's immune system. In some embodiments, a subject at risk of, or susceptible to, coronavirus infection is a human subject having existing health condition that affects the subject's major organs. In some embodiments, a subject at risk of, or susceptible to, coronavirus infection is a human subject having existing health condition that affects the subject's lung function. In some embodiments, a subject at risk of, or susceptible to, coronavirus infection is an elderly human subject having an existing health condition that affects the subject's immune system, or a major organ, such as lung function. In various embodiments described in this paragraph, a subject at risk of, or susceptible to, coronavirus infection can be either exhibiting symptoms of coronavirus infection or asymptomatic for coronavirus infection.

In some embodiments, a therapeutic nucleic acid described herein, a vaccine composition comprising the therapeutic nucleic acids described herein, a lipid-containing composition (e.g., lipid nanoparticles) comprising the therapeutic nucleic acids described herein, or a combination therapy described herein is administered to a subject who has been diagnosed positive for the coronavirus infection. In some embodiments, the subject diagnosed positive for coronavirus infection is asymptomatic for coronavirus infection, and the diagnosis is based on detecting the presence of a viral nucleic acid or protein from a sample taken from the subject. In some embodiments, the diagnosis is based on clinical symptoms exhibited by the patient. Exemplary symptoms that may serve as the basis of diagnosis include but are not limited to upper respiratory tract infection, lower respiratory tract infection, lung infection, renal infection, liver infection, enteric infection, hepatic infection, neurologic infections, respiratory syndrome, pneumonia, gastroenteritis, encephalomyelitis, encephalitis, sarcoidosis, diarrhea, hepatitis, and demyelinating disease. In some embodiments, the diagnosis is based on a subject's exhibited clinical symptom combined with the subject's history of being in contact with a geographical location, population, and/or individual considered of having a high risk of carrying the coronavirus, such as another individual diagnosed positive for the coronavirus infection.

In some embodiments, a therapeutic nucleic acid described herein, a vaccine composition comprising the therapeutic nucleic acids described herein, a lipid-containing composition (e.g., lipid nanoparticles) comprising the therapeutic nucleic acids described herein, or a combination therapy described herein is administered to a subject who has not previously received administration of the therapeutic nucleic acid, the vaccine composition, the lipid-containing composition (e.g., lipid nanoparticles), or the combination therapy.

In some embodiments, a therapeutic nucleic acid described herein, a vaccine composition comprising the therapeutic nucleic acids described herein, a lipid-containing composition (e.g., lipid nanoparticles) comprising the therapeutic nucleic acids described herein, or a combination therapy described herein is administered to a subject who has previously received administration of the therapeutic nucleic acid, the vaccine composition, the lipid-containing composition (e.g., lipid nanoparticles), or the combination therapy. In specific embodiments, the subject has been previously administered a therapeutic nucleic acid described herein, the vaccine composition comprising the therapeutic nucleic acids described herein, the lipid-containing composition (e.g., lipid nanoparticles) comprising the therapeutic nucleic acids described herein, or the combination therapy as described herein once, twice, three times or more.

In some embodiments, a therapeutic nucleic acid described herein, a vaccine composition comprising the therapeutic nucleic acids described herein, a lipid-containing composition (e.g., lipid nanoparticles) comprising the therapeutic nucleic acids described herein, or a combination therapy described herein is administered to a subject who has received a therapy prior to administration of the therapeutic nucleic acid, the vaccine composition, the lipid-containing composition (e.g., lipid nanoparticles), or the combination therapy. In some embodiments, the subject administered with a therapeutic nucleic acid described herein, a vaccine composition comprising the therapeutic nucleic acids described herein, a lipid-containing composition (e.g., lipid nanoparticles) comprising the therapeutic nucleic acids described herein, or a combination therapy described herein experienced adverse side effects to a prior therapy or a prior therapy was discontinued due to unacceptable levels of toxicity to the subject.

6.5.4 Administration Dosage and Frequency

The amount of therapeutic nucleic acid or a composition thereof which will be effective in the management, prevention and/or treatment of infectious disease will depend on the nature of the disease being treated, the route of administration, the general health of the subject, etc. and should be decided according to the judgment of a medical practitioner. Standard clinical techniques, such as in vitro assays, may optionally be employed to help identify optimal dosage ranges. Nevertheless, suitable dosage ranges of a therapeutic nucleic acid as described herein for administration are generally about 0.001 mg, 0.005 mg, 0.01 mg, 0.05 mg. 0.1 mg. 0.5 mg, 1.0 mg, 2.0 mg. 3.0 mg, 4.0 mg, 5.0 mg, 10.0 mg, 0.001 mg to 10.0 mg, 0.01 mg to 1.0 mg, 0.1 mg to 1 mg, and 0.1 mg to 5.0 mg. The therapeutic nucleic acid or a composition thereof can be administered to a subject once, twice, three, four or more times with intervals as often as needed. Effective doses may be extrapolated from dose response curves derived from in vitro or animal model test systems.

In certain embodiments, a therapeutic nucleic acid or a composition thereof is administered to a subject as a single dose followed by a second dose 1 to 6 weeks, 1 to 5 weeks, 1 to 4 weeks, 1 to 3 weeks, 1 to 2 weeks later. In accordance with these embodiments, booster inoculations may be administered to the subject at 6 to 12 month intervals following the second inoculation.

In certain embodiments, administration of a therapeutic nucleic acid or a composition thereof may be repeated and the administrations may be separated by at least 1 day, 2 days, 3 days, 5 days, 6 says, 7 days, 10 days, 14 days, 15 days, 21 days, 28 days, 30 days, 45 days, 2 months, 75 days, 3 months, or at least 6 months. In other embodiments, administration of therapeutic nucleic acid or a composition thereof may be repeated and the administrations may be separated by 1 to 14 days, 1 to 7 days, 7 to 14 days, 1 to 30 days, 15 to 30 days, 15 to 45 days, 15 to 75 days, 15 to 90 days, 1 to 3 months, 3 to 6 months, 3 to 12 months, or 6 to 12 months. In some embodiments, a first therapeutic nucleic acid or a composition thereof is administered to a subject followed by the administration of a second therapeutic nucleic acid or a composition thereof. In certain embodiments, the first and second therapeutic nucleic acids or compositions thereof may be separated by at least 1 day, 2 days, 3 days, 5 days, 6 days, 7 days, 10 days, 14 days, 15 days, 21 days, 28 days, 30 days, 45 days, 2 months, 75 days, 3 months, or at least 6 months. In other embodiments, the first and second therapeutic nucleic acids or compositions thereof may be separated by 1 to 14 days, 1 to 7 days, 7 to 14 days, 1 to 30 days, 15 to 30 days, 15 to 45 days, 15 to 75 days, 15 to 90 days, 1 to 3 months, 3 to 6 months, 3 to 12 months, or 6 to 12 months.

In certain embodiments, a therapeutic nucleic acid or composition thereof is administered to a subject in combination with one or more additional therapies, such as a therapy described in Section 6.5.2. The dosage of the other one or more additional therapies will depend upon various factors including, e.g., the therapy, the nature of the infectious disease, the route of administration, the general health of the subject, etc. and should be decided according to the judgment of a medical practitioner. In specific embodiments, the dose of the other therapy is the dose and/or frequency of administration of the therapy recommended for the therapy for use as a single agent is used in accordance with the methods disclosed herein. In other embodiments, the dose of the other therapy is a lower dose and/or less frequent administration of the therapy than recommended for the therapy for use as a single agent is used in accordance with the methods disclosed herein. Recommended doses for approved therapies can be found in the Physician's Desk Reference.

In certain embodiments, a therapeutic nucleic acid or composition thereof is administered to a subject concurrently with the administration of one or more additional therapies. In other embodiments, a therapeutic nucleic acid or composition thereof is administered to a subject every 3 to 7 days, 1 to 6 weeks, 1 to 5 weeks, 1 to 4 weeks, 2 to 4 weeks, 1 to 3 weeks, or 1 to 2 weeks and one or more additional therapies (such as described in Section 6.5.2) is administered every 3 to 7 days, 1 to 6 weeks, 1 to 5 weeks, 1 to 4 weeks, 1 to 3 weeks, or 1 to 2 weeks. In certain embodiments, a therapeutic nucleic acid or composition thereof is administered to a subject every 1 to 2 weeks and one or more additional therapies (such as described in Section 6.5.2) is administered every 2 to 4 weeks. In some embodiments, a therapeutic nucleic acid or composition thereof is administered to a subject every week and one or more additional therapies (such as described in Section 6.5.2) is administered every 2 weeks.

7. EXAMPLES

The examples in this section (i.e., Section 7) are offered by way of illustration, and not by way of limitation.

7.1 Example 1: mRNA Synthesis and Purification

DNA Linearization. DNA plasmid template containing the target sequence encoding the 51 subunit, a few different versions of the receptor binding domain (RBD), or the receptor binding motif (RBM) of the coronavirus SARS-CoV-2 Spike (S) protein, the 5' and 3'-UTR and polyA signal was linearized using restriction enzyme digestion. Every 10 μg of plasmid was mixed with 10 U of Esp3I/BsmBI, incubated at 37° C. for 4 hours to ensure complete linearization. The reaction was terminated by adding 1/10th volume of 3 M Na acetate (pH 5.5) and 2.5 volumes of ethanol, mix well and chill at −20° C. for 1 h. Linearized DNA was precipitated by centrifugation at 13800 g for 15 minutes at 4° C., washed twice with 70% ethanol, resuspended in nuclease-free $H_2O$.

In vitro Transcription of mRNA. Contents of a typical 20 μL reaction mixture are shown in the table below:

| | |
|---|---|
| Nuclease-free $H_2O$ | Up to 20 μL |
| RNase Inhibitor(40 U/μL) | 0.5 μL |
| rNTP mixture (100 mM each) | 8 μL (10 mM each final) |
| 10X IVT Reaction Buffer | 2 μL |
| 1M $MgCl_2$ | 0.8 μL |
| 0.1M DTT | 2 μL |
| 100 U/mL Pyrophosphatase Inorganic | 0.8 μL |
| 100 mM NaCl | 1 μL |
| Linearized DNA | 1 μg |
| T7 RNA Polymerase (50 U/μL) | 2 μL |

The reaction mixture was incubated at 37° C. for 6 hours followed by addition of 1 μl of DNase I (RNase-free, 1 U/μL) to remove the DNA template, incubate for 30 minutes at 37° C. The synthesized RNA was purified by adding 0.5 volume of 7.5 M LiCl 7.5 M LiCl, 50 mM EDTA and incubating at −20° C. for 45 minutes, followed by centrifugation at 4° C. for 15 minutes at 13800 g to pellet the mRNA. Then the supernatant was removed and the pellet was rinsed twice with 500 μL of ice cold 70% ethanol, mRNA was resuspended in nuclease-free $H_2O$, adjusted concentration to 1 mg/mL, and stored at −20° C.

mRNA Capping. Each 10 μg uncapped mRNA was heated at 65° C. for 10 minutes, placed on ice for 5 minutes, and mixed with 10 U Vaccinia Capping Enzyme, 50 U mRNA Cap 2'-O-Methyltransferase, 0.2 mM SAM, 0.5 mM GTP and 1U RNase inhibitor, and incubated at 37° C. for 60 minutes to generate cap1 modification structure. The modified mRNA was precipitated by LiCl as previously described and the RNA was resuspended in nuclease-free $H_2O$, and stored at −20° C.

HPLC Purification. RNA was purified by high performance liquid chromatography (HPLC) using a C4 column (5 μm) (10 mm×250 mm column). Buffer A contained 0.1 M triethylammonium acetate (rEAA), pH=7.0 and Buffer B contained 0.1 M rEAA, pH=7.0 and 25% acetonitrile.

FIG. 1 shows an exemplary HPLC purification of in vitro transcribed mRNA. As shown in FIG. 1, mRNA molecules were successfully produced by the in vitro transcription and maturation processes described above and were purified from the reaction system using HPLC.

7.2 Example 2: In Vitro Transfection and Antigen Expression Analysis

Different mRNAs molecules encoding SARS-CoV-2 S protein antigens produced in Example 1 were transfected into expression cell lines such as HEK293F and Hela cultured cells to evaluate efficiency of in vitro expression of the mRNA molecules.

To assemble the mRNA-lipid complex, two separate tubes were set up with 1 μL of Lipofectamine mixed with 30 μL Opti-MEM, and with 1 μg mRNA with 30 μL Opti-MEM, respectively. The two samples were mixed and incubated at room temperature for 5 minutes. Fifty microliter of such a complex was used to transfect cells present in 1 well of a 24-well plate, and the cells were incubated in humidified 37° C./5% CO2 incubator until analysis.

Expression analysis. Cells were transferred from 24 hours post-transfection culture, and centrifuged at 200 RCF for 5 minutes at room temperature. Next, cells were treated with 4% (v/v) paraformaldehyde for 30 min, and washed with PBS. Next, cells were treated with 0.2% (v/v) Triton X-100 for 10 min, and washed with PBS. Next, cells were blocked with 5% (w/v) bovine serum albumin for 1 h, and washed with PBS. Next, cells were incubated with several rabbit anti-SARS-CoV-2 S protein antibodies at 4° C. for 1 h, and labeled with FITC-labeled anti-rabbit antibody (1:200) as secondary antibody for 30 min, and washed with PBS and counter stained by DAPI. The signals were examined by confocal laser scanning microscopy.

Figure 2:
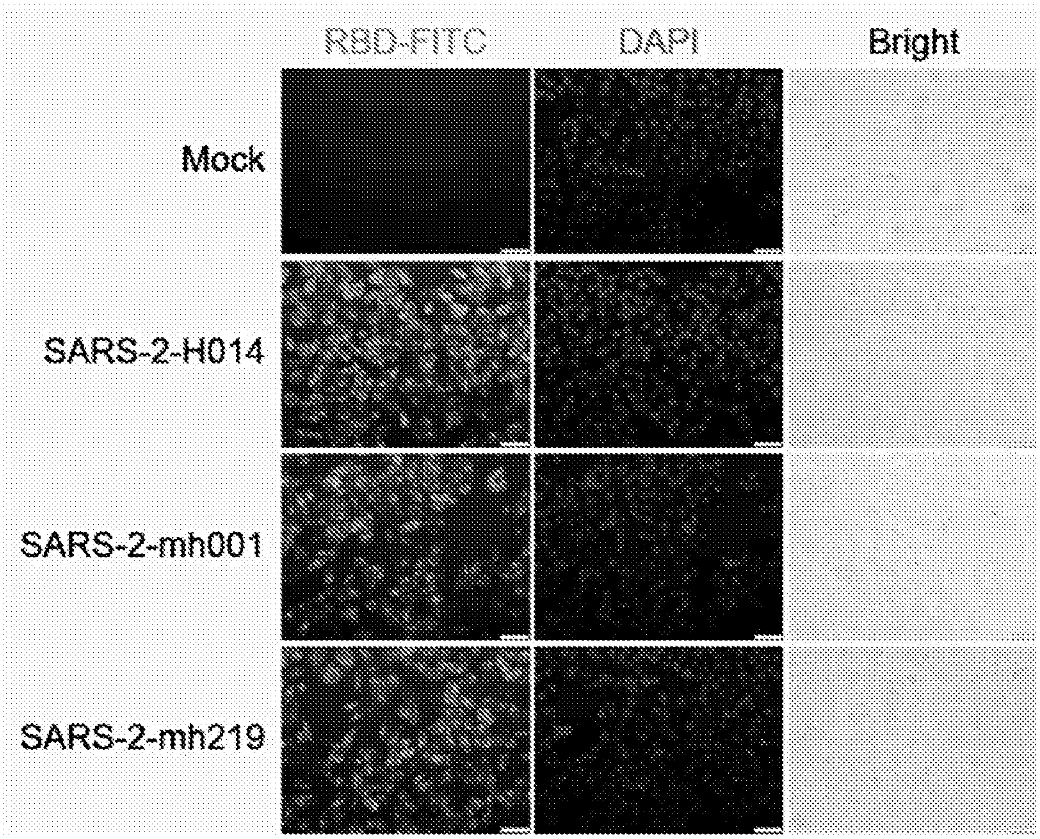

Particularly, FIG. 2 shows exemplary confocal fluorescence microscopy images of Hela cells transfected with an mRNA construct encoding a SARS-CoV-2 S protein RBD sequence (RBD sample 1). Cells were incubated with 3 different monoclonal antibodies recognizing the S protein RBD of SARS-CoV-2, namely SARS-2-H014, SARS-2-mh001 and SARS-2-mh219, respectively.

As shown in FIG. 2, in vitro transcribed mRNA molecules encoding the SARS-CoV-2 S protein RBD effectively transfected Hela cells. The transfected Hela cells expressed the encoded viral antigens at a satisfactory level, as can be recognized by the three monoclonal antibodies used in this study. The transfected Hela cells maintained normal cellular morphology, indicating a lack of cellular toxicity resulted from the expression of the encoded viral antigen.

Western blot. For the secreted proteins such as SARS-CoV-2 S protein or its fragments, cultures of cells transfected with the mRNA molecules produced in Example 1 was collected and analyzed by Western blot 24 hours post-transfection. Following SDS-PAGE, proteins were transferred onto blotting membrane. The blots were rinsed briefly with PBS and then incubated with added a rabbit anti-Spike RBD antibody for 2 hr at RT. The blots were washed extensively in PBS. HRP-conjugated anti-rabbit antibody was added and incubated for 1 hr at RT with gentle agitation. The membrane was washed with PBS, and incubated with added appropriate enzyme substrate solution to visualize protein bands.

Figure 3:
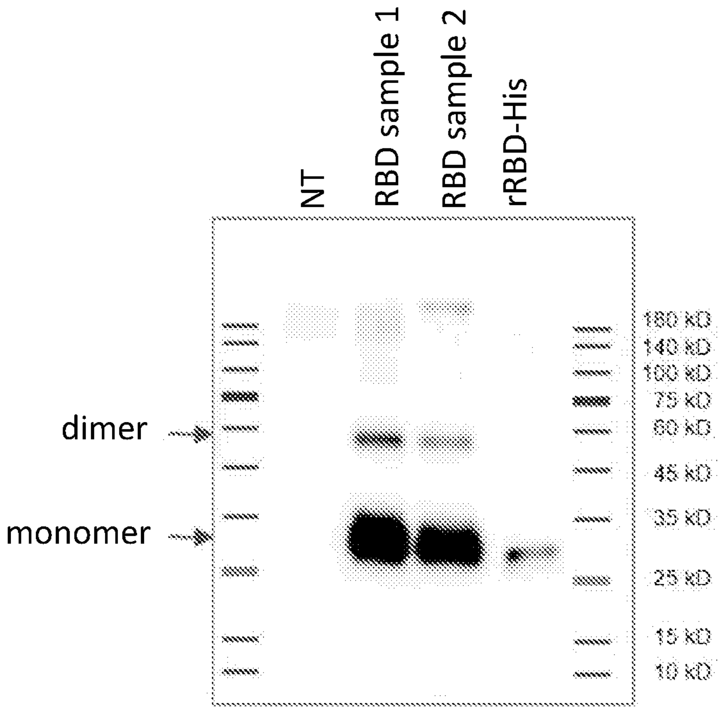

FIG. 3 shows an exemplary Western blot analysis of culture supernatant of Hela cells transfected with an mRNA molecule encoding a SARS-CoV-2 S protein RBD sequence. Particularly, the lanes labeled “RBD sample 1” and “RBD sample 2” were loaded with culture supernatant of Hela cells transfected with mRNA constructs encoding different SARS-CoV-2 S protein RBD sequences described herein, respectively. The lane labeled “rRBD-His” was loaded a recombinantly produced SARS-CoV-2 S protein RBD sequence fused to a C-terminal His-tag. The lane labeled “NT” was loaded cell culture supernatant of Hela cells transfected with an irrelevant mRNA construct as a negative control group.

As shown in FIG. 3, the in vitro transcribed mRNA constructs encoding the SARS-CoV-2 S protein RBD effectively transfected Hela cells. The transfected Hela cells expressed and secreted the encoded viral antigen at a satisfactory level. The bands around about 30 kD corresponded to secreted viral antigen in the monomeric form. The bands around about 60 kD corresponded to secreted viral antigen in the dimeric form. Without being bound by the theory, it is contemplated that multimerized forms of secreted viral antigen can be more immunogenic and effective in inducing humoral immune response upon administration to a vaccinated subject as compared to monomeric forms. As shown in FIG. 3, the viral antigen encoded by the mRNA construct can multimerize after expression, indicating usefulness of the mRNA construct in eliciting an immune response against the virus upon administration to a subject.

ELISA. The quantity of mRNA-encoded viral peptide or protein expressed in cell culture supernatant was determined by ELISA. Particularly, to perform the ELISA assays, microtiter plate wells was coated with 100 μl solution containing 5 μg/ml SARS-CoV-2 S Protein RBD, and incubated at 4° C. for 12 hours with closure plate membrane. Next, the plate was washed 3 times in washing buffer. Next, 300 μl of 5% BSA in PBST was added to each well and incubated for 60 minutes at 37° C. Next, the plate was washed 4 times in washing buffer. Next, culture supernatant samples and SARS-CoV-2 S protein RBD standards were diluted in washing buffer and 100 μl of suitably diluted samples and standards were added to the relevant wells in triplicates. Next, the wells were incubated for 60 minutes at 37° C., and washed 3 times in washing buffer. Next, 100 μL of rabbit anti-SARS-CoV-2 S protein antibody was added to each well of plate. Next, the plate was covered and incubated for 60 minutes at 37° C., and washed 3 times in washing buffer. Next, 100 μl of diluted HRP-conjugated anti-Rabbit antibody was added to each well, and incubated for 1 hour at 37° C., and washed 3 times in washing buffer. Next, 100 μl of TMB substrate solution was added to each well, incubated at room temperature (and in the dark if required) for approximately 10 min. Next, 100 μL of Stop Solution was added to each well, and gently and thoroughly mixed. Next, a Molecular Devices plate reader was used to read ODs at 450/620 nm subtracted for detection.

Figure 4:
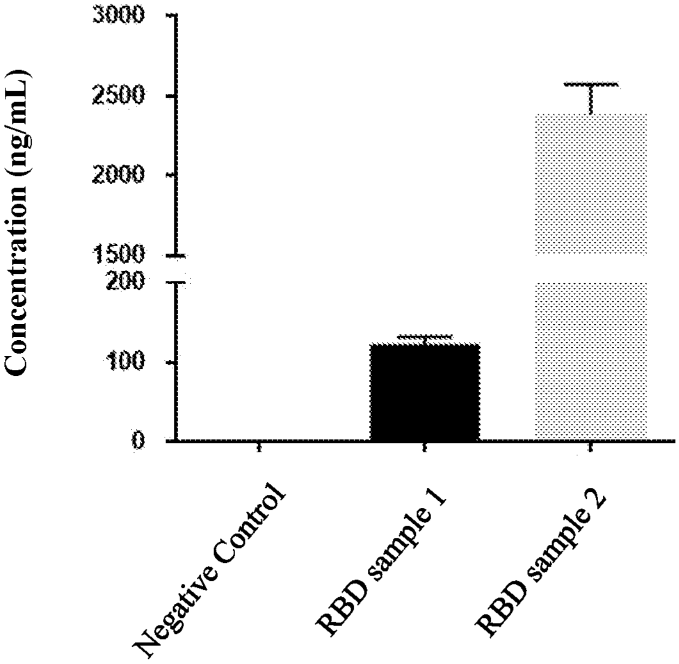
FIG. 4 shows exemplary quantification of mRNA-encoded SARS-CoV-2 S protein antigen concentrations (ng/mL) of in cell culture supernatant as determined by ELISA.

FIG. 4 shows an exemplary ELISA analysis measuring protein concentrations (ng/mL) of mRNA-encoded SARS-CoV-2 S protein RBD in culture supernatant of cells transfected with two mRNA constructs, designated as “RBD sample 1” and “RBD sample 2” respectively. BSA was used as a negative control for ELISA. This study further demonstrated that cells transfected with the mRNA constructs expressed and secreted the encoded viral antigen at satisfactory levels, as quantified by ELISA.

7.3 Example 3. Production of Neutralizing Antibodies by Mice Vaccinated with mRNA Containing LNP BALB/c mice were vaccinated by intramuscular injection of 100 μL of LNP formulation containing 10 μg of mRNA encoding a SARS-CoV-2 S protein RBD (RBD sample 1), and blood was collected from tail veins on day 7, 14, 21 and 28 post-vaccination, respectively. A group of vaccinated mice were also boosted by receiving a second intramuscular injection of the same dose of LNP formulation containing the mRNA 14 days after the first injection, and blood was collected from tail veins on day 7, 14, 21 and 28 after the second boosting injection. The 50% plaque reduction neutralization titer (PRNT 50) values of the collected mouse serum were determined to evaluate the production of neutralizing antibody by the vaccinated animals.

PRNT assays. To perform the plaque reduction neutralization titer (PRNT) assays, the serum sample or solution of antibody to be tested was diluted and mixed with a viral suspension. The mixture was then incubated to allow the antibody to react with the virus. Next, the mixture was poured over a confluent monolayer of host cells. The surface of the cell layer was covered in a layer of agarose or carboxymethyl cellulose to prevent the virus from spreading indiscriminately. The concentration of plaque forming units (PFU) can be estimated by the number of plaques (regions of infected cells) formed a few days later. Depending on the virus, the plaque forming units can be measured by microscopic observation, fluorescent antibodies or specific dyes that react with infected cells. The concentration of serum to reduce the number of plaques by 50% compared to the serum free virus gives the measure of how much antibody is present or how effective it is. This measurement is denoted as the PRNT 50 value.

Particularly, in this study, mouse serum collected as described above were heat inactivated at 55° C. for 30 min and then serially diluted to 1:50, 1:100, 1:200, 1:400, and 1:800 in PBS. Equal volume of PBS containing 100 PFU of SARS-CoV-2 pseudovirus was added to each serum dilution. Each mixture was incubated at 37° C. for 30 min, added to confluent cultures of Vero E6 monolayers, and allowed them to incubate at 37° C. for 60 minutes. The cell monolayers were covered with 4 ml of 0.8% agarose melted in standard Vero E6 cell medium, and plaques were resolved the with neutral red staining 2 days later. The PRNT 50 values were then calculated and plotted in FIG. 5. Particularly, Y axis shows the reciprocal of PRNT 50 values (i.e., 1/PRNT 50). X-axis shows the group of animals as follows: "RBD" denotes mice receiving only the first injection and the "RBD-B" denotes mice receiving the first and the boosting injection. "Control" denotes a group of mice received intramuscular injection of 100 μl LNP formulation without mRNA and boosted with the same dose of blank LNP 14 days later.

Figure 5:
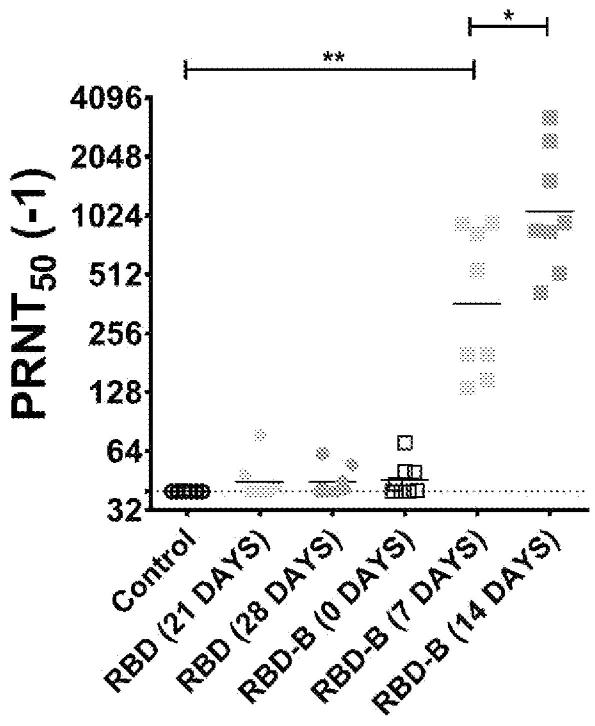
FIG. 5 shows neutralizing antibody titers in sera collected from mice vaccinated with lipid nanoparticles (LNP) containing mRNA encoding a SARS-CoV-2 antigen. Particularly, neutralizing antibody titer was measured as the PRNT50 value.

As shown in FIG. 5, animals vaccinated with the therapeutic mRNA-containing LNP produced neutralizing antibodies that significantly reduced infection of cells by SARS-CoV-2. This study demonstrated that the present therapeutic mRNA-containing LNP composition can be used for treating, managing or preventing infection by the coronavirus SARS-CoV-2.

7.4 Example 4: Study of Correlation Between RBD Expression in Mice and mRNA Contents of mRNA-LNP Samples The following experiment was performed to establish a method for detecting RBD expression in animals in response to a finished coronavirus SARS-CoV-2 mRNA vaccine product, so as to explore the correlation between the RBD expression and the mRNA contents in the finished product.

Animal grouping and dosing information were as follows:

| Group No. | Experimental groups | Number of animals | Dosing concentration (μg/mL) | Dosing volume (μL) | Dosing amount (μg) | Administration route |
|---|---|---|---|---|---|---|
| 1 | Blank control group | 10 | — | — | — | — |
| 2 | Vaccine sample group E | 4 | 10 | 100 | 1 | iv., once. |
| 3 | Vaccine sample group D | 4 | 20 | 100 | 2 | iv., once. |
| 4 | Vaccine sample group C | 4 | 30 | 100 | 3 | iv., once. |
| 5 | Vaccine sample group B | 4 | 40 | 100 | 4 | iv., once. |
| 6 | Vaccine sample group A | 4 | 50 | 100 | 5 | iv., once. |

Experimental animals, ICH mice, were administrated with different test substances by intravenous injection according to the table above. 6 hours after the administration, blood was collected from the heart after deep carbon dioxide anesthesia. After standing at room temperature for about 30 min, the serum was separated (4° C., 8000 rpm (5724 g), 10 min), sub packaged (in triplicate, each larger than 110 ul; if it was not able to guarantee that all of the three aliquots met the requirement, at least two of them would do, and the blood volume per tube was marked), and stored at −80° C. in a refrigerator. Serum samples were collected from the remaining 10 blank mice, mixed well and then dispensed into small tubes.

The RBD expression in the serum samples was detected by ELISA method as follows:

All the samples and reagents were recovered to room temperature before use.

1) 100 μL of ACE2 coating stock solution was added to the ELISA plate, and the plate was sealed with a sealing membrane, and incubated at 4° C. for 15 hours.
2) The liquid in the wells was discarded, and the plate was washed with a washing buffer for 3 times, 300 μL/well, and soaked for 2 min each time.
3) 300 μL/well of blocking solution was added, and the plate was sealed with a sealing membrane, and incubated at 37° C. for 1 hour.
4) The liquid in the wells was discarded, and the plate was washed with a washing buffer for 3 times, 300 μL/well, and soaked for 2 min each time.
5) 100 μL of diluted samples to be tested and a standard were added to the ELISA plate, and the plate was sealed with a sealing membrane, and incubated at 37° C. for 1 hour.
6) The liquid in the wells was discarded, and the plate was washed with a washing buffer for 3 times, 300 μL/well, and soaked for 2 min each time.
7) 100 μL of primary antibody stock solution was added to each well of the plate, and the plate was covered with a sealing membrane, and incubated at 37° C. for 1 hour.
8) The liquid in the wells was discarded, and the plate was washed with a washing buffer for 3 times, 300 μL/well, and soaked for 2 min each time.
9) 100 μL of HRP secondary antibody stock solution was added to each well of the plate, and the plate was covered with a sealing membrane, and incubated at 37° C. for 1 hour.
10) The liquid in the wells was discarded, and the plate was washed with a washing buffer for 3 times, 300 μL/well, and soaked for 2 min each time.
11) 100 μL of TMB substrate solution was added to each microwell, and the plate was incubated at room temperature, protected from the light, for about 5 min.
12) 100 μL of ELISA stop solution was added to each microwell.
13) The result was determined by using a multifunctional microplate reader, where the detection wavelengths were set as 450 nm and 620 nm, a Curve Fit/5-parameter regression model was set for the Standard Curve, and the Dilution Factor of the test samples was set as 2, while standard curve and sample settings being performed (the template settings can be set before the start of the reading), and where the absorption values were determined.
14) The result was calculated automatically via a software by using a 5-parameter regression model of the protein concentration (X) of the protein standard and its corresponding fluorescence value (Y), so as to calculate and obtain the protein concentrations (Unk-dilution/AdjResult) in the samples.

Figure 6:
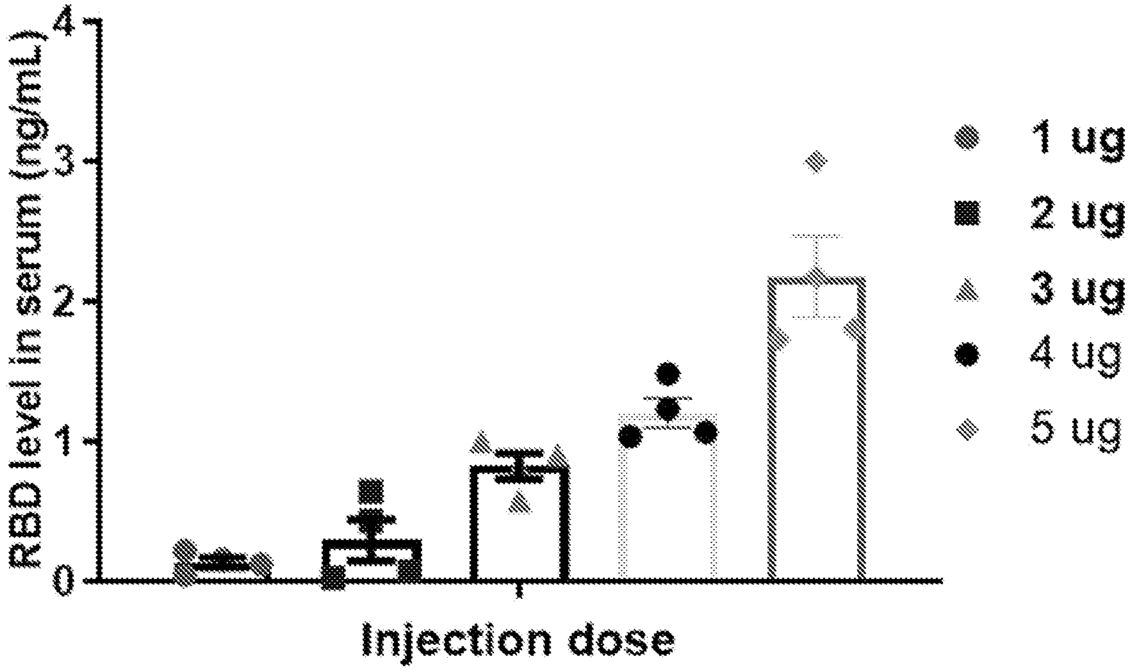
FIG. 6 shows the RBD expression levels in the serums of five groups of experimental mice which received 1 ug-5 ug dosing amounts.

The detection results of the RBD contents in the serum samples of the experimental animals were shown in FIG. 6 and Table 6. Among all mouse serum samples, no RBD concentration was detected in the "blank serum" sample. It was observed that there was a significant dose-dependence between 1 ug and 5 ug mRNA, and the expressed RBD contents were 0.14-2.18 ng/mL.

TABLE 6

| Sample | Value | Result (ng/mL) | Dilution | AdjResult (ng/mL) | Average (ng/mL) |
|---|---|---|---|---|---|
| Blank control group-1 | 0.101 | ND | 2 | ND | ND |
| Blank control group-2 | 0.130 | ND | 2 | ND | |
| Blank control group-3 | 0.118 | ND | 2 | ND | |
| Blank control group-4 | 0.131 | ND | 2 | ND | |
| Vaccine sample group E-1 | 0.163 | 0.079 | 2 | 0.158 | 0.14 |
| Vaccine sample group E-2 | 0.146 | 0.022 | 2 | 0.044 | |
| Vaccine sample group E-3 | 0.176 | 0.109 | 2 | 0.218 | |
| Vaccine sample group E-4 | 0.157 | 0.063 | 2 | 0.126 | |
| Vaccine sample group D-1 | 0.15 | 0.038 | 2 | 0.076 | 0.29 |
| Vaccine sample group D-2 | 0.237 | 0.217 | 2 | 0.434 | |
| Vaccine sample group D-3 | 0.308 | 0.321 | 2 | 0.642 | |
| Vaccine sample group D-4 | 0.145 | 0.014 | 2 | 0.027 | |
| Vaccine sample group C-1 | 0.44 | 0.501 | 2 | 1.002 | 0.83 |
| Vaccine sample group C-2 | 0.372 | 0.409 | 2 | 0.818 | |
| Vaccine sample group C-3 | 0.405 | 0.454 | 2 | 0.908 | |
| Vaccine sample group C-4 | 0.286 | 0.29 | 2 | 0.579 | |
| Vaccine sample group B-1 | 0.453 | 0.519 | 2 | 1.038 | 1.21 |
| Vaccine sample group B-2 | 0.464 | 0.534 | 2 | 1.067 | |
| Vaccine sample group B-3 | 0.611 | 0.743 | 2 | 1.486 | |
| Vaccine sample group B-4 | 0.524 | 0.618 | 2 | 1.236 | |
| Vaccine sample group A-1 | 1.029 | 1.499 | 2 | 2.998 | 2.18 |
| Vaccine sample group A-2 | 0.691 | 0.865 | 2 | 1.73 | |
| Vaccine sample group A-3 | 0.715 | 0.902 | 2 | 1.805 | |
| Vaccine sample group A-4 | 0.825 | 1.089 | 2 | 2.178 | |

7.5 Example 5: Antigen Immunogenicity Analysis

The purpose of the following experiment was to evaluate the immunogenicity of the mRNA molecular liposome (RBD mRNA-LNP) loaded with the SARS-CoV-2 coronavirus S-RBD protein of the present invention.

The number of animals in each group and the detailed immunization routes, doses and schedules were shown in the table below. Experimental animals, BALB/c mice, received the test antigen (10 μg/50 μL per mouse) via a single point intramuscular injection on the right hind limb on day 0. A same dose of the test vaccine was vaccinated again on day 14. The detailed administration methods, dosing amounts and administration routes were as follows:

| Group | Number of animals | Test antigen | Dose | Injection volume | Immunization method | Immunity cycle[a] |
|---|---|---|---|---|---|---|
| 1 | 8 | RBD mRNA-LNP | 10 μg per animal | 50 μL per animal | i.m. | Days 0 and 14 |
| 2 | 4 | Empty liposome | 10 μg per animal | 50 μL per animal | i.m. | Days 0 and 14 |
| 3 | 4 | 1 × PBS | N/A | 50 μL per animal | i.m. | Days 0 and 14 |

Note:
[a]The day of the first immunization was defined as day 0.

Before the first immunization, 4 mice were randomly selected to collect blood to prepare serum samples (above 150 μL), and the serum samples were collected without anticoagulants for monitoring, as shown in the following table.

| Group | Time point | Sample collection and processing method |
|---|---|---|
| RBD mRNA-LNP group | Day 14 | Collecting whole blood to prepare serum samples before the second immunization, serum amount >150 μL per animal |
| | Day 21 | Collecting whole blood to prepare serum samples, serum amount >150 μL per animal |
| | Day 28 | Collecting whole blood to prepare serum samples, serum amount >150 μL per animal, and Collecting spleens from 4 animals to prepare a single cell suspension |
| Empty liposome group | Day 14 | Collecting whole blood to prepare serum samples before the second immunization, serum amount >150 μL per animal |
| | Day 21 | Collecting whole blood to prepare serum samples, serum amount >150 μL per animal |
| | Day 28 | Collecting whole blood to prepare serum samples, serum amount >150 μL per animal, and Collecting spleen from 1 animal to prepare a single cell suspension |
| 1 × PBS group | Day 14 | Collecting whole blood to prepare serum samples before the second immunization, serum amount >150 μL per animal |
| | Day 21 | Collecting whole blood to prepare serum samples, serum amount >150 μL per animal |
| | Day 28 | Collecting whole blood to prepare serum samples, serum amount >150 μL per animal, and Collecting spleen from 1 animal to prepare a single cell suspension |

There were 52 samples in total as follows: 4 serum samples collected before the first immunization; 16 serum samples collected 14 days after the first immunization; 16 serum samples collected 21 days after the first immunization; and 16 serum samples collected 28 days after the first immunization, respectively. After the serum collection was completed, the coronavirus RBD IgG titers were detected together. In this experiment, a "Mouse Anti-New Coronavirus (2019-nCoV)S-RBD Protein IgG Antibody Detection Kit" developed by Wantai BioPharm was used for IgG titer detection. The test serum samples were diluted in a 10-fold gradient starting from 1:10 with a sample diluent, and shaken gently to mix well. 100 μL of each of the diluted samples, the negative control and the positive control was added to each well. The plate was sealed with a sealing membrane. The sealing membrane was cut off at 37° C. for 30 min, and the plate was washed for 5 times, 300 μL each time, and dried at the last time. 100 μL of ELISA reagent was added to each well, except for blank wells. The sealing membrane was cut off at 37° C. for 30 min, and the plate was washed for 5 times, 300 μL each time. 50 mL of each of color developer A and B was added to each well, shaken gently to mix well, and developed at 37° C., protected from the light, for 15 min. 50 μL of the stop solution was added to each well, and mixed well in a gentle manner. The result was measured within 10 min. The wavelength of the microplate reader was set at 450 nm. The maximum dilution factor for which the detection result was positive was selected, and Titer result was the OD value of the positive maximum dilution factor/0.1*corresponding dilution factor.

Figure 7:
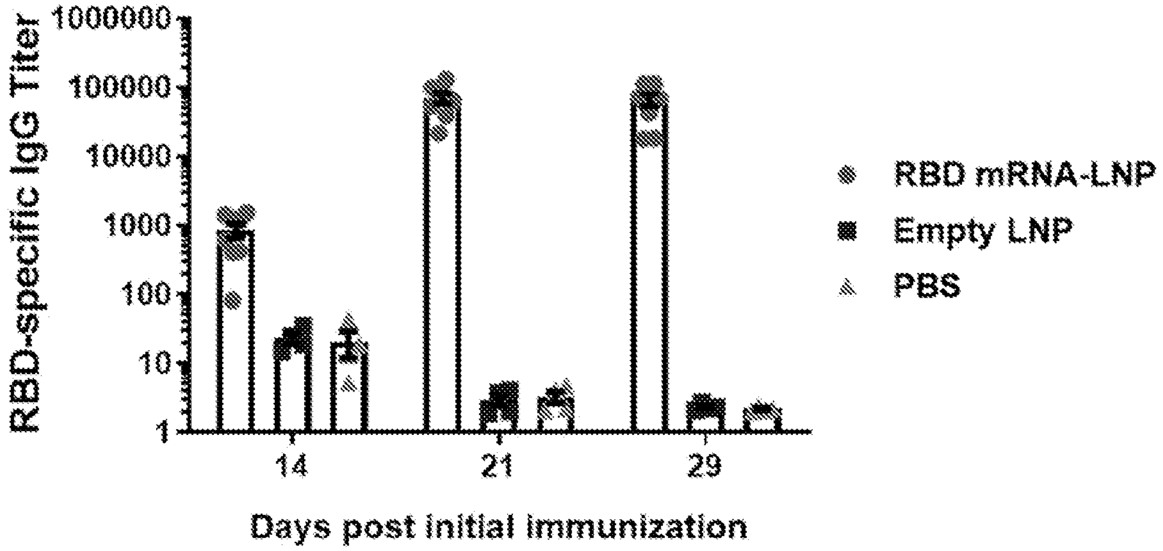
FIG. 7 shows the detection results of RBD-specific IgG antibody titers in immunized mice on days 14, 21 and 29 as measured by ELISA.

Specifically, the mice were immunized with a single dose (10 μg) of the mRNA vaccine on day 0, and a booster dose (10 μg) was given on day 14. The anti-S-RBD IgG antibody levels in the mouse serum samples were detected 14, 21, and 29 days after the immunization. The results were shown in FIG. 7. In the group of mice vaccinated with mRNA-LNP, one week after the second immunization, the specific IgG titer increased from about 1/900 on day 14 to 1/70,000 on day 21 and maintained at the same level on day 29. In contrast, neither of the empty liposome and PBS control groups had RBD-specific IgG expression. This result clearly showed that the vaccine product described in the present invention had strong immunogenicity and can specifically induce the production of related antibodies to achieve the effect of controlling or preventing the infection of the coronavirus SARS-CoV-2.

8. SEQUENCE LISTING

The present specification is being filed with a computer readable form (CRF) copy of the Sequence Listing. The CRF entitled 14639-009-999 Sequence_Listing.txt, which was created on Jan. 24, 2022 and is 199,425 bytes in size, and is incorporated herein by reference in its entirety.

What is claimed:

1. A pharmaceutical composition comprising a nucleic acid encoding a viral peptide or polypeptide derived from coronavirus SARS-CoV-2 and at least one lipid, wherein the viral peptide or polypeptide is an immunogenic fragment of the spike (S) protein of SARS-CoV-2;

wherein the immunogenic fragment of the S protein is the receptor binding domain (RBD) of the S protein;

wherein the nucleic acid comprises the sequence as set forth in any one of SEQ ID NOS:9, 11, 13, and 15, or a transcribed RNA sequence thereof; and wherein the at least one lipid forms lipid nanoparticles encapsulating the nucleic acid.

2. The pharmaceutical composition of claim 1, wherein the nucleic acid is an mRNA molecule.

3. The pharmaceutical composition of claim 1, wherein the nucleic acid further comprises a 5' untranslated region (5'-UTR), wherein the 5'-UTR comprises the DNA sequence set forth in any one of SEQ ID NO:46, SEQ ID NO:48 and SEQ ID NO:50, or the RNA sequence set forth in any one of SEQ ID NO:47, SEQ ID NO:49, and SEQ ID NO:51.

4. The pharmaceutical composition of claim 1, wherein the nucleic acid further comprises a 3' untranslated region (3'-UTR), wherein the 3'-UTR comprises the DNA sequence set forth in any one of SEQ ID NO:52, SEQ ID NO:54 and SEQ ID NO: 56, or the RNA sequence set forth in any one of SEQ ID NO:53, SEQ ID NO:55 and SEQ ID NO:57.

5. The pharmaceutical composition of claim 1, wherein the nucleic acid encodes a fusion protein comprising the viral peptide or polypeptide fused to a peptide or polypeptide selected from an Fc region of human immunoglobulin, a signal peptide, and a peptide facilitating multimerization of the fusion protein.

6. The pharmaceutical composition of claim 5, wherein the nucleic acid encodes a fusion protein comprising the (RBD) of the S protein fused to a signal peptide, and wherein the signal peptide comprises the sequence set forth in SEQ ID NO:36 or SEQ ID NO:38.

7. A method for, preventing or inhibiting an infectious disease caused by the coronavirus SARS-CoV-2 in a subject in need thereof, wherein the method comprises administering to the subject a therapeutically effective amount of the pharmaceutical composition of claim 1.

8. The method of claim 7, wherein the infectious disease is respiratory tract infection, lung infection, renal infection, liver infection, enteric infection, neurologic infections, respiratory syndrome, bronchitis, pneumonia, gastroenteritis, encephalomyelitis, encephalitis, sarcoidosis, diarrhea, hepatitis, or demyelinating disease.

9. The pharmaceutical composition of claim 5, wherein the nucleic acid encodes a fusion protein comprising the RBD of the S protein fused to the signal peptide, and wherein the signal peptide is encoded by the sequence set forth in SEQ ID NO: 37 or SEQ ID NO:39, or transcribed RNA sequence thereof.

10. The pharmaceutical composition of claim 5, wherein the nucleic acid encodes a fusion protein comprising the RBD of the S protein fused to the Fc region of human immunoglobulin, and wherein the Fc region is human IgG1 Fc or a variant thereof.

11. The pharmaceutical composition of claim 5, wherein the nucleic acid encodes a fusion protein comprising the RBD of the S protein fused to the peptide facilitating multimerization of the fusion protein, and wherein the fusion protein is configured to form a trimeric complex.

12. The pharmaceutical composition of claim 1, wherein the nucleic acid comprises one or more functional nucleotide analogs selected from pseudouridine, 1-methyl-pseudouridine and 5-methylcytosine.

13. The pharmaceutical composition of claim 1, wherein the composition comprises lipid nanoparticles comprising the at least one lipid.

14. The pharmaceutical composition of claim 13, wherein the lipid nanoparticles encapsulate the nucleic acid in a lipid shell.

15. The pharmaceutical composition of claim 1, wherein the composition is a vaccine.

16. The method of claim 7, wherein the subject is a human or a non-human mammal.

17. The method of claim 7, wherein the subject is at risk of, or is susceptible to, infection by the coronavirus.

18. The method of claim 7, wherein the subject is asymptomatic.

19. The method of claim 7, wherein upon administration of the pharmaceutical composition, the nucleic acid is expressed by the cells in the subject.

20. The method of claim 7, wherein upon administration of the pharmaceutical composition, an immune response against the coronavirus is elicited in the subject.

21. The method of claim 18, wherein the immune response comprises production of an antibody specifically binds to the viral peptide or protein encoded by the nucleic acid.

22. The method of claim 19, wherein the antibody is a neutralizing antibody against the coronavirus or cells infected by the coronavirus.

23. A method for administering the pharmaceutical composition of claim 1 to a subject in need thereof.

24. A method for preventing or inhibiting coronavirus disease 2019 (COVID-19) in a subject in need thereof, wherein the method comprises administering to the subject a therapeutically effective amount of the pharmaceutical composition of claim 1.

* * * * *

UNITED STATES PATENT AND TRADEMARK OFFICE
CERTIFICATE OF CORRECTION

PATENT NO. : 11,510,977 B2
APPLICATION NO. : 17/589703
DATED : November 29, 2022
INVENTOR(S) : Bo Ying It is certified that error appears in the above-identified patent and that said Letters Patent is hereby corrected as shown below:

In the Claims

In Column 329, Line 57 (part of Claim 7), delete the "," between "for" and "preventing".

In Column 330, Line 59 (part of Claim 21), replace "method of claim 18" with "method of claim 20".

In Column 330, Line 63 (part of Claim 22), replace "method of claim 19" with "method of claim 21".

Signed and Sealed this
Thirty-first Day of January, 2023

Katherine Kelly Vidal
*Director of the United States Patent and Trademark Office*